(12) United States Patent
Lichenstein et al.

(10) Patent No.: US 6,982,250 B2
(45) Date of Patent: Jan. 3, 2006

(54) METHODS OF PREVENTION AND TREATMENT OF INFLAMMATORY BOWEL DISEASE

(75) Inventors: Henry Lichenstein, Guilford, CT (US); Michael Jeffers, Branford, CT (US)

(73) Assignee: CuraGen Corporation, New Haven, CT (US)

(*) Notice: Subject to any disclaimer, the term of this patent is extended or adjusted under 35 U.S.C. 154(b) by 530 days.

(21) Appl. No.: 10/011,364

(22) Filed: Nov. 16, 2001

(65) Prior Publication Data

US 2003/0153495 A1 Aug. 14, 2003

Related U.S. Application Data

(63) Continuation-in-part of application No. 09/992,840, filed on Nov. 6, 2001.
(60) Provisional application No. 60/246,206, filed on Nov. 6, 2000.

(51) Int. Cl.
*A61K 38/00* (2006.01)
*C07K 17/00* (2006.01)

(52) U.S. Cl. .............................. 514/12; 514/2; 530/350
(58) Field of Classification Search ...................... 514/2, 514/12; 530/350; 435/69.1
See application file for complete search history.

(56) References Cited

U.S. PATENT DOCUMENTS

2002/0001825 A1    1/2002    Itoh

FOREIGN PATENT DOCUMENTS

| GB | 2365869 | 2/2002 |
|---|---|---|
| JP | 5301893 | 11/1993 |
| WO | WO 00/54813 | 9/2000 |
| WO | WO 01/07595 | 2/2001 |
| WO | WO 01/31008 A2 | 5/2001 |
| WO | WO 01/68854 | 9/2001 |
| WO | WO 01/72957 A2 | 10/2001 |
| WO | WO 01/92522 | 12/2001 |
| WO | WO 02/02625 | 1/2002 |
| WO | WO 02/24234 | 3/2002 |
| WO | WO 02/36732 | 5/2002 |
| WO | WO 02/46424 | 6/2002 |

OTHER PUBLICATIONS

Ngo et al., 1994, The Protein Folding Problem and Tertiary Structure Prediction, pp. 492–495.*
Wells, Aditivity of Mutational Effects in Proteins, 1990, Biochemistry, vol. 29, No.: 37, pp. 8509–8517.*
Jeffers et al. A Novel Human Fibroblast Growth Factor Treats Experimental Intestinal Inflammation. 2002, Gastroenterology, vol. 123, pp. 1151–1162.*

Pickering, et al. (1997). "Fibroblast Growth Factor–2 Potentiates Vascular Smooth Muscle Cell Migration to Platelet–Derived Growth Factor" and "Upregulation of $\alpha_2\beta_1$ Integrin and Disassembly of Actin Filaments" *Cir. Res.* 80:627–637.
Klein, et al. (1995). "Differential Modulation of Cell Phenotype by Different Molecular Weight Forms of Basic Fibroblast Growth Factor: Possible Intracellular Signaling by the High Molecular Weight Forms" *J. Cell Biol.* Apr.; 129(1):233–43. (ABSTRACT).
U.S. application No. 60/161,162, filed Oct. 22, 1999, Itch, et al.
U.S. Application No. 60/124,460, filed Mar. 15, 1999, Manning et al.
Bange et al. (2002). *Cancer Res* 62: 840–847.
Bikfalvi et al. (1997) *Endocrine Reviews* 18: 26–45.
Kirikoshi et al. (2000). *Biochemical and Biophysical Res Comm* 274: 337–343.
Ohmachi et al. (2000). *Biochemical and Biophysical Res Comm* 277: 355–360.
Wong et al. (2001). *Am J of Medical Genetics* 102: 282–285.
International Search Report for PCT/US02/19400, mailed Jun. 4, 2003.
Altschul, et al. (1990). "Basic local alignment search tool." *J. Mol Biol* 215(3): 403–10.
Basilico and Moscateli (1992). "The FGF family of growth factors and oncogenes." *Adv Cancer Res* 59: 115–65.
Danilenko (1999). "Preclinical and early clinical development of keratinocyte growth factor, an epithelial–specific tissue growth factor." *Toxicol Pathol* 27(1): 64–71.
Gasparini (1999). "The rationale and future potential of angiogenesis inhibitors in neoplasia." *Drugs* 58(1): 17–38.
GenBank Accession No.: A58788 (Mar. 6, 1998).
GenBank Accession No.: AA232729 (Nov. 27, 1996).
GenBank Accession No.: AA236522 (Nov. 27, 1996).

(Continued)

*Primary Examiner*—Janet Andres
*Assistant Examiner*—Jegatheesan Seharaseyon
(74) *Attorney, Agent, or Firm*—Ivor R. Elrifi; Naomi S. Biswas; Mintz, Levin, Cohn, Ferris, Glovsky and Popeo, P.C.

(57) ABSTRACT

The present invention is based upon methods of treating inflammatory conditions in the intestinal tract of mammals using growth factor related polypeptides. The invention includes methods of reducing the morality rate or delaying mortality in a subject suffering from an inflammatory pathology. Methods of using fibroblast growth factor-CX (FGF-CX) polynucleotide sequences and the FGF-CX polypeptides encoded by such nucleic acid sequences, or variants, fragments and homologs thereof, are claimed in the invention. Similarly, methods of using FCTRX polynucleotide sequences and the FCTRX polypeptides encoded by such nucleic acid sequences, or variants, fragments and homologs thereof, alone or in combination, are also claimed in the invention. FCTRX collectively refers to any of six variant FCTRX sequences, variously designated FCTR1, FCTR2, FCTR3, FCTR4, FCTR5 and FCTR6.

26 Claims, 44 Drawing Sheets

OTHER PUBLICATIONS

GenBank Accession No.: AAF00049 (Jun. 22, 2000).
GenBank Accession No.: AAF80597 (Aug. 27, 2001).
GenBank Accession No.: AB012615 (Sep. 8, 1999).
GenBank Accession No.: AB020858 (May 21, 1999).
GenBank Accession No.: AF091434 (Jun. 22, 2000).
GenBank Accession No.: AI272876 (Nov. 18, 1998).
GenBank Accession No.: AI272878 (Nov. 18, 1998).
GenBank Accession No.: BAB03265 (Jul. 26, 2000).
GenBank Accession No.: E05822 (Sep. 29, 1997).
GenBank Accession No.: P36364 (Nov. 1, 1997).
GenBank Accession No.: P54130 (Oct. 16, 2001).
GenBank Accession No.: P98070 (Oct. 16, 2001).
GenBank Accession No.: S82023 (May 5, 2002).
Gerwins, et al. (2000). "Function of fibroblast growth factors and vascular endothelial growth factors and their receptors in angiogenesis." *Crit Rev Oncol/Hematol 34*(3): 185–94.
Grisham (1994). "Oxidants and free radicals in inflammatory bowel disease." *Lancet 344*(8926): 859–61.
Klint and Claesson–Welsh (1999) "Signal transduction by fibroblast growth factor receptors" *Front. Biosci. 4*: d165–177.
Koga, et al. (1999). "Characterization of a novel member of the FGF family, XFGF–20, in *Xenopus laevis*." *Biochem Biophys Res Commun 261*(3): 756–65.
La Rocca, et al. (1990). "Suramin: prototype of a new generation of antitumor compounds." *Cancer Cells 2*(4): 106–15.
Li, et al. (1997). "Activation of FGF receptors by mutations in the transmembrane domain." *Oncogene 14*(12): 1397–406.
Lichtiger, et al. (1994). "Cyclosporine in severe ulcerative colitis refractory to steroid therapy." *N Engl J Med 330*(26): 1841–5.
Lorenzi, et al. (1996). "FRAG1, a gene that potently activates fibroblast growth factor receptor by C–terminal fusion through chromosomal rearrangement." *Proc Natl Acad Sci U S A 93*(17): 8956–61.
Matsumoto–Yoshitomi, et al. (1997). "Autocrine transformation by fibroblast growth factor 9 (FGF–9) and its possible participation in human oncogenesis." *Int J Cancer 71*(3): 442–50.
Miyakawa, et al. (1999). "A hydrophobic region locating at the center of fibroblast growth factor– 9 is crucial for its secretion." *J Biol Chem 274*(41): 29352–7.
Miyake, et al. (1998). "Structure and expression of a novel member, FGF–16, on the fibroblast growth factor family." *Biochem Biophys Res Commun 243*(1): 148–52.

Miyamoto, et al. (1993). "Molecular cloning of a novel cytokine cDNA encoding the ninth member of the fibroblast growth factor family, which has a unique secretion property." *Mol Cell Biol 13*(7): 4251–9.
Mount (1996). "AT–AC introns: an ATtACk on dogma." *Science 271*(5256): 1690–2.
Munkholm, et al. (1994). "Frequency of glucocorticoid resistance and dependency in Crohn's disease." *Gut 35*(3): 360–2.
Nakai and Kanehisa (1992). "A knowledge base for predicting protein localization sites in eukaryotic cells." *Genomics 14*(4): 897–911.
Naruo, et al. (1993). "Novel secretory heparin–binding factors from human glioma cells. (glia– activating factors) involved in glial cell growth. Purification and biological properties." *J Biol Chem 268*(4): 2857–64.
Pearson, et al. (1995). "Azathioprine and 6–mercaptopurine in Crohn disease. A meta–analysis." *Ann Intern Med 123*(2): 132–42.
Present, et al. (1999). "Infliximab for the treatment of fistulas in patients with Crohn's disease." *N Engl J Med 340*(18): 1398–405.
Revest, et al. (2000). "Fibroblast growth factor 9 secretion is mediated by a non–cleaved amino–terminal signal sequence." *J Biol Chem 275*(11): 8083–90.
Santos–Ocampo, et al. (1996). "Expression and biological activity of mouse fibroblast growth factor–9." *J Biol Chem 271*(3): 1726–31.
EMBL Database Accession No.: Q9Q1Y71 (May 1, 2000).
EMBL Database Accession No.: Q9UL22 (May 1, 2000).
Szebenyi and Fallon (1999). "Fibroblast growth factors as multifunctional signaling factors." *Int Rev Cytol 185*: 45–106.
Wozney, et al. (1988). "Novel regulators of bone formation: molecular clones and activities." *Science 242*(4885): 1528–34.
Xu, et al. (1999). "Fibroblast growth factor receptors (FGFRs) and their roles in limb development." *Cell Tissue Res 296*(1): 33–43.
Yates, et al. (1997). "Molecular diagnosis of thiopurine S–methyltransferase deficiency: genetic basis for azathioprine and mercaptopurine intolerance." *Ann Intern Med 126*(8): 608–14.

* cited by examiner

Figure 3.
Panel A
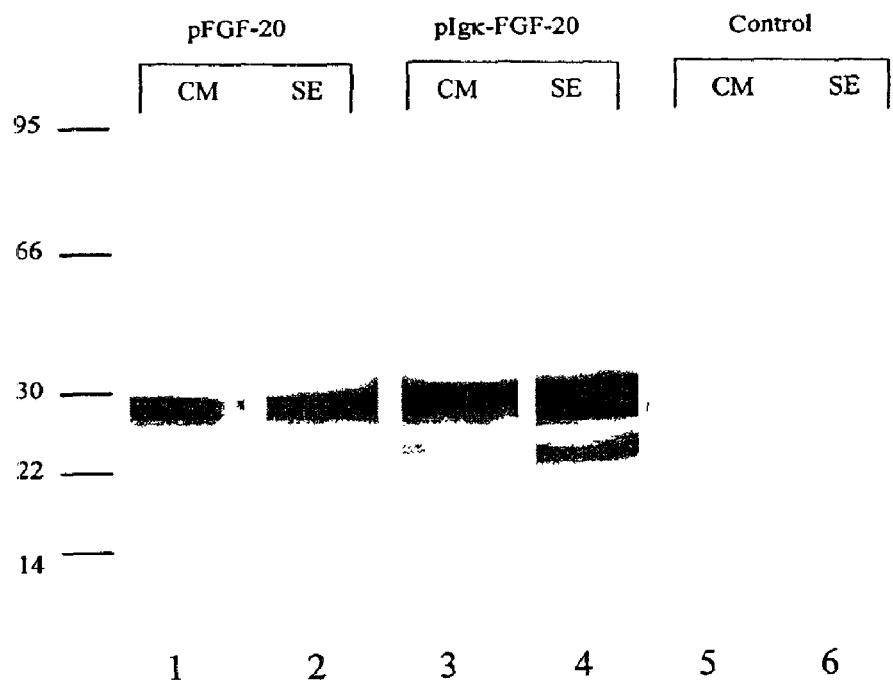
Panel B
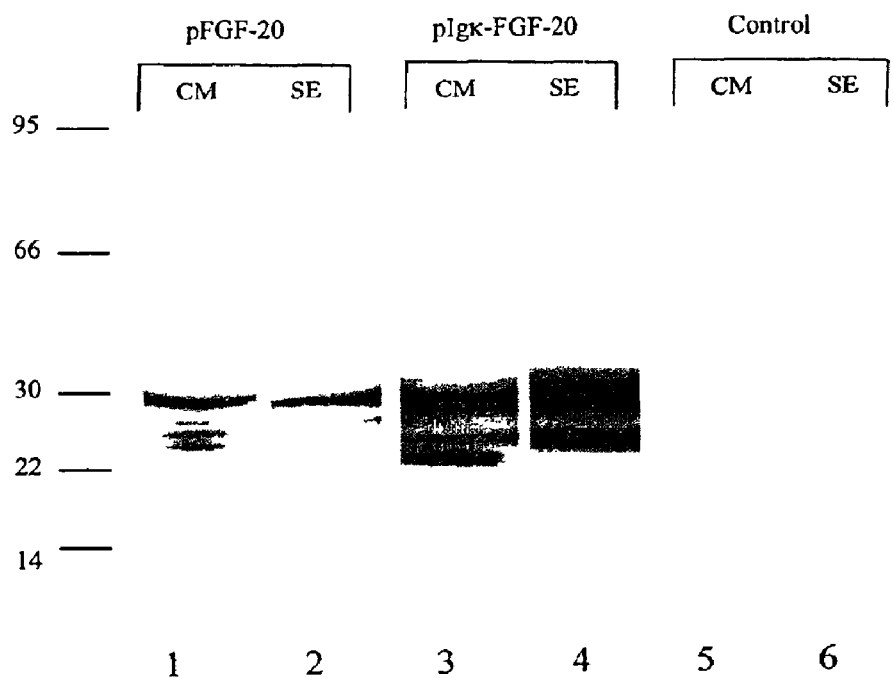

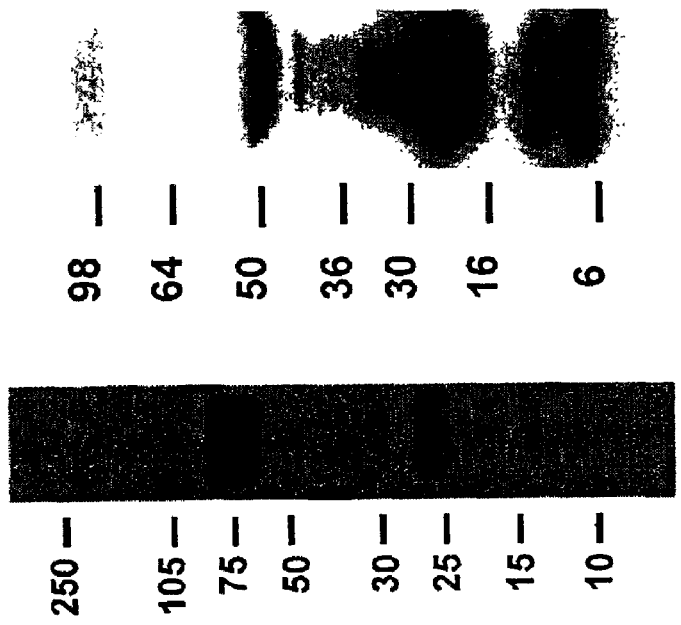
FIG. 11 Panel B
FIG. 11 Panel A

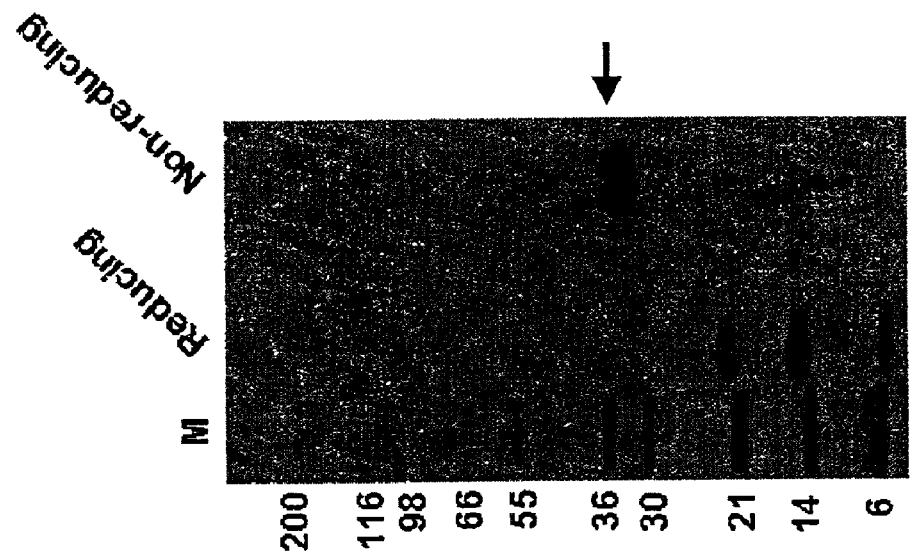
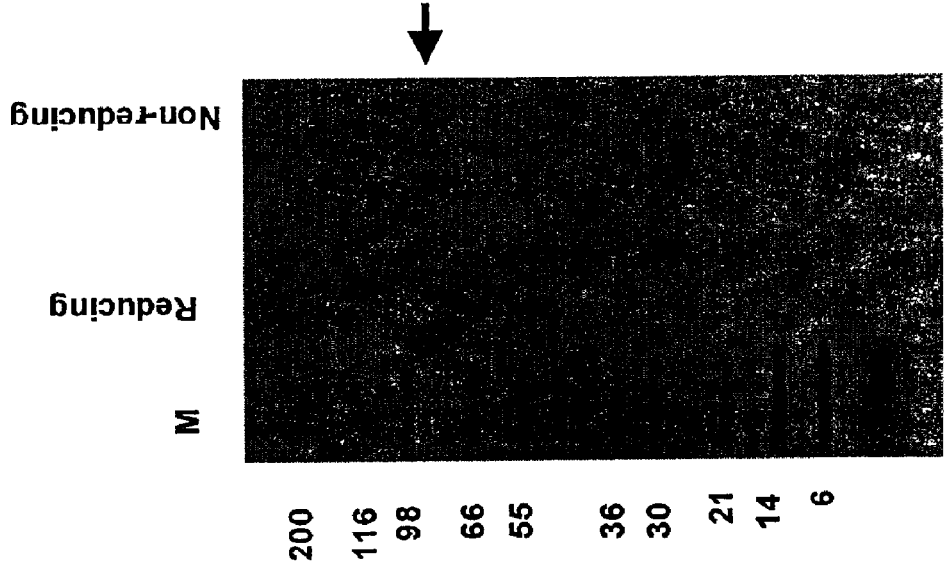
FIG. 17.

Figure 5. AB020858 or 30664188 (ip, QD, d0-6)
Effects on Dextran Sulfate induced Colitis in female balb/c mice (IBD/Cu-1)

Figure 6. AB020858 or 30664188 (ip, QD, d0-6)
Effects on Dextran Sulfate induced Colitis in female balb/c mice (IBD/Cu-1)

Figure 7. AB020858 or 30664188 (ip, QD, d0-6)
Effects on Dextran Sulfate induced Colitis in female balb/c mice (IBD/Cu-1)

Figure 8. AB020858 or 30664188 (ip, QD, d0-6)
Effects on Dextran Sulfate induced Colitis in female balb/c mice (IBD/Cu-1)

Figure 11. AB020858 or 30664188 (ip, QD, d0-6)
Effects on Dextran Sulfate induced Colitis in female balb/c mice (IBD/Cu-1)

Figure 12. AB020858 or 30664188 (ip, QD, d0-6)
Effects on Dextran Sulfate induced Colitis in female balb/c mice (IBD/Cu-1)

Figure 42.
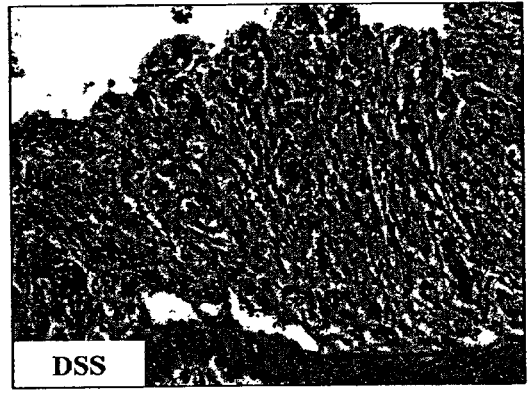
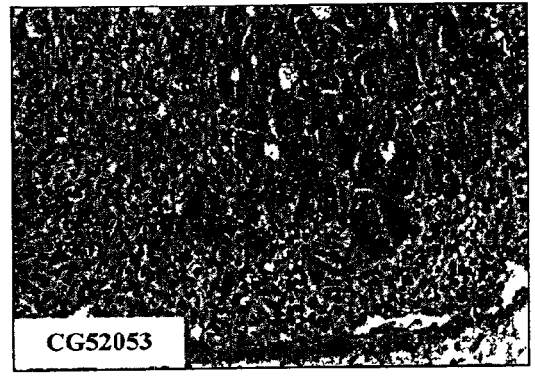

Figure 43.
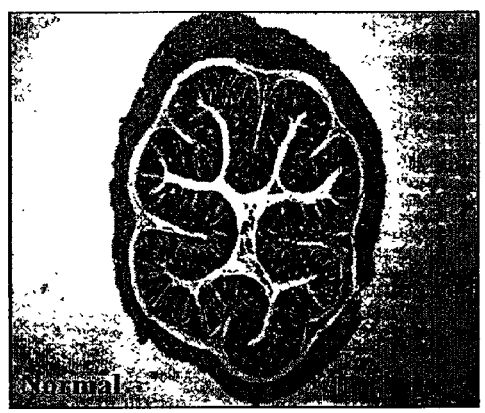
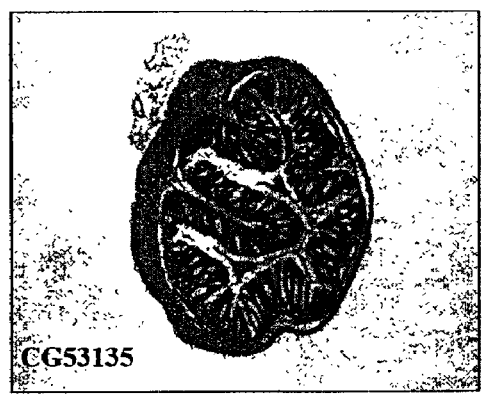
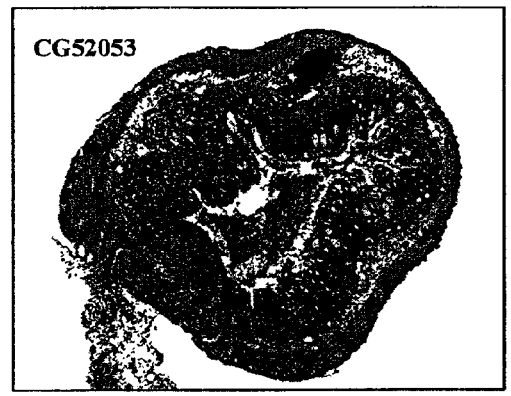

Figure 62.
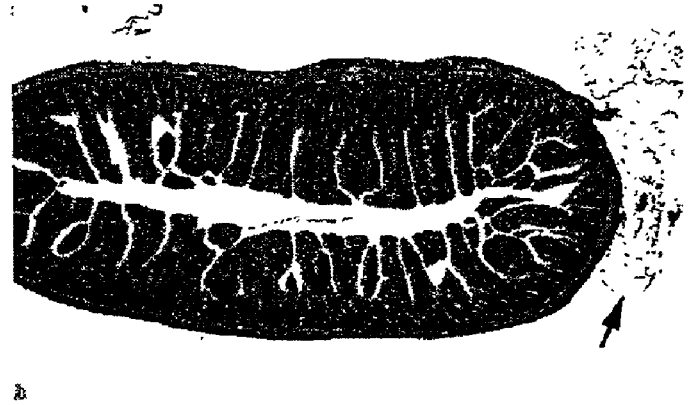
A. Normal Control
B. Disease Control
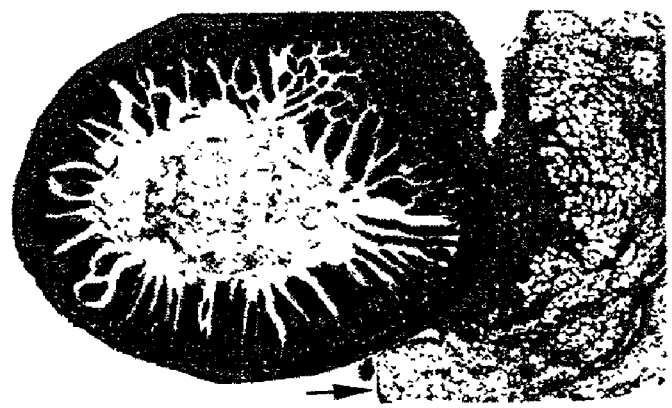
C. CG53135 0.2 mg/kg iv

Figure 63.
A. Normal Control
B. Disease Control
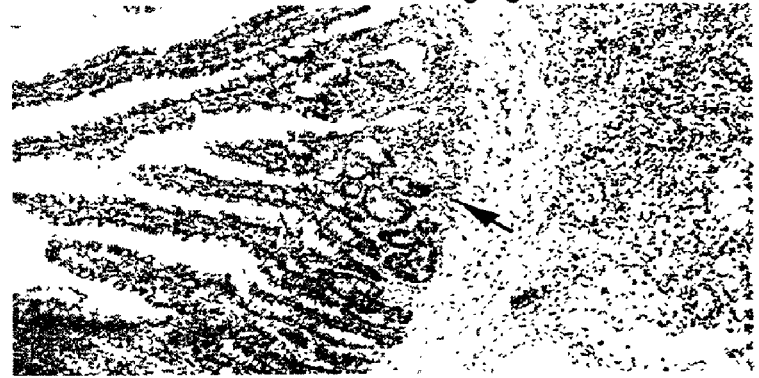
C. CG53135 0.2 mg/kg iv

US 6,982,250 B2

METHODS OF PREVENTION AND TREATMENT OF INFLAMMATORY BOWEL DISEASE

RELATED APPLICATION

This application claims the benefit of priority from U.S. Provisional application Ser. No. 60/246,206 filed Nov. 6, 2000, and is a continuation-in-part of U.S. Non-Provisional application Ser. No. 09/992,840, filed Nov. 6, 2001, the contents of which are incorporated herein in its entirety.

FIELD OF THE INVENTION

The present invention generally relates to methods of treatment of inflammatory conditions in the intestinal tract of mammals using growth factor related polypeptides. More specifically, the polypeptides employed in the methods of the invention are related to a member of the fibroblast growth factor family and to a member of the platelet derived growth factor family.

BACKGROUND OF THE INVENTION

Inflammatory bowel disease comprises two distinct subsets: ulcerative colitis and Crohn's disease. In 1999, approximately 1.7 million people were diagnosed with this debilitating disease. Satisfactory treatment of IBD is an unmet medical need, as existing therapeutics have not been successful in curtailing the disease and preventing surgeries. Up to forty percent of all ulcerative colitis patients undergo surgery, which typically includes the removal of part of the large intestine or a full colostomy. Such surgery is not curative for Crohn's disease, as 75% of all patients undergo at least one surgery in their lifetime, and up to 90% of these patients require additional surgeries. Consequently a therapeutic that can successfully treat inflammatory bowel disease will have the beneficial effects of improving a patient's quality of life, while potentially saving the healthcare system millions of dollars in costs associated with invasive surgical procedures.

SUMMARY OF THE INVENTION

The present invention is based upon methods of treating inflammatory conditions in the intestinal tract of mammals using growth factor related polypeptides. Methods of using fibroblast growth factor-CX (FGF-CX) polynucleotide sequences and the FGF-CX polypeptides encoded by such nucleic acid sequences, or variants, fragments and homologs thereof, are claimed in the invention. Similarly, methods of using FCTRX polynucleotide sequences and the FCTRX polypeptides encoded by such nucleic acid sequences, or variants, fragments and homologs thereof, alone or in combination, are also claimed in the invention. FCTRX collectively refers to any of six variant FCTRX sequences, designated FCTR1, FCTR2, FCTR3, FCTR4, FCTR5 and FCTR6.

In one aspect, the invention provides a method of promoting the growth of a population of cells whereby the cells are placed into contact with a composition including a FGF-CX or FCTRX polypeptide, or a composition including FGF-CX and FCTRX polypeptides. In another aspect, the invention provides a method of treating an inflammatory pathology in a subject, whereby an FGF-CX or an FCTRX polypeptide composition is administered to the subject. In yet another aspect, the invention provides a method of delaying the onset of an inflammatory pathology in a subject, whereby a composition including a FGF-CX or FCTRX polypeptide, or a composition including FGF-CX and FCTRX polypeptides, is administered to the subject. In a further aspect, the invention provides a method of ameliorating an inflammatory pathology in a subject, whereby a composition including a FGF-CX or FCTRX polypeptide, or a composition including FGF-CX and FCTRX polypeptides, is administered to the subject.

In one embodiment, the subject is a mammal. In another embodiment, the subject is human. In yet another embodiment, the inflammatory pathology is inflammatory bowel disease, an inflammatory condition occurring in the colon, an inflammatory condition occurring in the small intestine, or Crohn's disease. In yet another embodiment, the FGF-CX polypeptide is given by SEQ ID NO:2, or a variant, deletion mutant, or a variant of the deletion mutant thereof, wherein up to 15% of the residues of either variant are changed according to a conservative amino acid substitution. In still yet another embodiment, the FCTRX polypeptide is given by any one of SEQ ID NOS:4, 6, 8, 10, 12, and 14, or a variant, deletion mutant, variant of the deletion mutant, p35 form, or a variant of the p35 form thereof, wherein up to 15% of the residues of any variant are changed according to a conservative amino acid substitution. In yet a further embodiment, the polypeptide composition is administered intravenously or subcutaneously.

The invention further provides a method of preparing a pharmaceutical composition, whereby a polypeptide effective in treating an inflammatory pathology is combined with a pharmaceutically acceptable carrier.

In one embodiment, the pharmaceutical composition is suitable for intravenous, or subcutaneous administration to the subject. In another embodiment, the polypeptide is FGF-CX. In yet another embodiment, the FGF-CX polypeptide is given by SEQ ID NO:2, or a variant, deletion mutant, or a variant of the deletion mutant thereof, wherein up to 15% of the residues of either variant are changed according to a conservative amino acid substitution. In a further embodiment, the polypeptide is FCTRX. In yet a further embodiment, the FCTRX polypeptide is given by any one of SEQ ID NOS: 4, 6, 8, 10, 12, and 14, or a variant, deletion mutant, variant of the deletion mutant, p35 form, or a variant of the p35 form thereof, wherein up to 15% of the residues of any variant are changed according to a conservative amino acid substitution. In yet a further embodiment, the inflammatory pathology is inflammatory bowel disease, an inflammatory condition occurring in the colon, an inflammatory condition occurring in the small intestine, or Crohn's disease.

Contemplated within the invention is a method of reducing the mortality rate in a subject suffering from an inflammatory pathology comprising administering to the subject a composition comprising a first polypeptide wherein the first polypeptide comprises either a FGFCX polypeptide or a FCTRX polypeptide. A method of delaying mortality in a subject suffering from an inflammatory pathology comprising administering to the subject a composition comprising a first polypeptide wherein the first polypeptide comprises either a FGFCX polypeptide or a FCTRX polypeptide.

In one embodiment, a method of reducing the mortality rate or delaying mortality in a subject suffering from an inflammatory pathology includes providing a FGF-CX polypeptide or a FCTRX polypeptide suitable for intravenous, or subcutaneous administration to the subject. In another embodiment, the subject is mammalian. In a more specific embodiment, the subject is human. In a different embodiment, the polypeptide is FGF-CX. In further embodiments, the FGF-CX polypeptide includes at least one of the polypeptide of SEQ ID NO:2, or a variant, deletion mutant, or a variant of the deletion mutant thereof, wherein up to 15% of the residues of either variant are changed according to a conservative amino acid substitution. In another embodiment, the polypeptide is FCTRX. In yet further embodiments, the FCTRX polypeptide is given by at least one of SEQ ID NOS: 4, 6, 8, 10, 12, and 14, or a variant, deletion mutant, variant of the deletion mutant, p35 form, or a variant of the p35 form thereof, wherein up to 15% of the residues of any variant are changed according to a conservative amino acid substitution. In yet a further embodiment, the inflammatory pathology is at least one of an inflammatory bowel disease, an inflammatory condition occurring in the colon, an inflammatory condition occurring in the small intestine, or Crohn's disease.

Contemplated disorders within the invention include pathology such as inflammatory conditions in the gastrointestinal tract, including but not limited to inflammatory bowel disease such as ulcerative colitis and Crohn's disease, growth and proliferative diseases such as cancer, angiogenesis, atherosclerotic plaques, collagen formation, cartilage and bone formation, cardiovascular and fibrotic diseases and diabetic ulcers. In addition, FCTRX nucleic acids and their encoded polypeptides will be therapeutically useful for the prevention of aneurysms and the acceleration of wound closure through gene therapy. Furthermore, FCTRX nucleic acids and their encoded polypeptides can be utilized to stimulate cellular growth. wound healing, neovascularization and tissue growth, and similar tissue regeneration needs. More specifically, a FCTRX nucleic acid or polypeptide may be useful in treatment of anemia and leukopenia, intestinal tract sensitivity and baldness. Treatment of such conditions may be indicated, e.g., in patients having undergone radiation or chemotherapy, wherein treatment would minimize any hyperproliferative side effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

Other features and advantages of the invention will be apparent from the following detailed description and claims.

BRIEF DESCRIPTION OF THE DRAWINGS

FIG. 3 shows a Western analysis of FGF-CX. Samples from 293 cells (Panel A) or NIH 3T3 cells (Panel B) transiently transfected with the indicated construct were examined by Western analysis using anti-V5 antibody. CM=conditioned media, SE=suramin-extracted conditioned media. Molecular mass markers are indicated on the left.

FIG. 11. Panel A is a schematic representation of a scheme for the recombinant production, purification and apparent molecular weight of a mature form of the protein of clone 30664188.0.99. Panel B includes representations of two Western blot analyses showing expression of a 30664188.0.m99 polypeptide.

FIG. 17. Panel A is a representation of a western blot of 30664188.m99 expressed by HEK 293 cells cultured in the absence of serum. Panel B is a representation of SDS-PAGE 30664188.m99 protein expressed by HEK 293 cells cultured in the presence of serum.

FIG. 42 presents photomicrographs at 400× in the original image of mouse colon cross sections. Panel A, DSS plus Vehicle; Panel B, DSS+AB020858; Panel C, Normal mouse.

FIG. 43 presents photomicrographs at 50× in the original image of mouse colon crossections. Panel A, DSS plus Vehicle; Panel B, DSS+AB020858; Panel C, Normal mouse.

FIG. 62 presents images showing the protective effect of CG53135 on intestinal architecture. Panel A: Small intestine from normal control animal treated iv with vehicle (BSA). Panel. B: Small intestine from indomethacin-treated rat, further treated with vehicle (BSA) iv. Panel C: Small intestine from indomethacin-treated rat further treated with CG53135, 0.2 mg/kg iv. Sections were stained with H&E and visualized at a magnification of 25). FIG. 62 shows the protective Effect of CG53135 on Intestinal Architecturein indomethacin treated rats. Panel A, normal control; Panel B, disease control (indomethacin treated); Panel C, disease model animal treated with 0.2 mg/kg iv CG53135. Photomicrographs were obtained on sections stained with hemotoxylin and eosin, at 25× magnification.

FIG. 63 shows the effect of CG53135 treatment on BrdU Labeling in the Intestine. BrdU incorporation was detected by Immunoperoxidase staining. Panel A: Small intestine from normal control animal (100×). Panel B: Small intestine from indomethacin+vehicle (BSA) treated animal (50×). Panel C: Small intestine from indomethacin+CG53135 0.2 mg/kg iv treated rat (50×).

DETAILED DESCRIPTION OF THE INVENTION

Figure 1:
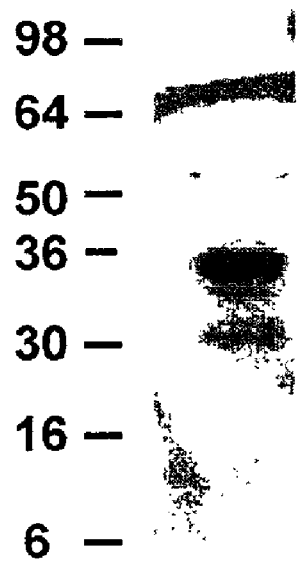
FIG. 1 shows a Western analysis of FGF-CX protein secreted by 293 cells.

This invention is related in part to the discovery of novel FGF-CX nucleic acid sequences that encode polypeptides that are members of the fibroblast growth factor ("FGF") family. As used herein the designation "FGF-CX" relates to nucleic acids, polynucleotides, proteins, polypeptides, and variants, derivatives and fragments of any of them, as well as to antibodies that bind immunospecifically to any of these classes of compounds. In the present disclosure, FGF-CX polypeptides are alternatively identified by the internal accession numbers AB020858, CG53135-01 and CG53135-02.

The invention further is based on the discovery of nucleic acids that encode polypeptides related to bone-morphogen protein-1 ("BMP-1"), to vascular endothelial growth factor ("VEGF-E"), and to platelet derived growth factors ("PDGF"). These sequences are collectively referred to as "FCTRX nucleic acids" or FCTRX polynucleotides" and the corresponding encoded polypeptide is referred to as a "FCTRX polypeptide" or "FCTRX protein." Unless indicated otherwise, "FCTRX" is meant to refer to any of the novel sequences disclosed herein. In addition, the polypeptides and nucleic acids of the invention are alternately referred to herein collectively as "PDGF D", since they are considered to represent a heretofore unknown PDGF, i.e., one that differs from PDGF A, PDGF B and PDGF C. Furthermore, when reference is made to "PDGFXX" or "PDGF XX" wherein "X" is either the A, B, C or D, this is meant to refer to homodimers of the particular PDGF. Alternately, when reference is made to "PDGFXY" wherein X and Y are either the A, B, C or D, and "X" is different from "Y" this is meant to refer to PDGF heterodimers.

It is shown herein that PDGF D has a high molecular weight latent form, designated p85, and a low molecular weight active form, designated p35. In the present disclosure, the FCTRX or PDGF D polypeptides are alternatively designated by the identifiers 30664188 and variations thereof such as 30664188.0.99 or 30664188.0.331, and CG52053 and variations thereof such as CG52053-01 and CG52053-02.

Inflammatory Bowel Disease

Inflammatory bowel disease ("IBD") refers to a group of chronic inflammatory disorders involving the gastrointestinal tract. Although IBD is diagnosed largely by exclusion, there are characteristic features associated with it that allows accurate diagnosis.

Chronic IBD is sub-divided into two major groups, namely, ulcerative colitis ("UC") and Crohn's disease ("CD"). Clinically IBD is characterized by recurrent inflammatory involvement of intestinal segments with diverse clinical manifestations. Typically UC affects the rectum and extends proximally to involve part or all of the colon. Lesions are restricted to the mucosal or submucosal layers of the colon with deeper layers unaffected except in fulminant disease. Symptoms include rectal bleeding, mucus containing diarrhea, abdominal pain and weight loss. CD affects the full thickness of the gut wall in both the small and large intestines in contrast to UC. The clinical symptoms of UC vary according to the region affected. In general, fever, malaise, weight loss, abdominal pain and cramps are the common symptoms of CD. Full thickness bowel lesions can progress to bowel perforations and local abscesses, fistulas in the adjoining abdominal and pelvic organs, and fibrosis of the bowel wall with obstruction.

The etiology of UC or CD remains unknown. However, a combination of factors including abnormalities in the immune system, genetic predisposition, environmental and psychological factors, may be of importance in determining the outcome of the disease.

In Europe and the United States, incidence and prevalence of CD is approximately 1–6 and 10–100 cases per 100,000 population respectively. For UC the incidence and prevalence rates are respectively 2–10 and 35–100 per 100,000. There is a slight preponderence in females over males for contracting the disease. UC and CD affect primarily individuals between the ages of 15 and 35 years.

Therapeutic Options for Inflammatory Bowel Disease

Choice of therapy for IBD is dependent on pharmacodynamic considerations that govern drug and patient characteristics. Clinical remission (relief of inflammatory symptoms) and mucosal healing are two vital aspects that need to be treated. Many of the current drugs of choice have a poor correlation between symptomatic relief and mucosal healing. Thus agents that can maintain remission as well as accomplish healing will be of particular interest in the management of IBD. In the past decade several drugs have been used in the treatment of IBD. These include conventional salicylates, antibiotics and corticosteroids as well as immunomodulators and biological response modifiers.

5-Aminosalicylates (5-ASAs)

The 5-ASAs (sulfasalazine and the sulfa-free agents) are known to alter the immune response by down-regulating antibody secretion and lymphocyte function, inhibit neutrophil and macrophage chemotaxis and protect intestinal epithelium by enhancing expression of heat shock proteins. In addition, they also inhibit the cyclooxygenase and 5-lipoxygenase pathways of arachidonic acid metabolism that may inhibit the release of chemotactic substances (Grisham, M. B. Lancet, 1994, 344:859–861). 5-ASAs are effective therapeutic agents for mild to moderate conditions of UC. However, 5-ASAs are not the drugs of choice for IBD due to their side effects that may include nausea, allergic reactions and reversible oligospermia.

Antibiotics

Historically, antibiotics like metronidazole and quinolones have been used to treat CD, although their effectiveness in ameliorating the condition has not been well documented. The presumed effect of these agents may be in the alteration of the bacterial flora associated with IBD. Antibiotics are not only less effective for IBD but also have associated side effects (anorexia, nausea, rash) and thus may not be the treatment of choice for IBD.

Corticosteroids

Corticosteroids have been the oldest of the nonspecific but effective therapeutic regimen used for IBD. Corticosteroids modulate both immunologic and inflammatory responses and inhibit an array of leukocyte functions such as adherence, chemotaxis, phagocytosis arachidocic acid metabolism and eicosanoids production. Although their use in short-term treatment of CD and UC have been shown, their efficacy in maintenance therapy is far from satisfactory (Munkholm et al., Gut, 1994, 35:360–362). The failure of corticosteroids in maintenance therapy coupled with the known detrimental side effects of this agent limit their use in the treatment for IBD.

Immunomodulators

The thiopurine agents 6-mercaptoputine ("6-MP") and azathioprine ("AZA") have been used in the treatment of CD and UC as steroid sparing agents (Pearson et al.. Annals of Internal Medicine, 1995, 123:1320142). Side effects such as leukopenia, thrombocytopenia associated with these drugs are further complicated by the genetic predisposition of the patient. (Yates et al Ann. Intern. Med. 1997, 126:608–614). Additional side effects such as pancreatitis, hepatitis, nausea and rash are also reported.

Methotrexate has been shown to be effective in steroid-dependent CD but not in UC The side effects of methotrexate include bone marrow suppression, interstitial pneumonitis and neuropathy.

Cyclosporine has been effective in the treatment of both CD and UC. Cyclosporine has been particularly shown to be effective in patients with active CD or UC that are resistant or intolerant to corticosteriods (Lichtiger et al., New England Journal of Medicine, 1994, 330:1841–1845). The side effects of cyclosporin include reversible or irreversible decrease in renal function, hypertension, tremor, and seizure.

Biological Response Modifiers

The agent Infliximab, a chimeric monoclonal IgG1 antibody directed against TNF-α, has been effectively used in the treatment of CD. Although it is effective in maintenance therapy and healing fistulas (Present et al., New England Journal of Medicine, 1999, 340:1398–1405), side effects include delayed hypersensitivity reactions and lymphoproliferative disorders.

Fibroblast Growth Factors

The fibroblast growth factor (FGF) group of cytokines includes at least 21 members that regulate diverse cellular functions such as growth, survival, apoptosis, motility and differentiation. These molecules transduce signals via high affinity interactions with cell surface tyrosine kinase FGF receptors (FGFRs). FGF receptors are expressed on most types of cells in tissue culture. Dimerization of FGF receptor monomers upon ligand binding has been reported to be a requisite for activation of the kinase domains, leading to receptor trans phosphorylation. FGF receptor-1 (FGFR-1), which shows the broadest expression pattern of the four FGF receptors, contains at least seven tyrosine phosphorylation sites. A number of signal transduction molecules are affected by binding with different affinities to these phosphorylation sites.

Previously described members of the FGF family regulate diverse cellular functions such as growth, survival, apoptosis, motility and differentiation (Szebenyi & Fallon (1999) Int. Rev. Cytol. 185, 45–106). These molecules transduce signals intracellularly via high affinity interactions with cell surface tyrosine kinase FGF receptors (FGFRs), four of which have been identified to date (Xu et al. (1999) Cell Tissue Res. 296, 33–43; Klint & Claesson-Welsh (1999) Front. Biosci. 4, 165–177). These FGF receptors are expressed on most types of cells in tissue culture. Dimerization of FGF receptor monomers upon ligand binding has been reported to be a requisite for activation of the kinase domains, leading to receptor trans phosphorylation. FGF receptor-1 (FGFR-1), which shows the broadest expression pattern of the four FGF receptors, contains at least seven tyrosine phosphorylation sites. A number of signal transduction molecules are affected by binding with different affinities to these phosphorylation sites.

FGFs also bind, albeit with low affinity, to heparin sulfate proteoglycans (HSPGs) present on most cell surfaces and extracellular matrices (ECM). Interactions between FGFs and HSPGs serve to stabilize FGF/FGFR interactions, and to sequester FGFs and protect them from degradation (Szebenyi. & Fallon (1999)). Due to its growth-promoting capabilities, one member of the FGF family, FGF-7, is currently in clinical trials for the treatment of chemotherapy-induced mucositis (Danilenko (1999) Toxicol. Pathol. 27, 64–71).

In addition to participating in normal growth and development, known FGFs have also been implicated in the generation of pathological states, including cancer (Basilico & Moscatelli (1992) Adv. Cancer Res. 59, 115–165). FGFs may contribute to malignancy by directly enhancing the growth of tumor cells. For example, autocrine growth stimulation through the co-expression of FGF and FGFR in the same cell leads to cellular transformation (Matsumoto-Yoshitomi, et al., (1997) Int. J. Cancer 71, 442–450). Likewise, the constitutive activation of FGFR via mutation or rearrangement leads to uncontrolled proliferation (Lorenzi, et al., (1996) Proc. Natl. Acad. Sci. USA. 93, 8956–8961; Li, et al., (1997) Oncogene 14, 1397–1406). Furthermore, some FGFs are angiogenic (Gerwins, et al., (2000) Crit. Rev. Oncol. Hematol. 34, 185–194). Such FGFs may contribute to the tumorigenic process by facilitating the development of the blood supply needed to sustain tumor growth. Not surprisingly, at least one FGF is currently under investigation as a potential target for cancer therapy (Gasparini (1999) Drugs 58, 17–38).

Expression of FGFs and their receptors in the brains of perinatal and adult mice has been examined. Messenger RNA all FGF genes, with the exception of FGF-4, is detected in these tissues. FGF-3, FGF-6, FGF-7 and FGF-8 genes demonstrate higher expression in the late embryonic stages than in postnatal stages, suggesting that these members are involved in the late stages of brain development. In contrast, expression of FGF-1 and FGF-5 increased after birth. In particular, FGF-6 expression in perinatal mice has been reported to be restricted to the central nervous system and skeletal muscles, with intense signals in the developing cerebrum in embryos but in cerebellum in 5-day-old neonates. FGF-receptor (FGFR)-4, a cognate receptor for FGF-6, demonstrate similar spatiotemporal expression, suggesting that FGF-6 and FGFR-4 plays significant roles in the maturation of nervous system as a ligand-receptor system. According to Ozawa et al., these results strongly suggest that the various FGFs and their receptors are involved in the regulation of a variety of developmental processes of brain, such as proliferation and migration of neuronal progenitor cells, neuronal and glial differentiation, neurite extensions, and synapse formation.

Glia-activating factor ("GAF"), another FGF family member, is a heparin-binding growth factor that was purified from the culture supernatant of a human glioma cell line. See, Miyamoto et al., 1993, Mol Cell Biol 13(7): 4251–4259. GAF shows a spectrum of activity slightly different from those of other known growth factors, and is designated as FGF-9. The human FGF-9 cDNA encodes a polypeptide of 208 amino acids. Sequence similarity to other members of the FGF family was estimated to be around 30%. Two cysteine residues and other consensus sequences found in other family members were also well conserved in the FGF-9 sequence. FGF-9 was found to have no typical signal sequence in its N terminus like those in acidic FGF and basic FGF.

Acidic FGF and basic FGF are known not to be secreted from cells in a conventional manner. However, FGF-9 was found to be secreted efficiently from cDNA-transfected COS cells despite its lack of a typical signal sequence. It could be detected exclusively in the culture medium of cells. The secreted protein lacked no amino acid residues at the N terminus with respect to those predicted by the cDNA sequence, except the initiation methionine. The rat FGF-9 cDNA was also cloned, and the structural analysis indicated that the FGF-9 gene is highly conserved.

Platelet Derived Growth Factors

Polypeptide growth factors exerting effects in a variety of tissues have been described. Among these growth factors are bone morphogenetic protein-1 ("BMP-1"), vascular endothelial growth factor (VEGF), and platelet-derived growth factor ("PDGF").

Multiple effects have been attributed to BMP-1. For example, BMP-1 is capable of inducing formation of cartilage in vivo. BMP1 is also identical to purified procollagen C proteinase ("PCP"), a secreted calcium-dependent metalloprotease that has been reported to be required for cartilage and bone formation. BMP-1 cleaves the C-terminal propeptides of procollagen I, II, and III and its activity is increased by the procollagen C-endopeptidase enhancer protein.

Vascular endothelial growth factor ("VEGF") polypeptides have been reported to act as mitogens primarily for vascular endothelial cells. The specificity for vascular endothelial cells contrasts VEGF polypeptides from other polypeptide mitogens, such as basic fibroblast growth factor and platelet-derived growth factors, which are active on a wider range of cell types.

VEGF has also been reported to affect tumor angiogenesis. For example, VEGF has been shown to stimulate the elongation, network formation, and branching of nonproliferating endothelial cells in culture that are deprived of oxygen and nutrients.

The platelet derived growth factor ("PDGF") family currently consists of at least 3 distinct genes, PDGF A, PDGF B, and PDGF C whose gene products selectively signal through two PDGFRs to regulate diverse cellular functions. PDGF A, PDGF B, and PDGF C dimerize in solution to form homodimers, as well as the heterodimer.

Expression of RNA encoding the PDGF A and PDGF B subunits of has been reported in vascular tissues involved in atherosclerosis. PDGF A and PDGF B mRNA have been reported to be present in mesenchymal-appearing intimal cells and endothelial cells, respectively, of atherosclerotic plaques. In addition, PDGF receptor mRNA has also been localized predominantly in plaque intimal cells.

The PDGF B is related to the transforming gene (v-sis) of simian sarcoma virus. The PDGF B has also been reported to be mitogen for cells of mesenchymal origin. The PDGF B has in addition been implicated in autocrine growth stimulation in the pathologic proliferation of endothelial cells characteristically found in glioblastomas. PDGF has also been reported to promote cellular proliferation and inhibits apoptosis.

FGF-CX

The present invention is related to a novel human FGF as well as its corresponding cDNA. The protein product of this gene has been shown to exhibit growth stimulatory and growth promoting properties.

The nucleotide sequence and translated polypeptide sequence of Fibroblast Growth Factor-CX ("FGF-CX," also referred to as AB020858) is presented in Table 1 (see Example 1; see also disclosure in U.S. Ser. No. 60/145,899, filed Jul. 27, 1999, U.S. Ser. No. 09/494585, filed Jan. 31, 2000 and U.S. Ser. No. 09/609,543, filed Jul. 3, 2000, all of which are incorporated herein by reference in their entireties). The start and stop codons are shown in bold.

TABLE 1

Nucleotide (SEQ ID NO:1) and Protein (SEQ ID NO:2) Sequence of Fibroblast Growth Factor-CX (FGF-CX)

```
  1  ATGGCTCCCTTAGCCGAAGTCGGGGGCTTTCTGGGCGGCCTGGAG
     MetAlaProLeuAlaGluValGlyGlyPheLeuGlyGlyLeuGlu

46  GGCTTGGGCCAGCAGGTGGGTTCGCATTTCCTGTTGCCTCCTGCC
     GlyLeuGlyGlnGlnValGlySerHisPheLeuLeuProProAla

91  GGGGAGCGGCCGCCGCTGCTGGGCGAGCGCAGGAGCGCGGCGGAG
     GlyGluArgProProLeuLeuGlyGluArgArgSerAlaAlaGlu

136  CGGAGCGCGCGCGGCGGGCCGGGGCTGCGCAGCTGGCGCACCTG
     ArgSerAlaArgGlyGlyProGlyAlaAlaGlnLeuAlaHisLeu

181  CACGGCATCCTGCGCCGCCGGCAGCTCTATTGCCGCACCGGCTTC
     HisGlyIleLeuArgArgArgGlnLeuTyrCysArgThrGlyPhe

226  CACCTGCAGATCCTGCCCGACGGCAGCGTGCAGGGCACCCGGCAG
     HisLeuGlnIleLeuProAspGlySerValGlnGlyThrArgGln

271  GACCACAGCCTCTTCGGTATCTTGGAATTCATCAGTGTGGCAGTG
     AspHisSerLeuPheGlyIleLeuGluPheIleSerValAlaVal

316  GGACTGGTCAGTATTAGAGGTGTGGACAGTGGTCTCTATCTTGGA
     GlyLeuValSerIleArgGlyValAspSerGlyLeuTyrLeuGly

361  ATGAATGACAAAGGAGAACTCTATGGATCAGAGAAACTTACTTCC
     MetAsnAspLysGlyGluLeuTyrGlySerGluLysLeuThrSer

406  GAATGCATCTTTAGGGAGCAGTTTGAAGAGAACTGGTATAACACC
     GluCysIlePheArgGluGlnPheGluGluAsnTrpTyrAsnThr

451  TATTCATCTAACATATATAAACATGGAGACACTGGCCGCAGGTAT
     TyrSerSerAsnIleTyrLysHisGlyAspThrGlyArgArgTyr

496  TTTGTGGCACTTAACAAAGACGGAACTCCAAGAGATGGCGCCAGG
     PheValAlaLeuAsnLysAspGlyThrProArgAspGlyAlaArg

541  TCCAAGAGGCATCAGAAATTTACACATTTCTTACCTAGACCAGTG
     SerLysArgHisGlnLysPheThrHisPheLeuProArgProVal
```

TABLE 1-continued

Nucleotide (SEQ ID NO:1) and Protein (SEQ ID NO:2) Sequence of Fibroblast Growth Factor-CX (FGF-CX)

```
586  GATCCAGAAAGAGTTCCAGAATTGTACAAGGACCTACTGATGTAC
     AspProGluArgValProGluLeuTyrLysAspLeuLeuMetTyr

631  ACT* (SEQ ID NO:1)
     Thr (SEQ ID NO:2)
```

Included in the invention is a nucleotide sequence (SEQ ID NO:1) encoding a novel fibroblast growth factor designated fibroblast growth factor-20X (FGF-CX) (see Table 1; SEQ ID NO:1). This coding sequence was identified in human genomic DNA sequences. The disclosed DNA sequence has 633 bases that encode a polypeptide predicted to have 211 amino acid residues (Table 1; SEQ ID NO:2). The predicted molecular weight of FGF-CX, based on the sequence shown in Table 1 and SEQ ID NO:2, is 23498.4 Da.

The FGF-CX nucleic acid sequence was used as a query nucleotide sequence in a BLASTN search to identify related nucleic acid sequences. The FGF-CX nucleotide sequence has a high similarity to murine fibroblast growth factor 9 ("FGF-9") (392 of 543 bases identical, or 72%; GenBank Accession Number S82023) and to human DNA encoding glia activating factor (GAP) (385 of 554 bases identical, or 69%; GenBank Accession Number E05822, also termed FGF-9). In addition, FGF-CX was found to have a comparable degree of identity (311 of 424 bases identical, or 73%) to a GAF sequence (SEQ ID NO:5) disclosed by Naruo et al. in Japanese Patent: JP 1993301893 entitled "Glia-Activating Factor And Its Production".

To verify that the open reading frame (ORF) identified by genomic mining was correct, PCR amplification was used to obtain a cDNA corresponding to the predicted genomic clone. The nucleotide sequence of the obtained product precisely matches that of the predicted gene (see Example 2).

The protein encoded by the cDNA is most closely related to Xenopus FGF-20X (designated XFGF-CX or XFGF-20X herein), as well as to human FGF-9 and human FGF-16 (80%, 70% and 64% amino acid identity, respectively). Based on the strong homology with XFGF-CX, the gene identified in the present disclosure is believed to represent its human ortholog, and is named FGF-CX herein.

A BLASTP analyses of the polypeptide of SEQ ID NO:2 shows that the first 208 amino acids of the FGF-CX polypeptide sequence (SEQ ID NO:2) aligns with a human FGF-9. See, e.g., SWISSPROT Accession Number P31371 for Glia-Activating Factor Precursor (GAF) (Fibroblast Growth Factor-9); Miyamoto et al. 1993 Mol. Cell. Biol. 13:4251–4259; and Naruo et al. 1993 J. Biol. Chem. 268:2857–2864. BLASTX analysis shows that the first 208 amino acids of the FGF-CX polypeptide (SEQ ID NO:2 aligns with the mouse FGF-9 and rat FGF-9 sequences. See, e.g., SWISSPROT Accession Number P54130 for Glia-Activating Factor Precursor (GAF) (Fibroblast Growth Factor-9), Santos-Ocampo et al., 1996 J. Biol. Chem. 271:1726–1731, for mouse FGF-9; and SWISSPROT Accession Number P36364 Glia-Activating Factor Precursor (GAF) (Fibroblast Growth Factor-9) (FGF-9), Miyamoto, 1993 Mol. Cell. Biol. 13:4251–4259, for rat FGF-9.

The full length FGF-CX polypeptide (SEQ ID NO:2) was also aligned by BLASTX with Xenopus XFGF-CX (See, Koga et al., 1999 Biochem Biophys Res Commun 261(3): 756–765). It was found that FGF-CX has 170 of 211 (80%) identical residues, and 189 of 211 (89%) positive residues compared with Xenopus XFGF-CX. The deduced 208 amino acid sequence of the XFGF-CX open reading frame contains a motif characteristic of the FGF family. XFGF-CX has a 73.1% overall similarity to XFGF-9 but differs from XFGF-9 in its amino-terminal region (33.3% similarity). This resembles the similarity seen for the presently disclosed SEQ ID NO:2 with respect to various mammalian FGF-9 and FGF-16 sequences, including human (see above).

Figure 4:
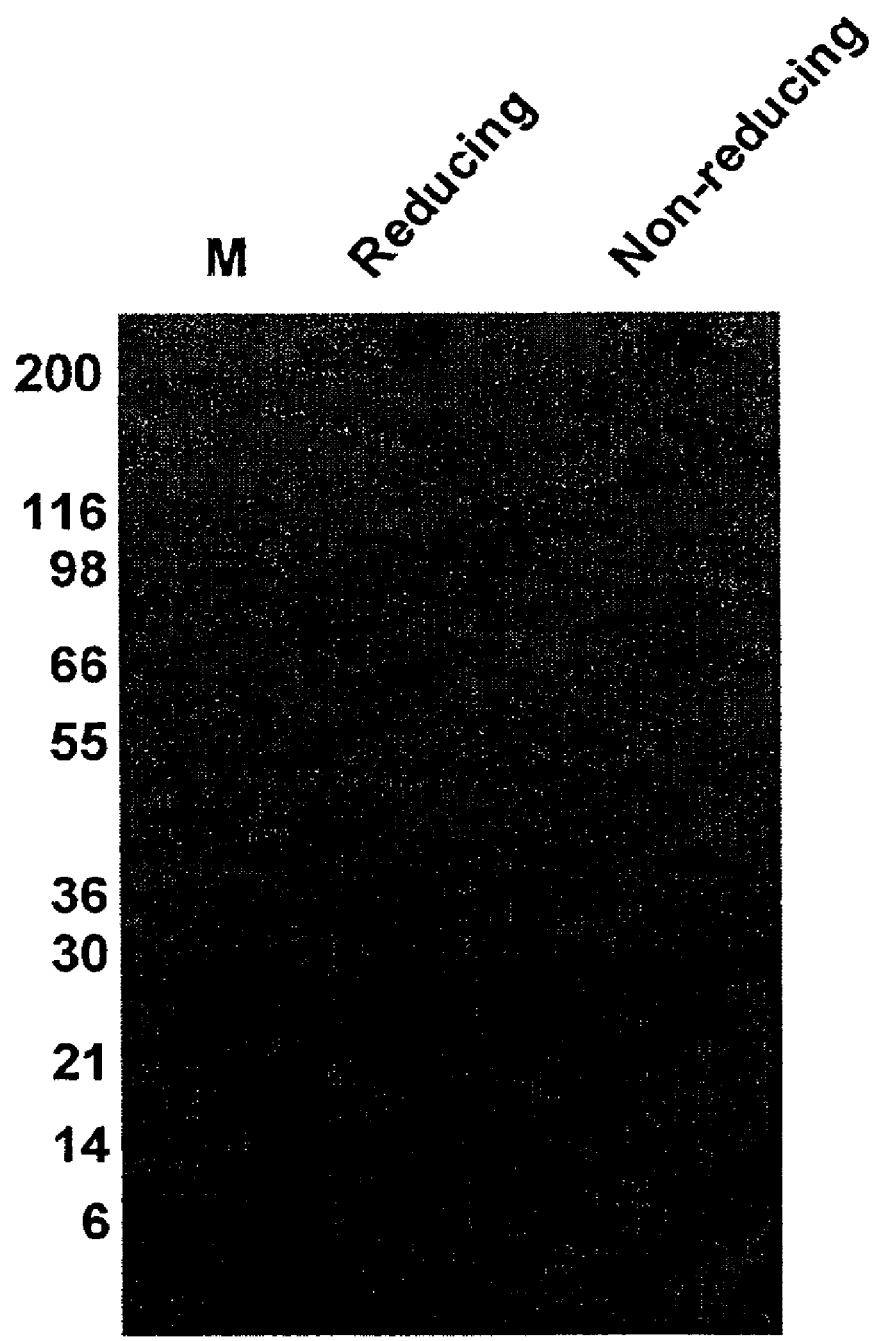
FIG. 4 presents an image of a Coomassie Blue stained SDS-PAGE gel of purified samples of FGF-CX prepared under reducing and nonreducing conditions.

FGF-CX lacks a classical amino-terminal signal sequence as predicted by PSORT (Nakai & Kanehisa (1992) Genomics 14, 897–911) and SIGNALP (Nielsen et al. (1997) Protein Eng. 10, 1–6) computer algorithms, just as found for some of its closest human family members (e.g. FGF-9 and FGF-16). Nonetheless, both FGF-9 and FGF-16 are secreted (Matsumoto-Yoshitomi et al. (1997) Int. J. Cancer 71, 442–450; Miyake et al. (1998) Biochem. Biophys. Res. Comm. 243, 148–152; Miyakawa et al. (1999) J. Biol. Chem. 274, 29352–29357; Revest et al. (2000) J Biol. Chem. 275, 8083–8090). To determine whether FGF-CX is also secreted, the cDNA encoding the full length FGF-CX protein was subcloned into a mammalian expression vector designated pFGF-CX. The protein expressed when human embryonic kidney 293 cells are transfected with this vector is found in the conditioned medium, and exhibits a band detected by an antibody to a C-terminal V5 epitope, with an apparent molecular weight in a Western blot of ~27 kDa (FIG. 4). An additional portion of the expressed protein is released from sequestration on the 293 cells by treatment with a substance that inhibits interaction with heparin sulfate proteoglycan (HSPG). The protein released in this way also exhibits a similar Western blot pattern (FIG. 4). Similarly when the protein is expressed in HEK293 cells from a recombinant plasmid incorporating an Ig Kappa signal sequence, a band is detected by Western blot with an apparent molecular weight of approximately 34 kDa (FIG. 1, Example 4).

FCTR1

A polynucleotide of the invention includes the nucleic acid of FCTR1 (also referred to as clone 30664188.0.99). FCTR1 is 1828 nucleotides in length. The nucleotide sequence of FCTR1 (also referred to as 30664188.0.99 or PDGFD) is reported in Table 2 (SEQ ID NO:3). The clone was orginally obtained from RNA from pituitary gland tissues is also present in RNA from human uterine microvascular endothelial cells (Clonetics, San Diego, Calif.), human erythroleukemia cells (ATCC, Manassas, Va.), thyroid, small intestine, lymphocytes, adrenal gland and salivary gland. The untranslated regions upstream of the start site and downstream of the stop codon are underlined, and the start and stop codons are shown in bold.

TABLE 2

Nucleotide (SEQ ID NO:3) and Protein (SEQ ID NO:4) Sequence of FCTR1

```
Translated Protein-Frame: 2-Nucleotide 182 to 1291
  1 CTAAAAAATATGTTCTCTACAACACCAAGGCTCATTAAAATATTT

46 TAAATATTAATATACATTTCTTCTGTCAGAAATACATAAAACTTT

91 ATTATATCAGCGCAGGGCGGCGCGGCGTCGGTCCCGGGAGCAGAA

136 CCCGGCTTTTTCTTGGAGCGACGCTGTCTCTAGTCGCTGATCCCA

181 AATGCACCGGCTCATCTTTGTCTACACTCTAATCTGCGCAAACTT
     MetHisArgLeuIlePheValTyrThrLeuIleCysAlaAsnPh
```

TABLE 2-continued

Nucleotide (SEQ ID NO:3) and Protein (SEQ ID NO:4) Sequence of FCTR1

```
226  TTGCAGCTGTCGGGACACTTCTGCAACCCCGCAGAGCGCATCCAT
     eCysSerCysArgAspThrSerAlaThrProGlnSerAlaSerIl

271  CAAAGCTTTGCGCAACGCCAACCTCAGGCGAGATGAGAGCAATCA
     eLysAlaLeuArgAsnAlaAsnLeuArgArgAspGluSerAsnHi

316  CCTCACAGACTTGTACCGAAGAGATGAGACCATCCAGGTGAAAGG
     sLeuThrAspLeuTyrArgArgAspGluThrIleGlnValLysGl

361  AAACGGCTACGTGCAGAGTCCTAGATTCCCGAACAGCTACCCCAG
     yAsnGlyTyrValGlnSerProArgPheProAsnSerTyrProAr

406  GAACCTGCTCCTGACATGGCGGCTTCACTCTCAGGAGAATACACG
     gAsnLeuLeuLeuThrTrpArgLeuHisSerGlnGluAsnThrAr

451  GATACAGCTAGTGTTTGACAATCAGTTTGGATTAGAGGAAGCAGA
     gIleGlnLeuValPheAspAsnGlnPheGlyLeuGluGluAlaGl

496  AAATGATATCTGTAGGTATGATTTTGTGGAAGTTGAAGATATATC
     uAsnAspIleCysArgTyrAspPheValGluValGluAspIleSe

541  CGAAACCAGTACCATTATTAGAGGACGATGGTGTGGACACAAGGA
     rGluThrSerThrIleIleArgGlyArgTrpCysGlyHisLysGl

586  AGTTCCTCCAAGGATAAAATCAAGAACGAACCAAATTAAAATCAC
     uValProProArgIleLysSerArgThrAsnGlnIleLysIleTh

631  ATTCAAGTCCGATGACTACTTTGTGGCTAAACCTGGATTCAAGAT
     rPheLysSerAspAspTyrPheValAlaLysProGlyPheLysIl

676  TTATTATTCTTTGCTGGAAGATTTCCAACCCGCAGCAGCTTCAGA
     eTyrTyrSerLeuLeuGluAspPheGlnProAlaAlaAlaSerGl

721  GACCAACTGGGAATCTGTCACAAGCTCTATTTCAGGGGTATCCTA
     uThrAsnTrpGluSerValThrSerSerIleSerGlyValSerTy

766  TAACTCTCCATCAGTAACGGATCCCACTCTGATTGCGGATGCTCT
     rAsnSerProSerValThrAspProThrLeuIleAlaAspAlaLe

811  GGACAAAAAATTGCAGAATTTGATACAGTGGAAGATCTGCTCAA
     uAspLysLysIleAlaGluPheAspThrValGluAspLeuLeuLy

856  GTACTTCAATCCAGAGTCATGGCAAGAAGATCTTGAGAATATGTA
     sTyrPheAsnProGluSerTrpGlnGluAspLeuGluAsnMetTy

901  TCTGGACACCCCTCGGTATCGAGGCAGGTCATACCATGACCGGAA
     rLeuAspThrProArgTyrArgGlyArgSerTyrHisAspArgLy

946  GTCAAAAGTTGACCTGGATAGGCTCAATGATGATGCCAAGCGTTA
     sSerLysValAspLeuAspArgLeuAsnAspAspAlaLysArgTy

991  CAGTTGCACTCCCAGGAATTACTCGGTCAATATAAGAGAAGAGCT
     rSerCysThrProArgAsnTyrSerValAsnIleArgGluGluLe

1036 GAAGTTGGCCAATGTGGTCTTCTTTCCACGTTGCCTCCTCGTGCA
     uLysLeuAlaAsnValValPhePheProArgCysLeuLeuValGl

1081 GCGCTGTGGAGGAAATTGTGGCTGTGGAACTGTCAACTGGAGGTC
     nArgCysGlyGlyAsnCysGlyCysGlyThrValAsnTrpArgSe

1126 CTGCACATGCAATTCAGGGAAAACCGTGAAAAAGTATCATGAGGT
     rCysThrCysAsnSerGlyLysThrValLysLysTyrHisGluVa

1171 ATTACAGTTTGAGCCTGGCCACATCAAGAGGAGGGGTAGAGCTAA
     lLeuGlnPheGluProGlyHisIleLysArgArgGlyArgAlaLy

1216 GACCATGGCTCTAGTTGACATCCAGTTGGATCACCATGAACGATG
     sThrMetAlaLeuValAspIleGlnLeuAspHisHisGluArgCy

1261 TGATTGTATCTGCAGCTCAAGACCACCTCGATAAGAGAATGTGCA
     SAspCysIleCysSerSerArgProProArg

1306 CATCCTTACATTAAGCCTGAAAGAACCTTTAGTTTAAGGAGGGTG

1352 AGATAAGAGACCCTTTTCCTACCAGCAACCAAACTTACTACTAGC
```

TABLE 2-continued

Nucleotide (SEQ ID NO:3) and Protein (SEQ ID NO:4) Sequence of FCTR1

```
1396 CTGCAATGCAATGAACACAAGTGGTTGCTGAGTCTCAGCCTTGCT

1441 TTGTTAATGCCATGGCAAGTAGAAAGGTATATCATCAACTTCTAT

1486 ACCTAAGAATATAGGATTGCATTTAATAATAGTGTTTGAGGTTAT

1531 ATATGCACAAACACACACAGAAATATATTCATGTCTATGTGTATA

1576 TAGATCAAATGTTTTTTTTGGTATATATAACCAGGTACACCAGAG

1621 CTTACATATGTTTGAGTTAGACTCTTAAAATCCTTTGCCAAAATA

1666 AGGGATGGTCAAATATATGAAACATGTCTTTAGAAAATTTAGGAG

1711 ATAAATTTATTTTTAAATTTTGAAACACAAAACAATTTTGAATCT

1756 TGCTCTCTTAAAGAAAGCATCTTGTATATTAAAAATCAAAAGATG

1801 AGGCTTTCTTACATATACATCTTAGTTG
```

Nucleotides 182 to 1292 of SEQ ID NO:3 encode a 370 amino acid protein (SEQ ID NO:4) that includes sequences characteristic of secreted proteins. The sequence of the encoded protein, which is also referred to herein as "FCTR1 protein," "30664188.0.99 protein," "30664188.0.99," "PDGFD," or "human PDGFD" is presented in Table 2. The predicted molecular weight of the 30664188.0.99 protein is 42847.8 daltons with a pI of 7.88.

BLASTN and BLASTP analyses indicate the 30664188.0.99 polypeptide has a similarity to human vascular endothelial growth factor E (VEGF-E), as well as to VEGF-E from other vertebrate species. For example, there is a 44% identity to human secretory growth factor-like protein (VEGF-E, or fallotein; Acc. No.: AAF00049 which references GenBank-ID: AF091434 for the nucleotide sequence). An alignment of the amino acid sequence of the 30664188.0.99 polypeptide with that of VEGF-E is shown in FIG. 1. BLASTP analyses also indicate that FCTR1 is related to human PDGF C, PDGF B, and PDGF A (42%, 27%, and 25% overall amino acid identity, respectively)

PFAM and PROSITE analyses indicte that 30664188.0.99 polypeptide amino acid sequence conatains a PDGF domain (aa 272–362) and a N-linked glycosylation site (residue 276).

The 30664188.0.99 polypeptide amino acid sequence shows similarity to the sequence of human procollagen C-endopeptidase (bone morphogenetic protein-1; BMP-1; PIR-ID:A58788), which is a polypeptide of 823 residues. Residues 54 to 169 of the 30664188.0.99 polypeptide show 30–41% identity over three segments of the BMP-1 polypeptide. The 30664188.0.99 polypeptide also shows a similar degree of identity is to BMP-1 from Xenopus laevis (ACC NO:P98070), which is a 707 residue protein. The latter protein may act as a zinc protease in promoting cartilage and bone formation (Wozney et al., Science 242: 1528–34, 1988).

The 30664188.0.99 polypeptide is also related to other growth factors. For example, it shows 42% identity and 59% similarity to chicken spinal cord-derived growth factor (TREMBLNEW-ACC:BAB03265), 42% identity and 59% identity to human secretory growth factor-like protein fallotein (SPTREMBL-ACC:Q9UL22), 42% identity and 39% similarity to human platelet-derived growth factor C (TREMBLNEW-ACC:AAF80597), and 39% identity and 59% similarity to mouse fallotein (SPTREMBL-ACC:Q9QY71).

The homologies discussed above identify the 30664188.0.99 polypeptide as a member of the BMP-1/VEGF-E/PDGF protein family. BMP-1 proteins include an EGF-like domain, three CUB domains, and PDGF/VEGF domains. BMP-1 proteins are also members of the astacin subfamily.

SignalP and PSORT analyses predict that the amino acid sequence for 30664188.0.99 includes a cleavable amino terminal signal peptide with a cleavage site between positions 23 and 24 (TSA-TP). The protein is most likely secreted and localized outside of the cell. The InterPro software program predicts the presence of a CUB domain in 30664188.0.99 from residue 53 to residue 167, a PDGF domain spanning residues 272–306 and 350–362, and a metallothionein domain from residue 302 to residue 365. A FCTR1 polypeptide of the invention includes a polypeptide having one, two, three, or four of these domains, or a combination thereof.

A FCTR1 polypeptide of the invention includes a mature form of a FCTR1 polypeptide that includes amino acids 24–370 of SEQ ID NO:4. These sequences are also encoded in a construct encoded by clone 30664188.0.m99, which is described in more detail below. Also within the invention are nucleic acids encoding FCTRX polypeptide fragments that include amino acid sequences 247–370, 247–338, or 339–370, or their variant forms. In some embodiments, the fragments stimulate proliferation of cells. Also within the invention are the FCTRX polypeptide fragments, or their variants, homologs or analogs encoded by these nucleic acids.

FCTR2 Nucleic Acids and Polypeptides

A polynucleotide of the invention includes the nucleic acid sequence of FCTR2 (also referred to as clone 30664188.0.331). FCTR2 is 1587 nucleotides in length and was originally isolated from RNA from pituitary gland tissues. The nucleotide sequence of FCTR2 is shown in Table 3 (SEQ ID NO:5). The untranslated regions upstream of the start site and downstream of the stop codon are underlined, and the start and stop codons are shown in bold.

TABLE 3

Nucleotide (SEQ ID NO:5) and Protein (SEQ ID NO:6) Sequence of FCTR2

Translated Protein—Frame: 3—Nucleotide 540 to 935
```
   1 AGAGGCTCTCAAATTAGATCAAGAAATGCCTTTAACAGAAGTGAA

46 GAGTGAACCTGCTCCTGACATGGCGGCTTCACTCTCAGGAGAATA

91 CACGGATACAGCTAGTGTTTGACAATCAGTTTGGATTAGAGGAAG

136 CAGAAAATGATATCTGTAGGTATGATTTTGTGGAAGTTGAAGATA

181 TATCCGAAACCAGTACCATTATTAGAGGACGATGGTGTGGACACA

226 AGGAAGTTCCTCCAAGGATAAAATCAAGAACGAACCAAATTAAAA

271 TCACATTCAAGTCCGATGACTACTTTGTGGCTAAACCTGGATTCA

316 AGATTTATTATTCTTTGCTGGAAGATTTCCAACCCGCAGCAGCTT

361 CAGAGACCAACTGGGAATCTGTCACAAGCTCTATTTCAGGGGTAT

406 CCTATAACTCTCCATCAGTAACGGATCCCACTCTGATTGCGGATG

451 CTCTGGACAAAAAAATTGCAGAATTTGATACAGTGGAAGATCTGC

496 TCAAGTACTTCAATCCAGAGTCATGGCAAGAAGATCTTGAGAATA
                                                  M
```

TABLE 3-continued

Nucleotide (SEQ ID NO:5) and Protein (SEQ ID NO:6) Sequence of FCTR2

```
 541 TGTATCTGGACACCCCTCGGTATCGAGGCAGGTCATACCATGACC
     etTyrLeuAspThrProArgTyrArgGlyArgSerTyrHisAspA

586 GGAAGTCAAAAGTTGACCTGGATAGGCTCAATGATGATGCCAAGC
     rgLysSerLysValAspLeuAspArgLeuAsNAspAspAlaLysA

631 GTTACAGTTGCACTCCCAGGAATTACTCGGTCAATATAAGAGAAG
     rgTyrSerCysThrProArgAsnTyrSerValAsnIleArgGluG

676 AGCTGAAGTTGGCCAATGTGGTCTTCTTTCCACGTTGCCTCCTCG
     luLeuLysLeuAlaAsnValValPhePheProArgCysLeuLeuV

721 TGCAGCGCTGTGGGAGGAAATTGTGGCTGTGGAACTGTCAACTGGA
     alGlnArgCysGlyGlyAsnCysGlyCysGlyThrValAsnTrpA

766 GGTCCTGCACATGCAATTCAGGGAAAACCGTGAAAAAGTATCATG
     rgSerCysThrCysAsnSerGlyLysThrValLysLysTyrHisG

811 AGGTATTACAGTTTGAGCCTGGCCACATCAAGAGGAGGGGTAGAG
     luValLeuGlnPheGluProGlyHisIleLysArgArgGlyArgA

856 CTAAGACCATGGCTCTAGTTGACATCCAGTTGGATCACCATGAAC
     laLysThrMetAlaLeuValAspIleGlnLeuAspHisHisGluA

901 GATGTGATTGTATCTGCAGCTCAAGACCACCTCGATAAGAGAATG
     RgCysAspCysIleCysSerSerArgProProArg

946 TGCACATCCTTACATTAAGCCTGAAAGAACCTTTAGTTTAAGGAG

991 GGTGAGATAAGAGACCCTTTTCCTACCAGCAACCAAACTTACTAC

1036 TAGCCTGCAATGCAATGAACACAAGTGGTTGCTGAGTCTCAGCCT

1081 TGCTTTGTTAATGCCATGGCAAGTAGAAAGGTATATCATCAACTT

1126 CTATACCTAAGAATATAGGATTGCATTTAATAATAGTGTTTGAGG

1171 TTATATATGCACAAACACACAGAAATATATTCATGTCTATGTG

1216 TATATAGATCAAATGTTTTTTTGGTATATATAACCAGGTACACC

1261 AGAGCTTACATATGTTTGAGTTAGACTCTTAAAATCCTTTGCCAA

1306 AATAAGGGATGGTCAAATATATGAAACATGTCTTTAGAAAATTTA

1351 GGAGATAAATTTATTTTTAAATTTTGAAACACAAAACAATTTTGA

1396 ATCTTGCTCTCTTAAAGAAAGCATCTTGTATATTAAAAATCAAAA

1441 GATGAGGCTTTCTTACATATACATCTTAGTTGATTATTAAAAAAG

1486 GAAAAATATGGTTTCCAGAGAAAAGGCCAATACCTAAGCATTTTT

1531 TCCATGAGAAGCACTGCATACTTACCTATGTGGACTATAATAACC

1576 TGTCTCCAAAAC
```

Clone 30664188.0.331 includes an open reading frame from nucleotides 540 to 936. The open reading frame encodes a polypeptide of 132 amino acids (SEQ ID NO:6). The encoded polypeptide is referred to herein as the "30664188.0.331 protein" or the "30664188.0.331 polypeptide". The predicted amino acid sequence of the 30664188.0.331 nucleic acid sequence is shown in Table 3 (SEQ ID NO:6).

Nucleotides 50 to 1472 of clone 30664188.0.331 are 100% identical to nucleotides 406–1828 of clone 30664188.0.99. The 132 amino acids of the clone 30664188.0.331 protein are 100% identical to the carboxy-terminal region of the protein sequence of 30664188.0.99. Thus, the nucleic acids of clones 30664188.0.99 and 30664188.0.331 are therefore related as splice variants of a common gene.

The 30664188.0.331 protein shows similarity to human growth factor FIGF (c-fos-induced growth factor; ptnr:SPTREMBL-ACC:O43915), a member of the platelet-derived growth factor/vascular endothelial growth factor (PDGF/VEGF) family, and to rat vascular endothelial growth factor D (ptnr:SPTREMBL-ACC:O35251).

FCTR3 Acids and Polypeptides

A FCTR3 (also referred to within the specification as PDGFD or murine PDGFD or mPDGFD) nucleic acid and polypeptide according to the invention includes the nucleic acid and encoded polypeptide sequence shown in Table 4 (SEQ ID NO:7 and 8). The start and stop codons are shown in bold. The FCTR3 nucleic acid sequence was identified from a murine brain library. The predicted open reading frame codes for a 370 amino acid long secreted protein. The FCTR3 has a predicted molecular weight of 42,808 daltons and a pI of 7.53. Protein structure analysis using PFAM and PROSITE identified the core PDGF domain within the FCTR3 polypeptide sequence.

FCTR4 Nucleic Acids and Polypeptides

A FCTR4 (also referred to within the specification as PDGFD or murine PDGFD or mPDGFD) nucleic acid and polypeptide according to the invention includes the nucleic acid and encoded polypeptide sequence shown in Table 5 (SEQ ID NO:9 and 10). The start and stop codons are shown in bold. The FCTR4 nucleic acid sequence was identified from a murine brain library and is a splice variant of FCTR3. FCTR4 has an internal stop codon in comparison with FCTR3. See Table 8. Unlike FCTR3, however, FCTR4 lacks a significant portion of the PDGF-like domain. See Table 9.

TABLE 5

Nucleotide (SEQ ID NO:9) and Protein (SEQ ID NO:10) Sequence of FCTR4

ATGCAACGGCTCGTTTTAGTCTCCATTCTCCTGTGCGCGAACTTTAGCTG

CTATCCGGACACTTTTGCGACTCCGCAGAGAGCATCCATCAAAGCTTTGC

GCAATGCCAACCTCAGGAGAGATGAGAGCAATCACCTCACAGACTTGTAC

CAGAGAGAGGAGAACATTCAGGTGACAAGCAATGGCCATGTGCAGAGTCC

TABLE 4

Nucleotide (SEQ ID NO:7) and Protein (SEQ ID NO:8) Sequence of FCTR3

```
   1 ATGCAACGGCTCGTTTTAGTCTCCATTCTCCTGTGCGCGAACTTTAGCTGCTATCCGGACACTTTTGCGACTCCGCAGAG
     M  Q  R  L  V  L  V  S  I  L  L  C  A  N  F  S  C  Y  P  D  T  F  A  T  P  Q  R

81 AGCATCCATCAAAGCTTTGCGCAATGCCAACCTCAGGAGAGATGAGAGCAATCACCTCACAGACTTGTACCAGAGAGAGG
     A  S  I  K  A  L  R  N  A  N  L  R  R  D  E  S  N  H  L  T  D  L  Y  Q  R  E  E

161 AGAACATTCAGGTGACAAGCAATGGCCATGTGCAGAGTCCTCGCTTCCCGAACAGCTACCCAAGGAACCTGCTTCTGACA
     N  I  Q  V  T  S  N  G  H  V  Q  S  P  R  F  P  N  S  Y  P  R  N  L  L  L  T

241 TGGTGGCTCCGTTCCCAGGAGAAAACACGGATACAACTGTCCTTTGACCATCAATTCGGACTAGAGGAAGCAGAAAATGA
     W  W  L  R  S  Q  E  K  T  R  I  Q  L  S  F  D  H  Q  F  G  L  E  E  A  E  N  D

321 CATTTGTAGGTATGACTTTGTGGAAGTTGAAGAAGTCTCAGAGAGCAGCACTGTTGTCAGAGGAAGATGGTGTGGCCACA
     I  C  R  Y  D  F  V  E  V  E  E  V  S  E  S  S  T  V  V  R  G  R  W  C  G  H  K

401 AGGAGATCCCTCCAAGGATAACGTCAAGAACAAACCAGATTAAAATCACATTTAAGTCTGATGACTACTTTGTGGCAAAA
     E  I  P  P  R  I  T  S  R  T  N  Q  I  K  I  T  F  K  S  D  D  Y  F  V  A  K

481 CCTGGATTCAAGATTTATTATTCATTTGTGGAAGATTTCCAACCGGAAGCAGCCTCAGAGACCAACTGGGAATCAGTCAC
     P  G  F  K  I  Y  Y  S  F  V  E  D  F  Q  P  E  A  A  S  E  T  N  W  E  S  V  T

561 AAGCTCTTTCTCTGGGGTGTCCTATCACTCTCCATCAATAACGGACCCCACTCTCACTGCTGATGCCCTGGACAAAACTG
     S  S  F  S  G  V  S  Y  H  S  P  S  I  T  D  P  T  L  T  A  D  A  L  D  K  T  V

641 TCGCAGAATTCGATACCGTGGAAGATCTACTTAAGCACTTCAATCCAGTGTCTTGGCAAGATGATCTGGAGAATTTGTAT
     A  E  F  D  T  V  E  D  L  L  K  H  F  N  P  V  S  W  Q  D  D  L  E  N  L  Y

721 CTGGACACCCCTCATTATAGAGGCAGGTCATACCATGATCGGAAGTCCAAAGTGGACCTGGACAGGCTCAATGATGATGT
     L  D  T  P  H  Y  R  G  R  S  Y  H  D  R  K  S  K  V  D  L  D  R  L  N  D  D  V

801 CAAGCGTTACAGTTGCACTCCCAGGAATCACTCTGTGAACCTCAGGGAGGAGCTGAAGCTGACCAATGCAGTCTTCTTCC
     K  R  Y  S  C  T  P  R  N  H  S  V  N  L  R  E  E  L  K  L  T  N  A  V  F  F  P

881 CACGATGCCTCCTCGTGCAGCGCTGTGGTGGCAACTGTGGTTGCGGAACTGTCAACTGGAAGTCCTGCACATGCAGCTCA
     R  C  L  L  V  Q  R  C  G  G  N  C  G  C  G  T  V  N  W  K  S  C  T  C  S  S

961 GGGAAGACAGTGAAGAAGTATCATGAGGTATTGAAGTTTGAGCCTGGACATTTCAAGAGAAGGGGCAAAGCTAAGAATAT
     G  K  T  V  K  K  Y  H  E  V  L  K  F  E  P  G  H  F  K  R  R  G  K  A  K  N  M

1041 GGCTCTTGTTGATATCCAGCTGGATCATCATGAGCGATGTGACTGTATCTGCAGCTCAAGACCACCTCGATAA
     A  L  V  D  I  Q  L  D  H  H  E  R  C  D  C  I  C  S  S  R  P  P  R
```

TABLE 5-continued

Nucleotide (SEQ ID NO:9) and Protein (SEQ ID NO:10) Sequence of FCTR4

TCGCTTCCCGAACAGCTACCCAAGGAACCTGCTTCTGACATGGTGGCTCC

GTTCCCAGGAGAAAACACGGATACAACTGTCCTTTGACCATCAATTCGGA

CTAGAGGAAGCAGAAAATGACATTTGTAGGTATGACTTTGTGGAAGTTGA

AGAAGTCTCAGAGAGCAGCACTGTTGTCAGAGGAAGATGGTGTGGCCACA

AGGAGATCCCTCCAAGGATAACGTCAAGAACAAACCAGATTAAAATCACA

TTTAAGTCTGATGACTACTTTGTGGCAAAACCTGGATTCAAGATTTATTA

TTCATTTGTGGAAGATTTCCAACCGGAAGCAGCCTCAGAGACCAACTGGG

AATCAGTCACAAGCTCTTTCTCTGGGGTGTCCTATCACTCTCCATCAATA

ACGGACCCCACTCTCACTGCTGATGCCCTGGACAAAACTGTCGCAGAATT

CGATACCGTGGAAGATCTACTTAAGCACTTCAATCCAGTGTCTTGGCAAG

ATGATCTGGAGAATTTGTATCTGGACACCCCTCATTATAGAGGCAGGTCA

TACCATGATCGGAAGTCCAAAGGTATTGAAGTTTGAGCCTGGACATTTCA

AGAGAAGGGGCAAAGCTAAGAATATGGCTCTTGTTGATATCCAGCTGGAT

CATCATGAGCGATGTGACTGTATCTGCAGCTCAAGACCACCTCGATAA

MQRLVLVSILLCANFSCYPDTFATPQRASIKALRNANLRRDESNHLTDLY

QREENIQVTSNGHVQSPRFPNSYPRNLLLTWWLRSQEKTRIQLSFDHQFG

LEEAENDTCRYDFVEVEEVSESSTVVRGRWCGHKEIPPRITSRTNQIKIT

FKSDDYFVAKPGFKIYYSFVEDFQPEAASETNWESVTSSFSGVSYHSPSI

TDPTLTADALDKTVAEFDTVEDLLKHFNPVSWQDDLENLYLDTPHYRGRS

YHDRKSKGIEV

FCTR5 Nucleic Acids and Polypeptides

A FCTR5 (also referred to within the specification as PDGFD or human PDGFD or hPDGFD or clone pCR2.1-S852_2B) nucleic acid and polypeptide according to the invention includes the nucleic acid and encoded polypeptide sequence of FCTR5 and is shown in Table 6 (SEQ ID NO:11 and SEQ ID NO:12). The FCTR5 nucleic acid sequence was identified as a splice variant of FCTR1.

Similar to FCTR1, protein structure analysis programs PSORT, PFAM and PROSITE predicted that FCTR5 contains a characteristic signal peptide (aa 1–23), PDGF domain (aa 272–362) and a N-linked glycosylation site (residue 276). BLASTP analysis revealed that the human FGTR5 is most closely related to human PDGF C, PDGF B, and PDGF A (42%, 27%, and 25% overall amino acid identity, respectively).

TABLE 6

Nucleotide (SEQ ID NO:11) and Protein (SEQ ID NO:12) Sequence of FCTR5

ATGCACCGGCTCATCTTGTTCTACACTCTAATCTGCGCAAACTTTTGCAG

CTGTCGGGACACTTCTGCAACCCCGCAGAGCGCATCCATCAAAGCTTTGC

GCAACGCCAACCTCAGGCGAGATGTTGACCTGGATAGGCTCAATGATGAT

GCCAAGCGTTACAGTTGCACTCCCAGGAATTACTCGGTCAATATAAGAGA

TABLE 6-continued

Nucleotide (SEQ ID NO:11) and Protein (SEQ ID NO:12) Sequence of FCTR5

AGAGCTGAAGTTGGCCAATGTGGTCTTCTTTCCACGTTGCCTCCTCGTGC

AGCCCTGTGGAGGAAATTGTGGCTGTGGAACTGTCAACTGGAGGTCCTGC

ACATGCAATTCAGGGAAAACCGTGAAAAAGTATCATGAGGTATTACAGTT

TGAGCCTGGCCACATCAAGAGGAGGGGTAGAGCTAAGACCATGGCTCTAG

TTGACATCCAGTTGGATCACCATGAACGATGCGATTGTATCTGCAGCTCA

AGACCACCTCGA

MHRLILFYTLICANFCSCRDTSATPQSASIKALRNANLRRDVDLDRLNDD

AKRYSCTPRNYSVNIREELKLANVVFFPRCLLVQRCGGNCGCGTVNWRSC

TCNSGKTVKKYHEVLQFEPGHIKRRGRAKTMALVDIQLDHHERCDCICSS

RPPR

FCTR6 Nucleic Acids and Polypeptides

A FCTR6 (also referred to within the specification as PDGFD or human PDGFD or hPDGFD) nucleic acid and polypeptide according to the invention includes the nucleic acid and encoded polypeptide sequence of FCTR6 and is shown in Table 7 (SEQ ID NO:13 and SEQ ID NO:14). The FCTR6 sequence (also referred to as clone pCR2.1-S869_4B) was identified as a splice variant of FCTR1.

FCTR6 contains much of the 5' end of the full length gene (FCTR1), but it is spliced to a cryptic, non-consensus splice site at the extreme 3' end of the coding sequence. This splicing introduces a STOP codon immediately downstream to the splice site. This splice variant contains the intact CUB domain of 30664188.0.99, but deletes the PDGF domains, indicating a possible regulatory function of the molecule.

Similar to FCTR1, however, protein structure analysis programs PSORT, PFAM and PROSITE predicted that FCTR6 contains a characteristic signal peptide (aa 1–23), a CUB domain (aa 53–167) and an N-linked glycosylation site (residue 276). BLASTP analysis revealed that the human FGTR5 is most closely related to human PDGF C, PDGF B, and PDGF A (42%, 27%, and 25% overall amino acid identity, respectively).

TABLE 7

Nucleotide (SEQ ID NO:13) and Protein (SEQ ID NO:14) Sequence of FCTR6

ATGCACCGGCTCATCTTTGTCTACACTCTAATCTGCGCAAACTTTTGCAG

CTGTCGGGACACTTCTGCAACCCCGCAGAGCGCATCCATCAAAGCTTTGC

GCAACGCCAACCTCAGGCGAGATGAGAGCAATCACCTCACAGACTTGTAC

CGAAGAGATGAGACCATCCAGGTGAAGGAAACGGCTACGTGCAGAGTCCT

AGATTCCCGAACAGCTACCCCAGGAACCTGCTCCTGACATGGCGGCTTCA

CTCTCAGGAGAATACACGGATACAGCTAGTGTTTGACAATCAGTTTGGAT

TAGAGGAAGCAGAAAATGATATCTGTAGGTAGAGCTAAGACCATGGCTCT

AGTTGACATCCAGTTGGATCACCATGAACGATGCGATTGTATCTGCAGCT

CAAGACCACCTCGA

MHRLIFVYTLICANFCSCRDTSATPQSASIKALRNANLRRDESNHLTDLY

TABLE 7-continued

Nucleotide (SEQ ID NO:13) and Protein (SEQ ID NO:14) Sequence of FCTR6

RRDETIQVKGNGYVQSPRFPNSYPRNLLLTWRLHSQENTRIQLVFDNQFG

LEEAENDICR

FCTRX Sequences

The various FCTRX nucleic acids and polypeptides are disclosed in related applications U.S. Ser. No. 60/158,083, filed Oct. 7, 1999; U.S. Ser. No. 60/159,231, filed Oct. 13, 1999; U.S. Ser. No. 60/174,485 filed Jan. 4, 2000; U.S. Ser. No. 60/186,707 filed Mar. 3, 2000; U.S. Ser. No. 60/188,250, filed Mar. 10, 2000; U.S. Ser. No. 60/223,879, filed Aug. 8, 2000; U.S. Ser. No. 60/234,082, filed on Sep. 20, 2000; U.S. Ser. No. 09/685,330, filed on Oct. 5, 2000; PCT Application US00/27671, filed Oct. 6, 2000; U.S. Ser. No. 09/688,312, filed Oct. 13, 2000; U.S. Ser. No. 09/715,332 filed Nov. 16, 2000; and U.S. Ser. No. 09/775,482 filed Feb. 2, 2001. Each of these applications is incorporated by reference in its entirety.

FCTRX amino acid sequence variants were analyzed with ClustalW software. The resulting sequence alignment is shown in Table 8.

TABLE 8

Alignment of FCTRX Polypeptide Sequences.

```
              10         20         30         40         50
        ....|....|....|....|....|....|....|....|....|....|
FCTR1   MHRLIFVYTLICANFCSCRDTSATPQSASIKALRNANLRRDESNHLTDLY   50
FCTR2   ---------------MYLDRPRYRGRSTHDRKS-----------------   18
FCTR3   MQRLVLVSILICANFSCYPDTFATPQRASIKALRNANLRRDESNHLTDLY   50
FCTR4   MQRLVLVSILICANFSCYPDTFATPQRASIKALRNANLRRDESNHLTDLY   50
FCTR5   MHRLILFYTLICANFCSCRDTSATPQSASIKALRNANLRRD---------   41
FCTR6   MHRLIFVYTLICANFCSCRDTSATPQSASIKALRNANLRRDESNHLTDLY   50

60         70         80         90        100
        ....|....|....|....|....|....|....|....|....|....|
FCTR1   RRDETIQVKGNGYVQSPRFPNSYPRNLLLTWRLHSQENTRIQLVFDNQFG   100
FCTR2   --------------------------------------------------   18
FCTR3   QREENIQVTSNGHVQSPRFPNSYPRNLLLTWWLRSQEKTRIQLSFDHQFG   100
FCTR4   QREENIQVTSNGHVQSPRFPNSYPRNLLLTWWLRSQEKTRIQLSFDHQFG   100
FCTR5   --------------------------------------------------   41
FCTR6   RRDETIQVKGNGYVQSPRFPNSYPRNLLLTWRLHSQENTRIQLVFDNQFG   100

110        120        130        140        150
        ....|....|....|....|....|....|....|....|....|....|
FCTR1   LEEAENDICRYDFVEVEDISETSTIIRGRWCGHKEVPPRIKSRTNQIKIT   150
FCTR2   --------------------------------------------------   18
FCTR3   LEEAENDICRYDFVEVERVSESSTVVRGRWCGHKEIPPRITSRTNQIKIT   150
FCTR4   LEEAENDICRYDFVEVEKVSESSTVVRGRWCGHKEIPPRITSRTNQIKIT   150
FCTR5   --------------------------------------------------   41
FCTR6   LEEAENDICR----------------------------------------   110

160        170        180        190        200
        ....|....|....|....|....|....|....|....|....|....|
FCTR1   FKSDDYFVAKPGFKIYYSLEEDFQPAAASETNWESVTSSISGVSYNSPSV   200
FCTR2   --------------------------------------------------   18
FCTR3   FKSDDYFVAKPGFKIYYSFVEDFQPEAASETNWESVTSSFSGVSYISPSI   200
FCTR4   FKSDDYFVAKPGFKIYYSFVEDFQPEAASETNWESVTSSFSGVSYISPSI   200
FCTR5   --------------------------------------------------   41
FCTR6   --------------------------------------------------   110

210        220        230        240        250
        ....|....|....|....|....|....|....|....|....|....|
FCTR1   TDPTLIADALDKKIAEFDTVEDLLKYFNEESWNEDLENMYLDTPRYRGRS   250
FCTR2   --------------------------------------------------   18
FCTR3   TDPTLTADALDKTVAEFDTVEDLLKHFNEVSWQDDLENLYLDTPHYRGRS   250
FCTR4   TDPTLTADALDKTVAEFDTVEDLLKHFNEVSWQDDLENLYLDTPHYRGRS   250
FCTR5   --------------------------------------------------   41
FCTR6   --------------------------------------------------   110

260        270        280        290        300
        ....|....|....|....|....|....|....|....|....|....|
FCTR1   YHDRKSK-VDLDRLNDDAKRYSCTPRNMSVNEREELKLANVVFFPRCLLV   299
FCTR2   ------K-VDLDRLNDDAKRYSCTPRNMSVNEREELKLANVVFFPRCLLV   61
FCTR3   YHDRKSK-VDLDRLNDDVKRYSCTPRNHSVNEREELKLTNAVFFPRCLLV   299
FCTR4   YHDRKSKTIKV---------------------------------------   261
FCTR5   --------VDLDRLNDDAKRYSCTPRNMSVNEREELKLANVVFFPRCLLV   83
FCTR6   --------------------------------------------------   110

310        320        330        340        350
        ....|....|....|....|....|....|....|....|....|....|
FCTR1   QRCGGNCGCGTVNWRSCTCNSGKTVKKYHEVLQFEPGHIKRRGRAKTMAL   349
FCTR2   QRCGGNCGCGRVNWRSCTCNSGKTVKKYHEVLQFEPGHIKRRGRAKTMAL   111
FCTR3   QRCGGNCGCGTVNWKSCTCSSGKTVKKYHEVLRFEPGHFKRRGKAKNMAL   349
FCTR4   --------------------------------------------------   261
FCTR5   QRCGGNCGCGTVNWRSCTCNSGKTVKKYHEVLQFEPGHIKRRGRAKTMAL   133
FCTR6   --------------------------------------------------   110
```

TABLE 8-continued

Alignment of FCTRX Polypeptide Sequences.

```
              360        370
         ....|....|....|....|.
FCTR1    VDIQLDHHERCDCICSSAPPR       370
FCTR2    VDIQLDHHERCDCICSSRPPR       132
FCTR3    VDIQLDHHERCDCICSSRPPR       370
FCTR4    ---------------------       261
FCTR5    VDIQLDHHERCDCICSSRPPR       154
FCTR6    ---------------------       110
```

Nucleic acids of FCTR1, FCTR3, FCTR4 and FCTR6 are aligned with each other over the nucleotide residues shown in Table 9.

TABLE 9

Alignment of SEQ ID NOS:3, 7, 9 and 13, respectively.

```
              160       170       180       190       200
         ....|....|....|....|....|....|....|....|....|....|
FCTR1    GAGCGACGCTGTCTCTAGTCGCTGATCCCAAATGCACCGGCTCATCTTTG    200
FCTR3    -------------------------------ATGCAACGGCTCGTTTTAG    19
FCTR4    -------------------------------ATGCAACGGCTCGTTTTAG    19
FCTR6    -------------------------------ATGCACCGGCTCATCTTTG    19

210       220       230       240       250
         ....|....|....|....|....|....|....|....|....|....|
FCTR1    TCTACACTCTAATCTGCGCAAACTTTTGCAGCTGTCGGGACACTTCTGCA    250
FCTR3    TCTCCATTCTCCTGTGCGCGAACTTTAGCTGCTATCCGGACACTTTTGCG    69
FCTR4    TCTCCATTCTCCTGTGCGCGAACTTTAGCTGCTATCCGGACACTTTTGCG    69
FCTR6    TCTACACTCTAATCTGCGCAAACTTTTGCAGCTGTCGGGACACTTCTGCA    69

260       270       280       290       300
         ....|....|....|....|....|....|....|....|....|....|
FCTR1    ACCCCGCAGAGCGCATCCATCAAAGCTTTGCGCAACGCCAACCTCAGGCG    300
FCTR3    ACTCCGCAGAGAGCATCCATCAAAGCTTTGCGCAATGCCAACCTCAGGAG    119
FCTR4    ACTCCGCAGAGAGCATCCATCAAAGCTTTGCGCAATGCCAACCTCAGGAG    119
FCTR6    ACCCCGCAGAGCGCATCCATCAAAGCTTTGCGCAACGCCAACCTCAGGCG    119

310       320       330       340       350
         ....|....|....|....|....|....|....|....|....|....|
FCTR1    AGATGAGAGCAATCACCTCACAGACTTGTACCGAAGAGATGAGACCATCC    350
FCTR3    AGATGAGAGCAATCACCTCACAGACTTGTACCAGAGAGAGGAGAACATTC    169
FCTR4    AGATGAGAGCAATCACCTCACAGACTTGTACCAGAGAGAGGAGAACATTC    169
FCTR6    AGATGAGAGCAATCACCTCACAGACTTGTACCGAAGAGATGAGACCATCC    169

360       370       380       390       400
         ....|....|....|....|....|....|....|....|....|....|
FCTR1    AGGTGAAAGGAAACGGCTACGTGCAGAGTCCTAGATTCCCGAACAGCTAC    400
FCTR3    AGGTGACAAGCAATGGCCATGTGCAGAGTCCTCGCTTCCCGAACAGCTAC    219
FCTR4    AGGTGACAAGCAATGGCCATGTGCAGAGTCCTCGCTTCCCGAACAGCTAC    219
FCTR6    AGGTGAAAGGAAACGGCTACGTGCAGAGTCCTAGATTCCCGAACAGCTAC    219

410       420       430       440       450
         ....|....|....|....|....|....|....|....|....|....|
FCTR1    CCCAGGAACCTGCTCCTGACATGGCGGCTTCACTCTCAGGAGAATACACG    450
FCTR3    CCAAGGAACCTGCTTCTGACATGGTGGCTCCGTTCCCAGGAGAAAACACG    269
FCTR4    CCAAGGAACCTGCTTCTGACATGGTGGCTCCGTTCCCAGGAGAAAACACG    269
FCTR6    CCCAGGAACCTGCTCCTGACATGGCGGCTTCACTCTCAGGAGAATACACG    269

460       470       480       490       500
         ....|....|....|....|....|....|....|....|....|....|
FCTR1    GATACAGCTAGTGTTTGACAATCAGTTTGGATTAGAGGAAGCAGAAAATG    500
FCTR3    GATACAACTGTCCTTTGACCATCAATTCGGACTAGAGGAAGCAGAAAATG    319
FCTR4    GATACAACTGTCCTTTGACCATCAATTCGGACTAGAGGAAGCAGAAAATG    319
FCTR6    GATACAGCTAGTGTTTGACAATCAGTTTGGATTAGAGGAAGCAGAAAATG    319

510       520       530       540       550
         ....|....|....|....|....|....|....|....|....|....|
FCTR1    ATATCTGTAGGTATGATTTTGTGGA-AGTTGAAGAT-ATATCCGAAACCA    548
FCTR3    ACATTTGTAGGTATGACTTTGTGGA-AGTTGAAGAA-CTCTCAGAGAGCA    367
FCTR4    ACATTTGTAGGTATGACTTTGTGGA-AGTTGAAGAA-CTCTCAGAGAGCA    367
FCTR6    ATATCTGTAGGTAGAGCTAAGACCATGCCTCTAGTTGACATCCAGTTCGA    369
```

TABLE 9-continued

Alignment of SEQ ID NOS:3, 7, 9 and 13, respectively.

```
                560       570       580       590       600
          ....|....|....|....|....|....|....|....|....|....|
FCTR1     GTACCATTATTAGAGGACGATGGTGTGGACACAAGGAAGTTCCTCCAAGG     598
FCTR3     GCACTGTTGTCAGAGGAAGATGGTGTGCCACAAGGAGATCCCTCCAAGG     417
FCTR4     GCACTGTTGTCAGAGGAAGATGGTGTGCCACAAGGAGATCCCTCCAAGG     417
FCTR6     TCACCATGAACGATG--CGATTGTATCTGCAGCTCAAGACCACCTCGA--     415

610       620       630       640       650
          ....|....|....|....|....|....|....|....|....|....|
FCTR1     ATAAAATCAAGAACGAACCAAATTAAAATCACATTCAAGTCCGATGACTA     648
FCTR3     ATAACGTCAAGAACAAACCAGATTAAAATCACATTTAAGTCTGATGACTA     467
FCTR4     ATAACGTCAAGAACAAACCAGATTAAAATCACATTTAAGTCTGATGACTA     467
FCTR6     --------------------------------------------------     415

660       670       680       690       700
          ....|....|....|....|....|....|....|....|....|....|
FCTR1     CTTTGTGGCTAAACCTGGATTCAAGATTTATTATTCTTTGCTGGAAGATT     698
FCTR3     CTTTGTGGCAAAACCTGGATTCAAGATTTATTATTCATTTGTGGAAGATT     517
FCTR4     CTTTGTGGCAAAACCTGGATTCAAGATTTATTATTCATTTGTGGAAGATT     517
FCTR6     --------------------------------------------------     415

710       720       730       740       750
          ....|....|....|....|....|....|....|....|....|....|
FCTR1     TCCAACCCGCAGCAGCTTCAGAGACCAACTGGGAATCTGTCACAAGCTCT     748
FCTR3     TCCAACCGGAAGCAGCCTCAGAGACCAACTGGGAATCAGTCACAAGCTCT     567
FCTR4     TCCAACCGGAAGCAGCCTCAGAGACCAACTGGGAATCAGTCACAAGCTCT     567
FCTR6     --------------------------------------------------     415

760       770       780       790       800
          ....|....|....|....|....|....|....|....|....|....|
FCTR1     ATTTCAGGGGTATCCTATAACTCTCCATCAGTAACGGATCCCACTCTGAT     798
FCTR3     TTCTCTGGGGTGTCCTATCACTCTCCATCAATAACGGACCCCACTCTCAC     617
FCTR4     TTCTCTGGGGTGTCCTATCACTCTCCATCAATAACGGACCCCACTCTCAC     617
FCTR6     --------------------------------------------------     415

810       820       830       840       850
          ....|....|....|....|....|....|....|....|....|....|
FCTR1     TGCGGATGCTCTGGACAAAAAAATTGCAGAATTTGATACAGTGGAAGATC     848
FCTR3     TGCTGATGCCCTGGACAAAACTGTCGCAGAATTCGATACCGTGGAAGATC     667
FCTR4     TGCTGATGCCCTGGACAAAACTGTCGCAGAATTCGATACCGTGGAAGATC     667
FCTR6     --------------------------------------------------     415

860       870       880       890       900
          ....|....|....|....|....|....|....|....|....|....|
FCTR1     TGCTCAAGTACTTCAATCCAGAGTCATGGCAAGAAGATCTTGAGAATATG     898
FCTR3     TACTTAAGCACTTCAATCCACTGTCTTGGCAAGATGATCTGGAGAATTTG     717
FCTR4     TACTTAAGCACTTCAATCCACTGTCTTGGCAAGATGATCTGGAGAATTTG     717
FCTR6     --------------------------------------------------     415

910       920       930       940       950
          ....|....|....|....|....|....|....|....|....|....|
FCTR1     TATCTGGACACCCCTCGGTATCGAGGCAGGTCATACCATGACCGGAAGTC     948
FCTR3     TATCTGGACACCCCTCATTATAGAGGCAGGTCATACCATGATCGGAAGTC     767
FCTR4     TATCTGGACACCCCTCATTATAGAGGCAGGTCATACCATGATCGGAAGTC     767
FCTR6     --------------------------------------------------     415

960       970       980       990      1000
          ....|....|....|....|....|....|....|....|....|....|
FCTR1     AAAAGTTGACCTGGATACAGCTCAATGATGATGCCAAGCGTTACAGTTGCA     998
FCTR3     CAAAGTGGACCTGGACACAGCTCAATGATGATGTCAAGCGTTACAGTTGCA     817
FCTR4     CAAAGGTATTGAACTTTCAGCC--TGGACATTTCAAGACAAGGGGCAAAG     815
FCTR6     --------------------------------------------------     415

1010      1020      1030      1040      1050
          ....|....|....|....|....|....|....|....|....|....|
FCTR1     CTCCCAGGAATTACTCGGTCAATATAAGAGAAGAGCTGAAGTTGGCCAAT    1048
FCTR3     CTCCCAGGAATCACTCTCTGAACCTCAGGGAGGAGCTGAAGCTGACCAAT     867
FCTR4     CTAAGAATATGGCTCTTGTTGATATCCAGCTGGATC--ATCATGAGCGAT     863
FCTR6     --------------------------------------------------     415

1060      1070      1080      1090      1100
          ....|....|....|....|....|....|....|....|....|....|
FCTR1     GTGGTCTTCTTTCCA---CGTTGCCTCCTCCGTGCAGCGCTGTGGAGAAA    1095
FCTR3     GCAGTCTTCTTCCCA---CGATGCCTCCTCCGTGCAGCGCTGTGGTGGCAA     914
FCTR4     GTGACTGTATCTGCAGCTCAAGACCACCTCGATAA---------------     898
FCTR6     --------------------------------------------------     415
```

TABLE 9-continued

Alignment of SEQ ID NOS:3, 7, 9 and 13, respectively.

```
                1110      1120      1130      1140      1150
            ....|....|....|....|....|....|....|....|....|....|
FCTR1       TTGTGGCTGTGGAACTGTCAACTGGAGGTCCTGCACATGCAATTCAGGGA      1145
FCTR3       CTGTGGTTGCGGAACTGTCAACTGGAAGTCCTGCACATGCAGCTCAGGGA      964
FCTR4       --------------------------------------------------      898
FCTR6       --------------------------------------------------      415

1160      1170      1180      1190      1200
            ....|....|....|....|....|....|....|....|....|....|
FCTR1       AAACCGTGAAAAAGTATCATGAGGTATTACAGTTTGAGCCTGGCCACATC      1195
FCTR3       AGACAGTGAAGAAGTATCATGAGGTATTGAAGTTTGAGCCTGGACATTTC      1014
FCTR4       --------------------------------------------------      898
FCTR6       --------------------------------------------------      415

1210      1220      1230      1240      1250
            ....|....|....|....|....|....|....|....|....|....|
FCTR1       AAGAGGAGGGGTAGAGCTAAGACCATGGCTCTAGTTGACATCCAGTTGGA      1245
FCTR3       AAGAGAAGGGGCAAAGCTAAGAATATGGCTCTTGTTGATATCCAGCTGGA      1064
FCTR4       --------------------------------------------------      898
FCTR6       --------------------------------------------------      415

1260      1270      1280      1290      1300
            ....|....|....|....|....|....|....|....|....|....|
FCTR1       TCACCATGAACGATGTGATTGTATCTGCAGCTCAAGACCACCTCGATAAG      1295
FCTR3       TCATCATGAGCGATGTGACTGTATCTGCAGCTCAAGACCACCTCGATAA-      1113
FCTR4       --------------------------------------------------      898
FCTR6       --------------------------------------------------      415
```

Amino acids of FCTR1, FCTR3, FCTR4 and FCTR6 are aligned with each other as shown in Table 10.

TABLE 10

Alignment of SEQ ID NOS:4, 8, 10 and 14, respectively.

```
                10        20        30        40        50
            ....|....|....|....|....|....|....|....|....|....|
FCTR1       MHRLIFVYTLICANFCSCRDTSATPQSASIKALRNANLRRDESNHLTDLY      50
FCTR3       MQRLVLVSILLCANFSCYPDTFATPQRASIKALRNANLRRDESNHLTDLY      50
FCTR4       MQRLVLVSILLCANFSCYPDTFATPQRASIKALRNANLRRDESNHLTDLY      50
FCTR6       MHRLIFVYTLICANFCSCRDTSATPQSASIKALRNANLRRDESNHLTDLY      50

60        70        80        90        100
            ....|....|....|....|....|....|....|....|....|....|
FCTR1       RRDETIQVKGNGKVQSPRFPNSYPRNLLLTWRLHSQENTRIQIVFDNQFG      100
FCTR3       QREENIQVTSNGHVQSPRFPNSYPRNLLLTWWLRSQEKTRIQISFDHQFG      100
FCTR4       QREENIQVTSNGHVQSPRFPNSYPRNLLLTWWLRSQEKTRIQISFDHQFG      100
FCTR6       RRDETIQVKGNGKVQSPRFPNSYPRNLLLTWRLHSQENTRIQIVFDNQFG      100

110       120       130       140       150
            ....|....|....|....|....|....|....|....|....|....|
FCTR1       LEEAENDICRYDFVEVEDISENSTIIRGRWCGHKEVPPRIKSRTNQIKIT      150
FCTR3       LEEAENDICRYDFVEVEKVSESSTVVRGRWCGHKEIPPRITSRTNQIKIT      150
FCTR4       LEEAENDICRYDFVEVEKVSESSTVVRGRWCGHKEIPPRITSRTNQIKIT      150
FCTR6       LEEAENDICR----------------------------------------      110

160       170       180       190       200
            ....|....|....|....|....|....|....|....|....|....|
FCTR1       FKSDDYFVAKPGFKIYYSLLEDFQPAAASETNWESVTSSISGVSYNSPSV      200
FCTR3       FKSDDYFVAKPGFKIYYSFVEDFQPEAASETNWESVTSSFSGVSYHSPSI      200
FCTR4       FKSDDYFVAKPGFKIYYSFVEDFQPEAASETNWESVTSSFSGVSYHSPSI      200
FCTR6       --------------------------------------------------      110

210       220       230       240       250
            ....|....|....|....|....|....|....|....|....|....|
FCTR1       TDPTLIADALDKKIAEFDTVEDLLKYFNPESWNEDLENMYLDTPRYRGRS      250
FCTR3       TDPTLTADALDKTVAEFDTVEDLLKHFNPVSWQDDLENLYLDTPHYRGRS      250
FCTR4       TDPTLTADALDKTVAEFDTVEDLLKHFNPVSWQDDLENLYLDTPHYRGRS      250
FCTR6       --------------------------------------------------      110
```

TABLE 10-continued

Alignment of SEQ ID NOS:4, 8, 10 and 14, respectively.

```
              260        270        280        290        300
         ....|....|....|....|....|....|....|....|....|....|
FCTR1    YHDRKSK-VDLDRLNDDAKRYSCTPRNMSVNTREELKLANVFFPRCLLV    299
FCTR3    YHDRKSK-VDLDRLNDDVKRYSCTPRNHSVNTREELKLTNAVFFPRCLLV    299
FCTR4    YHDRKSKTIEV---------------------------------------    261
FCTR6    --------------------------------------------------    110

310        320        330        340        350
         ....|....|....|....|....|....|....|....|....|....|
FCTR1    QRCGGNCGCGTVNWRSCTCNSGKTVKKYHEVLQPEPGHIKRRGRAKTMAL    349
FCTR3    QRCGGNCGCGTVNWKSCTCSSGKTVKKYHEVLKPEPGHFKRRGKAKNMAL    349
FCTR4    -------------------------------------------------    261
FCTR6    -------------------------------------------------    110

360        370
         ....|....|....|....|....|.
FCTR1    VDIQLDHHERCDCICSSAPPR          370
FCTR3    VDIQLDHHERCDCICSSRPPR          370
FCTR4    ---------------------          261
FCTR6    ---------------------          110
```

Nucleic acids of FCTR2 and FCTR5 are aligned with each other over the nucleotide residues shown in Table 11.

TABLE 11

Alignment of SEQ ID NO:5 and SEQ ID NO:11, respectively.

```
              460        470        480        490        500
         ....|....|....|....|....|....|....|....|....|....|
FCTR2    CTCTGGACAAAAAAATTGCAGAATTTGATACAGTGGAAGATCTGCTCAAG    500
FCTR5                             ATGCACCGGCTCATCTTGTTCTA     23

510        520        530        540        550
         ....|....|....|....|....|....|....|....|....|....|
FCTR2    TACTTCAATCCAGAGTCATGGCAAGAAGATCTTGAGAA---TATGTATCT    547
FCTR5    CACTCTAATCT-CCGCAAACTTTTGCAGCTGTCCGGACACTTCTGCAACC     72

560        570        580        590        600
         ....|....|....|....|....|....|....|....|....|....|
FCTR2    GGACACCCCTCGGT-ATGGAGGCAGGTCATACCAT-GACCGGAAGTCAAA    595
FCTR5    CCGCAGAGCGCATCCATCAAAGCTTTGCGCAACGCCAACCTCAGGCGAGA    122

610        620        630        640        650
         ....|....|....|....|....|....|....|....|....|....|
FCTR2    AGTTGACCTGGATAGGCTCAATGATGATGCCAAGCGTTACAGTTGCACTC    645
FCTR5    TGTTGACCTGGATAGGCTCAATGATGATGCCAAGCGTTACAGTTGCACTC    172

660        670        680        690        700
         ....|....|....|....|....|....|....|....|....|....|
FCTR2    CCAGGAATTACTCGGTCAATATAAGAGAAGAGCTGAAGTTGGCCAATGTG    695
FCTR5    CCAGGAATTACTCGGTCAATATAAGAGAAGAGCTGAAGTTGGCCAATGTG    222

710        720        730        740        750
         ....|....|....|....|....|....|....|....|....|....|
FCTR2    GTCTTCTTTCCACGTTGCCTCCTCGTGCAGCGCTGTGGAGGAAATTGTGG    745
FCTR5    GTCTTCTTTCCACGTTGCCTCCTCGTGCAGCGCTGTGGAGGAAATTGTGG    272

760        770        780        790        800
         ....|....|....|....|....|....|....|....|....|....|
FCTR2    CTGTGGAACTGTCAACTGGAGGTCCTGCACATGCAATTCAGGGAAAACCG    795
FCTR5    CTGTGGAACTGTCAACTGGAGGTCCTGCACATGCAATTCAGGGAAAACCG    322

810        820        830        840        850
         ....|....|....|....|....|....|....|....|....|....|
FCTR2    TGAAAAGTATCATGAGGTATTACAGTTTGAGCCTGGCCACATCAAGAGG    845
FCTR5    TGAAAAGTATCATGAGGTATTACAGTTTGAGCCTGGCCACATCAAGAGG    372

860        870        880        890        900
         ....|....|....|....|....|....|....|....|....|....|
FCTR2    AGGGGTAGAGCTAAGACCATGGCTCTAGTTGACATCCAGTTGGATCACCA    895
FCTR5    AGGGGTAGAGCTAAGACCATGGCTCTAGTTGACATCCAGTTGGATCACCA    422
```

TABLE 11-continued

Alignment of SEQ ID NO:5 and SEQ ID NO:11, respectively.

```
            910       920       930       940       950
       ....|....|....|....|....|....|....|....|....|....|
FCTR2  TGAACGATGTGATTGTATCTGCAGCTCAAGACCACCTCGATAAGAGAATG   945
FCTR5  TGAACGATGCGATTGTATCTGCAGCTCAAGACCACCTCGA             462
```

Amino acids of FCTR2 and FCTR5 are aligned with each other as shown in Table 12.

TABLE 12

Alignment of SEQ ID NO:6 and SEQ ID NO:12, respectively.

```
            10        20        30        40        50
       ....|....|....|....|....|....|....|....|....|....|
FCTR2  ----------MYLDRPRYRGRSTHDR------------KSKVDLDRLNDD   28
FCTR5  MHRLILFYTLICANFCSCRDTSATPQSASIKALRNANLRRDVDLDRLNDD   50

60        70        80        90        100
       ....|....|....|....|....|....|....|....|....|....|
FCTR2  AKRYSCTPRNYSVNIREELKLANVVFFPRCLLVQRCGGNCGCGRVNWRSC    78
FCTR5  AKRYSCTPRNYSVNIREELKLANVVFFPRCLLVQRCGGNCGCGTVNWRSC   100

110       120       130       140       150
       ....|....|....|....|....|....|....|....|....|....|
FCTR2  TCNSGKTVKKYHEVLQFEPGHIKRRGRAKTMALVDIQLDHHERCDCICSS   128
FCTR5  TCNSGKTVKKYHEVLQFEPGHIKRRGRAKTMALVDIQLDHHERCDCICSS   150

....
FCTR2  RPPR                                                 132
FCTR5  RPPR                                                 154
```

The similarities of the disclosed FCTRX polypeptides to previously described BMP-1 VEGF-E and PDGF polypeptides indicate a similarity of functions by the FCTRX nucleic acids and polypeptides of the invention. These utilities are described in more detail below.

FCTRX nucleic acids and polypeptides may be use to induce formation of cartilage, as BMP-1 is also capable of inducing formation of cartilage in vivo (Wozney et al., Science 242: 1528–1534 (1988)).

An additional use for the FCTRX nucleic acids and polypeptides is in the modulation of collagen formation. Recombinantly expressed BMP1 and purified procollagen C proteinase (PCP), a secreted metalloprotease requiring calcium and needed for cartilage and bone formation, are, in fact, identical. See, Kessler et al., Science 271:360–62 (1996). BMP-1 cleaves the C-terminal propeptides of procollagen I, II, and III and its activity is increased by the procollagen C-endopeptidase enhancer protein. FCTRX nucleic acids and polypeptides may play similar roles in collagen modulation pathways.

It is shown in the Examples below that FCTRX polypeptides have the ability to reduce or ameliorate the extent of inflammatory response in two animal models of inflammatory bowel disease.

The similarity between FCTRX polypeptides and PDGF polypeptides suggests that FCTRX nucleic acids and their encoded polypeptides can be used in various therapeutic and diagnostic applications. For example, FCTRX nucleic acids and their encoded polypeptides can be used to treat cancer, cardiovascular and fibrotic diseases and diabetic ulcers. In addition, FCTRX nucleic acids and their encoded polypeptides will be therapeutically useful for the prevention of aneurysms and the the acceleration of wound closure through gene therapy. Furthermore, FCTRX nucleic acids and their encoded polypeptides can be utilized to stimulate cellular growth.

A FCTRX nucleic acid or gene product, e.g., a nucleic acid encoding SEQ ID NO:4 or SEQ ID NO:6, is useful as a therapeutic agent in promoting wound healing, neovascularization and tissue growth, and similar tissue regeneration needs. More specifically, a FCTRX nucleic acid or polypeptide may be useful in treatment of anemia and leukopenia, intestinal tract sensitivity and baldness. Treatment of such conditions may be indicated in, e.g., patients having undergone radiation or chemotherapy. It is intended in such cases that administration of a FCTX nucleic acid or polypeptide, e.g., a polypeptide including the amino acid sequence of SEQ ID NO:4 or SEQ ID NO:6, or a nucleic acid sequence encoding these polypeptides (e.g., SEQ ID NO:3 or SEQ ID NO:5) will be controlled in dose such that any hyperproliferative side effects are minimized.

The invention also includes mature FGF-CX and/or FCTRX polypeptides, variants of mature FGF-CX and/or FCTRX polypeptides, fragments of mature and mature variant FGF-CX and/or FCTRX polypeptides, and nucleic acids encoding these polypeptides and fragments. As used herein, a "mature" form of a FGF-CX and/or FCTRX polypeptide or protein disclosed in the present invention is the product of a naturally occurring polypeptide or precursor form or proprotein. The naturally occurring polypeptide, precursor or proprotein includes, by way of nonlimiting example, the full length gene product, encoded by the corresponding gene. In some embodiments, the mature form include an FGF-CX and/or FCTRX polypeptide, precursor or proprotein encoded by an open reading frame described herein. The product "mature" form can arise, e.g., as a result of one or more naturally occurring processing steps as they may take place within the cell, or host cell, in which the gene product arises.

Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a FGF-CX or a FCTRX precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Additionally, a "mature" protein or fragment may arise from a cleavage event other than removal of an initiating methionine or removal of a signal peptide. Further as used herein, a "mature" form of a FGF-CX and/or a FCTRX polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

As used herein, "identical" residues correspond to those residues in a comparison between two sequences where the equivalent nucleotide base or amino acid residue in an alignment of two sequences is the same residue. Residues are alternatively described as "similar" or "positive" when the comparisons between two sequences in an alignment show that residues in an equivalent position in a comparison are either the same amino acid or a conserved amino acid as defined below.

Included within the invention are FGF-CX and FCTRX nucleic acids, isolated nucleic acids that encode FGF-CX and FCTRX polypeptides or a portion thereof, FGF-CX and FCTRX polypeptides, vectors containing these nucleic acids, host cells transformed with the FGF-CX and/or FCTRX nucleic acids, anti-FGF-CX and/or FCTRX antibodies, and pharmaceutical compositions. Also disclosed are methods of making FGF-CX and/or FCTRX polypeptides, as well as methods of screening, diagnosing, treating conditions using these compounds, and methods of screening compounds that modulate FGF-CX and/or FCTRX polypeptide activity. The FGF-CX and/or FCTRX nucleic acids and polypeptides, as well as FGF-CX and/or FCTRX antibodies, therapeutic agents and pharmaceutical compositions discussed herein, are useful, inter alia, in treating inflammatory conditions, as well as tissue proliferation-associated disorders.

FGF-CX and/or FCTRX Nucleic Acids and Polypeptides

A summary of the FGF-CX and/or FCTRX nucleic acids and proteins of the invention is provided in Table 13.

TABLE 13

Summary Of Nucleic Acids And Proteins Of The Invention

| Clone | Table | Clone alias | Nucleic Acid SEQ ID NO | Amino Acid SEQ ID NO |
|---|---|---|---|---|
| FGF-CX | 1 | AB020858; CG53135-01; CG53135-02; TA-AB02085-S274-F19; 20858 | 1 | 2 |
| FCTR1 | 2 | PDGFD; 30664188; 30664188.0.99; CG52053; CG52053-02; 30664188.0.m99; 30664188-S311a; 30664188-S11a | 3 | 4 |

TABLE 13-continued

Summary Of Nucleic Acids And Proteins Of The Invention

| Clone | Table | Clone alias | Nucleic Acid SEQ ID NO | Amino Acid SEQ ID NO |
|---|---|---|---|---|
| FCTR2 | 3 | PDGFD; 30664188.0.331; CG52053-01 | 5 | 6 |
| FCTR3 | 4 | PDGFD; murine PDGFD; mPDGFD | 7 | 8 |
| FCTR4 | 5 | PDGFD; murine PDGFD; mPDGFD | 9 | 10 |
| FCTR5 | 6 | PDGFD; human PDGFD; hPDGFD; clone pCR2.1-S852_2B | 11 | 12 |
| FCTR6 | 7 | PDGFD; human PDGFD; hPDGFD; clone pCR2.1-S869_4B | 13 | 14 |

One aspect of the invention pertains to isolated nucleic acid molecules that encode FGF-CX and/or FCTRX polypeptides or biologically active portions thereof. Also included in the invention are nucleic acid fragments sufficient for use as hybridization probes to identify FGF-CX and/or FCTRX-encoding nucleic acids (e.g., FGF-CX and/or FCTRX mRNAs) and fragments for use as PCR primers for the amplification and/or mutation of FGF-CX and/or FCTRX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

An FGF-CX and/or FCTRX nucleic acid can encode a mature FGF-CX and/or FCTRX polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as utilized herein, is one, which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated FGF-CX and/or FCTRX nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence of SEQ ID NOS:1, 3, 5, 7, 9, 11 and 13, or a complement of this aforementioned nucleotide sequence, can be isolated using standard molecular biology techniques and the sequence information provided herein. Using all or a portion of the nucleic acid sequence of SEQ ID NOS:1, 3, 5, 7, 9, 11 and 13 as a hybridization probe, FGF-CX and/or FCTRX molecules can be isolated using standard hybridization and cloning techniques (e.g., as described in Sambrook, et al., (eds.), MOLECULAR CLONING: A LABORATORY MANUAL 2$^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to FGF-CX and/or FCTRX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NOS:1, 3, 5, 7, 9, 11 and 13, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOS:1, 3, 5, 7, 9, 11 and 13, or a portion of this nucleotide sequence (e.g., a fragment that can be used as a probe or primer or a fragment encoding a biologically-active portion of an FGF-CX and/or FCTRX polypeptide). A nucleic acid molecule that is complementary to the nucleotide sequence shown in SEQ ID NOS:1, 3, 5, 7, 9, 11 and 13 is one that is sufficiently complementary to the nucleotide sequence shown in SEQ ID NOS:1, 3, 5, 7, 9, 11 and 13 that it can hydrogen bond with little or no mismatches to the nucleotide sequence shown SEQ ID NOS:1, 3, 5, 7, 9, 11 and 13, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of FGF-CX and/or FCTRX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for an FGF-CX and/or FCTRX polypeptide of species other than humans, including, but not limited to: vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human FGF-CX and/or FCTRX protein. Homologous nucleic acid sequences include those nucleic acid sequences that encode conservative amino acid substitutions (see below) in SEQ ID NOS:1, 3, 5, 7, 9, 11 and 13, as well as a polypeptide possessing FGF-CX and/or FCTRX biological activity. Various biological activities of the FGF-CX and/or FCTRX proteins are described below.

As used herein, "identical" residues correspond to those residues in a comparison between two sequences where the equivalent nucleotide base or amino acid residue in an alignment of two sequences is the same residue. Residues are alternatively described as "similar" or "positive" when the comparisons between two sequences in an alignment show that residues in an equivalent position in a comparison are either the same amino acid or a conserved amino acid as defined below.

An FGF-CX and/or FCTRX polypeptide is encoded by the open reading frame ("ORF") of an FGF-CX and/or FCTRX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bonafide cellular protein, a minimum size requirement is often set, e.g., a stretch of DNA that would encode a protein of 50 amino acids or more.

The nucleotide sequences determined from the cloning of the human FGF-CX and/or FCTRX genes allows for the generation of probes and primers designed for use in identifying and/or cloning FGF-CX and/or FCTRX homologues in other cell types, e.g. from other tissues, as well as FGF-CX and/or FCTRX homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NOS:1, 3, 5, 7, 9, 11 and 13; or an anti-sense strand nucleotide sequence of SEQ ID NOS:1, 3, 5, 7, 9, 11 and 13; or of a naturally occurring mutant of SEQ ID NOS:1, 3, 5, 7, 9, 11 and 13.

Probes based on the human FGF-CX and/or FCTRX nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express an FGF-CX and/or FCTRX protein, such as by measuring a level of an FGF-CX and/or FCTRX-encoding nucleic acid in a sample of cells from a subject e.g., detecting FGF-CX and/or FCTRX mRNA levels or determining whether a genomic FGF-CX and/or FCTRX gene has been mutated or deleted.

"A polypeptide having a biologically-active portion of an FGF-CX and/or FCTRX polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of FGF-CX and/or FCTRX" can be prepared by isolating a portion SEQ ID NOS:1, 3, 5, 7, 9, 11 and 13 that encodes a polypeptide having an FGF-CX and/or FCTRX biological activity (the biological activities of the FGF-CX and/or FCTRX proteins are described below), expressing the encoded portion of FGF-CX and/or FCTRX protein (e.g., by recombinant expression in vitro) and assessing the activity of the encoded portion of FGF-CX and/or FCTRX.

FGF-CX and/or FCTRX Nucleic Acid and Polypeptide Variants

The invention further encompasses nucleic acid molecules that differ from the nucleotide sequences shown SEQ ID NOS:1, 3, 5, 7, 9, 11 and 13 due to degeneracy of the genetic code and thus encode the same FGF-CX and/or FCTRX proteins as that encoded by the nucleotide sequences shown in SEQ ID NOS:1, 3, 5, 7, 9, 11 and 13. In another embodiment, an isolated nucleic acid molecule of the invention has a nucleotide sequence encoding a protein having an amino acid sequence shown in SEQ ID NOS:2, 4, 6, 8, 10, 12 and 14.

In addition to the human FGF-CX and/or FCTRX nucleotide sequences shown in SEQ ID NOS:1, 3, 5, 7, 9, 11 and 13 it will be appreciated by those skilled in the art that DNA sequence polymorphisms that lead to changes in the amino acid sequences of the FGF-CX and/or FCTRX polypeptides may exist within a population (e.g., the human population). Such genetic polymorphism in the FGF-CX and/or FCTRX genes may exist among individuals within a population due to natural allelic variation. As used herein, the terms "gene" and "recombinant gene" refer to nucleic acid molecules comprising an open reading frame (ORF) encoding an FGF-CX and/or FCTRX protein, preferably a vertebrate FGF-CX and/or FCTRX protein. Such natural allelic variations can typically result in 1–5% variance in the nucleotide sequence of the FGF-CX and/or FCTRX genes. Any and all such nucleotide variations and resulting amino acid polymorphisms in the FGF-CX and/or FCTRX polypeptides, which are the result of natural allelic variation and that do not alter the functional activity of the FGF-CX and/or FCTRX polypeptides, are intended to be within the scope of the invention.

Moreover, nucleic acid molecules encoding FGF-CX and/or FCTRX proteins from other species, and thus that have a nucleotide sequence that differs from the human sequence SEQ ID NOS:1, 3, 5, 7, 9, 11 and 13 are intended to be within the scope of the invention. Nucleic acid molecules corresponding to natural allelic variants and homologues of the FGF-CX and/or FCTRX cDNAs of the invention can be isolated based on their homology to the human FGF-CX and/or FCTRX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOS:1, 3, 5, 7, 9, 11 and 13. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding FGF-CX and/or FCTRX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% PVP; 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences of SEQ ID NOS:1, 3, 5, 7, 9, 11 and 13 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOS:1, 3, 5, 7, 9, 11 and 13 or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences of SEQ ID NOS:1, 3, 5, 7, 9, 11 and 13 or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789–6792.

Conservative Mutations

In addition to naturally-occurring allelic variants of FGF-CX and/or FCTRX sequences that may exist in the population, the skilled artisan will further appreciate that changes can be introduced by mutation into the nucleotide sequences of SEQ ID NOS:1, 3, 5, 7, 9, 11 and 13 thereby leading to changes in the amino acid sequences of the encoded FGF-CX and/or FCTRX proteins, without altering the functional ability of said FGF-CX and/or FCTRX proteins. For, example, nucleotide substitutions leading to amino acid substitutions at "non-essential" amino acid residues can be made in the sequence of SEQ ID NOS:2, 4, 6, 8, 10, 12 and 14. A "non-essential" amino acid residue is a residue that can be altered from the wild-type sequences of the FGF-CX and/or FCTRX proteins without altering their biological activity, whereas an "essential" amino acid residue is required for such biological activity. For example, amino acid residues that are conserved among the FGF-CX and/or FCTRX proteins of the invention are predicted to be particularly non-amenable to alteration. Amino acids for which conservative substitutions can be made are well-known within the art.

Another aspect of the invention pertains to nucleic acid molecules encoding FGF-CX and/or FCTRX proteins that contain changes in amino acid residues that are not essential for activity. Such FGF-CX and/or FCTRX proteins differ in amino acid sequence from SEQ ID NOS:2, 4, 6, 8, 10, 12 and 14 yet retain biological activity. In one embodiment, the isolated nucleic acid molecule comprises a nucleotide sequence encoding a protein, wherein the protein comprises an amino acid sequence at least about 45% homologous to the amino acid sequences of SEQ ID NOS:2, 4, 6, 8, 10, 12 and 14. Preferably, the protein encoded by the nucleic acid molecule is at least about 60% homologous to SEQ ID NOS:2, 4, 6, 8, 10, 12 and 14; more preferably at least about 70% homologous to SEQ ID NOS:2, 4, 6, 8, 10, 12 and 14; still more preferably at least about 80% homologous to SEQ ID NOS:2, 4, 6, 8, 10, 12 and 14; even more preferably at least about 90% homologous to SEQ ID NOS:2, 4, 6, 8, 10, 12 and 14; and most preferably at least about 95% homologous to SEQ ID NOS:2, 4, 6, 8, 10, 12 and 14.

An isolated nucleic acid molecule encoding an FGF-CX and/or FCTRX protein homologous to the protein of SEQ ID NOS:2, 4, 6, 8, 10, 12 and 14 can be created by introducing one or more nucleotide substitutions, additions or deletions into the nucleotide sequence of SEQ ID NOS:1, 3, 5, 7, 9, 11 and 13 such that one or more amino acid substitutions, additions or deletions are introduced into the encoded protein.

Mutations can be introduced into SEQ ID NOS:2, 4, 6, 8, 10, 12 and 14 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in the FGF-CX and/or FCTRX protein is replaced with another amino acid residue from the same side chain family. Alternatively, in another embodiment, mutations can be introduced randomly along all or part of an FGF-CX and/or FCTRX coding sequence, such as by saturation mutagenesis, and the resultant mutants can be screened for FGF-CX and/or FCTRX biological activity to identify mutants that retain activity. Following mutagenesis of SEQ ID NOS:1, 3, 5, 7, 9, 11 and 13, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, VLIM, HFY, wherein the letters within each group represent the single letter amino acid code.

In one embodiment, a mutant FGF-CX and/or FCTRX protein can be assayed for (i) the ability to form protein:protein interactions with other FGF-CX and/or FCTRX proteins, other cell-surface proteins, or biologically-active portions thereof, (ii) complex formation between a mutant FGF-CX and/or FCTRX protein and an FGF-CX and/or FCTRX ligand; or (iii) the ability of a mutant FGF-CX and/or FCTRX protein to bind to an intracellular target protein or biologically-active portion thereof; (e.g. avidin proteins).

In yet another embodiment, a mutant FGF-CX and/or FCTRX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NOS:1, 3, 5, 7, 9, 11 and 13, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence).

In specific aspects, antisense nucleic acid molecules are provided that comprise a sequence complementary to at least about 10, 25, 50, 100, 250 or 500 nucleotides or an entire FGF-CX and/or FCTRX coding strand, or to only a portion thereof. Nucleic acid molecules encoding fragments, homologs, derivatives and analogs of an FGF-CX and/or FCTRX protein of SEQ ID NOS:2, 4, 6, 8, 10, 12 and 14, or antisense nucleic acids complementary to an FGF-CX and/or FCTRX nucleic acid sequence of SEQ ID NOS:1, 3, 5, 7, 9, 11 and 13, are additionally provided.

In one embodiment, an antisense nucleic acid molecule is antisense to a "coding region" of the coding strand of a nucleotide sequence encoding an FGF-CX and/or FCTRX protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding the FGF-CX and/or FCTRX protein. The term "noncoding region" refers to 5' and 3' sequences which flank the coding region that are not translated into amino acids (i.e., also referred to as 5' and 3' untranslated regions).

Given the coding strand sequences encoding the FGF-CX and/or FCTRX protein disclosed herein, antisense nucleic acids of the invention can be designed according to the rules of Watson and Crick or Hoogsteen base pairing. The antisense nucleic acid molecule can be complementary to the entire coding region of FGF-CX and/or FCTRX mRNA, but more preferably is an oligonucleotide that is antisense to only a portion of the coding or noncoding region of FGF-CX and/or FCTRX mRNA. For example, the antisense oligonucleotide can be complementary to the region surrounding the translation start site of FGF-CX and/or FCTRX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g, phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyluracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, uracil-5-oxyacetic acid methylester, uracil-5-oxyacetic acid (v), 5-methyl-2-thiouracil, 2,6-diaminopurine, (acp3)w, and 3-(3-amino-3-N-2-carboxypropyl)uracil. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an FGF-CX and/or FCTRX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625–6641. The antisense nucleic acid molecule can also comprise a 2'-o-methylribonucleotide (see, e.g., Inoue, et al. 1987. *Nucl. Acids Res.* 15: 6131–6148) or a chimeric RNA-DNA analogue (see, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave FGF-CX and/or FCTRX mRNA transcripts to thereby inhibit translation of FGF-CX and/or FCTRX mRNA. A ribozyme having specificity for an FGF-CX and/or FCTRX-encoding nucleic acid can be designed based upon the nucleotide sequence of an FGF-CX and/or FCTRX cDNA disclosed herein (i.e., SEQ ID NOS:1, 3, 5, 7, 9, 11 and 13). For example, a derivative of a *Tetrahymena* L-19 IVS RNA can be constructed in which the nucleotide sequence of the active site is complementary to the nucleotide sequence to be cleaved in an FGF-CX and/or FCTRX-encoding mRNA. See, e.g., U.S. Pat. No. 4,987,071 to Cech, et al. and U.S. Pat. No. 5,116,742 to Cech, et al. FGF-CX and/or FCTRX mRNA can also be used to select a catalytic RNA having a specific ribonuclease activity from a pool of RNA molecules. See, e.g., Bartel et al., (1993) *Science* 261:1411–1418.

Alternatively, FGF-CX and/or FCTRX gene expression can be inhibited by targeting nucleotide sequences complementary to the regulatory region of the FGF-CX and/or FCTRX nucleic acid (e.g., the FGF-CX and/or FCTRX promoter and/or enhancers) to form triple helical structures that prevent transcription of the FGF-CX and/or FCTRX gene in target cells. See, e.g., Helene, 1991. *Anticancer Drug Des.* 6: 569–84; Helene, et al. 1992. *Ann. N.Y. Acad. Sci.* 660: 27–36; Maher, 1992. *Bioassays* 14: 807–15.

In various embodiments, the FGF-CX and/or FCTRX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of FGF-CX and/or FCTRX can be used in therapeutic and diagnostic applications. For example, PNAs can be used as antisense or antigene agents for sequence-specific modulation of gene expression by, e.g., inducing transcription or translation arrest or inhibiting replication. PNAs of FGF-CX and/or FCTRX can also be used, for example, in the analysis of single base pair mutations in a gene (e.g., PNA directed PCR clamping; as artificial restriction enzymes when used in combination with other enzymes, e.g., $S_1$ nucleases (see, Hyrup, et al., 1996.supra); or as probes or primers for DNA sequence and hybridization (see, Hyrup, et al., 1996, supra; Perry-O'Keefe, et al, 1996. supra).

In another embodiment, PNAs of FGF-CX and/or FCTRX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FGF-CX and/or FCTRX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

FGF-CX and/or FCTRX Polypeptides

A polypeptide according to the invention includes a polypeptide including the amino acid sequence of FGF-CX and/or FCTRX polypeptides whose sequences are provided in SEQ ID NOS:2, 4, 6, 8, 10, 12 and 14. The invention also includes a mutant or variant protein any of whose residues may be changed from the corresponding residues shown in SEQ ID NOS:2, 4, 6, 8, 10, 12 and 14 while still encoding a protein that maintains its FGF-CX and/or FCTRX activities and physiological functions, or a functional fragment thereof.

In general, an FGF-CX and/or FCTRX variant that preserves FGF-CX and/or FCTRX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated FGF-CX and/or FCTRX proteins, and biologically-active portions thereof, or derivatives, fragments, analogs or homologs thereof. Also provided are polypeptide fragments suitable for use as immunogens to raise anti-FGF-CX and/or FCTRX antibodies. In one embodiment, native FGF-CX and/or FCTRX proteins can be isolated from cells or tissue sources by an appropriate purification scheme using standard protein purification techniques. In another embodiment, FGF-CX and/or FCTRX proteins are produced by recombinant DNA techniques. Alternative to recombinant expression, an FGF-CX and/or FCTRX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the FGF-CX and/or FCTRX protein is derived, or substantially free from chemical precursors or other chemicals when chemically synthesized. The language "substantially free of cellular material" includes preparations of FGF-CX and/or FCTRX proteins in which the protein is separated from cellular components of the cells from which it is isolated or recombinantly-produced. In one embodiment, the language "substantially free of cellular material" includes preparations of FGF-CX and/or FCTRX proteins having less than about 30% (by dry weight) of non-FGF-CX and/or FCTRX proteins (also referred to herein as a "contaminating protein"), more preferably less than about 20% of non-FGF-CX and/or FCTRX proteins, still more preferably less than about 10% of non-FGF-CX and/or FCTRX proteins, and most preferably less than about 5% of non-FGF-CX and/or FCTRX proteins. When the FGF-CX and/or FCTRX protein or biologically-active portion thereof is recombinantly-produced, it is also preferably substantially free of culture medium, i.e., culture medium represents less than about 20%, more preferably less than about 10%, and most preferably less than about 5% of the volume of the FGF-CX and/or FCTRX protein preparation.

The language "substantially free of chemical precursors or other chemicals" includes preparations of FGF-CX and/or FCTRX proteins in which the protein is separated from chemical precursors or other chemicals that are involved in the synthesis of the protein. In one embodiment, the language "substantially free of chemical precursors or other chemicals" includes preparations of FGF-CX and/or FCTRX proteins having less than about 30% (by dry weight) of chemical precursors or non-FGF-CX and/or FCTRX chemicals, more preferably less than about 20% chemical precursors or non-FGF-CX and/or FCTRX chemicals, still more preferably less than about 10% chemical precursors or non-FGF-CX and/or FCTRX chemicals, and most preferably less than about 5% chemical precursors or non-FGF-CX and/or FCTRX chemicals.

Biologically-active portions of FGF-CX and/or FCTRX proteins include peptides comprising amino acid sequences sufficiently homologous to or derived from the amino acid sequences of the FGF-CX and/or FCTRX proteins (e.g., the amino acid sequence shown in SEQ ID NOS:2, 4, 6, 8, 10, 12 and 14) that include fewer amino acids than the full-length FGF-CX and/or FCTRX proteins, and exhibit at least one activity of an FGF-CX and/or FCTRX protein. Typically, biologically-active portions comprise a domain or motif with at least one activity of the FGF-CX and/or FCTRX protein. A biologically-active portion of an FGF-CX and/or FCTRX protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native FGF-CX and/or FCTRX protein.

In an embodiment, the FGF-CX and/or FCTRX protein has an amino acid sequence shown in SEQ ID NOS:2, 4, 6, 8, 10, 12 and 14. In other embodiments, the FGF-CX and/or FCTRX protein is substantially homologous to SEQ ID NOS:2, 4, 6, 8, 10, 12 and 14, and retains the functional activity of the protein of SEQ ID NOS:2, 4, 6, 8, 10, 12 and 14, yet differs in amino acid sequence due to natural allelic variation or mutagenesis, as described in detail, below. Accordingly, in another embodiment, the FGF-CX and/or FCTRX protein is a protein that comprises an amino acid sequence at least about 45% homologous to the amino acid sequence SEQ ID NOS:2, 4, 6, 8, 10, 12 and 14, and retains the functional activity of the FGF-CX and/or FCTRX proteins of SEQ ID NOS:2, 4, 6, 8, 10, 12 and 14.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOS:1, 3, 5, 7, 9, 11 and 13.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides FGF-CX and/or FCTRX chimeric or fusion proteins. As used herein, an FGF-CX and/or FCTRX "chimeric protein" or "fusion protein" comprises an FGF-CX and/or FCTRX polypeptide operatively-linked to a non-FGF-CX and/or FCTRX polypeptide. An "FGF-CX and/or FCTRX polypeptide" refers to a polypeptide having an amino acid sequence corresponding to an FGF-CX and/or FCTRX protein (SEQ ID NOS:2, 4, 6, 8, 10, 12 and 14), whereas a "non-FGF-CX and/or FCTRX polypeptide" refers to a polypeptide having an amino acid sequence corresponding to a protein that is not substantially homologous to the FGF-CX and/or FCTRX protein, e.g., a protein that is different from the FGF-CX and/or FCTRX protein and that is derived from the same or a different organism. Within an FGF-CX and/or FCTRX fusion protein the FGF-CX and/or FCTRX polypeptide can correspond to all or a portion of an FGF-CX and/or FCTRX protein. In one embodiment, an FGF-CX and/or FCTRX fusion protein comprises at least one biologically-active portion of an FGF-CX and/or FCTRX protein. In another embodiment, an FGF-CX and/or FCTRX fusion protein comprises at least two biologically-active portions of an FGF-CX and/or FCTRX protein. In yet another embodiment, an FGF-CX and/or FCTRX fusion protein comprises at least three biologically-active portions of an FGF-CX and/or FCTRX protein. Within the fusion protein, the term "operatively-linked" is intended to indicate that the FGF-CX and/or FCTRX polypeptide and the non-FGF-CX and/or FCTRX polypeptide are fused in-frame with one another. The non-FGF-CX and/or FCTRX polypeptide can be fused to the N-terminus or C-terminus of the FGF-CX and/or FCTRX polypeptide.

In one embodiment, the fusion protein is a GST-FGF-CX and/or FCTRX fusion protein in which the FGF-CX and/or FCTRX sequences are fused to the C-terminus of the GST (glutathione S-transferase) sequences. Such fusion proteins can facilitate the purification of recombinant FGF-CX and/or FCTRX polypeptides.

In another embodiment, the fusion protein is an FGF-CX and/or FCTRX protein containing a heterologous signal sequence at its N-terminus. In certain host cells (e.g., mammalian host cells), expression and/or secretion of FGF-CX and/or FCTRX can be increased through use of a heterologous signal sequence.

In yet another embodiment, the fusion protein is an FGF-CX and/or FCTRX-immunoglobulin fusion protein in which the FGF-CX and/or FCTRX sequences are fused to sequences derived from a member of the immunoglobulin protein family. The FGF-CX and/or FCTRX-immunoglobulin fusion proteins of the invention can be incorporated into pharmaceutical compositions and administered to a subject to inhibit an interaction between an FGF-CX and/or FCTRX ligand and an FGF-CX and/or FCTRX protein on the surface of a cell, to thereby suppress FGF-CX and/or FCTRX-mediated signal transduction in vivo. The FGF-CX and/or FCTRX-immunoglobulin fusion proteins can be used to affect the bioavailability of an FGF-CX and/or FCTRX cognate ligand. Inhibition of the FGF-CX and/or FCTRX ligand/FGF-CX and/or FCTRX interaction may be useful therapeutically for both the treatment of proliferative and differentiative disorders, as well as modulating (e.g. promoting or inhibiting) cell survival. Moreover, the FGF-CX and/or FCTRX-immunoglobulin fusion proteins of the invention can be used as immunogens to produce anti-FGF-CX and/or FCTRX antibodies in a subject, to purify FGF-CX and/or FCTRX ligands, and in screening assays to identify molecules that inhibit the interaction of FGF-CX and/or FCTRX with an FGF-CX and/or FCTRX ligand.

An FGF-CX and/or FCTRX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An FGF-CX and/or FCTRX-encoding nucleic acid can be cloned into such an expression vector such that the fusion moiety is linked in-frame to the FGF-CX and/or FCTRX protein.

FGF-CX and/or FCTRX Agonists and Antagonists

The invention also pertains to variants of the FGF-CX and/or FCTRX proteins that function as either FGF-CX and/or FCTRX agonists (i.e., mimetics) or as FGF-CX and/or FCTRX antagonists. Variants of the FGF-CX and/or FCTRX protein can be generated by mutagenesis (e.g., discrete point mutation or truncation of the FGF-CX and/or FCTRX protein). An agonist of the FGF-CX and/or FCTRX protein can retain substantially the same, or a subset of, the biological activities of the naturally occurring form of the FGF-CX and/or FCTRX protein. An antagonist of the FGF-CX and/or FCTRX protein can inhibit one or more of the activities of the naturally occurring form of the FGF-CX and/or FCTRX protein by, for example, competitively binding to a downstream or upstream member of a cellular signaling cascade which includes the FGF-CX and/or FCTRX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the FGF-CX and/or FCTRX proteins.

Variants of the FGF-CX and/or FCTRX proteins that function as either FGF-CX and/or FCTRX agonists (i.e., mimetics) or as FGF-CX and/or FCTRX antagonists can be identified by screening combinatorial libraries of mutants (e.g., truncation mutants) of the FGF-CX and/or FCTRX proteins for FGF-CX and/or FCTRX protein agonist or antagonist activity. In one embodiment, a variegated library of FGF-CX and/or FCTRX variants is generated by combinatorial mutagenesis at the nucleic acid level and is encoded by a variegated gene library. A variegated library of FGF-CX and/or FCTRX variants can be produced by, for example, enzymatically ligating a mixture of synthetic oligonucleotides into gene sequences such that a degenerate set of potential FGF-CX and/or FCTRX sequences is expressible as individual polypeptides, or alternatively, as a set of larger fusion proteins (e.g., for phage display) containing the set of FGF-CX and/or FCTRX sequences therein. There are a variety of methods which can be used to produce libraries of potential FGF-CX and/or FCTRX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FGF-CX and/or FCTRX sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the FGF-CX and/or FCTRX protein coding sequences can be used to generate a variegated population of FGF-CX and/or FCTRX fragments for screening and subsequent selection of variants of an FGF-CX and/or FCTRX protein. In one embodiment, a library of coding sequence fragments can be generated by treating a double stranded PCR fragment of an FGF-CX and/or FCTRX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the FGF-CX and/or FCTRX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FGF-CX and/or FCTRX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify FGF-CX and/or FCTRX variants. See, e.g., Arkin and Yourvan, 1992. *Proc. Natl. Acad. Sci. USA* 89: 7811–7815; Delgrave, et al., 1993. *Protein Engineering* 6:327–331.

Anti-FGF-CX and/or FCTRX Antibodies

Also included in the invention are antibodies to FGF-CX and/or FCTRX proteins, or fragments of FGF-CX and/or FCTRX proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated FGF-CX and/or FCTRX-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of FGF-CX and/or FCTRX-related protein that is located on the surface of the protein, e.g., a hydrophilic region. A hydrophobicity analysis of the human FGF-CX and/or FCTRX-related protein sequence will indicate which regions of a FGF-CX and/or FCTRX-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow and Lane, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., MONOCLONAL ANTIBODY PRODUCTION TECHNIQUES AND APPLICATIONS, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al,(*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–128.1) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 EMBO J., 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bisactive fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an FGF-CX and/or FCTRX protein is facilitated by generation of hybridomas that bind to the fragment of an FGF-CX and/or FCTRX protein possessing such a domain. Thus, antibodies that are specific for a desired domain within an FGF-CX and/or FCTRX protein, or derivatives, fragments, analogs or homologs thereof, are also provided herein.

Anti-FGF-CX and/or FCTRX antibodies may be used in methods known within the art relating to the localization and/or quantitation of an FGF-CX and/or FCTRX protein (e.g., for use in measuring levels of the FGF-CX and/or FCTRX protein within appropriate physiological samples, for use in diagnostic methods, for use in imaging the protein, and the like). In a given embodiment, antibodies for FGF-CX and/or FCTRX proteins, or derivatives, fragments, analogs or homologs thereof, that contain the antibody derived binding domain, are utilized as pharmacologically-active compounds (hereinafter "Therapeutics").

An anti-FGF-CX and/or FCTRX antibody (e.g., monoclonal antibody) can be used to isolate an FGF-CX and/or FCTRX polypeptide by standard techniques, such as affinity chromatography or immunoprecipitation. An anti-FGF-CX and/or FCTRX antibody can facilitate the purification of natural FGF-CX and/or FCTRX polypeptide from cells and of recombinantly-produced FGF-CX and/or FCTRX polypeptide expressed in host cells. Moreover, an anti-FGF-CX and/or FCTRX antibody can be used to detect FGF-CX and/or FCTRX protein (e.g., in a cellular lysate or cell supernatant) in order to evaluate the abundance and pattern of expression of the FGF-CX and/or FCTRX protein. Anti-FGF-CX and/or FCTRX antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

FGF-CX and/or FCTRX Recombinant Expression Vectors and Host Cells

Another aspect of the invention pertains to vectors, preferably expression vectors, containing a nucleic acid encoding an FGF-CX and/or FCTRX protein, or derivatives, fragments, analogs or homologs thereof. As used herein, the term "vector" refers to a nucleic acid molecule capable of transporting another nucleic acid to which it has been linked.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., FGF-CX and/or FCTRX proteins, mutant forms of FGF-CX and/or FCTRX proteins, fusion proteins, etc.).

The recombinant expression vectors of the invention can be designed for expression of FGF-CX and/or FCTRX proteins in prokaryotic or eukaryotic cells. For example, FGF-CX and/or FCTRX proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the FGF-CX and/or FCTRX expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, FGF-CX and/or FCTRX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to FGF-CX and/or FCTRX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, FGF-CX and/or FCTRX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding FGF-CX and/or FCTRX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) FGF-CX and/or FCTRX protein. Accordingly, the invention further provides methods for producing FGF-CX and/or FCTRX protein using the host cells of the invention. In one embodiment, the method comprises culturing the host cell of invention (into which a recombinant expression vector encoding FGF-CX and/or FCTRX protein has been introduced) in a suitable medium such that FGF-CX and/or FCTRX protein is produced. In another embodiment, the method further comprises isolating FGF-CX and/or FCTRX protein from the medium or the host cell.

Transgenic FGF-CX and/or FCTRX Animals

The host cells of the invention can also be used to produce non-human transgenic animals. For example, in one embodiment, a host cell of the invention is a fertilized oocyte or an embryonic stem cell into which FGF-CX and/or FCTRX protein-coding sequences have been introduced. Such host cells can then be used to create non-human transgenic animals in which exogenous FGF-CX and/or FCTRX sequences have been introduced into their genome or homologous recombinant animals in which endogenous FGF-CX and/or FCTRX sequences have been altered. Such animals are useful for studying the function and/or activity of FGF-CX and/or FCTRX protein and for identifying and/or evaluating modulators of FGF-CX and/or FCTRX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous FGF-CX and/or FCTRX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing FGF-CX and/or FCTRX-encoding nucleic acid into the male pronuclei of a fertilized oocyte (e.g., by microinjection, retroviral infection) and allowing the oocyte to develop in a pseudopregnant female foster animal. The human FGF-CX and/or FCTRX cDNA sequences of SEQ ID NOS:1, 3, 5, 7, 9, 11 and 13 can be introduced as a transgene into the genome of a non-human animal. Alternatively, a non-human homologue of the human FGF-CX and/or FCTRX gene, such as a mouse FGF-CX and/or FCTRX gene, can be isolated based on hybridization to the human FGF-CX and/or FCTRX cDNA (described further supra) and used as a transgene. Intronic sequences and polyadenylation signals can also be included in the transgene to increase the efficiency of expression of the transgene. A tissue-specific regulatory sequence(s) can be operably-linked to the FGF-CX and/or FCTRX transgene to direct expression of FGF-CX and/or FCTRX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the FGF-CX and/or FCTRX transgene in its genome and/or expression of FGF-CX and/or FCTRX mRNA in tissues or cells of the animals. A transgenic founder animal can then be used to breed additional animals carrying the transgene. Moreover, transgenic animals carrying a transgene-encoding FGF-CX and/or FCTRX protein can further be bred to other transgenic animals carrying other transgenes.

To create a homologous recombinant animal, a vector is prepared which contains at least a portion of an FGF-CX and/or FCTRX gene into which a deletion, addition or substitution has been introduced to thereby alter, e.g., functionally disrupt, the FGF-CX and/or FCTRX gene. The FGF-CX and/or FCTRX gene can be a human gene (e.g., the cDNA of SEQ ID NOS:1, 3, 5, 7, 9, 11 and 13), but more preferably, is a non-human homologue of a human FGF-CX and/or FCTRX gene. For example, a mouse homologue of human FGF-CX and/or FCTRX gene of SEQ ID NOS:1, 3, 5, 7, 9, 11 and 13 can be used to construct a homologous recombination vector suitable for altering an endogenous FGF-CX and/or FCTRX gene in the mouse genome. In one embodiment, the vector is designed such that, upon homologous recombination, the endogenous FGF-CX and/or FCTRX gene is functionally disrupted (i.e., no longer encodes a functional protein; also referred to as a "knock out" vector).

Alternatively, the vector can be designed such that, upon homologous recombination, the endogenous FGF-CX and/or FCTRX gene is mutated or otherwise altered but still encodes functional protein (e.g., the upstream regulatory region can be altered to thereby alter the expression of the endogenous FGF-CX and/or FCTRX protein). In the homologous recombination vector, the altered portion of the FGF-CX and/or FCTRX gene is flanked at its 5'- and 3'-termini by additional nucleic acid of the FGF-CX and/or FCTRX gene to allow for homologous recombination to occur between the exogenous FGF-CX and/or FCTRX gene carried by the vector and an endogenous FGF-CX and/or FCTRX gene in an embryonic stem cell. The additional flanking FGF-CX and/or FCTRX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced FGF-CX and/or FCTRX gene has homologously-recombined with the endogenous FGF-CX and/or FCTRX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The FGF-CX and/or FCTRX nucleic acid molecules, FGF-CX and/or FCTRX proteins, and anti-FGF-CX and/or FCTRX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an FGF-CX and/or FCTRX protein or anti-FGF-CX and/or FCTRX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express FGF-CX and/or FCTRX protein (e.g., via a recombinant expression vector in a host cell in gene therapy applications), to detect FGF-CX and/or FCTRX mRNA (e.g., in a biological sample) or a genetic lesion in an FGF-CX and/or FCTRX gene, and to modulate FGF-CX and/or FCTRX activity, as described further, below. In addition, the FGF-CX and/or FCTRX proteins can be used to screen drugs or compounds that modulate the FGF-CX and/or FCTRX protein activity or expression as well as to treat disorders characterized by insufficient or excessive production of FGF-CX and/or FCTRX protein or production of FGF-CX and/or FCTRX protein forms that have decreased or aberrant activity compared to FGF-CX and/or FCTRX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease(possesses anti-microbial activity) and the various dyslipidemias. In addition, the anti-FGF-CX and/or FCTRX antibodies of the invention can be used to detect and isolate FGF-CX and/or FCTRX proteins and modulate FGF-CX and/or FCTRX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to FGF-CX and/or FCTRX proteins or have a stimulatory or inhibitory effect on, e.g., FGF-CX and/or FCTRX protein expression or FGF-CX and/or FCTRX protein activity. The invention also includes compounds identified in the screening assays described herein.

In one embodiment, the invention provides assays for screening candidate or test compounds which bind to or modulate the activity of the membrane-bound form of an FGF-CX and/or FCTRX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol Biol.* 222: 301–310; Ladner, U.S. Pat. No. 5,233,409.).

In one embodiment, an assay is a cell-based assay in which a cell which expresses a membrane-bound form of FGF-CX and/or FCTRX protein, or a biologically-active portion thereof, on the cell surface is contacted with a test compound and the ability of the test compound to bind to an FGF-CX and/or FCTRX protein determined. The cell, for example, can of mammalian origin or a yeast cell. Determining the ability of the test compound to bind to the FGF-CX and/or FCTRX protein can be accomplished, for example, by coupling the test compound with a radioisotope or enzymatic label such that binding of the test compound to the FGF-CX and/or FCTRX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of FGF-CX and/or FCTRX protein, or a biologically-active portion thereof, on the cell surface with a known compound which binds FGF-CX and/or FCTRX to form an assay mixture, contacting the assay mixture with a test compound, and determining the ability of the test compound to interact with an FGF-CX and/or FCTRX protein, wherein determining the ability of the test compound to interact with an FGF-CX and/or FCTRX protein comprises determining the ability of the test compound to preferentially bind to FGF-CX and/or FCTRX protein or a biologically-active portion thereof as compared to the known compound.

In another embodiment, an assay is a cell-based assay comprising contacting a cell expressing a membrane-bound form of FGF-CX and/or FCTRX protein, or a biologically-active portion thereof, on the cell surface with a test compound and determining the ability of the test compound to modulate (e.g., stimulate or inhibit) the activity of the FGF-CX and/or FCTRX protein or biologically-active portion thereof. Determining the ability of the test compound to modulate the activity of FGF-CX and/or FCTRX or a biologically-active portion thereof can be accomplished, for example, by determining the ability of the FGF-CX and/or FCTRX protein to bind to or interact with an FGF-CX and/or FCTRX target molecule. As used herein, a "target molecule" is a molecule with which an FGF-CX and/or FCTRX protein binds or interacts in nature, for example, a molecule on the surface of a cell which expresses an FGF-CX and/or FCTRX interacting protein, a molecule on the surface of a second cell, a molecule in the extracellular milieu, a molecule associated with the internal surface of a cell membrane or a cytoplasmic molecule. An FGF-CX and/or FCTRX target molecule can be a non-FGF-CX and/or FCTRX molecule or an FGF-CX and/or FCTRX protein or polypeptide of the invention. In one embodiment, an FGF-CX and/or FCTRX target molecule is a component of a signal transduction pathway that facilitates transduction of an extracellular signal (e.g. a signal generated by binding of a compound to a membrane-bound FGF-CX and/or FCTRX molecule) through the cell membrane and into the cell. The target, for example, can be a second intercellular protein that has catalytic activity or a protein that facilitates the association of downstream signaling molecules with FGF-CX and/or FCTRX.

Determining the ability of the FGF-CX and/or FCTRX protein to bind to or interact with an FGF-CX and/or FCTRX target molecule can be accomplished by one of the methods described above for determining direct binding. In one embodiment, determining the ability of the FGF-CX and/or FCTRX protein to bind to or interact with an FGF-CX and/or FCTRX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an FGF-CX and/or FCTRX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an FGF-CX and/or FCTRX protein or biologically-active portion thereof with a test compound and determining the ability of the test compound to bind to the FGF-CX and/or FCTRX protein or biologically-active portion thereof. Binding of the test compound to the FGF-CX and/or FCTRX protein can be determined either directly or indirectly as described above. In one such embodiment, the assay comprises contacting the FGF-CX and/or FCTRX protein or biologically-active portion thereof with a known compound which binds FGF-CX and/or FCTRX to form an assay mixture, contacting the assay mixture with a test compound, and determining the ability of the test compound to interact with an FGF-CX and/or FCTRX protein, wherein determining the ability of the test compound to interact with an FGF-CX and/or FCTRX protein comprises determining the ability of the test compound to preferentially bind to FGF-CX and/or FCTRX or biologically-active portion thereof as compared to the known compound.

In still another embodiment, an assay is a cell-free assay comprising contacting FGF-CX and/or FCTRX protein or biologically-active portion thereof with a test compound and determining the ability of the test compound to modulate (e.g. stimulate or inhibit) the activity of the FGF-CX and/or FCTRX protein or biologically-active portion thereof. Determining the ability of the test compound to modulate the activity of FGF-CX and/or FCTRX can be accomplished, for example, by determining the ability of the FGF-CX and/or FCTRX protein to bind to an FGF-CX and/or FCTRX target molecule by one of the methods described above for determining direct binding. In an alternative embodiment, determining the ability of the test compound to modulate the activity of FGF-CX and/or FCTRX protein can be accomplished by determining the ability of the FGF-CX and/or FCTRX protein further modulate an FGF-CX and/or FCTRX target molecule. For example, the catalytic/enzymatic activity of the target molecule on an appropriate substrate can be determined as described, supra.

In yet another embodiment, the cell-free assay comprises contacting the FGF-CX and/or FCTRX protein or biologically-active portion thereof with a known compound which binds FGF-CX and/or FCTRX protein to form an assay mixture, contacting the assay mixture with a test compound, and determining the ability of the test compound to interact with an FGF-CX and/or FCTRX protein, wherein determining the ability of the test compound to interact with an FGF-CX and/or FCTRX protein comprises determining the ability of the FGF-CX and/or FCTRX protein to preferentially bind to or modulate the activity of an FGF-CX and/or FCTRX target molecule.

The cell-free assays of the invention are amenable to use of both the soluble form or the membrane-bound form of FGF-CX and/or FCTRX protein. In the case of cell-free assays comprising the membrane-bound form of FGF-CX and/or FCTRX protein, it may be desirable to utilize a solubilizing agent such that the membrane-bound form of FGF-CX and/or FCTRX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl) dimethylamminiol-2-hydroxy-1-propane sulfonate (CHAPSO).

In more than one embodiment of the above assay methods of the invention, it may be desirable to immobilize either FGF-CX and/or FCTRX protein or its target molecule to facilitate separation of complexed from uncomplexed forms of one or both of the proteins, as well as to accommodate automation of the assay. Binding of a test compound to FGF-CX and/or FCTRX protein, or interaction of FGF-CX and/or FCTRX protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-FGF-CX and/or FCTRX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or FGF-CX and/or FCTRX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of FGF-CX and/or FCTRX protein binding or activity determined using standard techniques.

Other techniques for immobilizing proteins on matrices can also be used in the screening assays of the invention. For example, either the FGF-CX and/or FCTRX protein or its target molecule can be immobilized utilizing conjugation of biotin and streptavidin. Biotinylated FGF-CX and/or FCTRX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with FGF-CX and/or FCTRX protein or target molecules, but which do not interfere with binding of the FGF-CX and/or FCTRX protein to its target molecule, can be derivatized to the wells of the plate, and unbound target or FGF-CX and/or FCTRX protein trapped in the wells by antibody conjugation. Methods for detecting such complexes, in addition to those described above for the GST-immobilized complexes, include immunodetection of complexes using antibodies reactive with the FGF-CX and/or FCTRX protein or target molecule, as well as enzyme-linked assays that rely on detecting an enzymatic activity associated with the FGF-CX and/or FCTRX protein or target molecule.

In another embodiment, modulators of FGF-CX and/or FCTRX protein expression are identified in a method wherein a cell is contacted with a candidate compound and the expression of FGF-CX and/or FCTRX mRNA or protein in the cell is determined. The level of expression of FGF-CX and/or FCTRX mRNA or protein in the presence of the candidate compound is compared to the level of expression of FGF-CX and/or FCTRX mRNA or protein in the absence of the candidate compound. The candidate compound can then be identified as a modulator of FGF-CX and/or FCTRX mRNA or protein expression based upon this comparison.

For example, when expression of FGF-CX and/or FCTRX mRNA or protein is greater (i.e., statistically significantly greater) in the presence of the candidate compound than in its absence, the candidate compound is identified as a stimulator of FGF-CX and/or FCTRX mRNA or protein expression. Alternatively, when expression of FGF-CX and/or FCTRX mRNA or protein is less (statistically significantly less) in the presence of the candidate compound than in its absence, the candidate compound is identified as an inhibitor of FGF-CX and/or FCTRX mRNA or protein expression. The level of FGF-CX and/or FCTRX mRNA or protein expression in the cells can be determined by methods described herein for detecting FGF-CX and/or FCTRX mRNA or protein.

In yet another aspect of the invention, the FGF-CX and/or FCTRX proteins can be used as "bait proteins" in a two-hybrid assay or three hybrid assay (see, e.g., U.S. Pat. No. 5,283,317; Zervos, et al., 1993. Cell 72: 223–232; Madura, et al., 1993. J. Biol. Chem. 268: 12046–12054; Bartel, et al., 1993. Biotechniques 14: 920–924; Iwabuchi, et al., 1993. Oncogene 8: 1693–1696; and Brent WO 94/10300), to identify other proteins that bind to or interact with FGF-CX and/or FCTRX ("FGF-CX and/or FCTRX-binding proteins" or "FGF-CX and/or FCTRX-bp") and modulate FGF-CX and/or FCTRX activity. Such FGF-CX and/or FCTRX-binding proteins are also likely to be involved in the propagation of signals by the FGF-CX and/or FCTRX proteins as, for example, upstream or downstream elements of the FGF-CX and/or FCTRX pathway.

The two-hybrid system is based on the modular nature of most transcription factors, which consist of separable DNA-binding and activation domains. Briefly, the assay utilizes two different DNA constructs. In one construct, the gene that codes for FGF-CX and/or FCTRX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an FGF-CX and/or FCTRX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with FGF-CX and/or FCTRX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the FGF-CX and/or FCTRX sequences, SEQ ID NOS:1, 3, 5, 7, 9, 11 and 13, or fragments or derivatives thereof, can be used to map the location of the FGF-CX and/or FCTRX genes, respectively, on a chromosome. The mapping of the FGF-CX and/or FCTRX sequences to chromosomes is an important first step in correlating these sequences with genes associated with disease.

Briefly, FGF-CX and/or FCTRX genes can be mapped to chromosomes by preparing PCR primers (preferably 15–25 bp in length) from the FGF-CX and/or FCTRX sequences. Computer analysis of the FGF-CX and/or FCTRX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the FGF-CX and/or FCTRX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. Science 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the FGF-CX and/or FCTRX sequences to design oligonucleotide primers, sublocalization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature,* 325: 783–787.

Moreover, differences in the DNA sequences between individuals affected and unaffected with a disease associated with the FGF-CX and/or FCTRX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The FGF-CX and/or FCTRX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the FGF-CX and/or FCTRX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The FGF-CX and/or FCTRX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NOS:1, 3, 5, 7, 9, 11 and 13 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining FGF-CX and/or FCTRX protein and/or nucleic acid expression as well as FGF-CX and/or FCTRX activity, in the context of a biological sample (e.g., blood, serum, cells, tissue) to thereby determine whether an individual is afflicted with a disease or disorder, or is at risk of developing a disorder, associated with aberrant FGF-CX expression or activity, aberrant FCTRX expression or activity, or both. The disorders include pathology such as inflammatory conditions in the gastrointestinal tract, including but not limited to inflammatory bowel disease such as ulcerative colitis and Crohn's disease, growth and proliferative diseases such as cancer, angiogenesis, atherosclerotic plaques, collagen formation, cartilage and bone formation, cardiovascular and fibrotic diseases and diabetic ulcers. In addition, FCTRX nucleic acids and their encoded polypeptides will be therapeutically useful for the prevention of aneurysms and the acceleration of wound closure through gene therapy. Furthermore, FCTRX nucleic acids and their encoded polypeptides can be utilized to stimulate cellular growth, wound healing, neovascularization and tissue growth, and similar tissue regeneration needs. More specifically, a FCTRX nucleic acid or polypeptide may be useful in treatment of anemia and leukopenia, intestinal tract sensitivity and baldness. Treatment of such conditions may be indicated, e.g., in patients having undergone radiation or chemotherapy, wherein treatment would minimize any hyperproliferative side effects.

The invention also provides for prognostic (or predictive) assays for determining whether an individual is at risk of developing a disorder associated with FGF-CX and/or FCTRX protein, nucleic acid expression or activity. For example, mutations in an FGF-CX and/or FCTRX gene can be assayed in a biological sample. Such assays can be used for prognostic or predictive purpose to thereby prophylactically treat an individual prior to the onset of a disorder characterized by or associated with FGF-CX and/or FCTRX protein, nucleic acid expression, or biological activity.

Another aspect of the invention provides methods for determining FGF-CX and/or FCTRX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of FGF-CX and/or FCTRX in clinical trials.

These and other agents are described in further detail in the following sections.

Diagnostic Assays

An exemplary method for detecting the presence or absence of FGF-CX and/or FCTRX in a biological sample involves obtaining a biological sample from a test subject and contacting the biological sample with a compound or an agent capable of detecting FGF-CX and/or FCTRX protein or nucleic acid (e.g., mRNA, genomic DNA) that encodes FGF-CX and/or FCTRX protein such that the presence of FGF-CX and/or FCTRX is detected in the biological sample. An agent for detecting FGF-CX and/or FCTRX mRNA or genomic DNA is a labeled nucleic acid probe capable of hybridizing to FGF-CX and/or FCTRX mRNA or genomic DNA. The nucleic acid probe can be, for example, a full-length FGF-CX and/or FCTRX nucleic acid, such as the nucleic acid of SEQ ID NOS:1, 3, 5, 7, 9, 11 and 13, or a portion thereof, such as an oligonucleotide of at least 15, 30, 50, 100, 250 or 500 nucleotides in length and sufficient to specifically hybridize under stringent conditions to FGF-CX and/or FCTRX mRNA or genomic DNA. Other suitable probes for use in the diagnostic assays of the invention are described herein.

An agent for detecting FGF-CX and/or FCTRX protein is an antibody capable of binding to FGF-CX and/or FCTRX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect FGF-CX and/or FCTRX mRNA, protein, or genomic DNA in a biological sample in vitro as well as in vivo. For example, in vitro techniques for detection of FGF-CX and/or FCTRX mRNA include Northern hybridizations and in situ hybridizations. In vitro techniques for detection of FGF-CX and/or FCTRX protein include enzyme linked immunosorbent assays (ELISAs), Western blots, immunoprecipitations, and immunofluorescence. In vitro techniques for detection of FGF-CX and/or FCTRX genomic DNA include Southern hybridizations. Furthermore, in vivo techniques for detection of FGF-CX and/or FCTRX protein include introducing into a subject a labeled anti-FGF-CX and/or FCTRX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting FGF-CX and/or FCTRX protein, mRNA, or genomic DNA, such that the presence of FGF-CX and/or FCTRX protein, mRNA or genomic DNA is detected in the biological sample, and comparing the presence of FGF-CX and/or FCTRX protein, mRNA or genomic DNA in the control sample with the presence of FGF-CX and/or FCTRX protein, mRNA or genomic DNA in the test sample.

The invention also encompasses kits for detecting the presence of FGF-CX and/or FCTRX in a biological sample. For example, the kit can comprise: a labeled compound or agent capable of detecting FGF-CX and/or FCTRX protein or mRNA in a biological sample; means for determining the amount of FGF-CX and/or FCTRX in the sample; and means for comparing the amount of FGF-CX and/or FCTRX in the sample with a standard. The compound or agent can be packaged in a suitable container. The kit can further comprise instructions for using the kit to detect FGF-CX and/or FCTRX protein or nucleic acid.

Prognostic Assays

The diagnostic methods described herein can furthermore be utilized to identify subjects having or at risk of developing a disease or disorder associated with aberrant FGF-CX and/or FCTRX expression or activity. For example, the assays described herein, such as the preceding diagnostic assays or the following assays, can be utilized to identify a subject having or at risk of developing a disorder associated with FGF-CX and/or FCTRX protein, nucleic acid expression or activity. Alternatively, the prognostic assays can be utilized to identify a subject having or at risk for developing a disease or disorder. Thus, the invention provides a method for identifying a disease or disorder associated with aberrant FGF-CX and/or FCTRX expression or activity in which a test sample is obtained from a subject and FGF-CX and/or FCTRX protein or nucleic acid (e.g., mRNA, genomic DNA) is detected, wherein the presence of FGF-CX and/or FCTRX protein or nucleic acid is diagnostic for a subject having or at risk of developing a disease or disorder associated with aberrant FGF-CX and/or FCTRX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant FGF-CX and/or FCTRX expression or activity. For example, such methods can be used to determine whether a subject can be effectively treated with an agent for a disorder. Thus, the invention provides methods for determining whether a subject can be effectively treated with an agent for a disorder associated with aberrant FGF-CX and/or FCTRX expression or activity in which a test sample is obtained and FGF-CX and/or FCTRX protein or nucleic acid is detected (e.g., wherein the presence of FGF-CX and/or FCTRX protein or nucleic acid is diagnostic for a subject that can be administered the agent to treat a disorder associated with aberrant FGF-CX and/or FCTRX expression or activity).

The methods of the invention can also be used to detect genetic lesions in an FGF-CX and/or FCTRX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an FGF-CX and/or FCTRX-protein, or the misexpression of the FGF-CX and/or FCTRX gene. For example, such genetic lesions can be detected by ascertaining the existence of at least one of: (i) a deletion of one or more nucleotides from an FGF-CX and/or FCTRX gene; (ii) an addition of one or more nucleotides to an FGF-CX and/or FCTRX gene; (iii) a substitution of one or more nucleotides of an FGF-CX and/or FCTRX gene, (iv) a chromosomal rearrangement of an FGF-CX and/or FCTRX gene; (v) an alteration in the level of a messenger RNA transcript of an FGF-CX and/or FCTRX gene, (vi) aberrant modification of an FGF-CX and/or FCTRX gene, such as of the methylation pattern of the genomic DNA, (vii) the presence of a non-wild-type splicing pattern of a messenger RNA transcript of an FGF-CX and/or FCTRX gene, (viii) a non-wild-type level of an FGF-CX and/or FCTRX protein, (ix) allelic loss of an FGF-CX and/or FCTRX gene, and (x) inappropriate post-translational modification of an FGF-CX and/or FCTRX protein. As described herein, there are a large number of assay techniques known in the art which can be used for detecting lesions in an FGF-CX and/or FCTRX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. Science 241: 1077–1080; and Nakazawa, et al., 1994. Proc. Natl. Acad. Sci. USA 91: 360–364), the latter of which can be particularly useful for detecting point mutations in the FGF-CX and/or FCTRX-gene (see, Abravaya, et al., 1995. Nucl. Acids Res. 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an FGF-CX and/or FCTRX gene under conditions such that hybridization and amplification of the FGF-CX and/or FCTRX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. Proc. Natl. Acad. Sci. USA 87: 1874–1878), transcriptional amplification system (see, Kwoh, et al., 1989. Proc. Natl. Acad. Sci. USA 86: 1173–1177); Qβ Replicase (see, Lizardi, et al, 1988. BioTechnology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an FGF-CX and/or FCTRX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in FGF-CX and/or FCTRX can be identified by hybridizing a sample and control nucleic acids, e.g., DNA or RNA, to high-density arrays containing hundreds or thousands of oligonucleotides probes. See, e.g., Cronin, et al., 1996. Human Mutation 7: 244–255; Kozal, et al., 1996. Nat. Med. 2: 753–759. For example, genetic mutations in FGF-CX and/or FCTRX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the FGF-CX and/or FCTRX gene and detect mutations by comparing the sequence of the sample FGF-CX and/or FCTRX with the corresponding wild-type (control) sequence. Examples of sequencing reactions include those based on techniques developed by Maxim and Gilbert, 1977. Proc. Natl. Acad. Sci. USA 74: 560 or Sanger, 1977. Proc. Natl. Acad. Sci. USA 74: 5463. It is also contemplated that any of a variety of automated sequencing procedures can be utilized when performing the diagnostic assays (see, e.g., Naeve, et al., 1995. Biotechniques 19: 448), including sequencing by mass spectrometry (see, e.g., PCT International Publication No. WO 94/16101; Cohen, et al., 1996. Adv. Chromatography 36: 127–162; and Griffin, et al., 1993. Appl. Biochem. Biotechnol. 38: 147–159).

Other methods for detecting mutations in the FGF-CX and/or FCTRX gene include methods in which protection from cleavage agents is used to detect mismatched bases in RNA/RNA or RNA/DNA heteroduplexes. See, e.g., Myers, et al., 1985. Science 230: 1242. In general, the art technique of "mismatch cleavage" starts by providing heteroduplexes of formed by hybridizing (labeled) RNA or DNA containing the wild-type FGF-CX and/or FCTRX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. Proc. Natl. Acad. Sci. USA 85: 4397; Saleeba, et al., 1992. Methods Enzymol. 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in FGF-CX and/or FCTRX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on an FGF-CX and/or FCTRX sequence, e.g., a wild-type FGF-CX and/or FCTRX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in FGF-CX and/or FCTRX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control FGF-CX and/or FCTRX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al, 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an FGF-CX and/or FCTRX gene.

Furthermore, any cell type or tissue, preferably peripheral blood leukocytes, in which FGF-CX and/or FCTRX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on FGF-CX and/or FCTRX activity (e.g., FGF-CX and/or FCTRX gene expression), as identified by a screening assay described herein can be administered to individuals to treat (prophylactically or therapeutically) disorders. The disorders include pathology such as inflammatory conditions in the gastrointestinal tract, including but not limited to inflammatory bowel disease such as ulcerative colitis and Crohn's disease, growth and proliferative diseases such as cancer, angiogenesis, atherosclerotic plaques, collagen formation, cartilage and bone formation, cardiovascular and fibrotic diseases and diabetic ulcers. In addition, FCTRX nucleic acids and their encoded polypeptides will be therapeutically useful for the prevention of aneurysms and the acceleration of wound closure through gene therapy. Furthermore, FCTRX nucleic acids and their encoded polypeptides can be utilized to stimulate cellular growth. wound healing, neovascularization and tissue growth, and similar tissue regeneration needs. More specifically, a FCTRX nucleic acid or polypeptide may be useful in treatment of anemia and leukopenia, intestinal tract sensitivity and baldness. Treatment of such conditions may be indicated, e.g., in patients having undergone radiation or chemotherapy, wherein treatment would minimize any hyperproliferative side effects.

In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of FGF-CX and/or FCTRX protein, expression of FGF-CX and/or FCTRX nucleic acid, or mutation content of FGF-CX and/or FCTRX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of FGF-CX and/or FCTRX protein, expression of FGF-CX and/or FCTRX nucleic acid, or mutation content of FGF-CX and/or FCTRX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an FGF-CX and/or FCTRX modulator, such as a modulator identified by one of the exemplary screening assays described herein.

Monitoring of Effects During Clinical Trials

Monitoring the influence of agents (e.g., drugs, compounds) on the expression or activity of FGF-CX and/or FCTRX (e.g., the ability to modulate aberrant cell proliferation and/or differentiation) can be applied not only in basic drug screening, but also in clinical trials. For example, the effectiveness of an agent determined by a screening assay as described herein to increase FGF-CX and/or FCTRX gene expression, protein levels, or upregulate FGF-CX and/or FCTRX activity, can be monitored in clinical trails of subjects exhibiting decreased FGF-CX and/or FCTRX gene expression, protein levels, or downregulated FGF-CX and/or FCTRX activity. Alternatively, the effectiveness of an agent determined by a screening assay to decrease FGF-CX and/or FCTRX gene expression, protein levels, or downregulate FGF-CX and/or FCTRX activity, can be monitored in clinical trails of subjects exhibiting increased FGF-CX and/or FCTRX gene expression, protein levels, or upregulated FGF-CX and/or FCTRX activity. In such clinical trials, the expression or activity of FGF-CX and/or FCTRX and, preferably, other genes that have been implicated in, for example, a cellular proliferation or immune disorder can be used as a "read out" or markers of the immune responsiveness of a particular cell.

By way of example, and not of limitation, genes, including FGF-CX and/or FCTRX, that are modulated in cells by treatment with an agent (e.g., compound, drug or small molecule) that modulates FGF-CX and/or FCTRX activity (e.g., identified in a screening assay as described herein) can be identified. Thus, to study the effect of agents on cellular proliferation disorders, for example, in a clinical trial, cells can be isolated and RNA prepared and analyzed for the levels of expression of FGF-CX and/or FCTRX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of FGF-CX and/or FCTRX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an FGF-CX and/or FCTRX protein, mRNA, or genomic DNA in the preadministration sample; (iii) obtaining one or more post-administration samples from the subject; (iv) detecting the level of expression or activity of the FGF-CX and/or FCTRX protein, mRNA, or genomic DNA in the post-administration samples; (v) comparing the level of expression or activity of the FGF-CX and/or FCTRX protein, mRNA, or genomic DNA in the pre-administration sample with the FGF-CX and/or FCTRX protein, mRNA, or genomic DNA in the post administration sample or samples; and (vi) altering the administration of the agent to the subject accordingly. For example, increased administration of the agent may be desirable to increase the expression or activity of FGF-CX and/or FCTRX to higher levels than detected, i.e., to increase the effectiveness of the agent. Alternatively, decreased administration of the agent may be desirable to decrease expression or activity of FGF-CX and/or FCTRX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant FGF-CX and/or FCTRX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Ostoeodystrophy, and other diseases, disorders and conditions of the like.

These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endoggenous function of an aforementioned peptide by homologous recombination (see, e.g., Capecchi, 1989. *Science* 244:1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant FGF-CX and/or FCTRX expression or activity, by administering to the subject an agent that modulates FGF-CX and/or FCTRX expression or at least one FGF-CX and/or FCTRX activity. Subjects at risk for a disease that is caused or contributed to by aberrant FGF-CX and/or FCTRX expression or activity can be identified by, for example, any or a combination of diagnostic or prognostic assays as described herein. Administration of a prophylactic agent can occur prior to the manifestation of symptoms characteristic of the FGF-CX and/or FCTRX aberrancy, such that a disease or disorder is prevented or, alternatively, delayed in its progression. Depending upon the type of FGF-CX and/or FCTRX aberrancy, for example, an FGF-CX and/or FCTRX agonist or FGF-CX and/or FCTRX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating FGF-CX and/or FCTRX expression or activity for therapeutic purposes. The modulatory method of the invention involves contacting a cell with an agent that modulates one or more of the activities of FGF-CX and/or FCTRX protein activity associated with the cell. An agent that modulates FGF-CX and/or FCTRX protein activity can be an agent as described herein, such as a nucleic acid or a protein, a naturally-occurring cognate ligand of an FGF-CX and/or FCTRX protein, a peptide, an FGF-CX and/or FCTRX peptidomimetic, or other small molecule. In one embodiment, the agent stimulates one or more FGF-CX and/or FCTRX protein activity. Examples of such stimulatory agents include active FGF-CX and/or FCTRX protein and a nucleic acid molecule encoding FGF-CX and/or FCTRX that has been introduced into the cell. In another embodiment, the agent inhibits one or more FGF-CX and/or FCTRX protein activity. Examples of such inhibitory agents include antisense FGF-CX and/or FCTRX nucleic acid molecules and anti-FGF-CX and/or FCTRX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an FGF-CX and/or FCTRX protein or nucleic acid molecule. In one embodiment, the method involves administering an agent (e.g., an agent identified by a screening assay described herein), or combination of agents that modulates (e.g., up-regulates or down-regulates) FGF-CX and/or FCTRX expression or activity. In another embodiment, the method involves administering an FGF-CX and/or FCTRX protein or nucleic acid molecule as therapy to compensate for reduced or aberrant FGF-CX and/or FCTRX expression or activity.

Stimulation of FGF-CX and/or FCTRX activity is desirable in situations in which FGF-CX and/or FCTRX is abnormally downregulated and/or in which increased FGF-CX and/or FCTRX activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The FGF-CX and/or FCTRX nucleic acids and proteins of the invention are useful in potential prophylactic and therapeutic applications implicated in a variety of disorders including, but not limited to: inflammatory bowel disease and disorders associated with FGF-CX, with FCTRX, or with both FGF-CX and/or FCTRX.

As an example, a cDNA encoding the FGF-CX and/or FCTRX protein of the invention may be useful in gene therapy, and the protein may be useful when administered to a subject in need thereof. By way of non-limiting example, the compositions of the invention will have efficacy for treatment of patients suffering from: inflammatory conditions in the gastrointestinal tract, including but not limited to inflammatory bowel disease such as ulcerative colitis and Crohn's disease, growth and proliferative diseases such as cancer, angiogenesis, atherosclerotic plaques, collagen formation, cartilage and bone formation, cardiovascular and fibrotic diseases and diabetic ulcers. In addition, FCTRX nucleic acids and their encoded polypeptides will be therapeutically useful for the prevention of aneurysms and the acceleration of wound closure through gene therapy. Furthermore, FCTRX nucleic acids and their encoded polypeptides can be utilized to stimulate cellular growth, wound healing, neovascularization and tissue growth, and similar tissue regeneration needs. More specifically, a FCTRX nucleic acid or polypeptide may be useful in treatment of anemia and leukopenia, intestinal tract sensitivity and baldness. Treatment of such conditions may be indicated, e.g., in patients having undergone radiation or chemotherapy, wherein treatment would minimize any hyperproliferative side effects.

Both the novel nucleic acid encoding the FGF-CX and/or FCTRX protein, and the FGF-CX and/or FCTRX protein of the invention, or nucleic acid or protein fragments, analogs, homologs or derivative thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies which immunospecifically-bind to the novel substances of the invention for use in therapeutic or diagnostic methods.

EXAMPLES

It is shown in several Examples below that both FGF-CX and FCTRX induce the growth and proliferation of various mammalian cells in culture. It is further demonstrated in animal models of inflammatory bowel disease that these proteins have beneficial effects in treating, ameliorating and delaying the onset of inflammatory bowel disease. By "treating" is meant the administration of a protein used in the present invention to a subject suffering from a pathology such as inflammatory bowel disease with the objective of providing a beneficial therapeutic effect. By "ameliorating" a pathology such as inflammatory bowel disease, it is meant that a) in a subject in which the pathology is becoming more severe, one or more symptoms of the pathology cease becoming more severe and stabilize or improve; or b) in a subject in which the pathology is considered to be at a stable state, one or more symptoms of the pathology improve or become less severe. By "delaying the onset" of a pathology such as inflammatory bowel disease, it is meant that administering a prophylactic dose or dosing regimen of a therapeutic agent such as the FGF-CX and FCTRX proteins employed in the present invention results in the delay of appearance, or the delay of worsening, of one or more symptoms of a pathology such as inflammatory bowel disease. Such a delay may be for an indeterminate period, in which the symptoms essentially never appear or never worsen, or it may be for A more limited period, in which the symptoms appear or worsen at a later time than would be expected, based on the experience of patients not treated by the compositions envisioned in the present methods, in the absence of administering the therapeutic agent.

The results of experiments reported below in three Examples indicate that, in mice in which inflammatory bowel disease is induced by oral administration of DSS for 7 days, simultaneous treatment with the growth factors employed here during the course of exposure to DSS lead to significant therapeutic benefits compared to untreated DSS controls.

An additional Example reports results on rats treated with indomethacin which results in gross and histopathologic intestinal alterations that are similar to those occurring in Crohn's Disease. Administration of CG53135 (0.2 mg/kg iv) to indomethacin-treated rats results in significant reductions in weight loss, small intestine weight, absolute neutrophil counts, and jejunal necrosis and inflammation scores.

Example 1

Identification of the FGF-CX Gene

The FGF-CX gene was identified following a TBLASTN (Altschul, S. F., Gish, W., Miller, W., Myers, E. W. & Lipman, D. J. (1990) *J. Mol. Biol.* 215, 403–410) search of Genbank human genomic DNA sequences with Xenopus FGF-CX (Koga, C., Adati, N., Nakata, K., Mikoshiba, K., Furuhata, Y., Sata, S., Tei, H., Sakati, Y., Kurokawa, T., Shiokawa, K. & Yokoyama, K. K. (1999) *Biochem. Biophys. Res. Comm.* 261, 756–765; Accession No. AB012615) as query. This search identified a locus (Accession No. AB020858) of high homology on chromosome 8. Intron/exon boundaries were deduced using standard consensus splicing parameters (Mount, S. M. (1996) *Science* 271, 1690–1692), together with homologies derived from known FGFs. The FGF-CX initiation codon localizes to bp 16214 of the sequence of AB020858, and the remaining 3' portion of this exon continues to bp 15930. The 5' UTR of FGF-CX was extended upstream of the initiation codon by an additional 606 bp using public ESTs (Accession Nos. AA232729, AA236522, AI272876 and AI272878). The remaining structure of the FGF-CX gene as it relates to locus AB020858 is as follows: intron 1 (bp 15929–9942); exon 2 (bp 9941–9838); intron 2 (bp 9837–7500); exon 3 (begins at bp 7499).

The gene discovered by the procedure in the preceding paragraph includes 3 exons and 2 introns. The DNA sequence predicts an ORF of 211 amino acid residues (see Table 1), with an in-frame stop codon 117 bp upstream of the initiator methionine. The DNA segment from which the gene was mined maps to chromosome 8p21.3–p22, a location that was confirmed by radiation hybrid analysis.

Example 2

Molecular Cloning of the Sequence Encoding a FGF-CX Protein

Oligonucleotide primers were designed for the amplification by PCR of a DNA segment, representing an open reading frame, coding for the full length FGF-CX. The forward primer includes a BglII restriction site (AGATCT) and a consensus Kozak sequence (CCACC). The reverse primer contains an in-frame XhoI restriction site for further subcloning purposes. Both the forward and the reverse primers contain a 5' clamp sequence (CTCGTC). The sequences of the primers are the following:

```
FGF-CX-Forward:
5'-CTCGTC AGATCT CCACC ATG GCT CCC    (SEQ ID NO:15)
TTA GCC GAA GTC-3'

FGF-CX-Reverse:
5'-CTCGTC CTCGAG AGT GTA CAT CAG TAG (SEQ ID NO:16)
GTC CTT G-3'
```

PCR reactions were performed using a total of 5ng human prostate cDNA template, 1 µM of each of the FGF-CX-Forward and FGF-CX-Reverse primers, 5 micromoles dNTP (Clontech Laboratories, Palo Alto Calif.) and 1 microliter of 50xAdvantage-HF 2 polymerase (Clontech Laboratories) in 50 microliter volume. The following PCR reaction conditions were used:

| a) | 96° C. | 3 minutes |
|---|---|---|
| b) | 96° C. | 30 seconds denaturation |
| c) | 70° C. | 30 seconds, primer annealing. This temperature was gradually decreased by 1° C./cycle. |
| d) | 72° C. | 1 minute extension. Repeat steps (b)–(d) ten times |
| e) | 96° C. | 30 seconds denaturation |
| f) | 60° C. | 30 seconds annealing |
| g) | 72° C. | 1 minute extension Repeat steps (e)–(g) 25 times |
| h) | 72° C. | 5 minutes final extension |

A single PCR product, with the expected size of approximately 640 bp, was isolated after electrophoresis on agarose gel and ligated into a pCR2.1 vector (Invitrogen, Carlsbad, Calif.). The cloned insert was sequenced using vector specific M13 Forward(–40) and M13 Reverse primers, which verified that the nucleotide sequence was 100% identical to the sequence in Table 1 (SEQ ID NO:1) inserted directly between the upstream BglII cloning site and the downstream XhoI cloning site. The cloned sequence constitutes an open reading frame coding for the predicted FGF-CX full length protein. The clone is called TA-AB02085-S274-F19.

Example 3

Preparation of Mammalian Expression Vector pCEP4/Sec

The oligonucleotide primers pSec-V5-His Forward CTCGT CCTCG AGGGT AAGCC TATCC CTAAC (SEQ ID NO:17) and pSec-V5-His Reverse CTCGT CGGGC CCCTG ATCAG CGGGT TTAAA C (SEQ ID NO:18), were designed to amplify a fragment from the pcDNA3.1-V5His (Invitrogen, Carlsbad, Calif.) expression vector that includes V5 and His6. The PCR product was digested with XhoI and ApaI and ligated into the XhoI/ApaI digested pSecTag2 B vector harboring an Ig kappa leader sequence (Invitrogen, Carlsbad Calif.). The correct structure of the resulting vector, pSecV5His, including an in-frame Ig-kappa leader and V5-His6 was verified by DNA sequence analysis. The vector pSecV5His was digested with PmeI and NheI to provide a fragment retaining the above elements in the correct frame. The PmeI-NheI fragment was ligated into the BamHI/Klenow and NheI treated vector pCEP4 (Invitrogen, Carlsbad, Calif.). The resulting vector was named pCEP4/Sec and includes an in-frame Ig kappa leader, a site for insertion of a clone of interest, and the V5 epitope and 6xHis under control of the PCMV and/or the PT7 promoter. pCEP4/Sec is an expression vector that allows heterologous protein expression and secretion by fusing any protein into a multiple cloning site following the Ig kappa chain signal peptide. Detection and purification of the expressed protein are aided by the presence of the V5 epitope tag and 6xHis tag at the C-terminus (Invitrogen, Carlsbad, Calif.).

Example 4

Expression of FGF-CX in Human Embryonic Kidney (HEK) 293 Cells

The BglII-XhoI fragment containing the FGF-CX sequence was isolated from TA-AB02085-S274-F19 (Example 2) and subcloned into the BamHI-XhoI digested pCEP4/Sec to generate the expression vector pCEP4/Sec-FGF-CX. The pCEP4/Sec-FGF-CX vector was transfected into 293 cells using the LipofectaminePlus reagent following the manufacturer's instructions (Gibco/BRL/Life Technologies, Rockville, Md.). The cell pellet and supernatant were harvested 72 hours after transfection and examined for FGF-CX expression by Western blotting (reducing conditions) with an anti-V5 antibody. FIG. 1 shows that FGF-CX is expressed as a polypeptide having an apparent molecular weight (Mr) of approximately 34 kDa proteins secreted by 293 cells. In addition a minor band is observed at about 31 kDa.

Example 5

Expression of FGF-CX in E. coli

The vector pRSETA (In Vitrogen Inc., Carlsbad, Calif.) was digested with XhoI and NcoI restriction enzymes. Oligonucleotide linkers of the sequence 5' CATGGTCAGCCTAC 3' (SEQ ID NO:19) and

Figure 2:
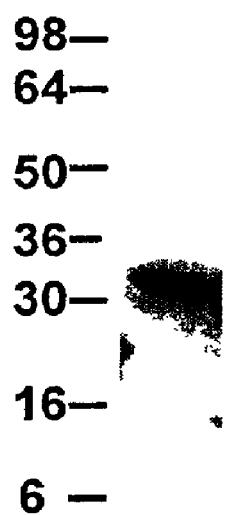
FIG. 2 shows a Western analysis of FGF-CX protein expressed in *E. coli* cells.

5' TCGAGTAGGCTGAC 3' (SEQ ID NO:20)

were annealed at 37 degree Celsius and ligated into the XhoI-NcoI treated pRSETA. The resulting vector was confirmed by restriction analysis and sequencing and was named pETMY. The BglII-XhoI fragment of the sequence encoding FGF-CX (see Example 2) was ligated into vector pETMY that was digested with BamHI and XhoI restriction enzymes. The expression vector is named pETMY-FGF-CX. In this vector, hFGF-CX was fused to the 6xHis tag and T7 epitope at its N-terminus. The plasmid pETMY-FGF-CX was then transfected into the E. coli expression host BL21 (DE3, pLys) (Novagen, Madison, Wis.) and expression of protein FGF-CX was induced according to the manufacturer's instructions. After induction, total cells were harvested, and proteins were analyzed by Western blotting using anti-HisGly antibody (Invitrogen, Carlsbad, Calif.). FIG. 2 shows that FGF-CX was expressed as a protein of apparent molecular weight Mr approximately 32 kDa.

Example 6

Comparison of Expression of Recombinant FGF-CX Protein With and Without a Cloned Signal Peptide a) Expression Without a Signal Peptide As noted in the Detailed Description of the Invention, FGF-CX apparently lacks a classical amino-terminal signal sequence. To determine whether FGF-CX is secreted from mammalian cells, cDNA obtained as the BglII-XhoI fragment, encoding the full length FGF-CX protein, was subcloned from TA-AB02085-S274-F19 (Example 2) into BamHI/XhoI-digested pcDNA3.1 (Invitrogen). This provided a mammalian expression vector designated pFGF-CX. This construct incorporates the V5 epitope tag and a polyhistidine tag into the carboxy-terminus of the protein to aid in its identification and purification, respectively, and should generate a polypeptide of about 27 kDa. Following transient transfection into 293 human embryonic kidney cells, conditioned media was harvested 48 hr post transfection.

In addition to secretion of FGF-CX into conditioned media, it also found to be associated with the cell pellet/ECM (data not shown). Since FGFs are known to bind to heparin sulfate proteoglycan (HSPG) present on the surface of cells and in the extracellular matrix (ECM), the inventors investigated the possibility that FGF-CX was sequestered in this manner. To this end, FGF-CX-transfected cells were extracted by treatment with 0.5 ml DMEM containing 100 $\mu$M suramin, a compound known to disrupt low affinity interactions between growth factors and HSPGs (La Rocca, R. V., Stein, C. A. & Myers, C. E. (1990) Cancer Cells 2, 106–115), for 30 min at 4° C. The suramin-extracted conditioned media was then harvested and clarified by centrifigation (5 min; 2000×g).

The conditioned media and the suramin extract were then mixed with equal volumes of 2×gel-loading buffer. Samples were boiled for 10 min, resolved by SDS-PAGE on 4–20% gradient polyacrylamide gels (Novex, Dan Diego, Calif.) under reducing conditions, and transferred to nitrocelluose filters (Novex). Western analysis was performed according to standard procedures using HRP-conjugated anti-V5 antibody (Invitrogen) and the ECL detection system (Amersham Pharmacia Biotech, Piscataway, N.J.).

One band having the expected Mr was identified in conditioned media from 293 cells transfected with pFGF-CX (FIG. 3, Panel A, lane 1). Conditioned media from cells transfected with control vector did not react with the antibody (FIG. 3, Panel A, lane 5). After suramin treatment, it was found that a significant quantity of FGF-CX could in fact be released from the cell surface/ECM, indicating that HSPGs are likely to play a role in sequestering this protein (FIG. 3, Panel A, lane 2). These results indicate that FGF-CX can be secreted without a classical signal peptide.

Recombinant FGF-CX protein stimulates DNA synthesis and cell proliferation, effects that are likely to be mediated via high affinity binding of FGF-CX to a cell surface receptor, and modulated via low affinity interactions with HSPGs. The suramin extraction data suggests that FGF-CX binds to HSPGs present on the cell surface and/or the ECM.

b) Expression With a Signal Peptide

With the goal of enhancing protein secretion, a construct (pCEP4/Sec-FGF-CX) was generated in which the FGF-CX cDNA was fused in frame with a cleavable amino-terminal secretory signal sequence derived from the Igκ gene. The resulting protein also contained carboxy-terminal V5 and polyhistidine tags as described above for pFGF-CX. Following transfection into 293 cells, a protein product having the expected Mr of about 31 kDa was obtained, and suramin was again found to release a significant quantity of sequestered FGF-CX protein (FIG. 3, Panel A; lanes 3 and 4). As expected, pCEP4/Sec-FGF-CX generated more soluble FGF-CX protein than did pFGF-CX.

Results similar to those described above for 293 cells were also obtained with NIH 3T3 cells (FIG. 3, Panel B).

Example 7

Expression of FGF-CX

FGF-CX was expressed essentially as described in Example 5. The protein was purified using $Ni^{2+}$-affinity chromatography, subjected to SDS-PAGE under both reducing and nonreducing conditions, and stained using Coomassie Blue. The results are shown in FIG. 4. It is seen that under both sets of conditions, the protein migrates with an apparent molecular weight of approximately 29–30 kDa.

Example 8

Stimulation of Bromodeoxyuridine Incorporation by Recombinant FGF-CX

A dose response experiment for incorporation of BrdU was carried out using human renal carcinoma cells (786-0; American Type Culture Collection, Manassas, Va.). 293-EBNA cells (Invitrogen) were transfected using Lipofectamine 2000 according to the manufacturer's protocol (Life Technologies, Gaithersburg, Md.). Cells were supplemented with 10% fetal bovine serum (FBS; Life Technologies) 5 hr post-transfection. To generate protein for BrdU and growth assays (Example 10), cells were washed and fed with Dulbecco's modified Eagle medium (DMEM; Life Technologies) 18 hr post-transfection. After 48 hr, the media was discarded and the cell monolayer was incubated with 100 $\mu$M suramin (Sigma, St. Louis, Mo.) in 0.5 ml DMEM for 30 min at 4° C. The suramin-extracted conditioned media was then removed, clarified by centrifugation (5 min; 2000×g), and subjected to TALON metal affinity chromatography according to the manufacturer's instructions (Clontech, Palo Alto, Calif.) taking advantage of the carboxy-terminal polyhistidine tag. Retained fusion protein was released by washing the column with imidazole.

To generate control protein, 293-EBNA cells were transfected with pCEP4 plasmid (Invitrogen) and subjected to the purification procedure outlined above.

Recombinant FGF-CX was tested for its ability to induce DNA synthesis in a bromodeoxyuridine (BrdU) incorporation assay. 786-0 cells were cultured in 96-well plates to approximately 100% confluence, washed with DMEM, and serum-starved in DMEM for 24 hr. Recombinant FGF-CX or control protein was then added to the cells for 18 hr. The BrdU assay was performed according to the manufacturer's specifications (Roche Molecular Biochemicals, Indianapolis, Ind.) using a 5 hr BrdU incorporation time.

Figure 5:
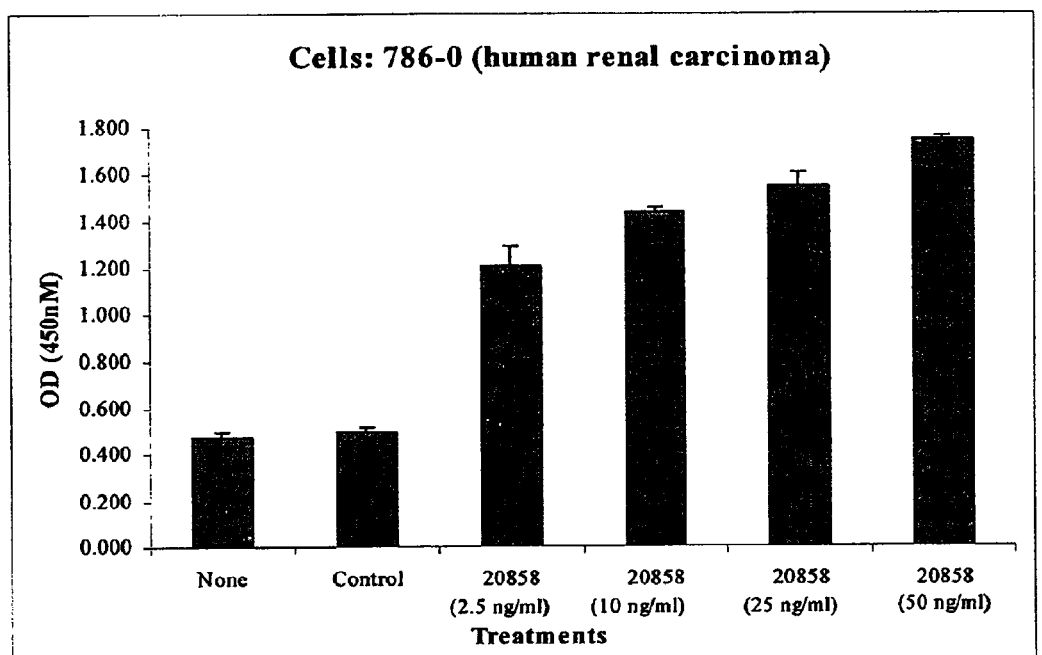
FIG. 5 provides the results of a dose titration growth experiment carried out using 786-0 human renal carcinoma cells. In this experiment incorporation of bromodeoxyuridine induced by varying amounts of FGF-CX (designated in FIG. 5 as 20858) was determined.

The results are shown in FIG. 5, in which FGF-CX is designated "20858". It is seen that FGF-CX stimulates proliferation of renal carcinoma cells by more than 4-fold over controls, with a half-effective dose being about 2.5 ng/mL.

Example 9

Receptor Binding Specificity of FGF-CX

Figure 6:
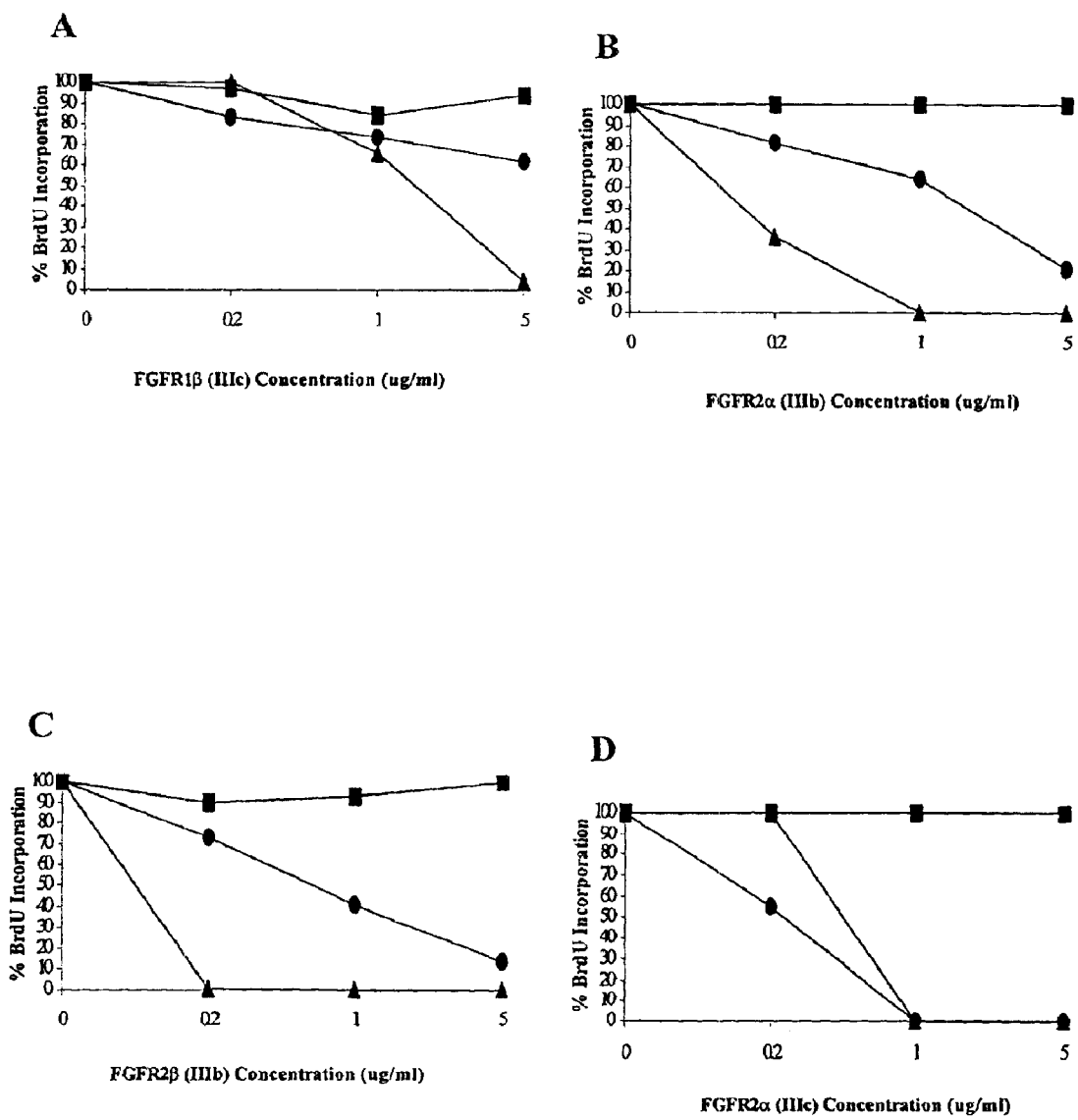
FIG. 6 shows the results of experiments assessing the receptor binding specificity of FGF-CX. NIH 3T3 cells were serum-starved, incubated with the indicated growth factor (square=PDGF-BB; triangle=aFGF; circle=FGF-CX) either alone or together with the indicated soluble FGFR, and analyzed by a BrdU incorporation assay. Experiments were performed in triplicate and are represented as the percent BrdU increase in incorporation of BrdU relative to cells receiving the growth factor alone.
Figure 6:
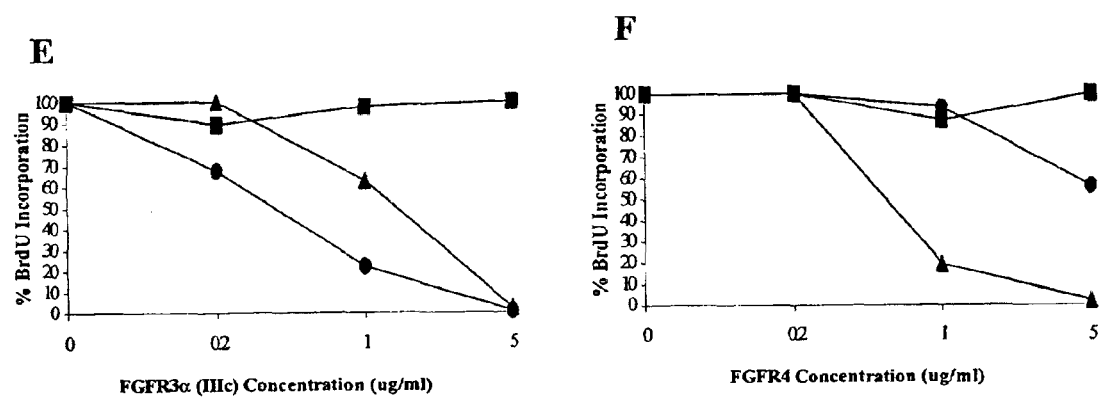

To determine the receptor binding specificity of FGF-CX, we examined the effect of soluble FGF receptors (FGFRs)

on the induction of DNA synthesis in NIH 3T3 cells by recombinant FGF-CX. Four receptors have been identified to date (Klint P and Claesson-Welsh L. Front. Biosci., 4: 165–177, 1999; Xu X, et al. Cell Tissue Res., 296: 33–43, 1999). Soluble receptors for FGFR1β(IIIc), FGFR2α(IIIb), FGFR2β(IIIb), FGFR2α(IIIc), FGFR3α (IIIc) and FGFR4 were utilized. It was found that soluble forms of each of these FGFRs were able to specifically inhibit the biological activity of FGF-CX (see FIG. 6). Complete or nearly complete inhibition was obtained with soluble FGFR2α(IIIb), FGFR2β(IIIb), FGFR2α(IIIc), and FGFR3α(IIIc), whereas partial inhibition was achieved with soluble FGFR1β(IIIc) and FGFR4. None of the soluble receptor reagents interfered with the induction of DNA synthesis by PDGF-BB, thereby demonstrating their specificity. The integrity of each soluble receptor reagent was demonstrated by showing its ability to inhibit the induction of DNA synthesis by aFGF (acidic FGF), a factor known to interact with all of the FGFRs under analysis.

Example 10

Cloning and Expression of an N-terminal Deletion Form of FGF-CX

Figure 7:
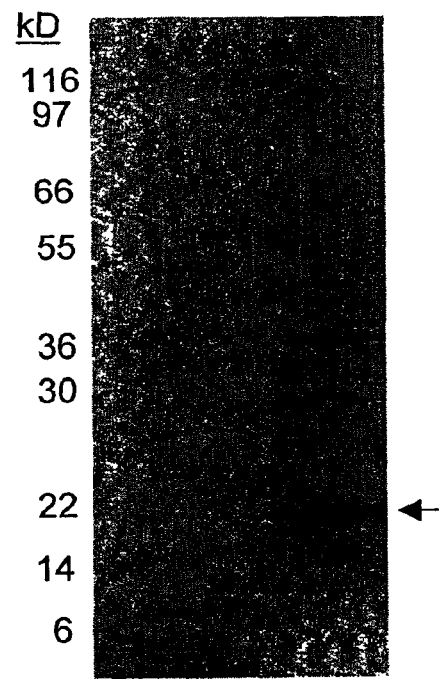
FIG. 7 shows an image of a Coomassie Blue stained SDS-PAGE gel of the arginine supernatant obtained when plasmid pET24a-FGF20X-del54-codon was expressed in *E.coli* strain BL21 (DE3).

E. coli strain BL21 (DE3) (Invitrogen) harboring the plasmid pET24a- FGF20X-del54-codon were grown in LB medium at 37° C. This plasmid encodes the C-terminal portion of FGF-CX beginning at position 55. When cell densities reached an OD of 0.6, IPTG was added to final concentration of 1 mM. Induced cultures were then incubated for an additional 4 hours at 37° C. Cells were harvested by centrifugation at 3000×g for 15 minutes at 4° C., suspended in PBS and then disrupted with two passes through a microfluidizer. To separate soluble and insoluble proteins, the lysate was subjected to centrifugation at 10,000×g for 20 minutes at 4° C. The insoluble fraction (pellet) was extracted with PBS containing 1M L-arginine. The remaining insoluble material was then removed by centrifugation and the soluble fraction of the arginine extract was filtered through 0.2 micron low-protein binding membrane and analyzed by SDS PAGE. The result is shown in FIG. 7, which indicates that the product is a polypeptide with an apparent molecular weight of approximately 20 kDa (see arrow). N-terminal sequencing of the expressed polypeptide provides the sequence AQLAHLHGILRRRQL which is 100% identical to residues 54–64 of FGF-CX (Table 1, SEQ ID NO:2).

Example 11

Stimulation of Bromodeoxyuridine Incorporation into NIH 3T3 Cells in Response to a Truncated Form of FGF-CX A vector expressing residues 24–211 of FGF-CX, referred to as (d1-23)FGF-CX, was prepared. See Table 1 and SEQ ID NO:2. The incorporation of BrdU by NIH 3T3 cells treated with conditioned medium obtained using the vector incorporating this truncated form was compared to the incorporation in response to treatment with conditioned medium using a vector encoding full length FGF-CX. This experiment was carried out as described in Example 8.

Figure 8:
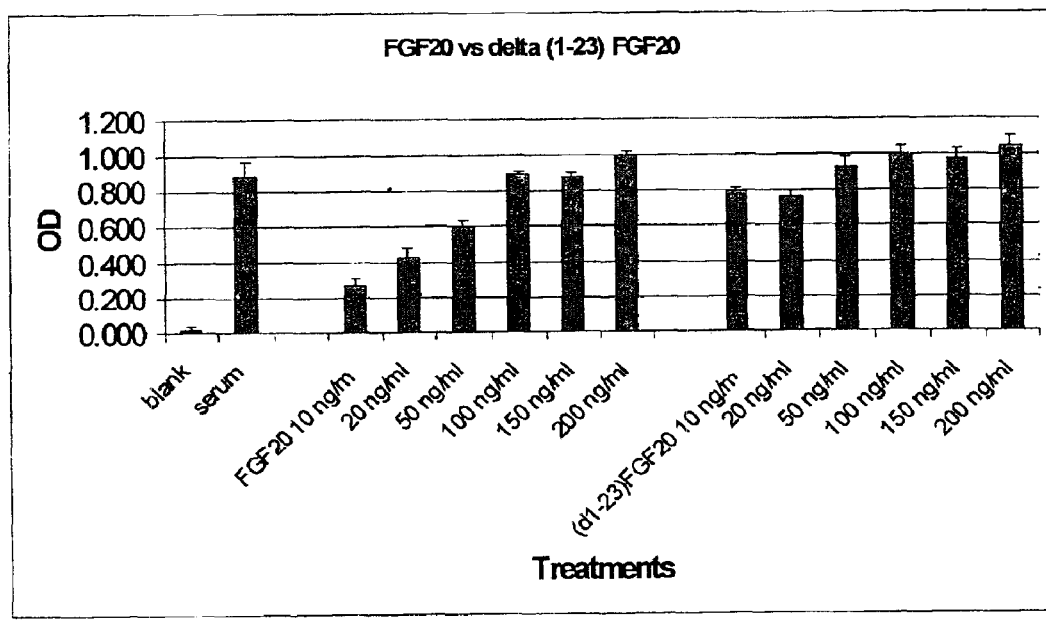
FIG. 8 displays the biological activity of a truncated form of recombinant FGF-CX (denoted by (d1-23)FGF20 in the FIG.) as represented by its effects on DNA synthesis, compared to that of full length FGF-CX (denoted FGF20 in the FIG.). NIH 3T3 mouse fibroblasts were serum-starved, incubated with the indicated factor for 18 hr, and analyzed by a BrdU incorporation assay.

The results are shown in FIG. 8. It is seen that (d1-23) FGF-CX retains high activity at the lowest concentration tested, 10 ng/mL. At this concentration, the activity of full length FGF-CX has fallen considerably, approaching the level of the control. It is estimated that (d1-23)FGF-CX may be at least 5-fold more active than full length FGF-CX.

Example 12

Molecular Cloning of a Mature FCTR1 Form (30664188.0.m99) Polypeptide from Cline 30664188.0.99

A mature form of clone 30664188.0.99, coding for residues 24 to 370 of the amino acid sequence of Table 2 (SEQ ID NO:4) was cloned. This fragment was designated 30664188.0.m99 and corresponds to the polypeptide sequence remaining after a signal peptide predicted to be cleaved between residues 23 and 24 has been removed. The following oligonucleotide primers were designed to PCR amplify the predicted mature form of 30664188.0.99: 30664188 Eco Forward—CTCGTC GAATTC ACC CCG CAG AGC GCA TCC ATC AAA GC (SEQ ID NO:21), and 3066418 Xho Reverse—CTCGTC CTC GAG TCG AGG TGG TCT TGA GCT GCA GAT ACA (SEQ ID NO:22).

The forward primer included an in frame EcoRI restriction site, and the reverse primer included an XhoI restriction site. The EcoRI/XhoI fragment is compatible with the pET28a E. coli expression vector and with the pMelV5His baculovirus expression vector.

PCR reactions were set up using 5 ng human spleen and fetal lung cDNA templates. The reaction mixtures contained 1 microM of each of the 30664188 Eco Forward and 30664188 Xho Reverse primers, 5 micromoles dNTP (Clontech Laboratories, Palo Alto Calif.) and 1 microliter of 50xAdvantage-HF 2 polymerase (Clontech Laboratories, Palo Alto Calif.) in 50 microliter volume. The following reaction conditions were used:

a)  96° C. 3 minutes
b)  96° C. 30 seconds denaturation
c)  70° C. 30 seconds, primer annealing. This temperature was gradually decreased by 1° C. per cycle
d)  72° C. 1 minute extension.
Repeat steps b–d 10 times
e)  96° C. 30 seconds denaturation
f)  60° C. 30 seconds annealing
g)  72° C. 1 minute extension
Repeat steps e–g 25 times
h)  72° C. 5 minutes final extension The amplified product expected to have 1041 bp was detected by agarose gel electrophoresis in both samples. The fragments were purified from agarose gel and ligated to pCR2.1 vector (Invitrogen, Carlsbad, Calif.). The cloned inserts were sequenced using M13 Forward, M13 Reverse and the following gene specific primers:

```
3066418 S1:
GGA CGA TGG TGT GGA CAC AAG,      (SEQ ID NO:23)

3066418 S2:
CTT GTG TCC ACA CCA TCG TCC,      (SEQ ID NO:24)

3066418 S3:
TAT CGA GGC AGG TCA TAC CAT and  (SEQ ID NO:25)

3066418 S4:
ATG GTA TGA CCT GCC TCG ATA.      (SEQ ID NO:26)
```

The cloned inserts were verified as an open reading frame coding for the predicted mature form of 30664188.0.99. The construct derived from fetal lung, called 30664188-S311a, was used for further subcloning into expression vectors (see below). The nucleotide sequence of 30664188-S11a within the restriction sites was found to be 100% identical to the corresponding fragment in the ORF of 30664188.0.99 (Table 2; SEQ ID NO:4).

Example 13

Expression of 30664188.m99 Polypeptide in *E. coli*

Figure 9:
FIG. 9 is a representation of a Western blot of a 30664188.m99 protein expressed in *E. coli* cells.

The vector pRSETA (InVitrogen Inc., Carlsbad, Calif.) was digested with XhoI and NcoI restriction enzymes. Oligonucleotide linkers CATGGTCAGCCTAC (SEQ ID NO:27); and TCGAGTAGGCTGAC (SEQ ID NO:28) were annealed at 37 degrees Celsius and ligated into the XhoI-NcoI treated pRSETA. The resulting vector was confirmed by restriction analysis and sequencing and was named pETMY. The BamHI-XhoI fragment containing the 30664188 sequence (Example 12) was ligated into BamHI-XhoI digested pETMY. The resulting expression vector was named pETMY-30664188. In this vector, 30664188 is fused to the T7 epitope and a 6xHis tag at its N-terminus The plasmid pETMY-30664188 was then transfected into the *E. coli* expression host BL21(DE3, pLys) (Novagen, Madison, Wis.) and expression of the protein was induced according to the manufacturer's instructions. After induction, the *E. coli* cells were harvested, and proteins were analyzed by Western blotting using anti-His6Gly antibody (Invitrogen, Carlsbad, Calif.). FIG. 9 shows that the resulting polypeptide, termed 30664188.m99 herein, was expressed as a protein of apparent molecular weight 40 kDa. This approximates the molecular weight expected for the 30664188.m99 sequence.

Example 14

Expression of 30664188.m99 Polypeptide in Human Embryonic Kidney 293 Cells

Figure 10:
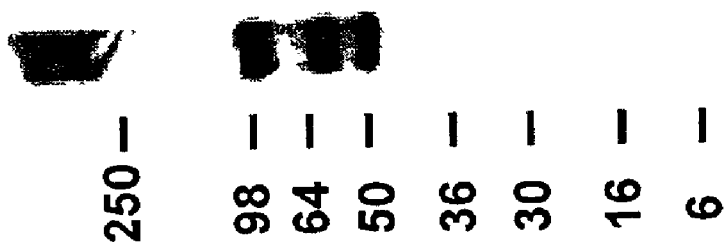
FIG. 10 is a representation of a Western blot of a 30664188.m99 protein secreted by human 293 cells.

The EcoRI-XhoI fragment containing the 30664188.m99 sequence was isolated from 30664188-S311a (Example 12) and subcloned into the vector pE28a (Novagen, Madison, Wis.) to give the plasmid pET28a-30664188. Subsequently, pET28a-30664188 was partially digested with BamHI restriction enzyme, and then completely digested with XhoI. A fragment of 1.1 kb was isolated and ligated into BamHI-XhoI digested pCEP4/Sec (Example 3) to generate expression vector pCEP4/Sec-30664188.m99. The pCEP4/Sec-30664188.m99. vector was transfected into human embryonic kidney 293 cells (ATCC No. CRL-1573, Manassas, Va.) using the LipofectaminePlus reagent following the manufacturer's instructions (Gibco/BRL/Life Technologies, Rockville, Md.). The cell pellet and supernatant were harvested 72 hours after transfection and examined for expression of the 30664188.m99 protein by Western blotting of an SDS-PAGE run under reducing conditions using an anti-V5 antibody. FIG. 10 shows that 30664188.m99 is expressed as three discrete protein bands of apparent molecular weight 50, 60, and 98 kDa secreted by 293 cells. The 50 kDa band migrated at a sized expected for a monomer glycosylated form of 30664188.m99, and the 98 kDa band migrated at a size consistent with a dimer of the monomer form.

Example 15

Expression and Purification of 30664188.m99 Protein

HEK 293 cells were grown in Dulbecco's modified eagle's medium (DMEM)/10% fetal bovine serum medium to 90% confluence. The cells were transfected with pCEP4sec or pCEP4sec/30664188.m99 using Lipofectamine 2000 according to the manufacturer's specifications (Gibco/BRL/Life Technologies, Rockville, Md.). Transfected cells were incubated for 2 days with DMEM and conditioned medium was prepared by collection of cell supernatants. The conditioned medium was enriched by Talon metal affinity chromatography (Clontech, Palo Alto, Calif.). Briefly, 7 ml of conditioned medium was incubated with 1 ml of Talon metal affinity resin in spin columns. The spin columns were washed twice with one ml of PBS. The columns were then eluted twice with 0.65 ml of PBS/0.5M imidazole pH 8.0 and the eluates pooled. Imidazole was removed by buffer exchange dialysis into PBS using Microcon centrifugal filter devices (Millipore Corp., Bedford, Mass.). The enriched gene products were stored at 4° C.

The purified protein obtained was subjected to SDS-PAGE under reducing conditions and probed with an anti-V5 antibody, which was detected with an enzyme label. The results of two separate transfection and purification runs are shown in the gels. They show that the product is a mixture of V5-containing polypeptides. The largest has an apparent molecular weight of about 50 kDa (FIG. 11, Panel B). The program ProSite predicts one N-glycosylation site in the mature protein. Glycosylation may explain the apparent molecular weight found. Thus the 50 kDa band is consistent with the length expected for full length gene product. Other bands, preponderantly having apparent molecular weights of about 20–25 kDa also arise. These are presumed to be the result of proteolysis occurring either intracellularly within the 293 cells or extracellularly after secretion from them. In another run (not shown) the broad band extending from about 6 kDa to about 14 kDa is reolved into two bands of about 7–8 kDa and about 10 kDa.

Example 16

The Clone 30664188.0.m99 Protein Induces Cellular DNA Synthesis

Human CCD-1070 fibroblast cells (ATCC No. CRL-2091, Manassas, Va.) or murine NIH 3T3 (ATCC No. CRL-1658, Manassas, Va.) fibroblast cells were cultured in DMEM supplemented with 10% fetal bovine serum or 10% calf serum respectively. Fibroblasts were grown to confluence at 37° C. in 10% $CO_2$/air. Cells were then starved in DMEM for 24 h. pCEP4/Sec (Example 3) or pCEP4/Sec/30664188.m99 (Example 14) enriched conditioned medium was added (10 microL/100 microL of culture ) for 18 h. BrdU (10 uM) was then added and incubated with the cells for 5 h. BrdU incorporation was assayed by colorimetric immunoassay according to the manufacturer's specifications (Boehringer Mannheim, Indianapolis, Ind.).

Figure 12:
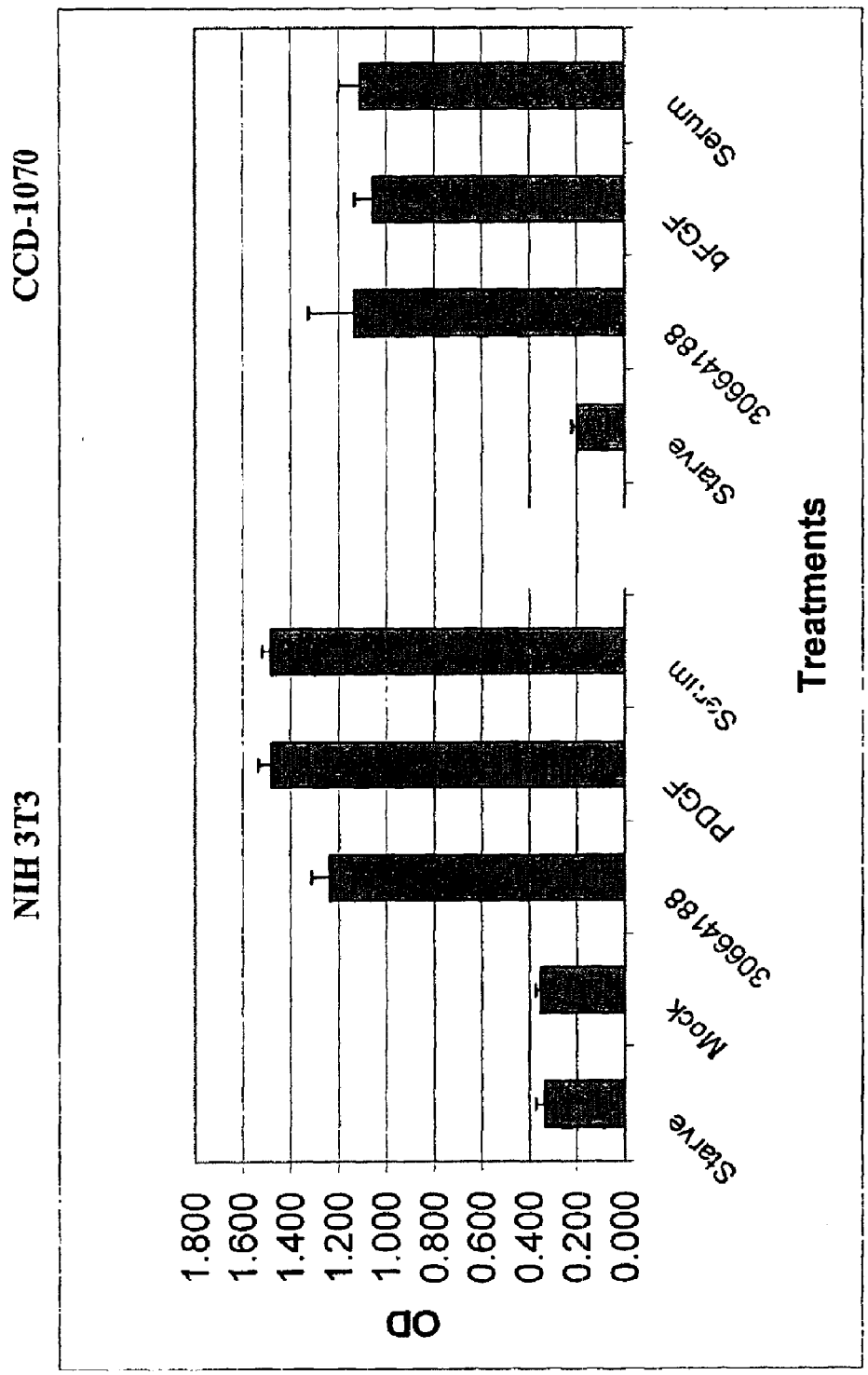
FIG. 12 is a graph showing incorporation of BrdU into NIH 3T3 cells and CCD-1070 cells in response to various treatments.

FIG. 12 demonstrates that 30664188.m99 induced an approximate four- to five-fold increase in BrdU incorporation in either cell type compared to cells treated with control conditioned medium or untreated cells. The proliferative increase observed was similar to the increase in BrdU incorporation induced by platelet derived FCTRX (PDGF), basic fibroblast growth factor (bFGF), or serum treatment. Additionally, 30664188.m99 partially purified conditioned medium did not induce BrdU incorporation in human MG-63 epithelial cells or CCD1106 keratinocytes (data not shown). These results suggest that 30664188 selectively induces DNA synthesis in human and mouse fibroblasts, but not in epithelial cell lines.

Figure 13:
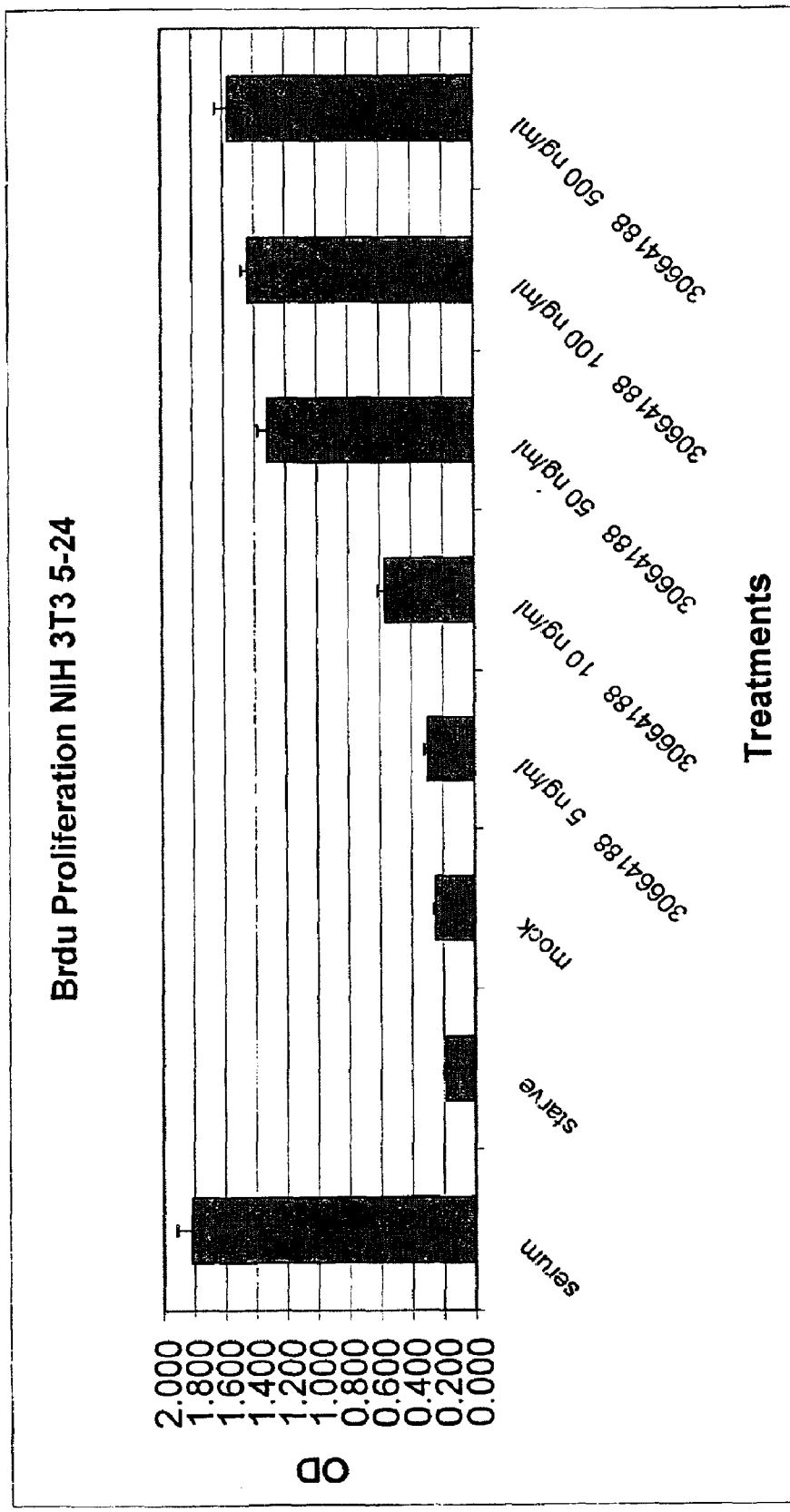
FIG. 13 is a graph showing proliferation of NIH 3T3 5–24 cells in response to various treatments.

In separate experiments, CCD-1070 cells and MG-63 osteosarcoma cells (ATCC Cat. No. CRL-1427) treated with pCEP4/Sec/30664188 each incorporated BrdU in a dose-dependent fashion, with 1 ug/mL providing the full effect (approximately 2.5- to 3-fold increase over control), 100 ng/mL providing slightly less than one-half the effect, and 10 and 1 ng/mL providing approximately control levels of incorporation. Furthermore, the dose response of NIH 3T3 cells shows that a 50% response occurs between doses of 10 and 50 ng/mL of pCEP4/Sec/30664188.M99 (FIG. 13).

In additional dose titration experiments using both NIH/3T3 cells and CCD 1070 cells, the half maximal effect occurred at or below 25 ng/mL.

Example 17

Induction of Proliferation of NIH 3T3 Cells by 30664188.m99

Murine NIH 3T3 fibroblasts were plated at 40% confluency and cultured in DMEM supplemented with 10% fetal bovine serum or 10% calf serum for 24 hrs. The culture medium was removed and replaced with an equivalent volume of pCEP4/Sec (Example 3) or pCEP4/Sec/30664188.m99.m99. (Example 14) conditioned medium. After 48 h, cells were photographed with a Zeiss Axiovert 100. Cell numbers were determined by trypsinization followed by counting using a Coulter Z1 Particle Counter.

Figure 14:
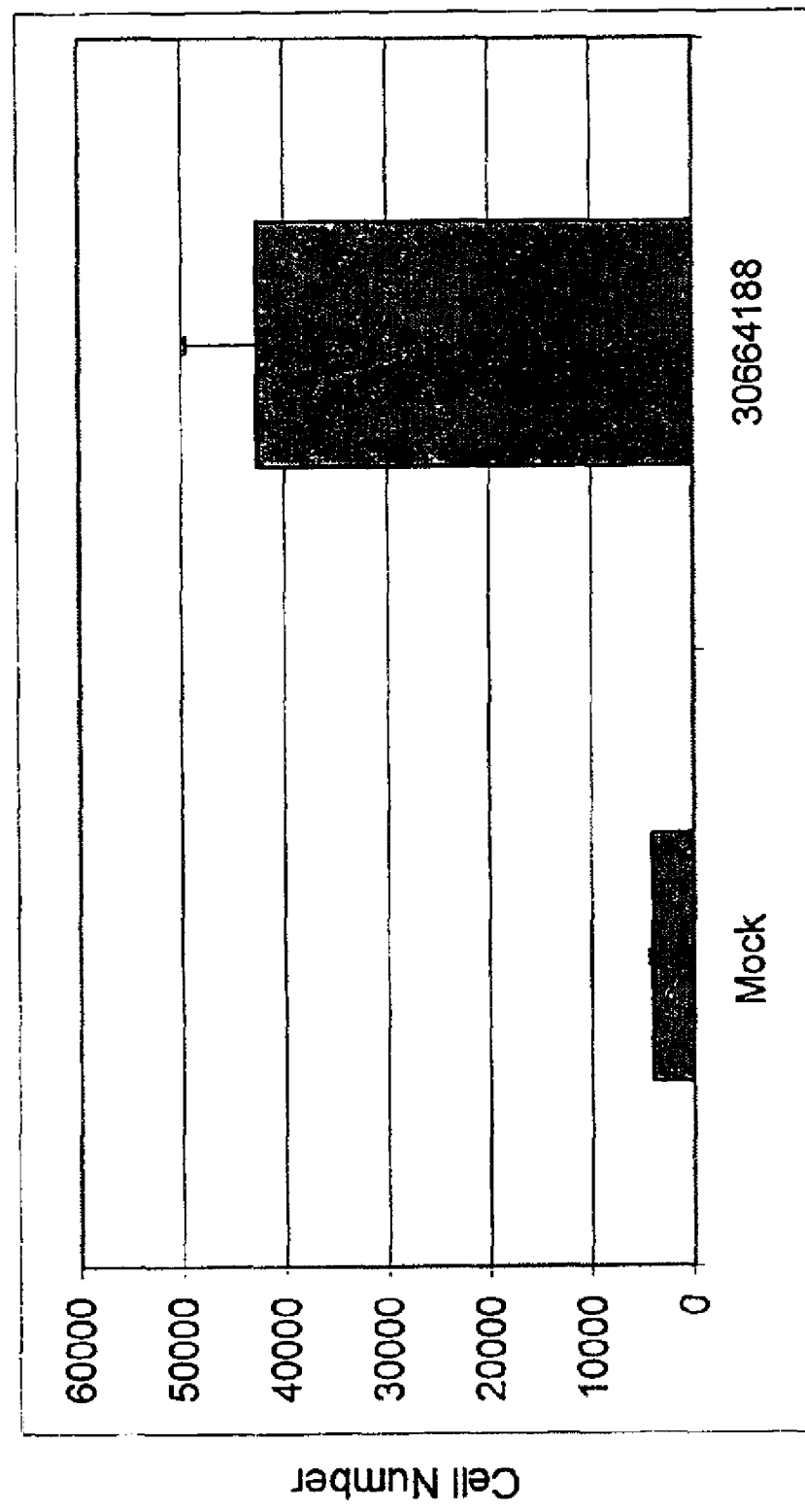
FIG. 14 is a graph showing cell number in NIH 3T3 cells exposed to a mock treatment or 30664188.

Treatment of NIH 3T3 fibroblasts with conditioned medium from 30664188 transfected HEK293 kidney epithelial cells resulted in a 6 to 8 fold increase in cell number over a two day period (FIG. 14). Cells treated with control conditioned medium from HEK293 cells transfected with the pCEP4/Sec vector alone demonstrated little or no growth (FIG. 14).

Figure 15:
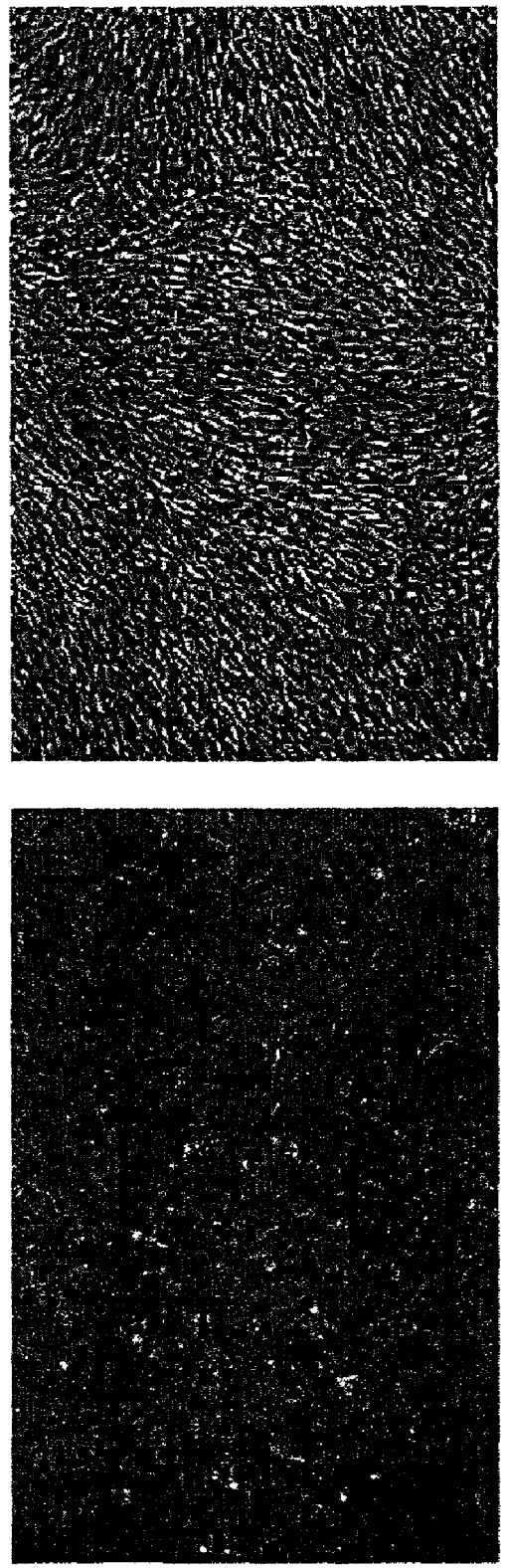
FIG. 15 is a depiction of a photomicrograph showing cell density and cell morphology of NIH 3T3 cells in response to treatment with pCEP4sec CM or 30664188 protein.

To determine whether 30664188.m99 conditioned medium was able to induce phenotypic changes characteristic of cellular transformation, cells treated with either 30664188 conditioned medium or mock conditioned medium were examined by light microscopy. FIG. 15 shows that NIH 3T3 cells treated with 30664188.m99, but not control treated NIH 3T3 cells, showed a marked increase in cell number, as well as refractile properties. Loss of contact inhibition of growth was evident. The cobblestone appearance characteristic of confluent NIH 3T3 cells was lost and density independent growth was evident. The latter was also suggested by the more rounded appearance of the NIH 3T3 cells due to subtle retraction. Transfection of pCEP4/Sec/30664188.m99.m99 also showed nearly identical potency in transformation potential 2 to 5 days in culture. After 7 to 10 days in culture, however, the morphologically transformed phenotype appeared to revert.

Example 18

Figure 16:
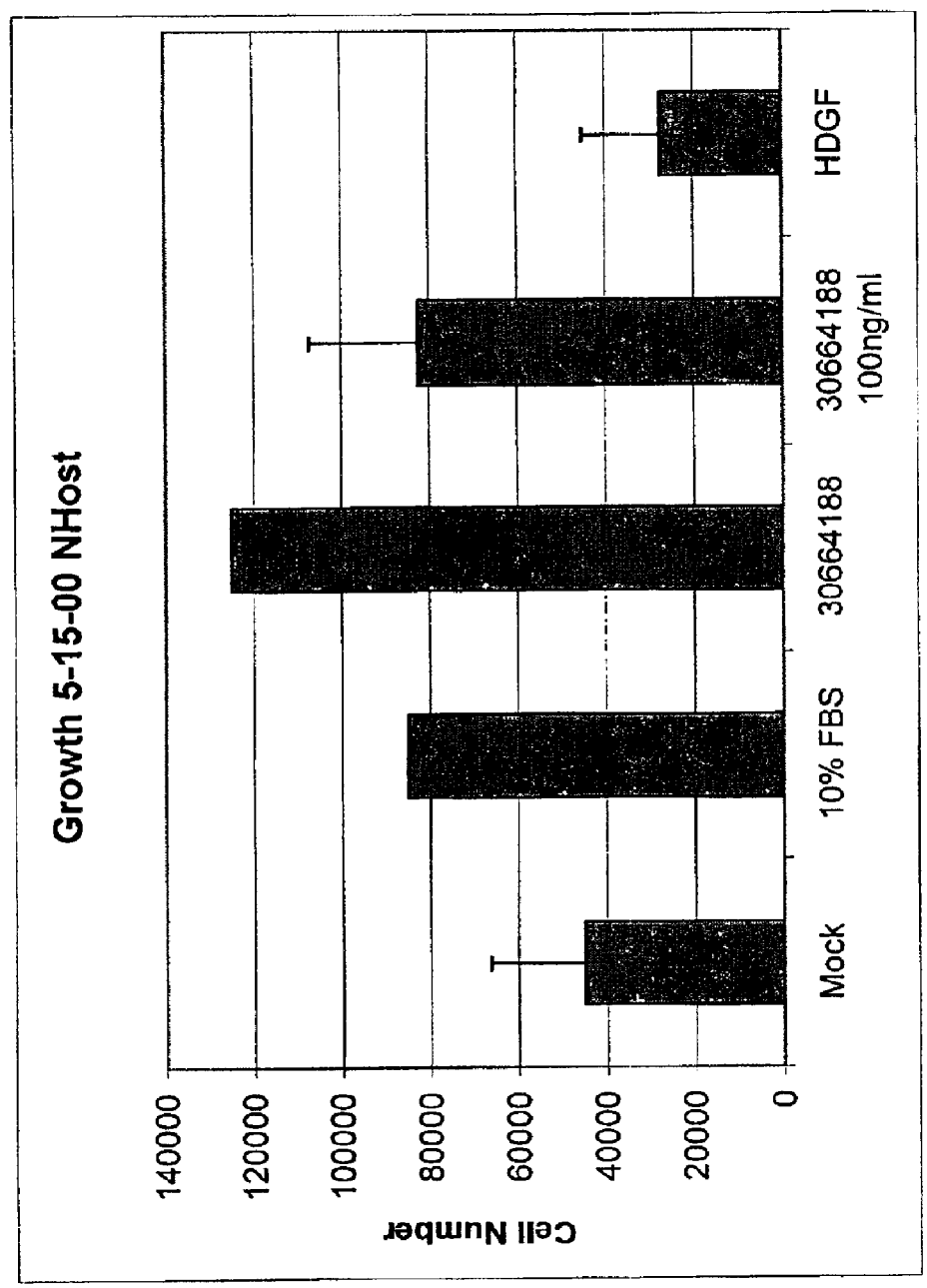
FIG. 16 is a depiction of a photomicrograph showing changes in cell number in NHost osteoblast cells in response to various treatments.

Induction of Proliferation of Human Primary Osteoblast Cells by the 30664188 Protein In an experiment similar to that described in Example 17, human primary osteoblast cells (NHost; Clonetics)also underwent a dose-dependent increase in cell number by 3- to 4-fold (FIG. 16). The dose required to elicit a 50% response in FIG. 16 is below 100 ng/mL of pCEP4/Sec/30664188.m99. In addition, Jurkat cells contacted with partially purified conditioned medium containing the 30664188 gene product exhibited a doubling of BrdU uptake compared to the medium from mock transfection, whereas the same cells contacted with 13 other CuraGen Corporation gene products thought to have growth promoting activity elicited no effect.

In summary, the observations that the 30664188 protein induces DNA synthesis (Example 16), cell growth (Examples 16 and 17), and morphological transformation (Example 17) indicate that the 30664188 protein possesses growth promoting and stimulating properties.

Example 19

Purification of Intact and Cleaved Products of the 30664188.m99 Protein

It was observed that in certain experiments treatment with the vector pCEP4/Sec/30664188.m99 did not result in DNA synthesis or cell proliferation. In additional experiments, medium conditioned with 30664188.m99 was obtained from HEK 293 cells grown in the presence of serum (Examples 15–17). The 30664188.m99 gene product was purified by cation exchange chromatography, followed by nickel affinity chromatography. The protein product was run under nonreducing and reducing conditions on SDS-PAGE, and developed by Coomassie stain. The results are shown in FIG. 17, Panels A and B. In the presence of serum, the 30664188.m99 gene product appeared as a protein of about 35 kDa under nonreducing conditions (FIG. 17 Panel B). However, this polypeptide appears as three degraded bands when run under reducing conditions. The apparent molecular weights of the two bands were 22–25 kDa (band I), about 16 kDa (band II) and about 5–6 kDa (band III). N-terminal amino acid analysis of these fragments indicates that bands I and II both appear to result from cleavage between residues 247 and 248, such that the peptide product begins at residue 248 of the 30664188.0.99 (Table 2, SEQ ID NO:4) amino acid sequence, and that band III begins at residue 339. These results are consistent with cleavage of the polypeptide corresponding to band I to provide the fragments of bands II and III. It is possible that the 35 kDa band observed under nonreducing conditions is a dimer composed of band I, and/or the bonded polypeptide composed of bands II and III, observed under reducing conditions.

Amino terminal analysis indicates that the gene product from pCEP4sec/30664188.m99-transfected 293 cells grown in the presence of serum, isolated according to the procedure described above, is a carboxyl-terminal fragment of the full length protein. The 35 kDa band found under nonreducing conditions is termed p35 below. These results are expanded in Example 21.

When 293 cells were cultured in the absence of serum, and the same isolation and detection procedure described in the preceding paragraph is followed, a different gene product is observed. Under nonreducing conditions a band was found at about 85 kDa (FIG. 17 Panel A). This protein is termed p85 below. The corresponding gene product observed under reducing conditions a major band is found at about 53–54 kDa. N-terminal amino acid analysis of this gene product provides the amino acids at the multiple cloning site used in pCEP4sec/30664188.m99 (Example 14). The residues corresponding to the Ig kappa leader sequence, cloned upstream from the multiple cloning site, are absent. These results indicate that the gene product obtained in the absence of serum represents the full amino acid sequence encoded in pCEP4sec/30664188.m99. The p85 polypeptide is thought to be a dimer of the 50 kDa species observed on reducing SDS-PAGE. These results are expanded in Example 21.

Example 20

Activity of Intact and Cleaved Fragments of the 30664188.m99 Protein

Purified p85 and p35 FCTRX proteins were separately applied to NIH 3T3 cells in a range of concentrations.

Figure 18:
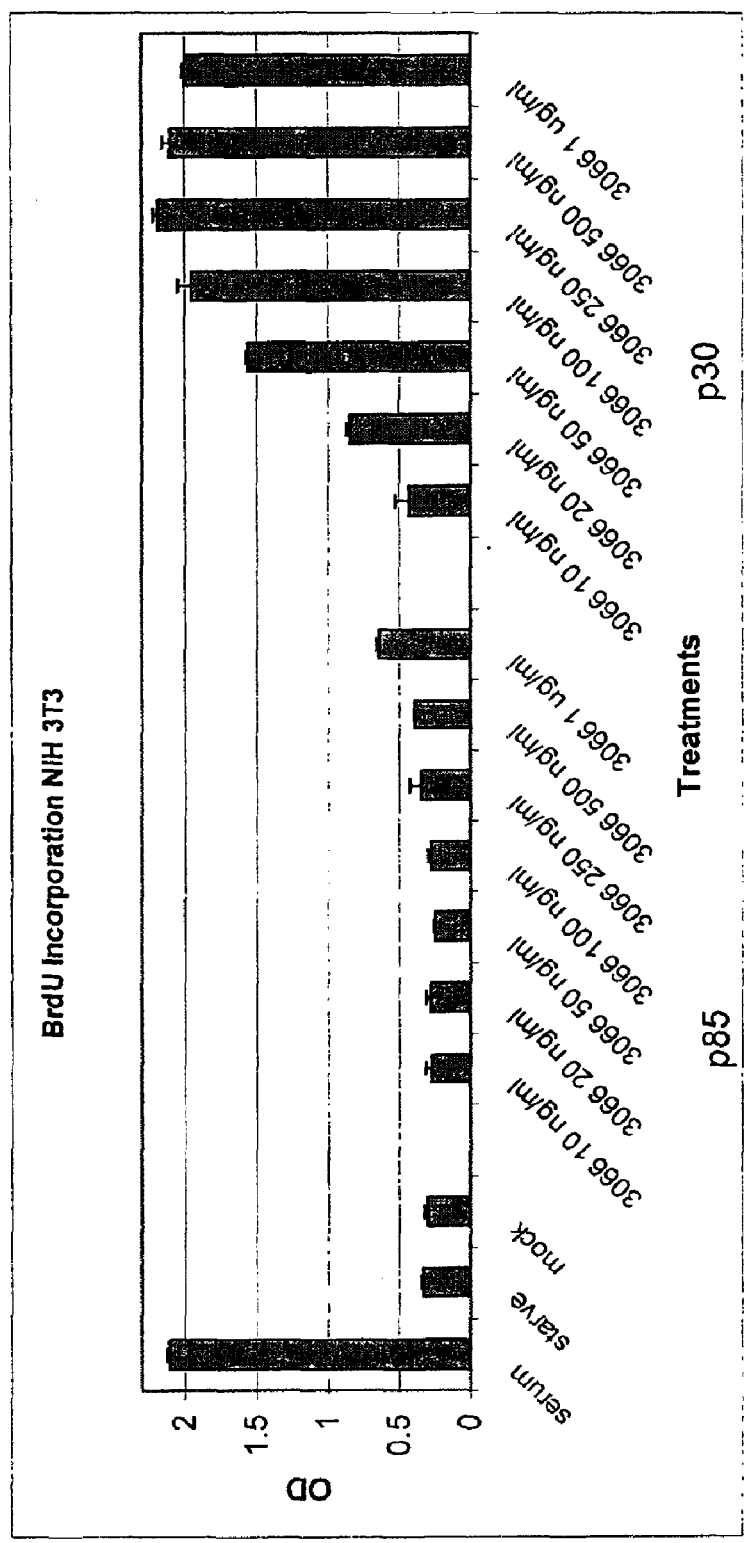
FIG. 18 is a representation of dose titration of BrdU incorporation into NIH 3T3 cells stimulated by p85 (bars 4–10) and by the p35 fragment of 30664188.m99 protein (bars 11–17).

Incorporation of BrdU was evaluated as described in Example 8. The results are shown in FIG. 18. It is seen that p85 has growth-promoting activity that does not differ from control levels except at the highest concentration used (bars 4–10). p35, on the other hand, was at least as active, if not more so, than unfractionated pCEP4/Sec/30664188.m99 conditioned medium (bars 11–17). The concentration of p35 giving 50% of the maximum DNA synthesis falls between 20 and 50 ng/mL.

These results suggest that the p35 fragment derived from intact 30664188.m99 has growth-promoting activity but that the intact dimeric form of the .m99 protein, p85, does not.

Example 21

Purification of Recombinant PDGF DD

The gene product of PDGFD was expressed in HEK293 cells grown on porous microcarriers (Cultisphere-GL, Hyclone; Logan, Utah) in 1 L spinner flasks. As noted in Examples 2 and 4, the recombinant PDGF D gene includes a 6xHis fusion at the 3' end. Cells were grown in DMEM/F12 media containing 1% penicillin/streptomycin in the presence or absence of 5% fetal bovine serum (FBS). The conditioned medium was harvested by centrifugation (4000×g for 15 minutes at 4° C.) and loaded onto a POROS HS50 column (PE Biosystems; Foster City, Calif.), pre-equilibrated with 20 mM Tris-acetate (pH 7.0). After washing with the equilibration buffer, bound proteins were eluted with a NaCl step gradient (0.25 M, 0.5 M, 1.0 M and 2.0 M). Fractions containing PDGF DD p35 (1.0 M NaCl step elution) or p85 (0.5 M NaCl step elution) (see Example 19) were pooled and diluted with an equal volume of phosphate-buffered saline (PBS), pH 8.0 containing 0.5 M NaCl, then loaded onto a POROS MC20 column pre-charged with nickel sulfate (PE Biosystems). After washing with PBS/0.5 M NaCl, bound proteins were eluted with a linear gradient of imidazole (0–0.5 M). Fractions containing PDGF DD (homodimers of PDGFD) (100–150 mM imidazole) were pooled and dialyzed twice against 1000 volumes of 20 mM Tris-HCl, pH 7.5, 50 mM NaCl. The protein purity was estimated to be >95% by sodium dodecyl sulfate-polyacrylamide gel electrophoresis (SDS-PAGE; 4–20% Tris-glycine gradient gel; Invitrogen, Carlsbad, Calif.) analysis (See, for example, the results in Example 19, including FIG. 17).

Biochemical Properties of PDGF D. To examine the biochemical properties of the gene product of PDGF D, the cDNA encoding PDGF D protein was subcloned into a mammalian expression vector, pCEP4/Sec-30664188m99 (Example 14). This construct incorporates an epitope tag (V5) and a polyhistidine tag into the COOH terminus of the protein to aid in its identification and purification (expression vector pCEP4/Sec-30664188m99; Example 14).

Figure 19:
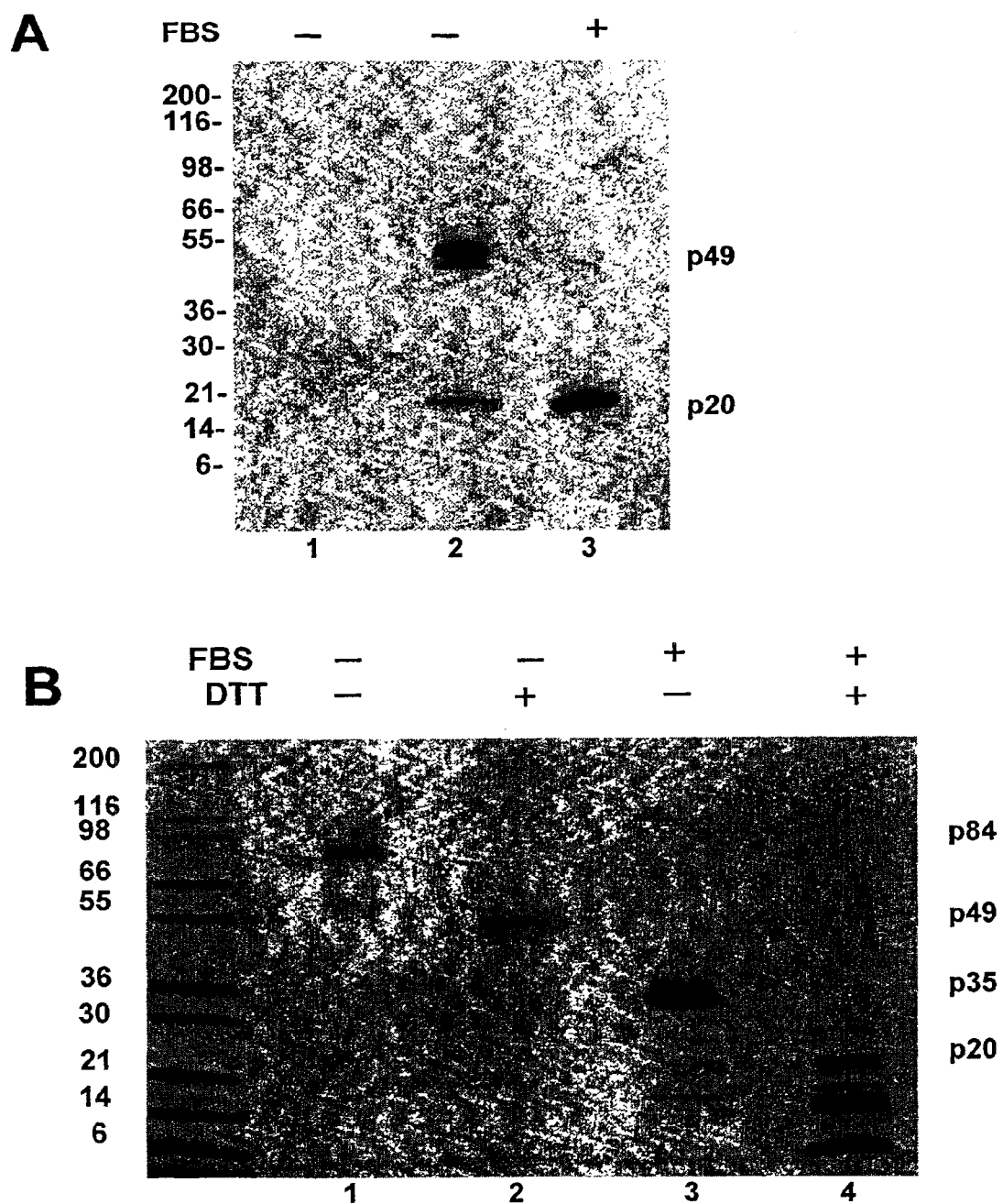
FIG. 19 is a representation of a Western blot and SDS PAGE analysis of PDGF D. In Panel A, samples from the conditioned medium of HEK 293 cells transiently transfected with pCEP4/Sec (lane 1) or pCEP4/Sec-PDGF D (lanes 2 & 3) and cultured in the presence (lane 3) or absence (lanes 1 & 2) of FBS were examined by SDS-PAGE under reducing conditions, followed by immunoblot analysis using anti-V5 antibody. In Panel B, purified PDGF-D from pCEP4/Sec-PDGF D transfected HEK 293 cells cultured in the presence (lanes 3 & 4) or absence (lanes 1 & 2) of FBS was resolved by SDS-PAGE and stained with Coomassie Blue. Samples were treated with (+) and without (−) DTT. Molecular weight markers are indicated on the left.

Following transfection into 293 HEK cells and growth in serum-free culture, a secreted polypeptide with an apparent molecular weight of ~49 kDa (p49 species) was identified by Western blot analysis under reducing conditions (FIG. 19 Panel A, lane 2). The fact that the apparent molecular weight of p49 is greater than the expected value of ~43-kDa may be attributable to glycosylation. In contrast, a 20-kD protein was secreted when PDGF D-transfected cells were grown in the presence of FBS (FIG. 19 Panel A, lane 3). Conditioned media from mock transfected cells did not react with the anti-V5 antibody (FIG. 19 Panel A, lane 1).

In addition, PDGF D was expressed in the presence or absence of FBS and purified to >95% homogeneity. As shown in FIG. 19 Panel B (lane 2), expression of PDGF D under serum-free conditions resulted in the detection of the expected 49-kD gene product under reducing conditions, when the gel was stained using Coomassie Blue. A polypeptide species with an apparent molecular weight of about 84 kDa, corresponding to a dimeric p85 species of p49, was seen under non-reducing conditions (FIG. 19 Panel B, lane 1). When PDGF DD was purified from serum-containing conditioned medium and run under nonreducing conditions, a species with an apparent molecular weight of about 35 kDa (p35) was observed (FIG. 19 Panel B, lane 3). Under reducing conditions, p35 was found to yield three bands when visualized with Coomassie Blue, which migrate with apparent molecular weights of approximately 20, 14, and 6 kDa (FIG. 19 Panel B, lane 4).

Figure 20:
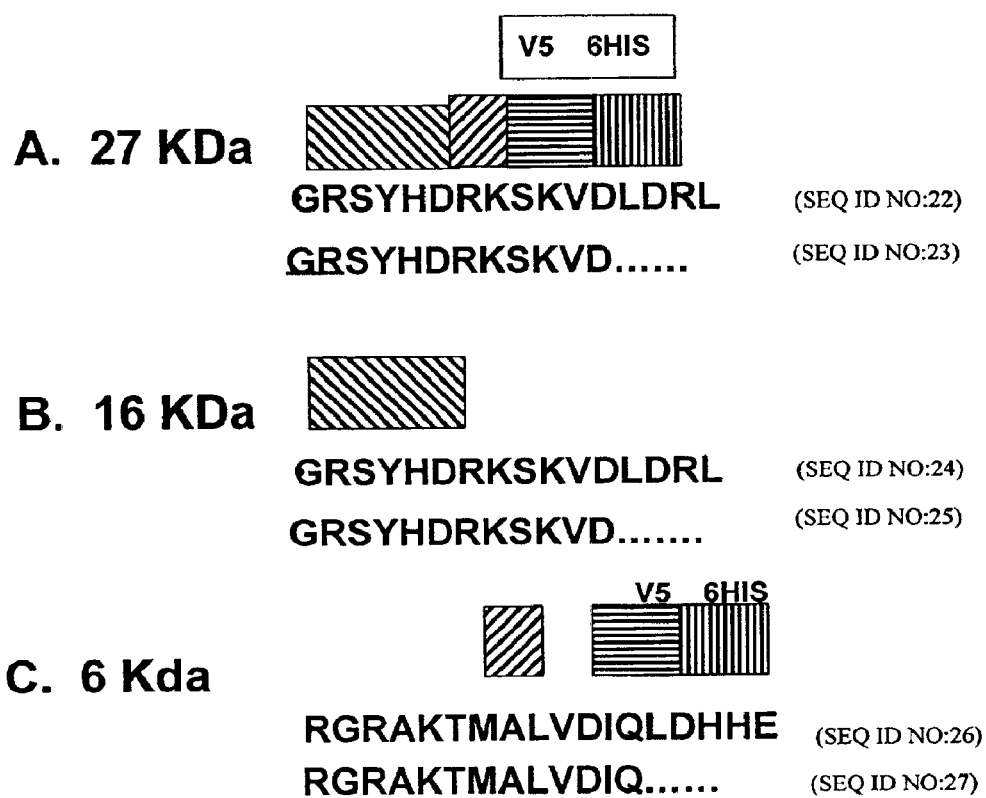
FIG. 20 is a representation of fragments obtained from p35 and identified by N-terminal sequencing. In each panel, the upper sequence in black is the predicted sequence from the clone, and the lower sequence in gray is the sequence provided by N-terminal sequencing. The diagonal shadings represent two fragments of p35. Horizontal shading represents the V5 epitope and vertical shading represents the 6His tag, both of which originate from vector pCEP4/Sec-30664188 (Example 3). In Panel A, two sequences were identified, one beginning with GlyArg (shown with these two residues underlined), and the second beginning with the third residue, Ser.

Amino terminal sequence analysis of p35 demonstrated proteolytic cleavage after Arg247 (R247) or Arg249 (R249) (FIG. 20). As indicated in Panel A of FIG. 20, two peptides were found, one beginning with GlyArg (GRSYHDR . . . ; shown with the GR residues underlined), and the second beginning with the third residue, Ser (SYHDR . . . ). The ratio of these peptides was found to be SYHDR:GRSYHDR=4:1. The additional sequencing results in FIG. 20 (Panels B and C) indicate that further processing produces the remaining polypeptides seen with Coomassie blue staining but not with anti-V5 Westerns, namely the 16 kDa and 6 kDa species shown. These are joined together to provide p35.

The results presented in this Example indicate that the PDGF D gene products are dimers in both the holoprotein form (p85) and the C-terminal fragment (p35). The p85 form appears to be processed in the presence of FBS to provide the p35 form. These dimeric forms are designated PDGF DD.

Example 22

Figure 21:
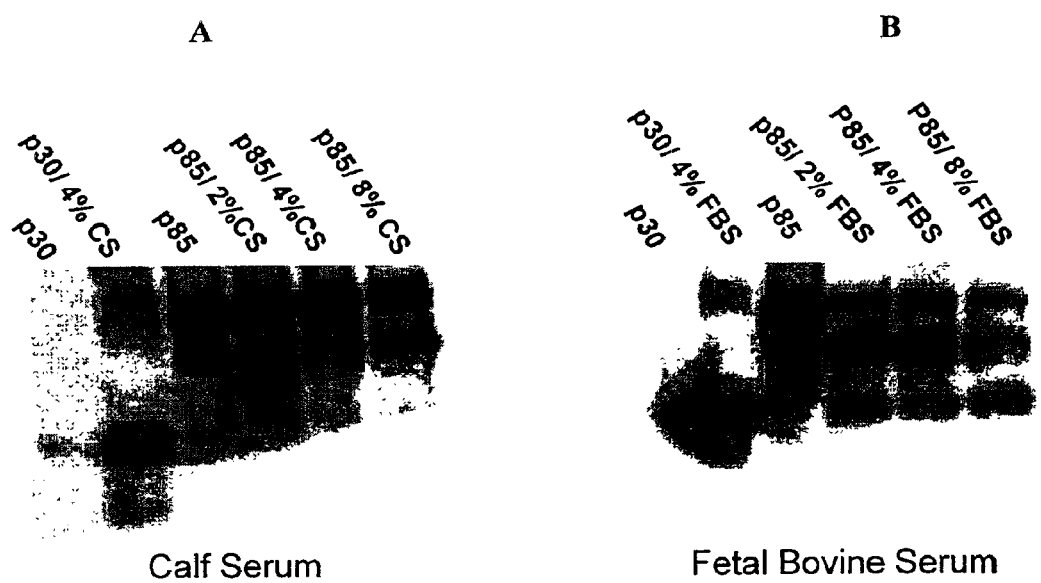
FIG. 21 is a depiction of the SDS-PAGE of the 30664188 gene product in the presence of fetal bovine serum (Panel B) and Calf Serum (Panel A). Lanes 1 and 2 in each panel show authentic 30664188 p35 alone or in the presence of serum, respectively. Lane 3 in each panel shows p85 in the absence of serum, and lanes 4–6 show p85 in the presence of increasing concentrations of the respective serum.

Processing of the 30664188 Gene Product in the Presence of Fetal Bovine Serum and Calf Serum The 30664188 gene product was incubated in the presence of increasing concentrations of calf serum (FIG. 21, Panel A) or fetal bovine serum (Panel B). The results demonstrate that only fetal bovine serum (Panel B) but not calf serum (Panel A) processes the p85 form of the 30664188 gene product to provide p35.

Example 23

Stimulation of Growth of Pulmonary Artery Smooth Muscle Cells by Growth Factors

This Example demonstrates the ability of PDGF DD to stimulate growth of pulmonary artery smooth muscle cells.

The p35 dimer of 30664188, PDGF AA or PDGF BB were added at various concentrations to pulmonary artery smooth muscle cells (Clonetics) after being cultured in 6-well plates to approximately 35% confluence, washed with DMEM, and starved overnight. After 18 hrs, BrdU was added, and 5 hrs later the cells were analyzed for BrdU incorporation using a BrdU-directed ELISA.

Figure 22:
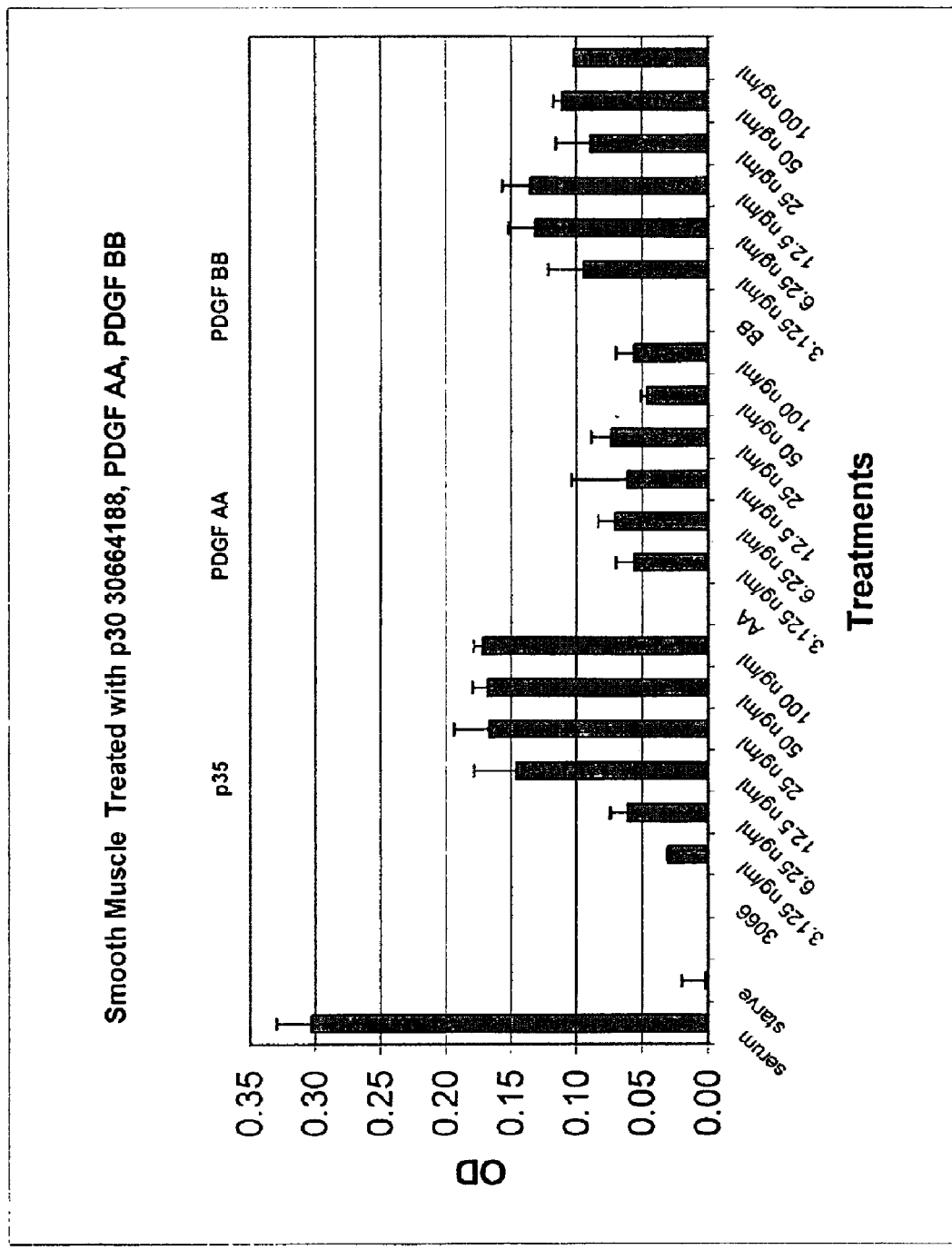
FIG. 22 is a depiction of the stimulation of the growth of pulmonary artery smooth muscle cells by growth factors. Smooth muscle cells were treated with purified p35 PDGF DD, PDGF AA or PDGF BB at the concentrations indicated, and the amount of BrdU incorporated into DNA was determined.

The results are shown in FIG. 22. It is seen that the maximal effect achieved by treatment with p35 dimer exceeds that given by both PDGF AA and PDGF BB. It is seen that the effects of p35 dimer and PDGF BB resemble each other more closely than the effect obtained with PDGF AA. Of all three growth factors tested, p35 dimer induced the greatest growth in smooth muscle cells, as determined by BrdU incorporation, with 50% maximal effect obtained at less than 12.5 ng/mL.

Example 24

Proliferation of Pulmonary Artery Smooth Muscle Cells in Response to Various Growth-Promoting Treatments This Example demonstrates the ability of PDGF DD to stimulate proliferation of pulmonary artery smooth muscle cells.

Pulmonary artery smooth muscle cells were cultured in 6-well plates to approximately 35% confluence, washed with DMEM, and starved overnight. Cells were then fed with DMEM supplemented with recombinant 30664188, a known PDGF (200 ng/ml) or 10% FBS for three days. Culture fluids were removed and replaced with same media for an additional 2–3 days. To quantitate the smooth muscle cell growth assay, cells were trypsinized and counted with a Beckman Coulter Z1 series counter (Beckman Coulter, Fullerton, Calif.).

Figure 23:
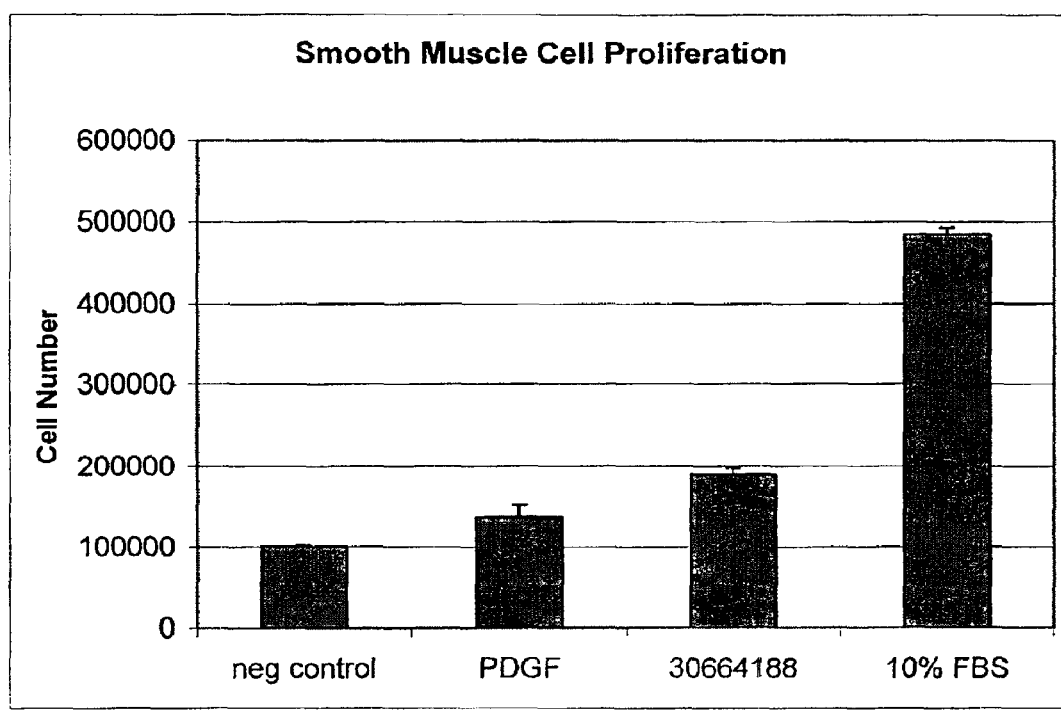
FIG. 23 is a diagram showing the proliferation of pulmonary artery smooth muscle cells in response to various treatments.

The results are shown in FIG. 23. It is seen that PDGF produces a modest increase in cell number, whereas treatment with 30664188 provides an effect, compared with control, that is almost double that observed with PDGF. A positive control using treatment with 10% FBS gave a very pronounced effect. Treatment of smooth muscle cells with 30664188 and PDGF BB led to elongated bipolar spindle shaped phenotype in contrast to the flat club shaped phenotype observed with serum.

30664188 is an effective stimulant of pulmonary artery smooth muscle cell proliferation, and suggests that 30664188 has a therapeutic use in wound healing, tissue repair and cartilage repair. Furthermore, antibodies directed against 30664188 may have therapeutic use in inhibiting or preventing restenosis of patent vasculature.

Example 25

Proliferation of Saphenous Vein Cells in Response to Various Growth-Promoting Treatments This Example illustrates the ability of PDGF DD to stimulate proliferation in saphenous vein cells. Saphenous vein cells (Clonetics) were treated and analyzed as described in Example 24. The results (not shown) indicate that PDGF produces a slightly lower increase in cell number than does treatment with 30664188, which provides proliferation to almost 5 times the cell number seen with the control. A positive control using treatment with 10% FBS gave a very pronounced effect. 30664188 is an effective stimulant of saphenous vein cell proliferation, and suggests that 30664188 and 30664188 antibodies has a therapeutic use in wound healing, tissue repair and cartilage repair. Furthermore, antibodies directed against 30664188 may have therapeutic use in inhibiting or preventing restenosis of patent vasculature.

Example 26

Mouse Model for Inflammatory Bowel Disease

A widely recognized animal model for inflammatory bowel disease is the mouse dosed with the sodium form of dextran sulfate.

Materials and Methods

Colitis Study Design. Normal female Balb/c mice (Harlan Labs), 6–8 weeks old weighing approximately 20 g, were housed 3–5 animals per cage in polycarbonate cages with filter tops and given food (Harlan Teklad mouse chow) and tap water ad libitum. Mice were acclimated for 6 days (Day-7 through Day-1) and then given water orally (po) ad libitum containing 5% dextran sulfate sodium (DSS) or control water ad libitum for 7 days (Day 0 through Day 6). DSS (Spectrum Chemicals, Gardena Calif.) was made as a 5% solution in tap water; DSS was made every other day and stored at 4° C. Mice were divided into 4 treatment groups (Table 14). On Day 0, daily intraperitoneal (ip) treatments with vehicle (1M L-arginine in phosphate buffered saline) or protein (CG53135 or CG52053, 5 mg/kg) were initiated and continued each morning through Day 6. On Day 7, mice were sacrificed by exposure to $CO_2$.

TABLE 14

Treatment Groups

| Group | N[a] | Treatment |
|---|---|---|
| 1 | 5 | Normal control: no DSS water + vehicle ip |
| 2 | 10 | Disease control: DSS water po + vehicle ip |
| 3 | 10 | CG53135: DSS water po + 5 mg/kg CG 53135 ip |
| 4 | 5 | DSS water po + 5mg/kg CG52053 ip |

[a]N = number of animals per group

Protein production. The cDNA for CG52053 was identified and cloned into the pCEP4/Sec vector (Invitrogen, Carlsbad, Calif.) and transfected into human embryonic kidney cells (HEK 293). The transfected cells were selected using Hygromycin B and then scaled up in 10 L bioreactors using DMEM medium containing 10% FBS. The CG52053 protein was purified from the culture medium by ion-exchange and metal affinity chromatography. The final purified CG52053 was diluted in 20 mM Tris HCl (pH 7.4) and 50 mM NaCl.

The cDNA for CG53135 was identified and cloned into the pRSET vector (Invitrogen) to provide the vector pETMY-FGF-CX described in Example 5. The gene product of this construct provides a polypeptide incorporating (His)$_6$-(enterokinase cleavage site)-(multicloning site) at the N-terminal end of the polypeptide; in addition, in this construct, the FGF-CX sequence begins with the Ala at position 2 of Table 1 (SEQ ID NO:2). This vector was transformed into Escherichia coli. The E. coli cells were grown up to 10 L scale and infected with CE6 phage to produce the recombinant CG53135. The recombinant protein was purified by disrupting the E. coli cells in a microfluidizer and extraction with 1M L-arginine solution, followed by multiple metal affinity chromatography steps. The final purified protein was dialyzed into phosphate buffered saline containing 1M L-arginine. Protein purity was determined by SDS-PAGE analysis and identities were confirmed by Western blot analysis. Activity of proteins was determined by BrdU incorporation assay (Roche Molecular Biochemicals) using a 5 hr incorporation time and NIH 3T3 cells.

Body weights were measured daily and at termination on day 7. Additional parameters measured at necropsy included colon length, colon weight and spleen weights. Colon and spleen were collected into formalin for histopathologic evaluation.

Colon content was scored at necropsy according to the following criteria:

0=normal to semi-solid stool, no blood observed

1=normal to semi-solid stool, blood tinged

2=semi-solid to fluid stool with definite evidence of blood

3=bloody fluid

Pathology Methods

Three sections approximately 1 cm apart from the distal end (area that is most severely affected in this model) and 3 sections approximately 1 cm apart from the proximal end (less severely affected area) were processed for paraffin embedding, sectioned and stained with hematoxylin and eosin for pathologic evaluation.

For each section, submucosal edema was quantitated by measuring the distance from the muscularis mucosa to the internal border of the outer muscle layer. Inflammation (foamy macrophage, lymphocyte and PMN infiltrate) was assigned severity scores according to the following:

Normal=0
Minimal=1
Mild=2
Moderate=3
Marked=4
Severe=5

Splenic lymphoid atrophy was also scored by the above criteria.

The parameters reflecting epithelial cell loss/damage were scored individually using a % area involved scoring method:

None=0
1–10% of the mucosa affected=1
11–25% of the mucosa affected=2
26–50% of the mucosa affected=3
51–75% of the mucosa affected=4
76–100% of the mucosa affected=5

Parameters that were scored using % involvement included:

Colon glandular epithelial loss—this includes crypt epithelial as well as remaining gland epithelial loss and would equate to crypt damage score.

Colon Erosion—this reflects loss of surface epithelium and generally was associated with mucosal hemorrhage (reflective of the bleeding seen clinically and at necropsy).

For each animal, 3 proximal (less severe lesions) and 3 distal (most severe lesion) areas were scored and the mean of the scores for each of the regions was determined. Group means and % inhibition from disease control were determined. By doing it this way (rather than summing the scores from various sections) one can look at the mean±SE for in individual Aparameter (represented by 3 sections) and equate it to a delineated severity. As an example, if the mean is 4 for gland epithelial loss one knows that 51–75% of the mucosa was devoid of epithelium.

The 3 important scored parameters (inflammation, glandular epithelial loss, erosion) were ultimately summed to arrive at a sum of histopathology score which indicates the overall damage and would have a maximum score of 15.

One final summation of proximal+distal summed scores was done to reflect the overall total colonic severity score.

Statistics. The mean and standard error (SE) for each treatment group was determined for each parameter scored; the data were compared to the data for the disease controls (Group 2) using a 2-tailed Student's t test with significance at $p \leq 0.05$.

Results

Live Phase, Necropsy and Organ Weight

All animals except DSS+vehicle control mouse 4 survived to study termination. Mouse 4 was found dead the morning of necropsy on day 7.

Figure 24:
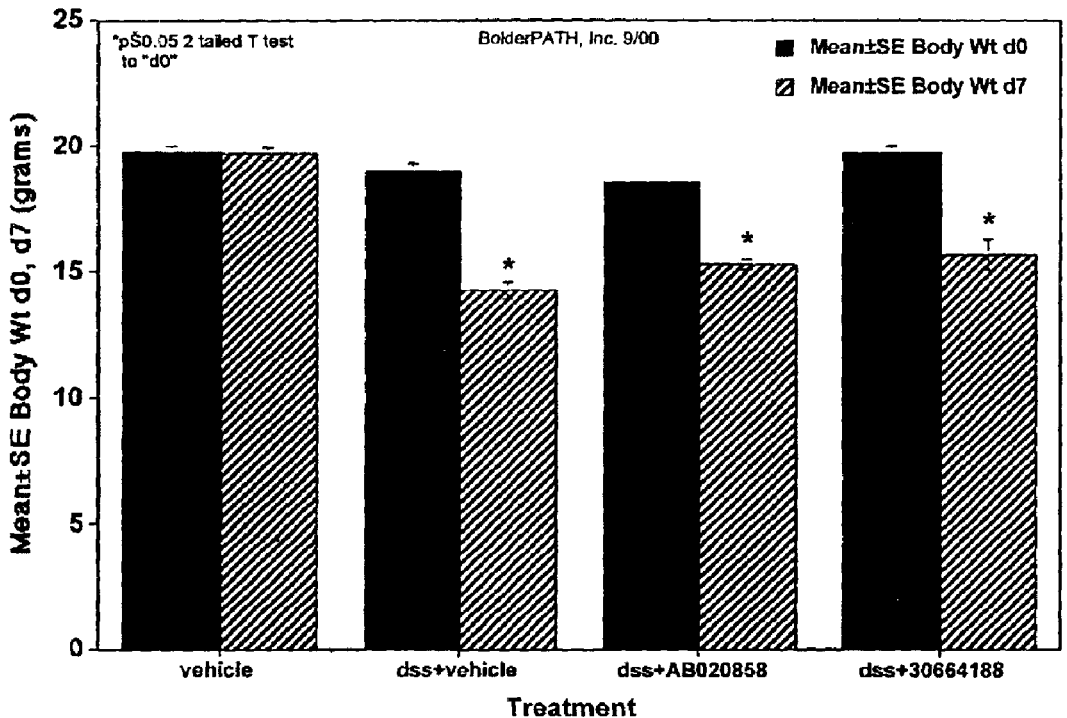
FIG. 24 presents bar graphs representing mean body weights of mice on day 0, and on day 6 after various treatments.
Figure 25:
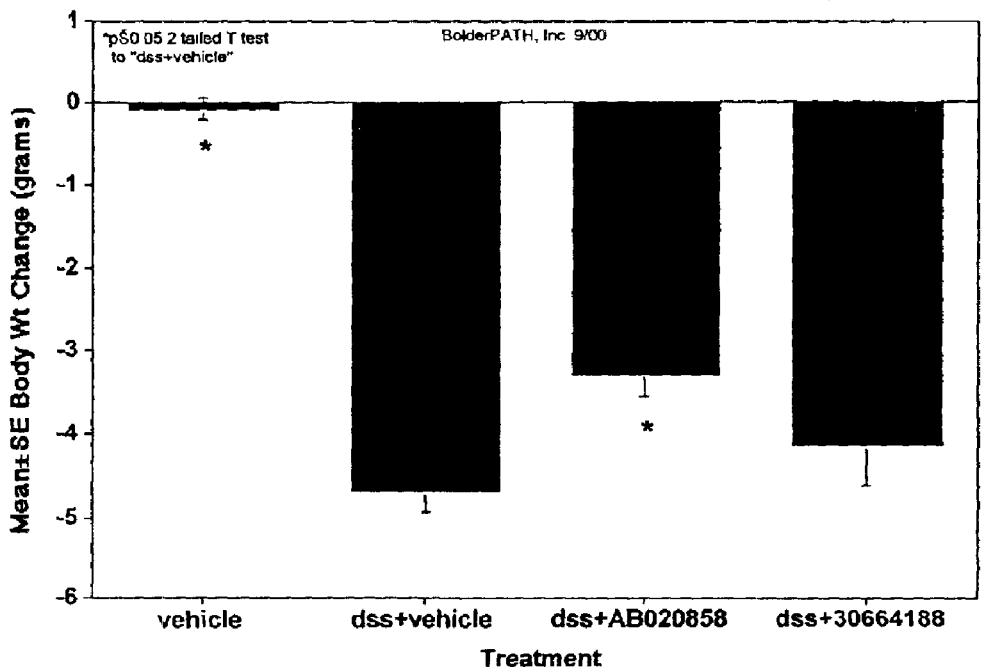
FIG. 25 presents bar graphs representing changes in mean body weights of mice between day 0 and day 6 after various treatments.
Figure 26:
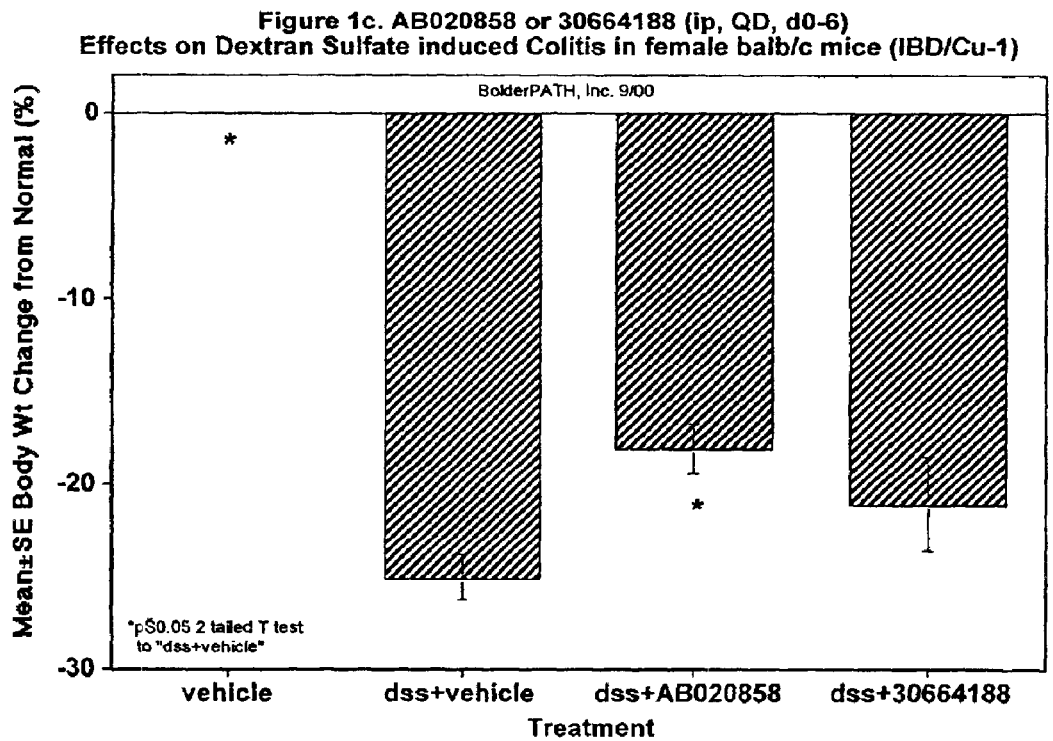
FIG. 26 presents bar graphs representing percent changes in mean body weights of mice between day 0 and day 6 after various treatments.

DSS treatment-related changes in body weight were present by day 3 in all DSS treated mice. At study termination, DSS+vehicle controls had a 25% decrease in body weight (FIGS. 24, 25 and 26). A significant beneficial effect on DSS induced weight loss was seen in mice given FGF-CX, referred to as AB020858 (FIGS. 25 and 26).

Clinical evidence of bloody diarrhea was evident in all DSS+vehicle animals except animal 1. At necropsy all DSS controls had blood or blood tinged fluid in the colon. In contrast, mice treated with AB020858 generally had semisolid stool and little evidence of blood. Similar findings occurred in mice treated with 30664188.

Figure 34:
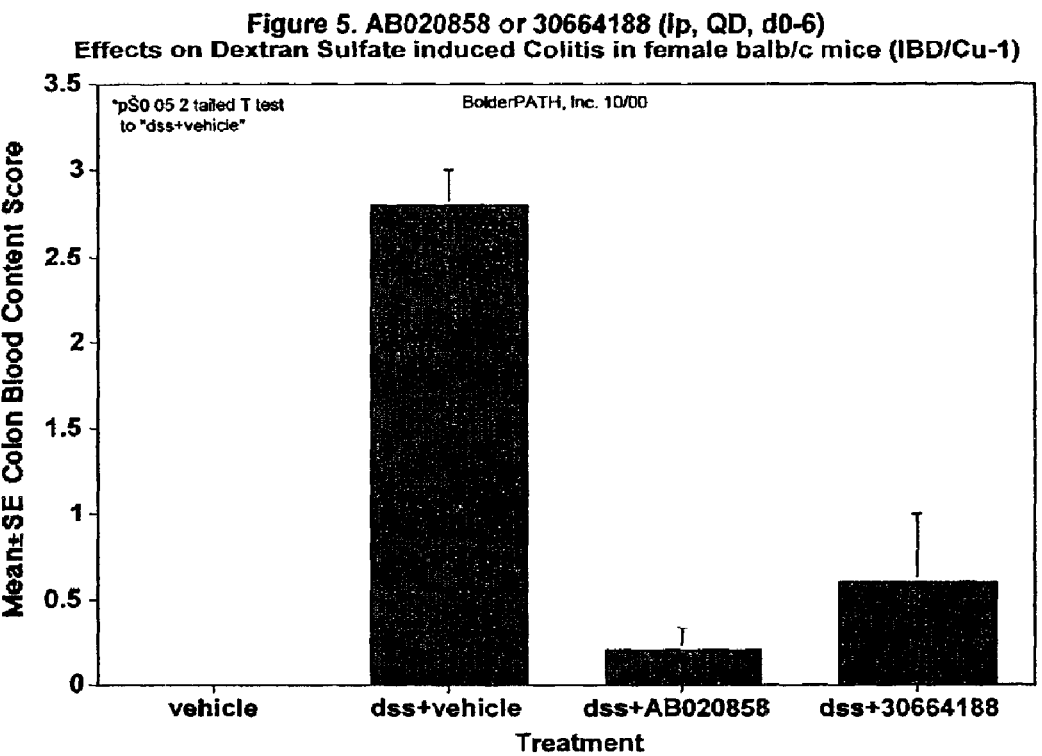
FIG. 34 presents bar graphs representing mean colon blood content scores in mice after various treatments.

Colon content scores reflecting colonic hemorrhage were dramatically decreased (93%) in mice treated with AB020858 and (79%) in mice treated with 30664188 (FIG. 34).

Figure 27:
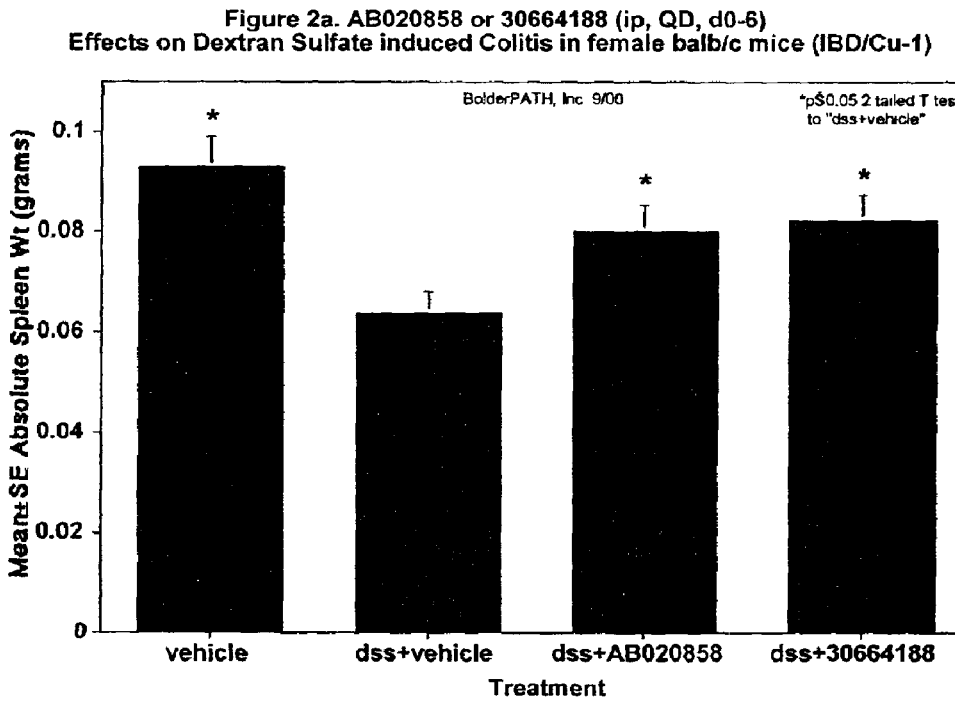
FIG. 27 presents bar graphs representing changes in mean weights of the spleens of mice between day 0 and day 6 after various treatments.
Figure 28:
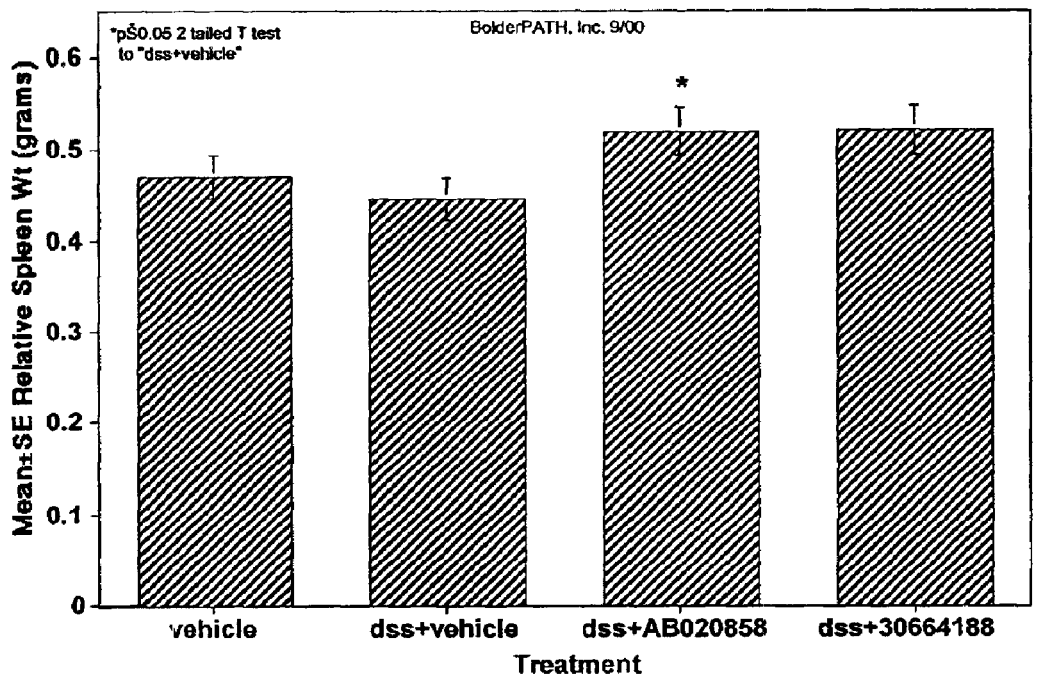
FIG. 28 presents bar graphs representing changes in mean spleen weights of mice between day 0 and day 6 after various treatments.

Absolute spleen weights (FIGS. 27 and 28) were decreased approximately 30% in mice treated with vehicle. Treatment with AB020858 resulted in 55% reduction of the DSS-induced losses in spleen weights. Treatment with 30664188 reduced the splenic weight losses by 62%.

Figure 29:
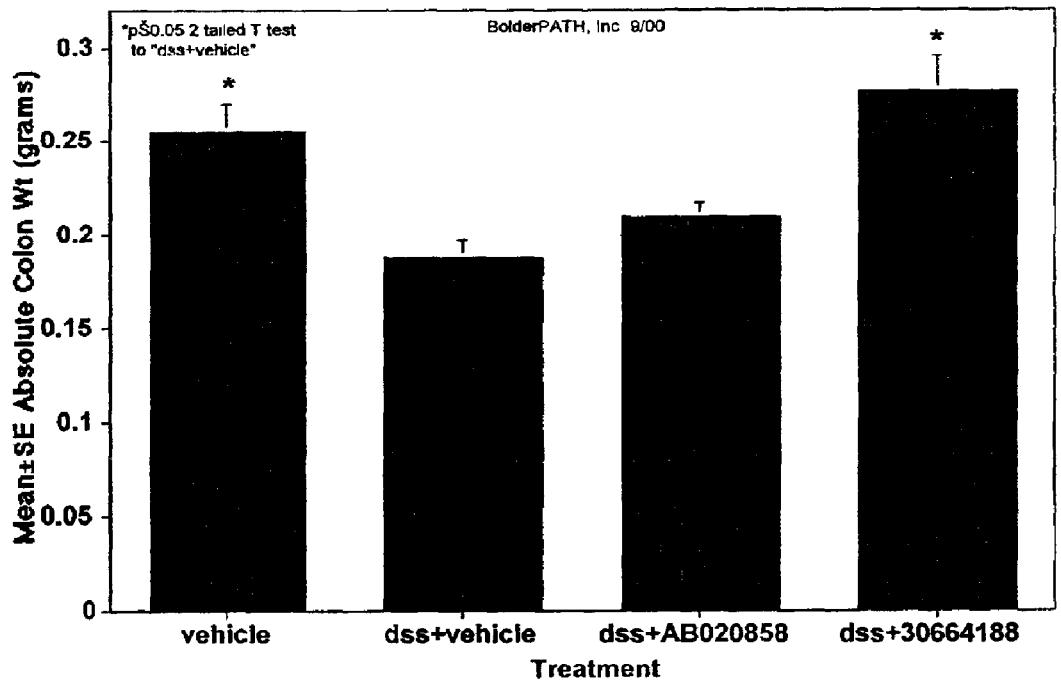
FIG. 29 presents bar graphs representing changes in mean colon weights of mice between day 0 and day 6 after various treatments.
Figure 30:
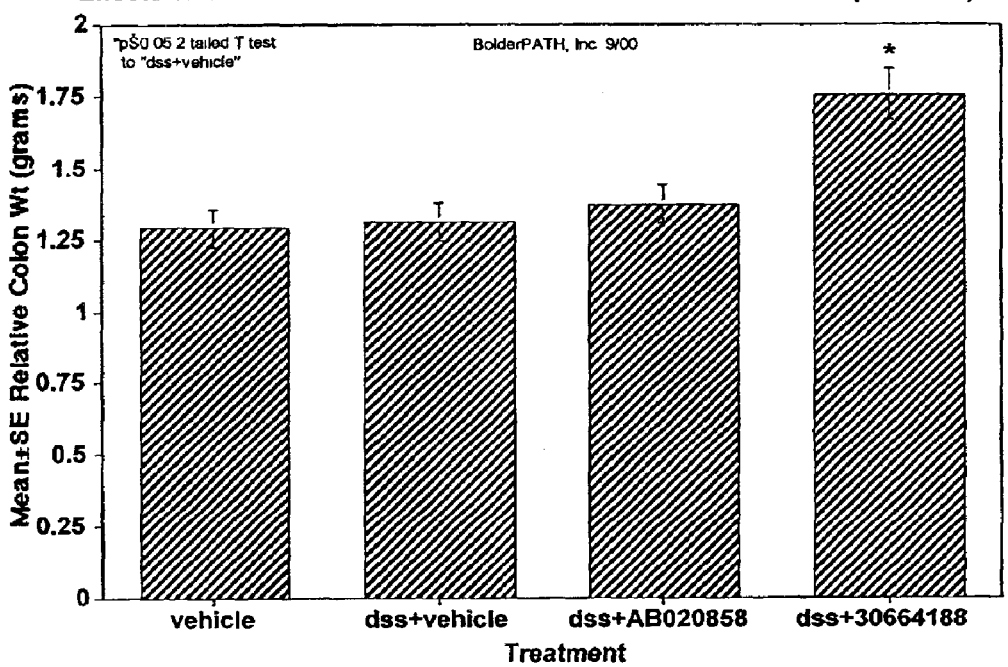
FIG. 30 presents bar graphs representing changes in mean colon weights of mice between day 0 and day 6 after various treatments.
Figure 31:
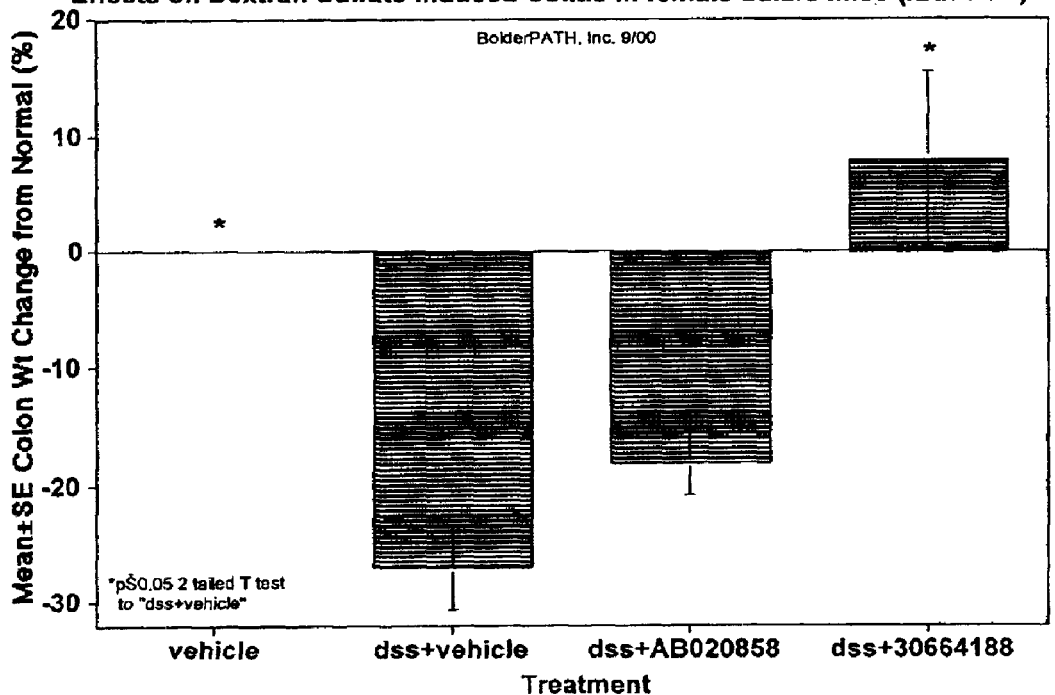
FIG. 31 presents bar graphs representing percent changes in mean colon weights of mice between day 0 and day 6 after various treatments.

Absolute colon weights (FIGS. 29 and 30) were decreased approximately 26% in mice treated with vehicle. Treatment with AB020858 resulted in slight but not significant reduction of the DSS-induced changes in colon weights. Treatment with 30664188 reversed the colon weight decreases (FIGS. 30 and 31).

Figure 32:
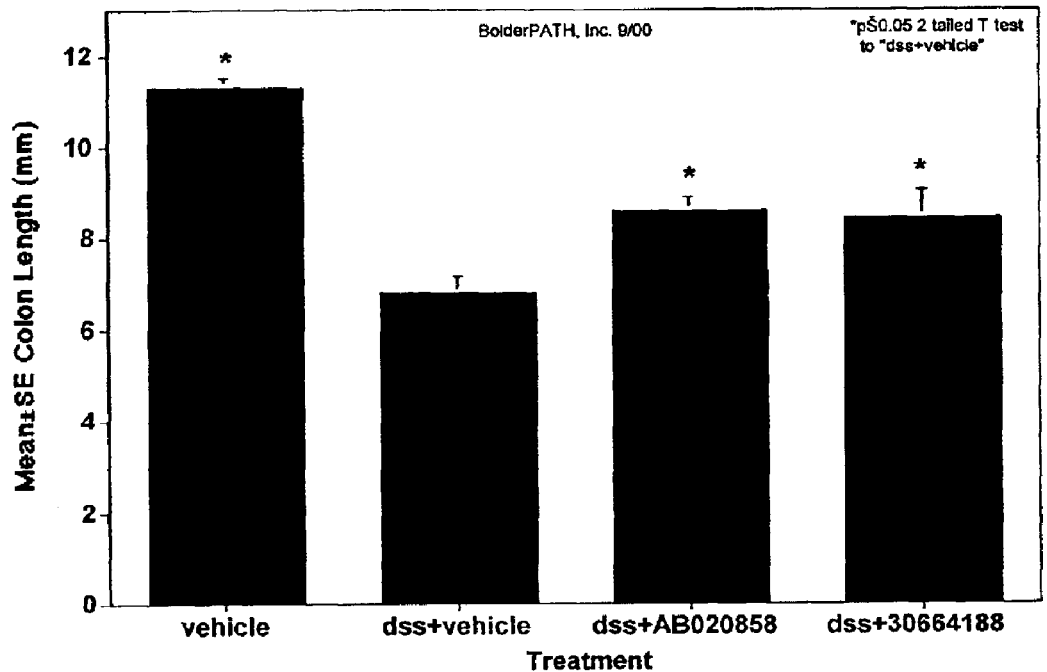
FIG. 32 presents bar graphs representing changes in mean colon lengths of mice between day 0 and day 6 after various treatments.
Figure 33:
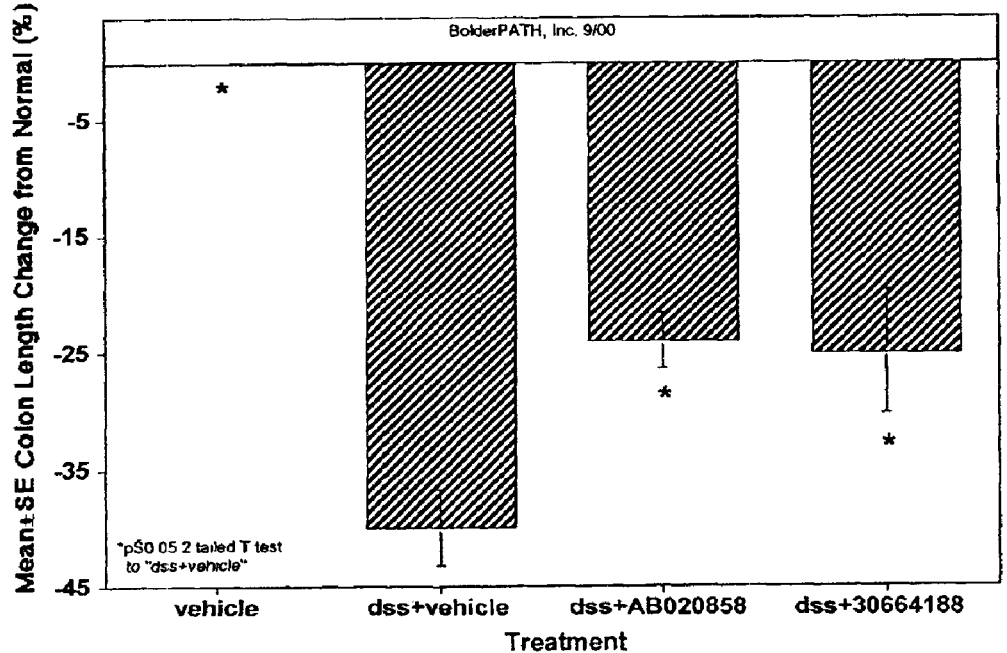
FIG. 33 presents bar graphs representing percent changes in mean colon lengths of mice between day 0 and day 6 after various treatments.

Absolute colon lengths (FIGS. 32 and 33) were decreased approximately 40% in mice treated with DSS+vehicle. Treatment with AB020858 resulted in significant (40%) reduction of the DSS-induced changes in colon length. Treatment with 30664188 reduced the colon length loss 36%.

Histopathology Findings

Figure 35:
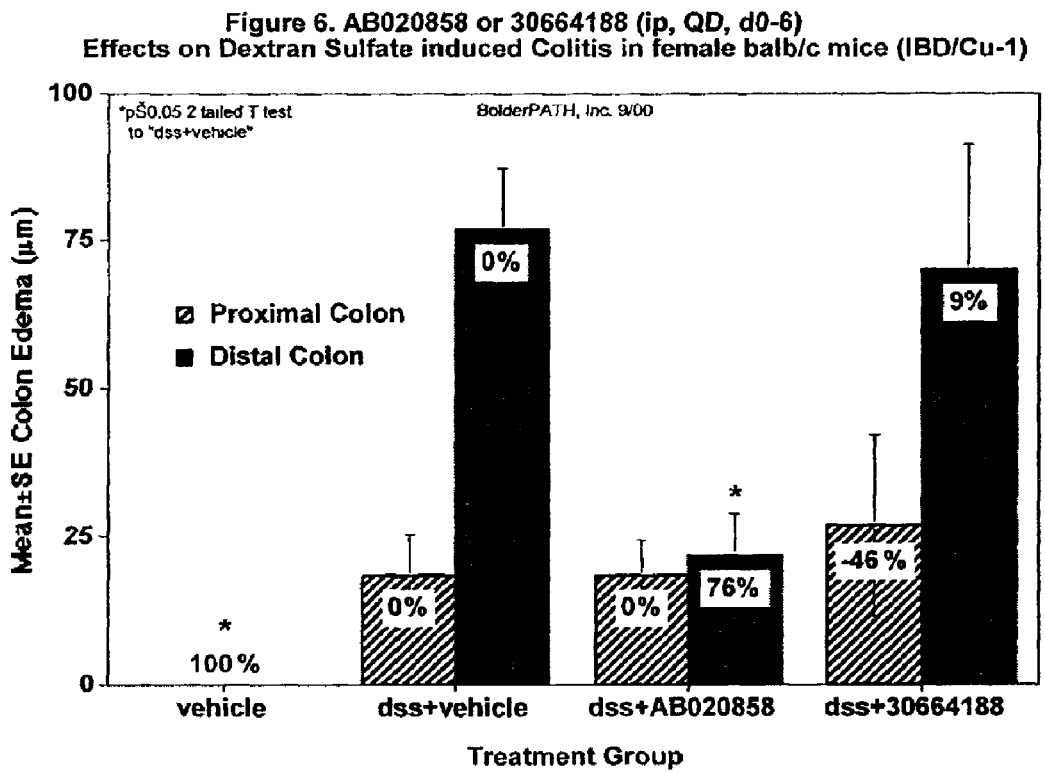
FIG. 35 presents bar graphs representing mean colon edema scores in mice after various treatments.

Histopathology was conducted on the full length of the colon. Lesions were much greater in the distal vs. proximal colon, as expected. Quantitation of efficacy of treatment is based primarily on inhibition of pathological changes in this location. Colonic edema in the distal colon was inhibited 76% by treatment with AB020858 whereas treatment with 30664188 did not inhibit the edema (FIG. 35).

Figure 36:
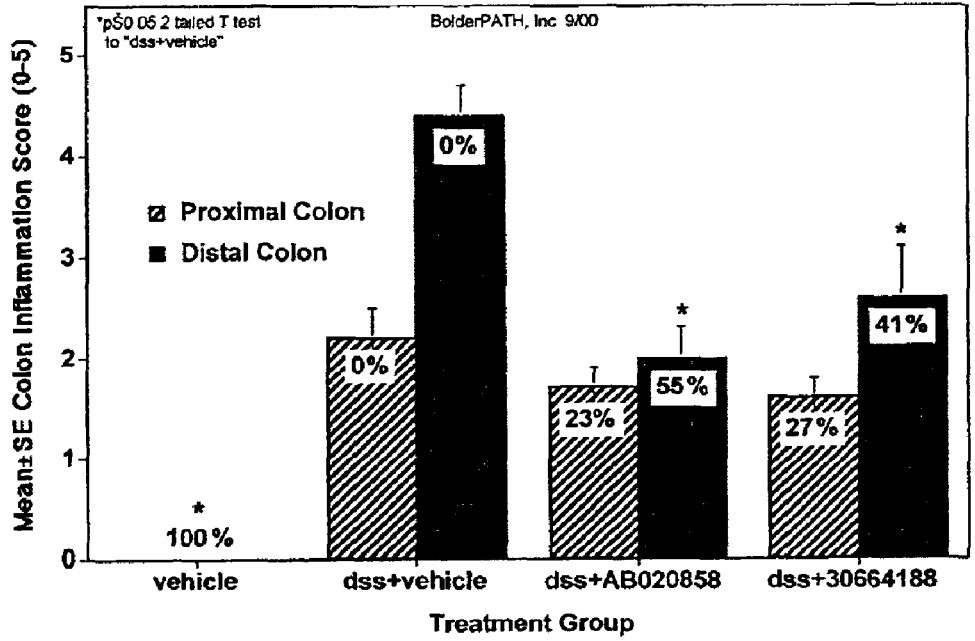
FIG. 36 presents bar graphs representing mean colon inflammation scores in mice after various treatments.

Colonic inflammation in the distal colon was inhibited 55% by treatment with AB020858 and 41% by treatment with 30664188 (FIG. 36).

Figure 37:
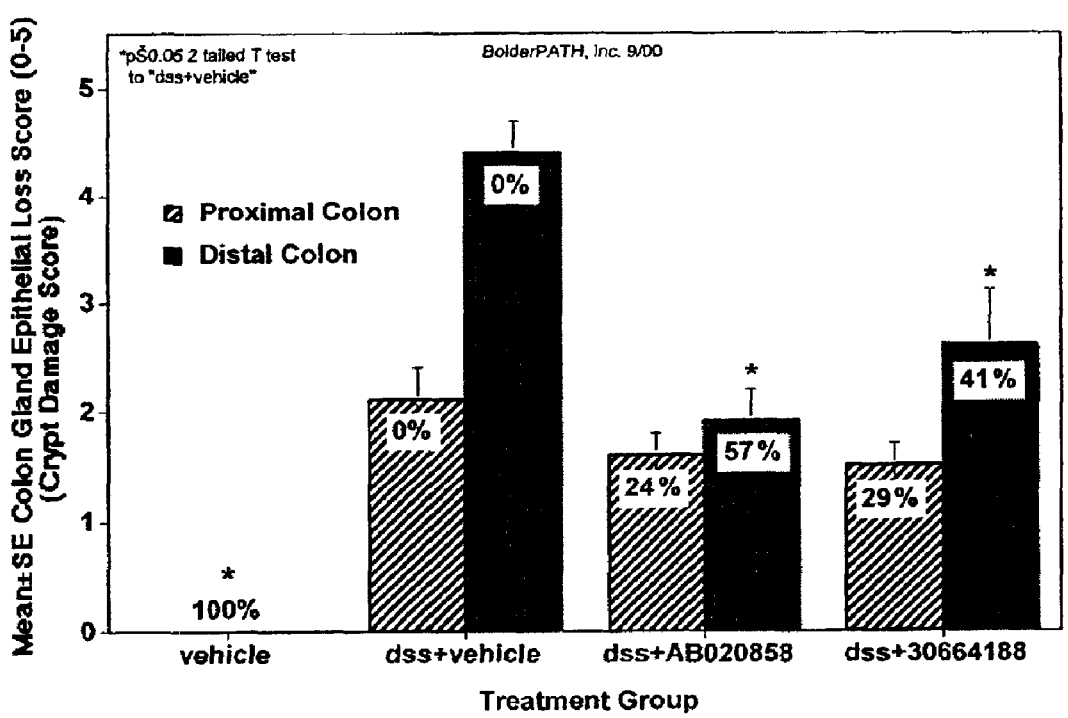
FIG. 37 presents bar graphs representing mean colon epithelial loss scores in mice after various treatments.
Figure 38:
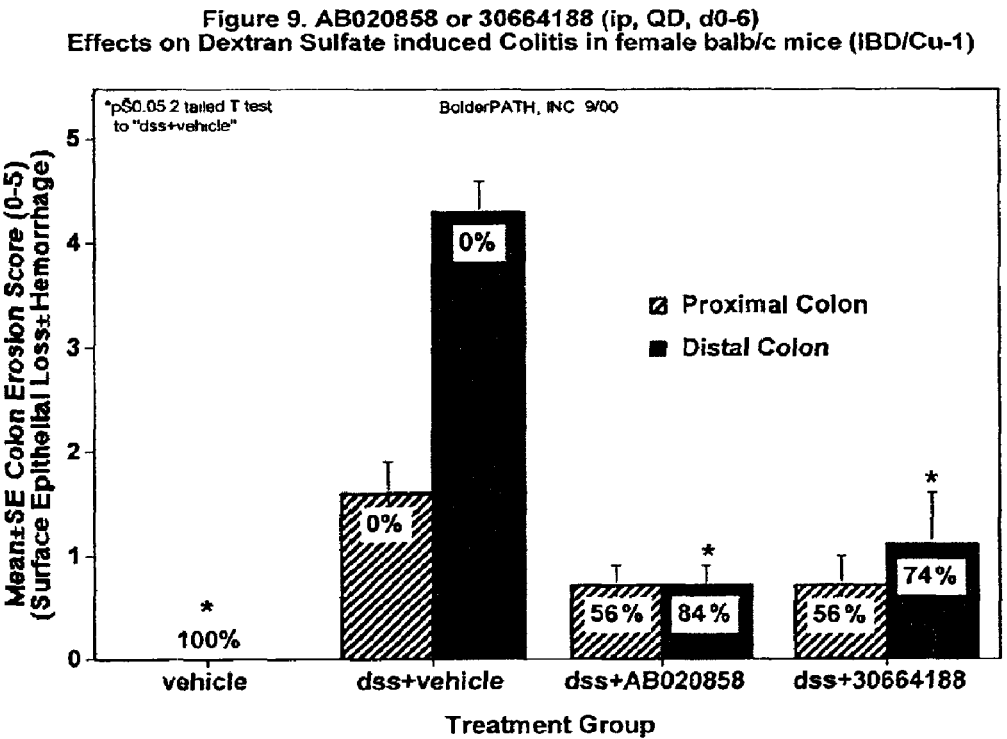
FIG. 38 presents bar graphs representing mean colon erosion content scores in mice after various treatments.

Protection of colonic epithelium (both crypts and remainder of the gland), as determined by the epithelial loss score, was 57% in mice given AB020858 and 41% in those treated with 30664188 (FIG. 37). Further evidence of mucosal epithelial protection in the distal colon was evident on evaluation of degree of surface epithelial loss leading to erosion/ulceration. As shown by the colon erosion scores, AB020858 treatment gave 84% inhibition of the erosive lesions and 30664188 treatment resulted in 74% inhibition (FIG. 38).

Figure 39:
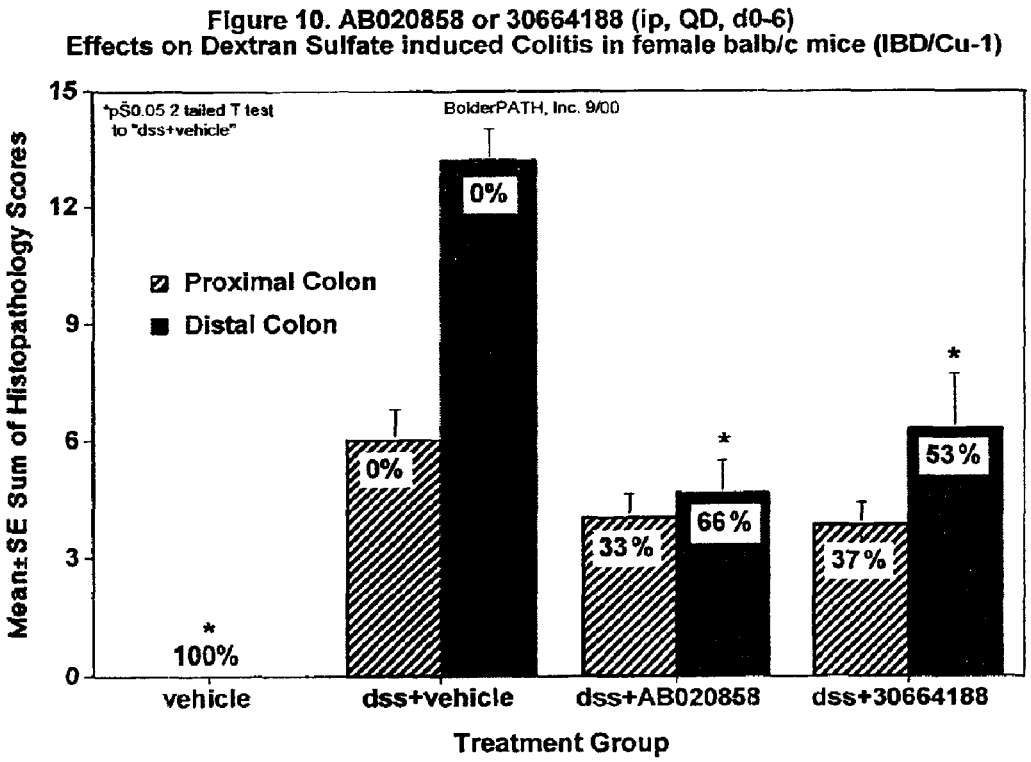
FIG. 39 presents bar graphs representing sum of histopathology scores in mice after various treatments.
Figure 40:
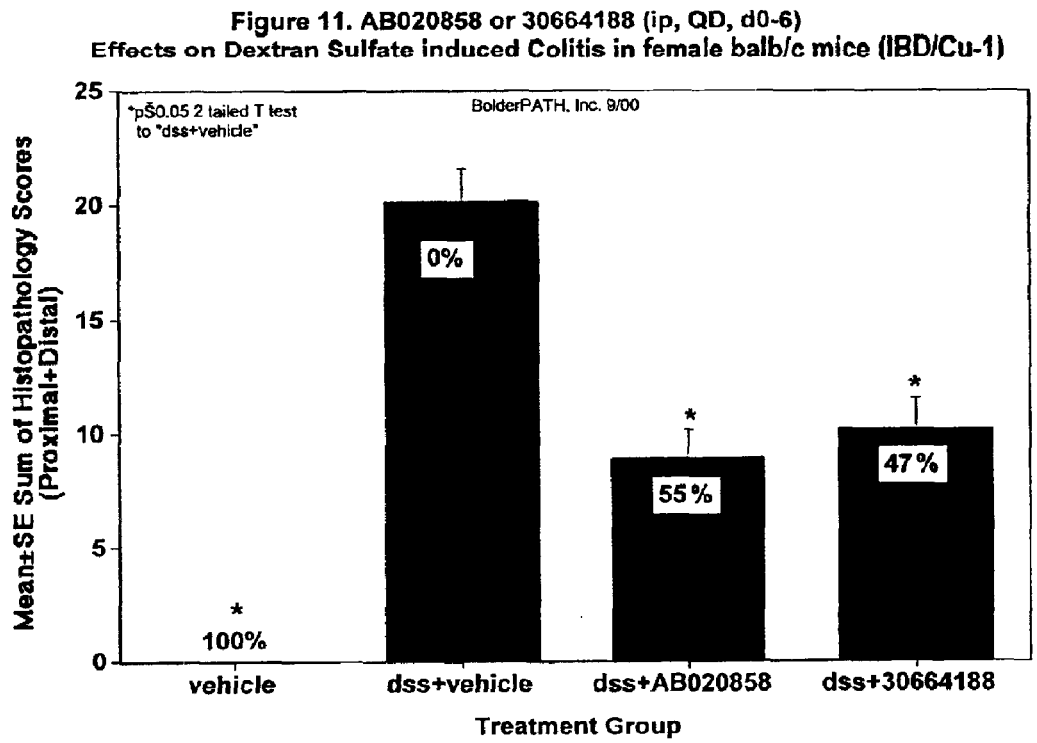
FIG. 40 presents bar graphs representing histopathology score differencess in mice after various treatments.

Summing the important histologic scores for inflammation, glandular epithelial damage and erosion (FIG. 39), it is seen that an overall protective effect results from the treatment with AB020858, which provides 66% inhibition of the pathology. Treatment with 30664188 resulted in 53% inhibition of the overall score. Slight but not significant (33–37%) inhibition of the total histologic scores was evident for proximal colon. Results for the colon overall are shown in FIG. 40.

Figure 41:
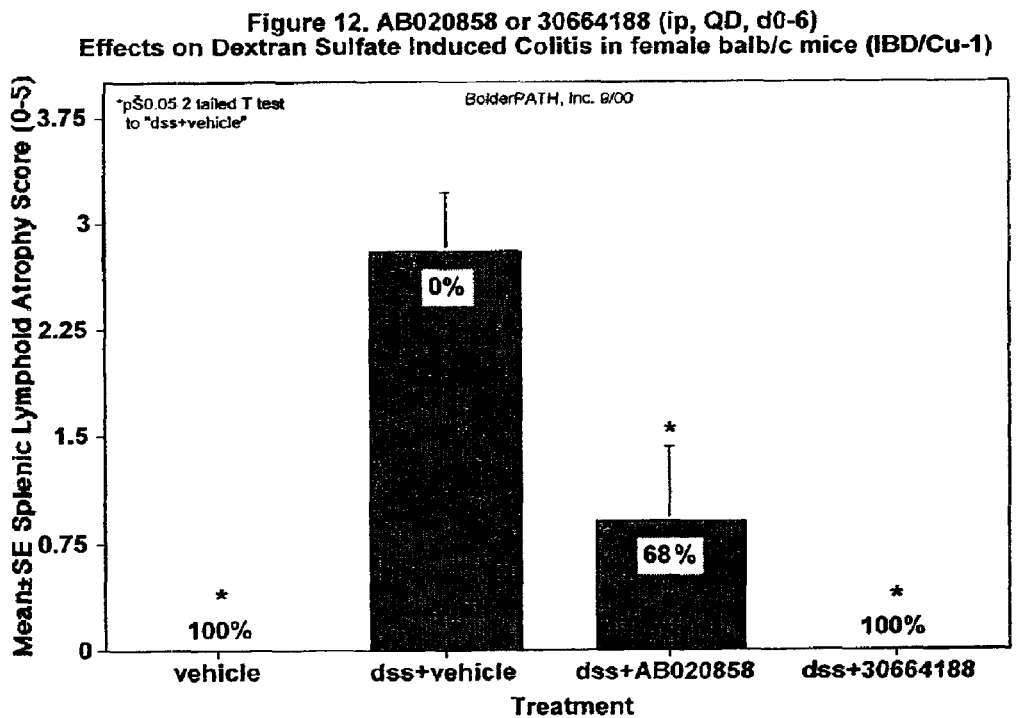
FIG. 41 presents bar graphs representing mean splenic lymphoid atrophy scores in mice after various treatments.

Splenic weight decreases were largely a result of splenic lymphoid atrophy. Treatment with both proteins inhibited this parameter as well (FIG. 41).

Discussion and Conclusions

In this model of inflammatory bowel disease, in which mice are exposed to 5% DSS for 7 days, most animals develop marked to severe distal colonic inflammation/edema in association with crypt and colonic glandular epithelial loss and erosion/ulceration leading to marked hemorrhage. Lesions in the proximal colon are much milder but similar in character.

Cotemporaneous treatment with AB020858 (5 mg/kg, qd, d0–6) resulted in clinical benefit (reduced body weight loss) as well as protection against development of hemorrhagic diarrhea, a common feature of this model. Stressed unhealthy DSS treated mice have splenic lymphoid atrophy. This parameter (reflected by weight changes and histologic alterations) was also benefited by treatment with AB020858.

Colonic shortening (due to inflammation and mucosal tissue loss) was inhibited 40% by treatment with AB020858. This gross observation was strongly supported by the histologic observations of mucosal epithelial preservation in the crypts, colonic glands and surface epithelium (see FIGS. 42 and 43). In FIG. 42, viewed at 400× in the original images, the normal colonic mucosa has uniform glandular architecture and no submucosal edema (upper left). The disease control has no mucosal glands and surface epithelium, exposing blood vessels of the severely inflamed lamina propria to the lumen and resulting in hemorrhage (upper right). treatment with CG53135 preserves mucosal integrity and results in decreased epithelial loss and reduced inflammation in the lamina propria (lower left). Treatment with CG52053 decreases epithelial loss and mucosal inflammation, although to a lesser degree than treatment with CG53135 (lower right). In FIG. 43, viewed at 50× in the original images, the normal control shows normal colonic mucosa with uniform glandular architecture and no submucosal edema (upper left). DSS-induced colitis results in loss of glandular architecture and edema that separates the mucosa from the outer muscle layers (upper right). Treatment with CG53135 inhibits the severe mucosal changes and submucosal edema induced by DSS (lower left). Treatment with CG52053 results in some inhibition of inflammation and loss of glandular architecture but no inhibition of submucosal edema (lower right). This histologic evidence of mucosal protection corroborates the dramatic necropsy observation that very little hemorrhagic diarrhea occurs.

The results of the experiments reported in this Example indicate that, in mice in which inflammatory bowel disease is induced by oral administration of DSS for 7 days, simultaneous treatment with the growth factors employed here during the course of exposure to DSS led to significant therapeutic benefits compared to untreated DSS controls.

Example 27

Dose Responsive Effects of AB020858 Female Swiss Webster Mice with Dextran Sulfate-induced Colitis The experiments reported in this Example report the results of dose titration experiments in an animal model of inflammatory bowel disease using a different strain of mouse than that used in Example 26.

Introduction and General Methods

Colitis Study Design. Normal female Swiss-Webster mice (Harlan Labs), 6–8 weeks old weighing approximately 20 g, were acclimated for 4 days (Day-4 through Day-1) and then given water orally (po) ad libitum containing 5% dextran sulfate sodium (DSS) or control water ad libitum for 7 days (Day 0 through Day 6). DSS (Spectrum Chemicals, Gardena Calif.) was made as a 5% solution in tap water; DSS was made every other day and stored at 4° C. Mice were divided into 8 treatment groups including QD doses of 0.3, 1, 3 and 10 mg/kg, and a BID dose regimen of 5 mg/kg per dose (Table 15). On Day 0, daily intraperitoneal (ip) treatments with vehicle (1M L-arginine in phosphate buffered saline) or CG53135 protein in vehicle were initiated and continued through Day 6. On Day 7, mice were sacrificed with $CO_2$.

TABLE 15

Treatment Groups

| Treatment Group | Normal Control[a] | Disease Control[b] QD | CG53135 QD | CG53135 QD | CG53135 QD | CG53135 QD | Disease Control[b] BID | CG53135 BID |
|---|---|---|---|---|---|---|---|---|
| Group # | 1 | 2 | 3 | 4 | 5 | 6 | 7 | 8 |
| CG 53135 (mg/kg) | 0 | 0 | 10 | 3 | 1 | 0.3 | 0 | 5 |
| Number of Test Animals | 4 | 10 | 10 | 10 | 10 | 10 | 10 | 10 |

[a]normal control = vehicle only;
[b]disease control = 5% DSS + vehicle

Protein production. The CG53135 protein was produced in *E. coli* as described in Example 26. The recombinant protein was purified by disrupting the *E. coli* cells (resuspended in a 1 M L-arginine solution) in a microfluidizer, followed by multiple metal affinity chromatography steps. The final purified protein was dialyzed into phosphate buffered saline containing 1M L-arginine.

Colon content was scored as described in Example 1.

Pathology Methods

Three sections equidistant apart from the distal one third of the colon (area that is most severely affected in this model) were processed for paraffin embedding, sectioned and stained with hematoxylin and eosin for pathologic evaluation.

For each section, scoring was done as described in Example 26.

Splenic lymphoid atrophy was also scored by the above criteria.

Epithelial cell loss/damage was scored as described in Example 26.

Parameters that were scored using % involvement included:

Colon glandular epithelial loss—this includes crypt epithelial as well as remaining gland epithelial loss and would equate to crypt damage score.

Colon Erosion—this reflects loss of surface epithelium and generally was associated with mucosal hemorrhage (reflective of the bleeding seen clinically and at necropsy).

For each animal, 3 distal (most severe lesion) areas were scored. Scoring and analysis was done as described in Example 26.

Live Phase, Necropsy and Organ Weight Results

Four animals died during the course of the study (#10 in vehicle control group 2 on day 7, #3 in group 6, 0.3 mg/kg on day 6, #5 in group 8 vehicle control BID on day 7, and #6 in group 7 5 mg/kg BID on day 6).

Figure 44:
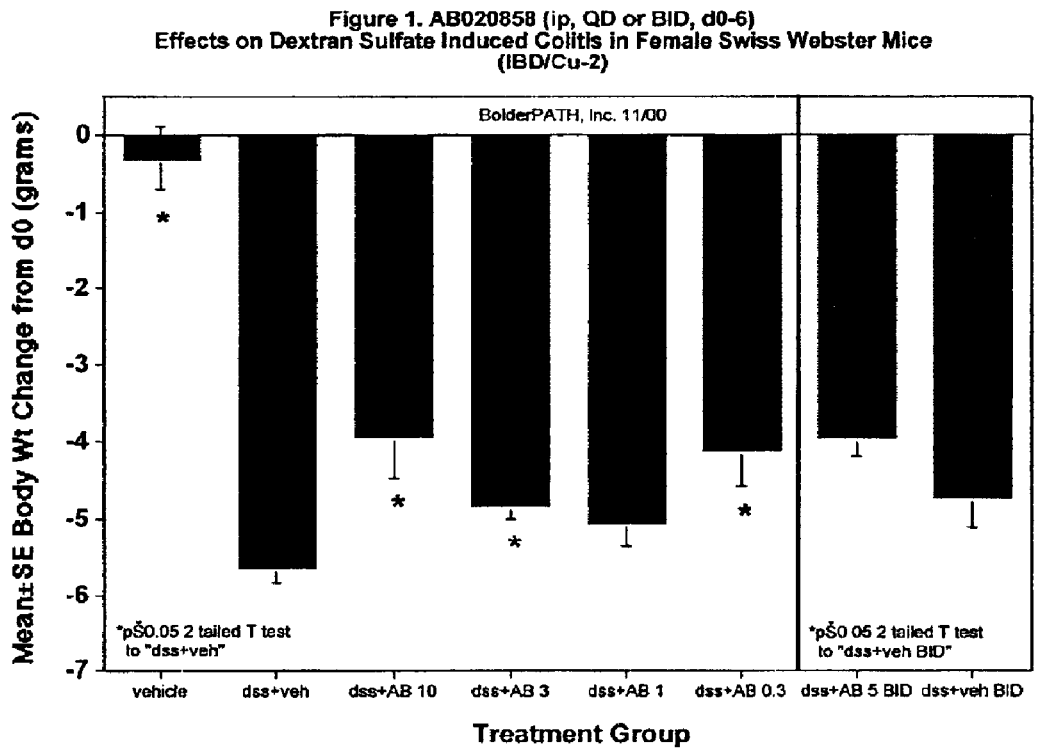
FIG. 44 presents the change in mean body weight from day 0 upon treating mice with varying doses of AB020858.
Figure 45:
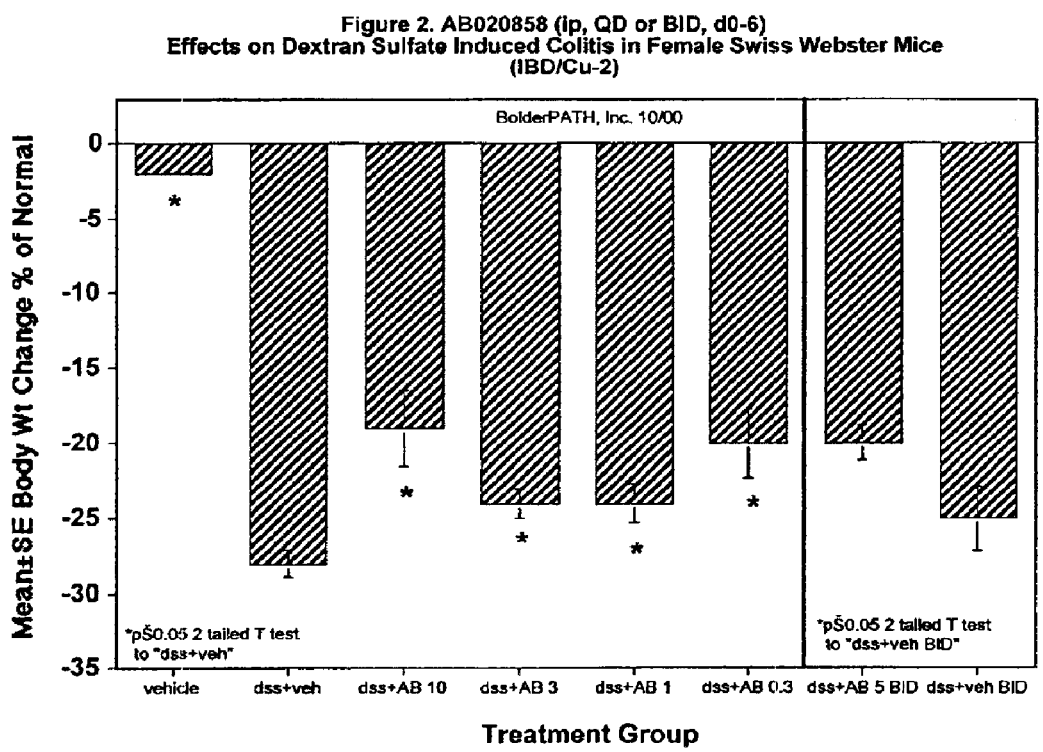
FIG. 45 presents the percent change in mean body weight from day 0 upon treating mice with varying doses of AB020858.

DSS treatment-related changes in body weight were obvious by day 5 in all DSS treated mice and ultimately were most severe in animals treated with vehicle (FIG. 44). At study termination, DSS+vehicle controls had a 28% decrease in body weight. A significant beneficial effect on DSS induced weight loss was seen in mice given AB020858 QD at all doses (FIG. 45).

Figure 46:
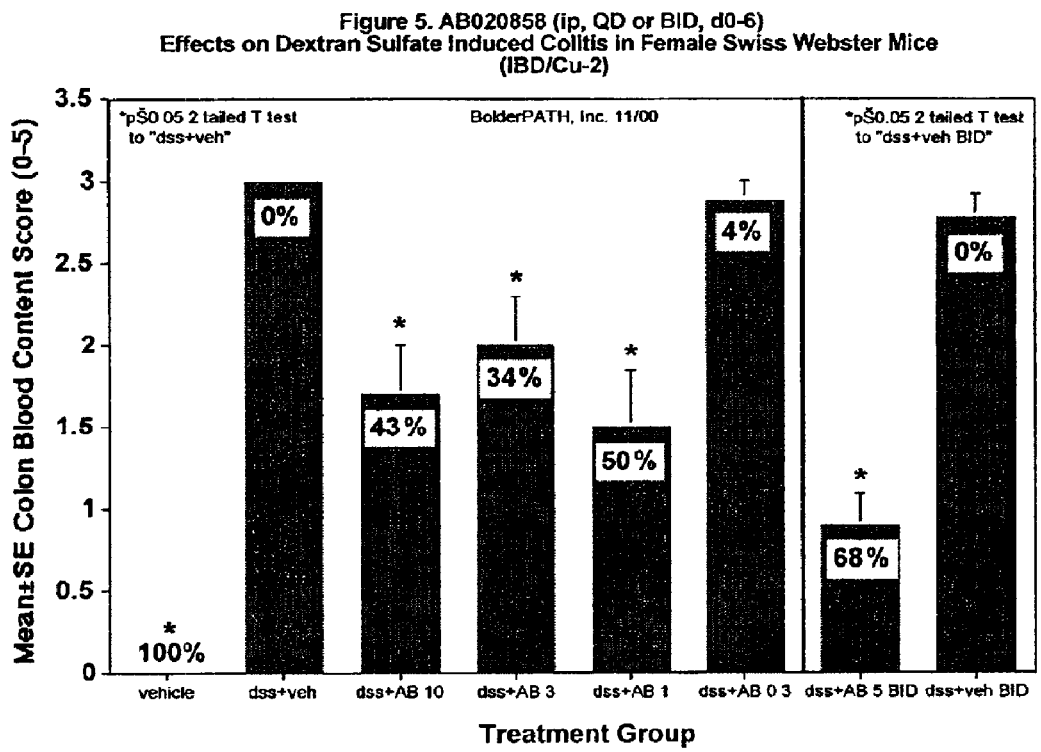
FIG. 46 presents mean colon blood content score upon treating mice with varying doses of AB020858.

Clinical evidence of bloody diarrhea was evident in all DSS+vehicle animals. At necropsy all DSS controls had blood or blood tinged fluid in the colon. In contrast, mice treated QD with 10 mg/kg AB020858 generally had semi-solid stool and less blood (except animals #5). Clinical benefit was also evident but less impressive in those given doses of 3 or 1 mg/kg QD and absent in those treated with 0.3 mg/kg (FIG. 46). Mice treated BID with 5 mg/kg had the most impressive clinical benefit (68% inhibition) and clinically these mice had the best overall improvement.

Figure 47:
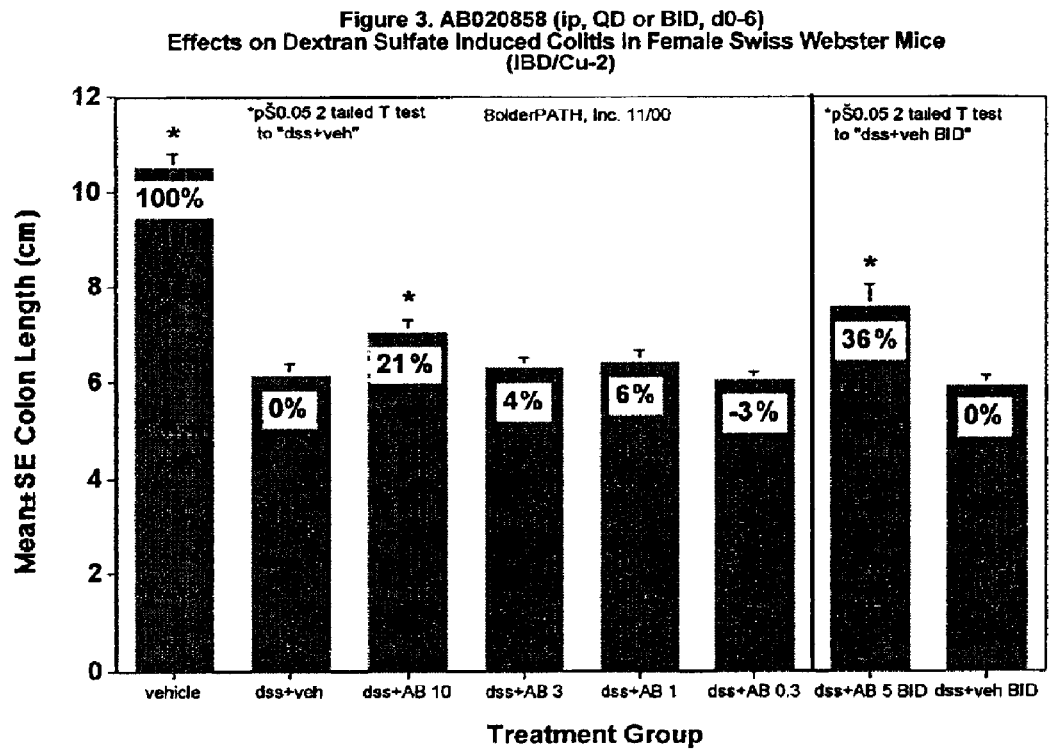
FIG. 47 presents mean colon lengths upon treating mice with varying doses of AB020858.
Figure 48:
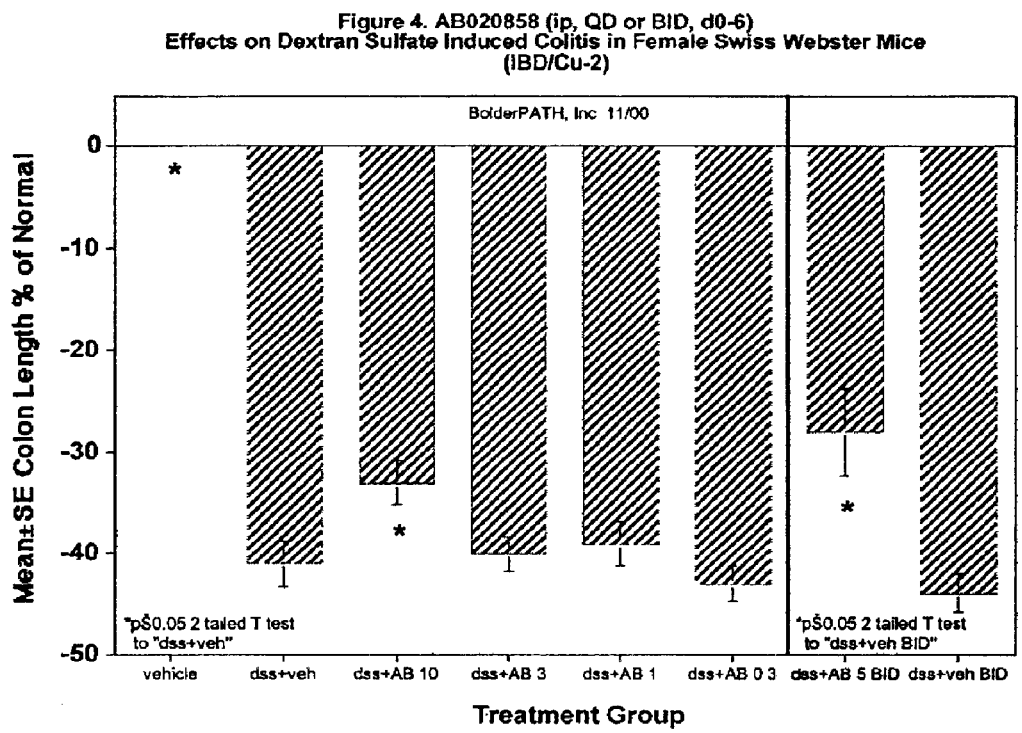
FIG. 48 presents mean colon lengths as a percent of normal, upon treating mice with varying doses of AB020858.

Absolute colon lengths (FIGS. 47 and 48) were decreased 41% in mice treated with vehicle. Treatment with AB020858 QD at 10 mg/kg resulted in significant (21%) inhibition of the DSS-induced changes in colon length. Treatment with AB020858 BID at 5 mg/kg reduced the colon length decrease 36%.

Figure 49:
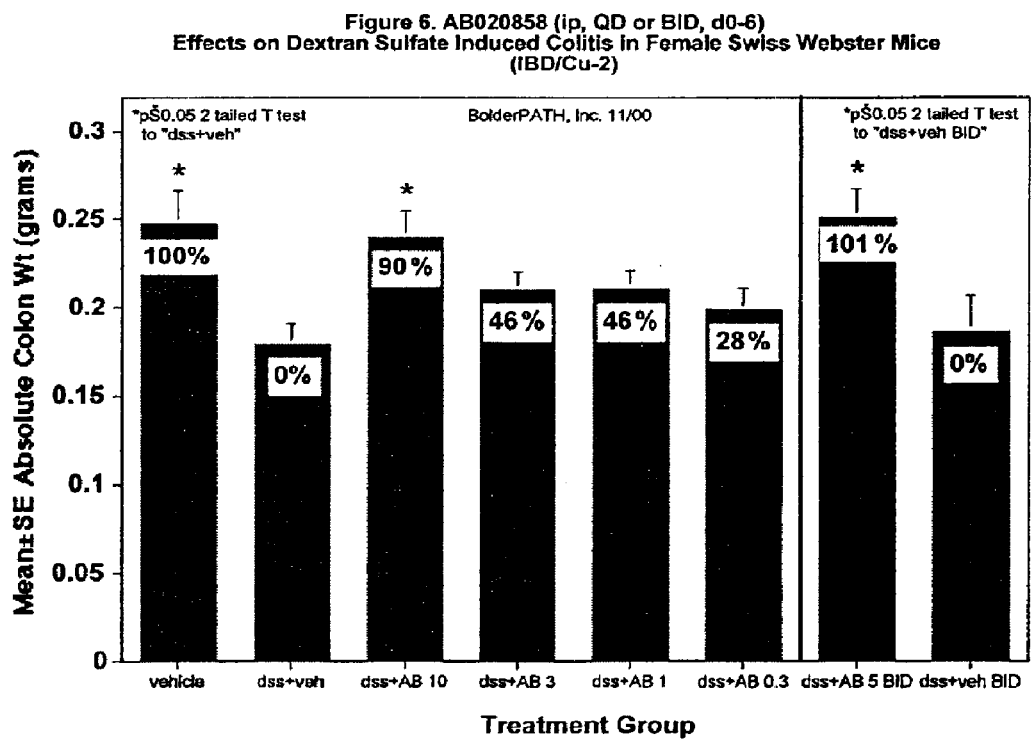
FIG. 49 presents mean colon weights upon treating mice with varying doses of AB020858.
Figure 50:
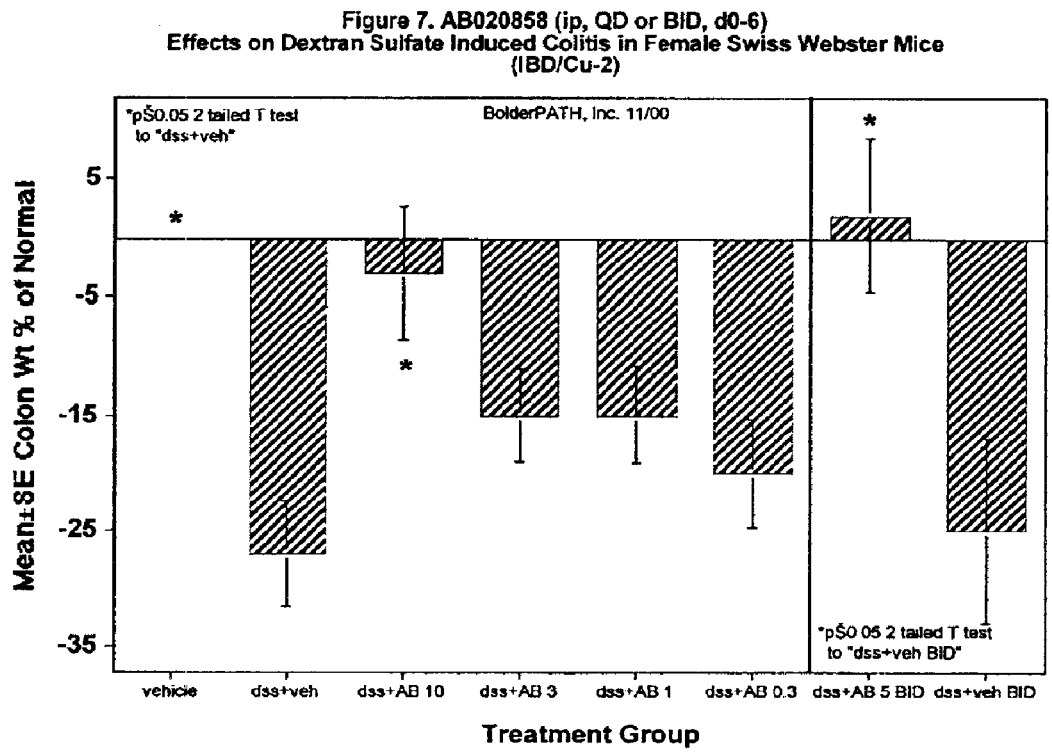
FIG. 50 presents mean colon colon weights as a percent of normal, upon treating mice with varying doses of AB020858.

Absolute colon weights (FIGS. 49 and 50) were decreased approximately 26% in mice treated with DSS in vehicle. Treatment with AB020858 at 10 mg/kg QD or 5 mg/kg BID resulted in significant reduction of the DSS-induced changes in colon weights.

Figure 51:
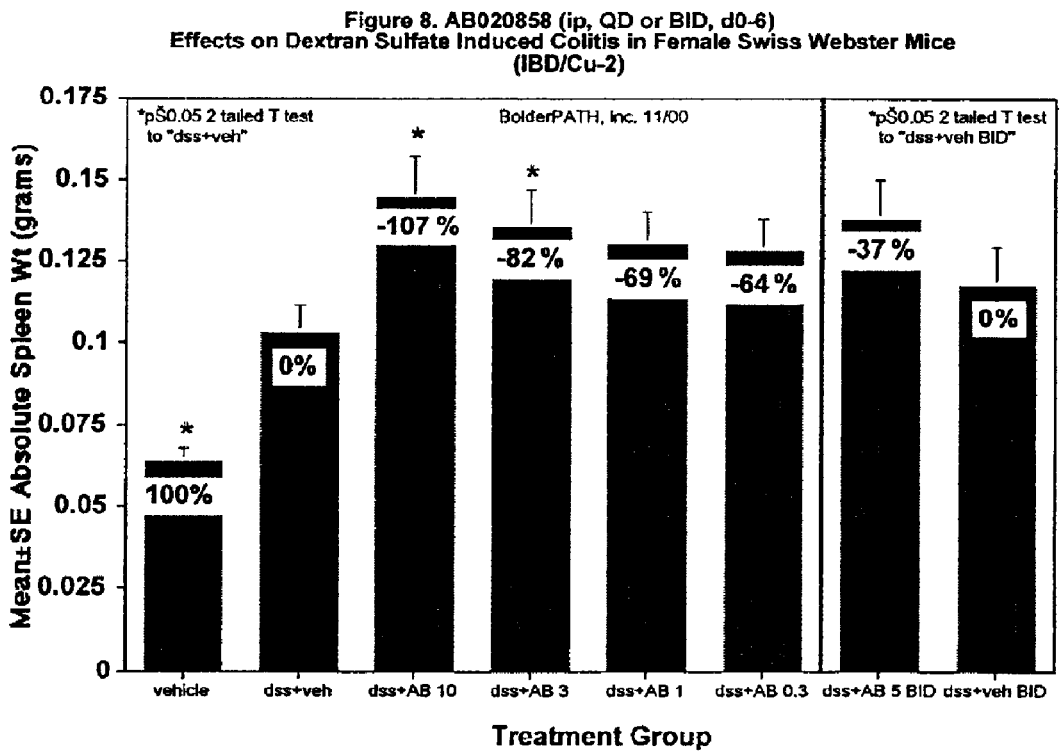
FIG. 51 presents mean spleen weights upon treating mice with varying doses of AB020858.
Figure 52:
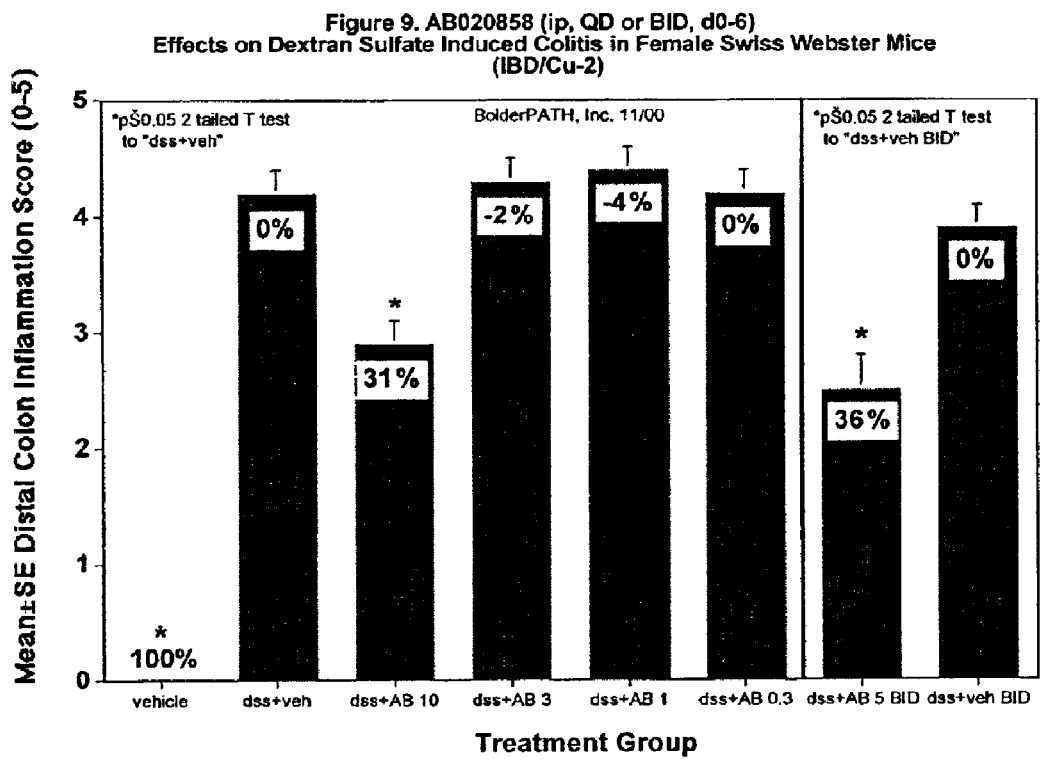
FIG. 52 presents mean distal colon inflammation score upon treating mice with varying doses of AB020858.
Figure 53:
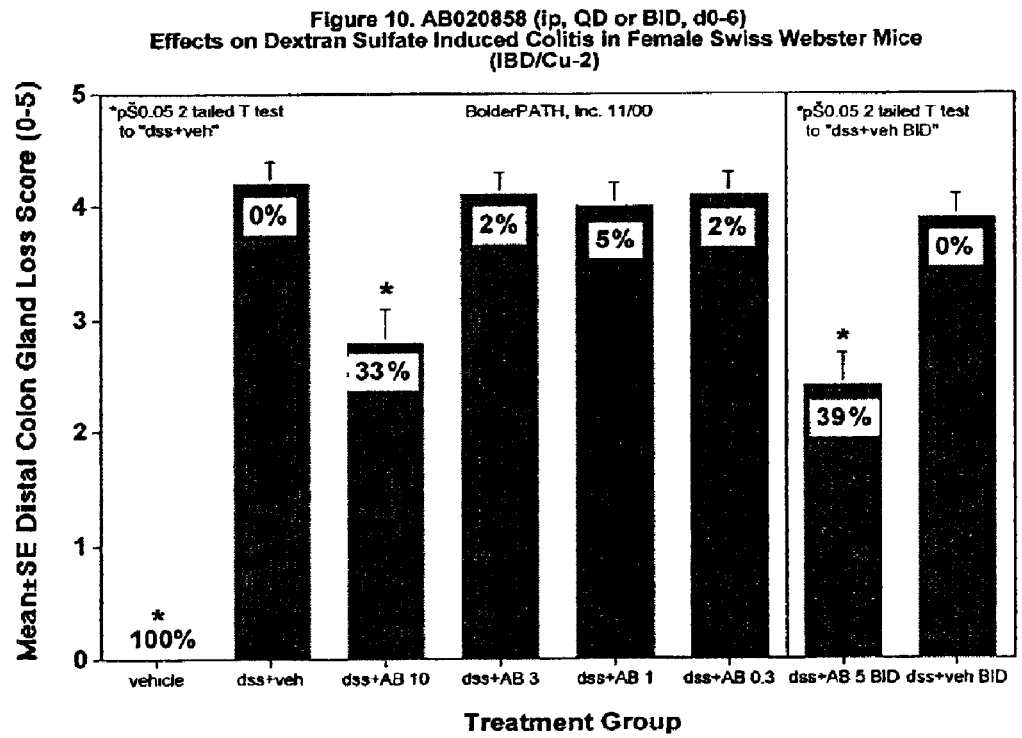
FIG. 53 presents mean distal colon gland loss score upon treating mice with varying doses of AB020858.
Figure 54:
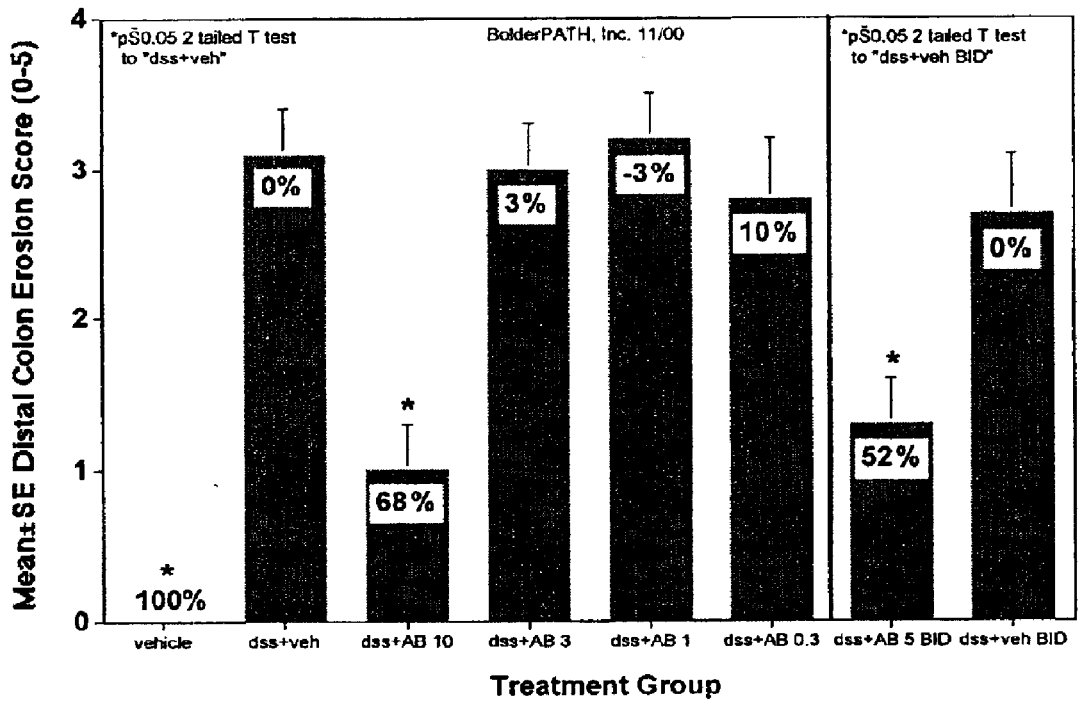
FIG. 54 presents mean distal colon erosion score upon treating mice with varying doses of AB020858.
Figure 55:
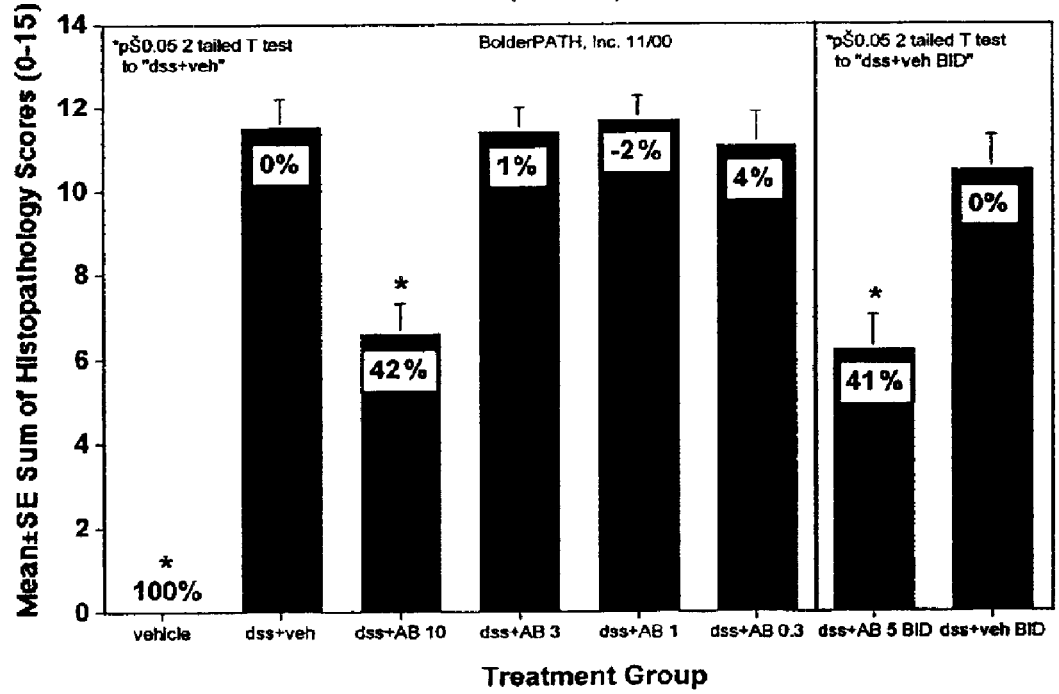
FIG. 55 presents mean sums of histopathology scores upon treating mice with varying doses of AB020858.

Absolute spleen weights (FIG. 51) were increased approximately 40% in mice treated with DSS+vehicle (due to extreme extramedullary hematopoiesis). Spleen weights were significantly greater in all DSS treated animals vs. normal.

Histopathology Findings

Significant reduction of colonic inflammation, gland loss, erosion and total histopathology scores occurred in mice treated with AB020858 QD (10 mg/kg) and BID (5 mg/kg) and was of approximately equal magnitude (FIGS. 52, 53, 54 and 55).

Figure 56:
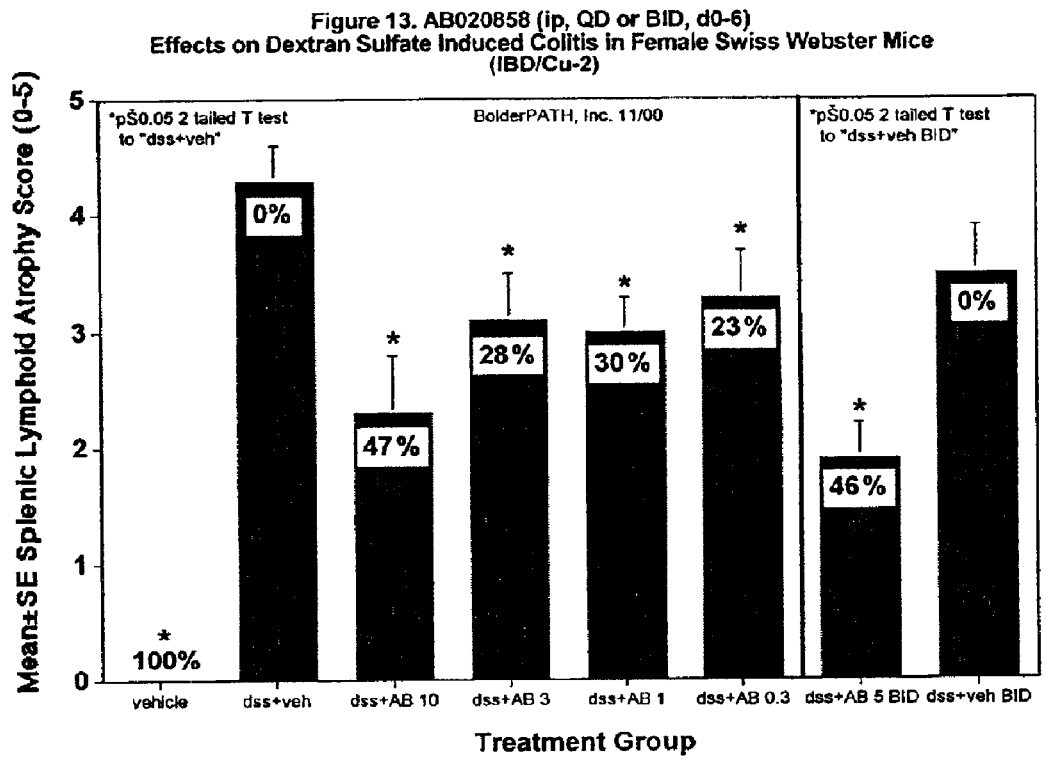
FIG. 56 presents mean splenic lymphoid atrophy score upon treating mice with varying doses of AB020858.
Figure 57:
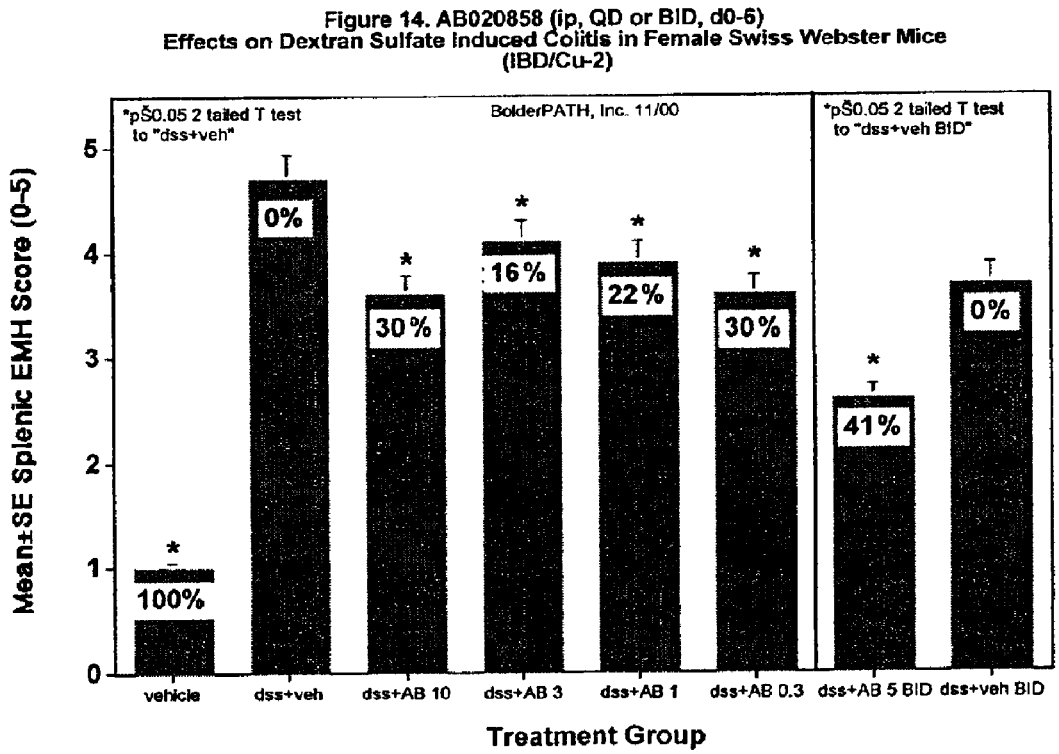
FIG. 57 presents mean splenic extramedullary hematopoiesis score upon treating mice with varying doses of AB020858.

Splenic lymphoid atrophy (an indication of stress) was inhibited in these same animals 47% and 46% respectively (FIG. 56). Inhibition of induction of splenic extramedullary hematopoiesis was greater in mice treated BID vs. QD and occurred in all treatment groups (FIG. 57).

Discussion and Conclusions

The experiments reported in this Example provide dose-response information for the administration of AB020858, using a different strain of mouse than those in Example 26 (which used Balb/c mice). The results indicate that simultaneous administration of AB020858 is effective in inhibiting the appearance of markers of DSS-induced inflammatory bowel disease, especially with the highest doses used.

Example 28

Administering CG53135 Subcutaneously

An additional experiment was carried out in which mice were also treated subcutaneously with CG531135. Together with the results in Examples 26 and 27, these studies demonstrate that prophylactic administration of CG53135 at doses of 5 or 10 mg/kg ip and 5 or 1 mg/kg sc significantly reduce the extent and severity of mucosal damage induced by dextran sulfate sodium in a murine model of colitis.

Example 29

Effects of Administering CG53135 to Indomethacin-treated Rats

Treatment of rats with indomethacin results in gross and histopathologic intestinal alterations that are similar to those occurring in Crohn's Disease. The experiments provided in this Example report on the efficacy of CG53135 in treating the rat model of indomethacin-induced intestinal injury. The efficacy of this protein in an alternate model of intestinal injury adds support to the therapeutic potential of CG53135 in treatment of inflammatory bowel disease.

Materials & Methods

Protein production. Preparation of CG53135 protein was the same as described in Example 26.

Study Design. Female Lewis rats (Harlan, Indianapolis, Ind.) weighing 175–200 g were acclimated for 8 days (Day-8 through Day-1). Rats were divided into 8 treatment groups: four groups receiving CG53135 (three groups iv and one group sc), two iv controls for normal and the disease model, and two sc controls for normal and the disease model. On Day-1, treatments with CG53135 or vehicle were initiated and continued through Day 4. CG53135 was injected iv (tail vein) at doses of 5, 1 or 0.2 mg/kg, or 1 mg/kg sc; vehicle controls were injected with BSA (5 mg/mL in PBS+1M L-arginine). On Days 0 and 1 rats were treated with indomethacin (Sigma Chemical Co., St. Louis, Mo.; 7.5 mg/kg doses) in order to induce gross and histopathologic intestinal alterations similar to those occurring in Crohn's Disease. Indomethacin was prepared in 5% sodium bicarbonate. On Day 5, rats were injected with a single ip dose of 50 mg/kg 5-bromo-2'deoxyuridine (BrdU, Calbiochem, LaJolla, Calif.) 1 hour prior to necropsy in order to pulse label proliferating cells in the intestine and spleen. Following termination, a 10 cm section of jejunum in the area at risk for lesions was weighed, given a gross pathology score, and then collected into formalin for histopathologic evaluation and scoring of necrosis and inflammation. Blood was collected for CBC analysis.

Observations and Analysis of Markers of Pathology

Gross Observations. Body weight was measured daily beginning on Day 0. At necropsy, liver and spleen weights were measured, and a 10 cm section of jejunum in the area at risk was weighed, scored for gross pathology, and collected into formalin for histopathologic evaluation and scoring of necrosis and inflammation. The area at risk for indomethacin-induced injury was scored at necropsy according to the following criteria:

0=normal

1=minimal thickening of the mesentery/mesenteric border of the intestine

2=mild to moderate thickening of the mesentery/mesenteric border of intestine, but no adhesions 3=moderate thickening with 1 or more definite adhesions that are easily separated 4=marked thickening with 1 to numerous hard to separate adhesions 5=severe intestinal lesions resulting in death.

Histopathology. Five sections (approximately equally spaced) taken from the weighed 10 cm area at risk of small intestine for indomethacin-induced lesions were fixed in 10% neutral buffered formalin, processed for paraffin embedding, sectioned at 5 μm and stained with hematoxylin and eosin for histopathologic evaluation. Necrosis was scored according to the percent area of the section affected in the same way as described in Example 26 for scoring epithelial cell loss.

Inflammation was scored according to the following criteria:

0=none

1=minimal inflammation in mesentery and muscle or lesion

2=mild inflammation in mesentery and muscle or lesion

3=moderate inflammation in mesentery and muscle or lesion

4=marked inflammation in lesion

5=severe inflammation in lesion.

The means for inflammation and necrosis were determined for each animal, and then the means for each group were calculated.

Statistics. The mean and standard error (SE) for each treatment group were determined for each parameter scored; the data were compared to the data for the disease controls using a 2-tailed Student's T test with significance at $p<0.05$.

Results

Figure 58:
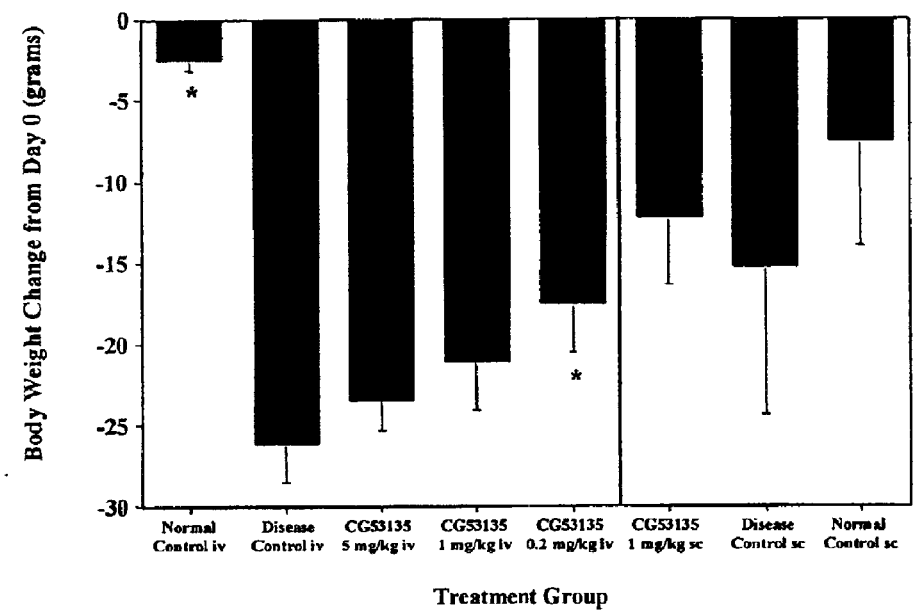
FIG. 58 presents the effect of CG53135 Treatment on Weight Loss in Indomethacin-treated rats. Body weight change from Day 0 to Day 5 is shown in grams.

Weight loss was observed in all animals treated with indomethacin. A slight, but significant reduction in weight loss was observed in animals treated with CG53135 (0.2 mg/kg iv) as compared with disease controls (iv). Other doses of CG53135 (both iv and sc routes of administration) provided diminished, but not statistically significant, indomethacin-induced weight loss (FIG. 58).

Figure 59:
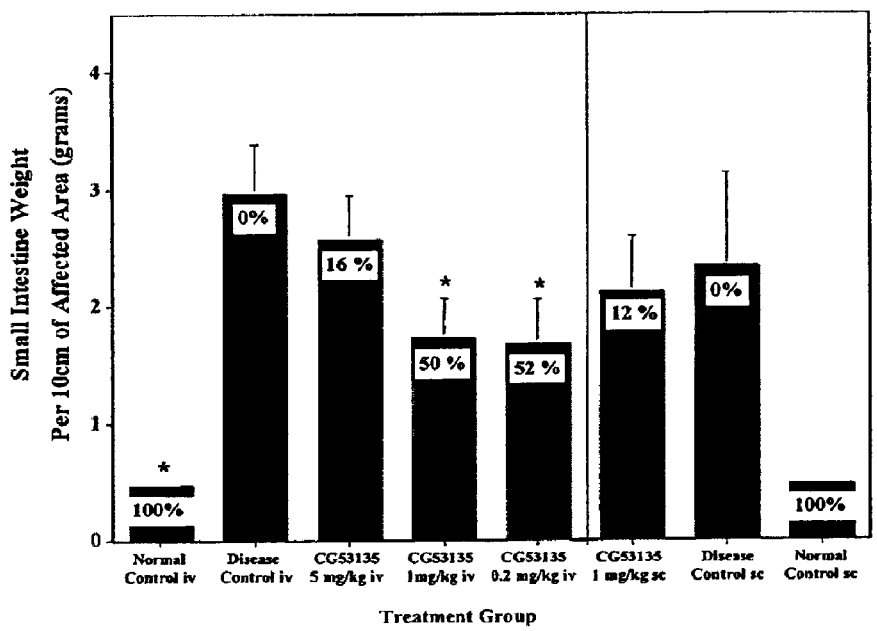
FIG. 59 presents the effect of CG53135 Treatment on Small Intestine Weight in Indomethacin-treated rats.

At necropsy, a 10 cm section of jejunum in the area at risk from each animal was weighed. Indomethacin treatment resulted in an elevation in small intestine weight as compared with normal iv and sc controls, consistent with edema and inflammation associated with this model of intestinal injury. Treatment with CG53135 (1 mg/kg or 0.2 mg/kg iv) resulted in significant reductions in small intestine weight as compared with disease controls (FIG. 59). A slight reduction in the small intestine clinical score was observed, with the greatest benefit occurring with the 1.0 mg/kg iv dose (38%) and the 0.2 mg/kg iv dose (25%); these benefits, however, were not statistically significant. Relative spleen and liver weights were increased in animals treated with indomethacin. Administration of CG53135 produced moderate additional increases in these weights (data not shown).

Figure 60:
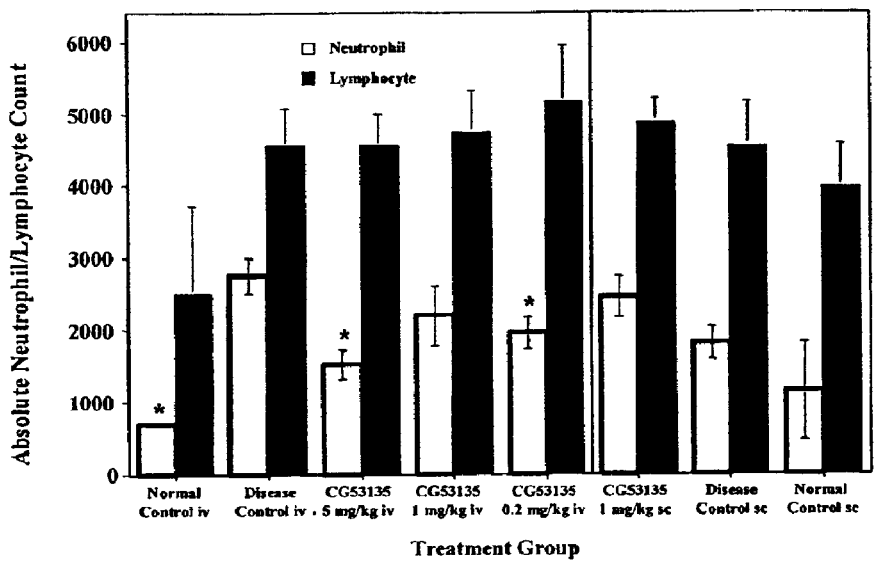
FIG. 60 presents effect of CG53135 Treatment on absolute neutrophil and lymphocyte counts in indomethacin-treated rats. Blood was collected on Day 5 at necropsy and the cell counts were determined.

Hematology. Administration of 2 doses of indomethacin to rats increased the total white blood cell count as a result of increased neutrophils and lymphocytes. Reductions in red blood cell count, hematocrit, and hemoglobin concentration were also observed. Treatment with CG53135 (5 mg/kg and 0.2 mg/kg iv) resulted in significant reductions in absolute neutrophil counts as compared with disease controls (FIG. 60). Hemoglobin concentration was diminished in the indomethacin controls compared to normal controls, and slightly further diminished in rates treated with CG53135 (data not shown).

Figure 61:
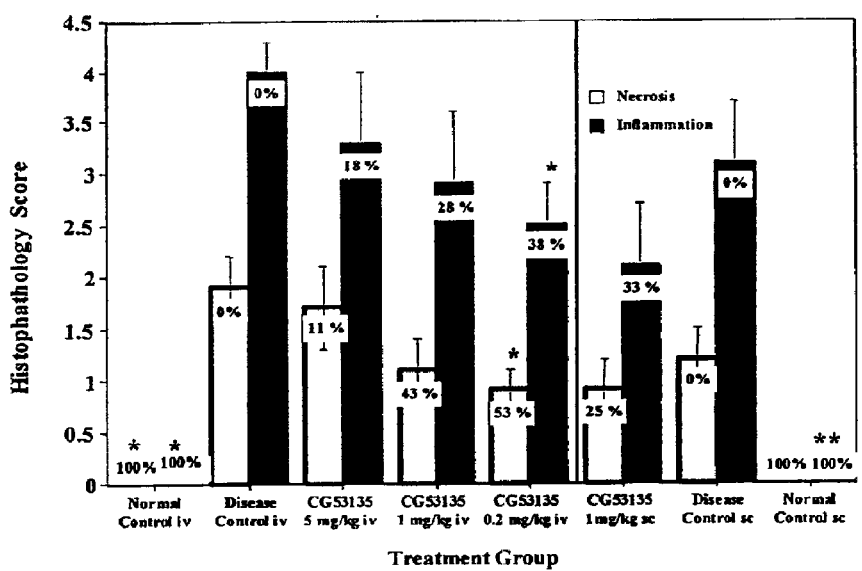
FIG. 61 presents effect of CG53135 Treatment on Histopathology Scores in Indomethacin-treated rats. Five sections of affected intestine were evaluated and scored for necrosis and inflammation as described in the methods.

Histopathology. Evaluation and scoring of 5 sections of intestine were conducted for each animal. Histologic evidence of a protective effect on the intestine was observed only in animals treated with CG53135 (0.2 mg/kg iv). A 53% reduction in jejunal necrosis and 38% reduction in inflammation score were observed for the 0.2 mg/kg iv CG53135 dose as compared with disease controls iv (FIG. 61). Photomicrographs of affected small intestine are shown in FIG. 62 for a normal and disease control, and a rat treated with 0.2 mg/kg CG53135. Panel A shows the small intestine from a normal control animal treated iv with vehicle (BSA). Normal villous architecture and mesentery (arrow) are apparent. Panel B presents a photomicrograph of the small intestine from an indomethacin-treated rat, with vehicle (BSA) iv. Focal mucosal necrosis extending across most of the area associated with attachment of the mesentery is apparent (see, for example, the asterisks at upper right intestinal wall and lower right intestinal wall). Marked inflammatory cell infiltrate is present in the mesentery (arrow). Panel C shows the image of the small intestine from an indomethacin-treated rat further treated with CG53135, 0.2 mg/kg iv. There is no apparent necrosis, in contrast to the disease control shown in Panel B. There is a focal area of attenuated villi and cellular infiltration into muscle layer (see, for example, the three asterisks at the upper right, right and lower right of the intestinal wall). Mesentery (arrow) is infiltrated by inflammatory cells. The photomicrographs in FIG. 62 provide further support for the protective effect of 0.2 mg/kg iv CG53135

BrdU labeling was carried out by injecting 50 mg/kg 1 hr prior to necropsy. In the small intestine from a normal control animal, normal pattern of crypt labeling is seen at 100× (FIG. 63, Panel A). BrdU incorporation in the disease model was decreased or absent in eptithelial cells in mucosal areas of necrosis, but increased in subajacent inflammatory tissue in which fibroblast labeling was prominent (FIG. 63, Panel B, visualized at 50×). Focal mucosal necrosis (arrow) is delineated by an absence of BrdU immunostaining as well as severe infiltration of inflammatory cells and fibroblast proliferation. Small intestine from a rat treated with indomethacin+CG53135 0.2 mg/kg iv shows an absence of crypt labeling, but relatively intact mucosa (arrow in FIG. 63, Panel C, visualized at 50×). Subadjacent smooth muscle and mesentery is only mildly infiltrated with inflammatory cells, compared with that seen in the disease control (Panel B). In certain animals treated with CG53135, in which preservation of mucosal integrity occurred, increased crypt labeling was also observed; this is in the direction found in the normal control.

The results of the experiments in this Example may be summarized as follows. Treatment of rats with indomethacin results in gross and histopathologic intestinal alterations that are similar to those occurring in Crohn's Disease. Administration of CG53135 (0.2 mg/kg iv) to indomethacin-treated rats resulted in significant reductions in weight loss, small intestine weight, absolute neutrophil counts, and jejunal necrosis and inflammation scores. Higher doses of CG53135 (5, 1 mg/kg iv and 1 mg/kg sc) were less efficacious. The morphological appearance of tissues collected from animals injected with BrdU 1 hour prior to necropsy suggested that the beneficial effects of CG53135 in this model of intestinal injury were the result of mucosal protection rather than a proliferative effect on target cells.

Example 30

Therapeutic Administration of CG53135 Enhances Survival in the Murine DSS Model

Figure 64:
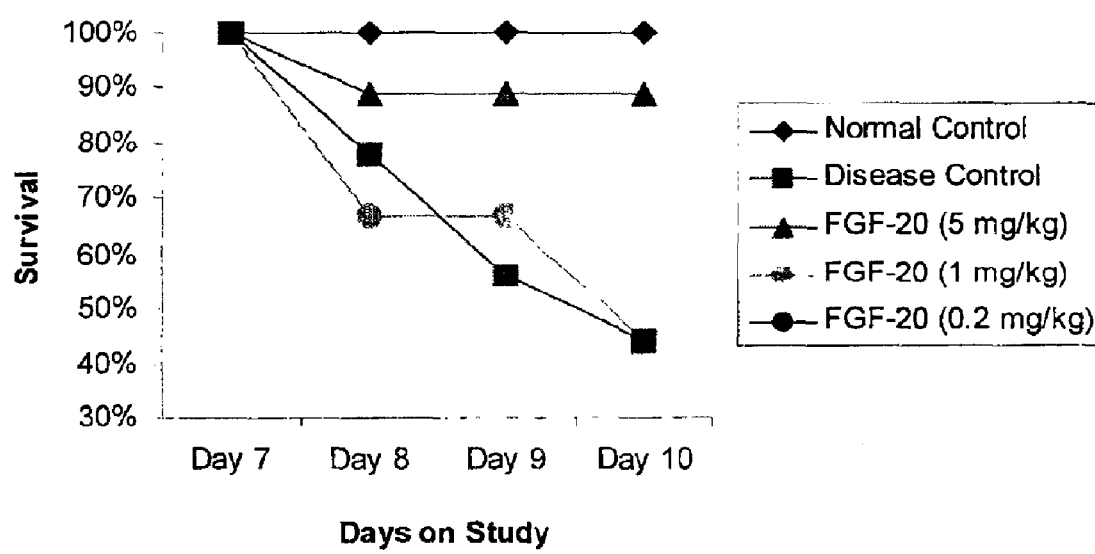
FIG. 64. Effect of therapeutically-administered CG53135 on survival in the DSS model of colitis. Female Balb/c mice were exposed to 4% DSS in drinking water for 7 days (day 0 to day 6) and then switched to normal drinking water for 4 additional days (day 7 to day 10). CG53135 is identified as FGF-20 in FIG. 64. Disease control animals (n=9) received daily SC injections of vehicle solution on day 4 to day 9. CG53135 groups (n=9) received daily SC injections of the indicated concentrations of CG53135 on day 4 to day 9. Normal control animals (n=3) were not exposed to DSS, but did receive daily SC injections of vehicle solution on day 4 to day 9. Animal survival was recorded on a daily basis and the experiment was concluded on day 10. Note that the disease control and the 0.2 mg/kg CG53135 groups overlap.

In the experiments described in Examples 26–28, DSS exposure and CG53135 administration were initiated simultaneously on day 0. In the present Example, the effect of CG53135 administered after the initiation of DSS treatment was examined. CG53135 was prepared as described in Example 26. Balb/c mice were exposed to DSS for 7 days (day 0 to day 6). The mice were injected daily subcutaneously with various concentrations of CG53135 (5, 1 and 0.2 mg/kg) beginning on the fifth day of DSS exposure (i.e. day 4) and ending 3 days after the termination of DSS exposure (i.e. day 9), or with vehicle only. Animal survival was recorded on a daily basis and the experiment was concluded on day 10. As shown in FIG. 64, therapeutic administration of CG53135 at 5 mg/kg enhanced survival relative to the disease control group. Thus, while only 44% (4 of 9) of the animals in the disease control group survived until the end of the study, 89% (8 of 9) of the animals treated with CG53135 at 5 mg/kg survived. CG53135 administered therapeutically at lower doses had no effect on survival relative to control.

EQUIVALENTS

From the foregoing detailed description of the specific embodiments of the invention, it should be apparent that particular novel compositions and methods involving nucleic acids, polypeptides, antibodies, detection and treatment have been described. Although these particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made as a matter of routine for a person of ordinary skill in the art to the invention without departing from the spirit and scope of the invention as defined by the claims. Indeed, various modifications of the invention in addition to those described herein will become apparent to those skilled in the art from the foregoing description and accompanying figures. Such modifications are intended to fall within the scope of the appended claims.

What is claimed is:

1. A method of ameliorating a symptom associated with an inflammatory bowel disease comprising administering to a subject an amount effective to ameliorate said inflammatory disease of a polypeptide comprising an amino acid SEQ ID NO: 2.

2. A method of ameliorating a symptom associated with an inflammatory bowel disease comprising administering to a subject a compsition comprising a pharmaceutically acceptable carrier and an amount effective to ameliorate said inflammatory disease of a polypeptide comprising an amino acid SEQ ID NO: 2.

3. A method of treating an inflammatory bowel disease comprising administering to a subject an amount effective to treat said inflammatory bowel disease of a polypeptide comprising an amino acid sequence of SEQ ID NO:2.

4. A method of treating an inflammatory bowel disease comprising administering to a subject a composition comprising a pharmaceutically acceptable carrier and an amount effective to treat said inflammatory bowel disease of a polypeptide comprising an amino acid sequence of SEQ ID NO:2.

5. The method of claim 3 or 4, wherein said inflammatory bowel disease is Crohn's disease.

6. The method of claim 3 or 4, wherein said inflammatory bowel disease is ulcerative colitis.

7. The method of claim 3 or 4, wherein said administering is parenteral administration.

8. The method of claim 7, wherein said parenteral administration is intravenous administration.

9. The method of claim 7, wherein said parenteral administration is subcutaneous administration.

10. The method of claim 3 or 4, wherein said administration is rectal administration.

11. The method of claim 3 or 4, wherein said administration is transdermal administration.

12. The method of claim 3 or 4, wherein said administration is transmucosal administration.

13. The method of claim 12, wherein said transmucosal administration is nasal administration.

14. The method of claim 3 or 4, wherein said subject is a mammal.

15. The method of claim 3 or 4, wherein said subject is a human.

16. The method of claim 1 or 2, wherein said inflammatory bowel disease is Crohn's disease.

17. The method of claim 1 or 2, wherein said inflammatory bowel disease is ulcerative colitis.

18. The method of claim 1 or 2, wherein said administering is parenteral administration.

19. The method of claim 18, wherein said parenteral administration is intravenous administration.

20. The method of claim 18, wherein said parenteral administration is subcutaneous administration.

21. The method of claim 1 or 2, wherein said administration is rectal administration.

22. The method of claim 1 or 2, wherein said administration is transdermal administration.

23. The method of claim 1 or 2, wherein said administration is transmucosal administration.

24. The method of claim 23, wherein said transmucosal administration is nasal administration.

25. The method of claim 1 or 2, wherein said subject is a mammal.

26. The method of claim 1 or 2, wherein said subject is a human.

* * * * *

UNITED STATES PATENT AND TRADEMARK OFFICE
CERTIFICATE OF CORRECTION

PATENT NO. : 6,982,250 B2
DATED : January 3, 2006
INVENTOR(S) : Lichenstein et al.

It is certified that error appears in the above-identified patent and that said Letters Patent is hereby corrected as shown below:

Title page,
Item [75], Inventors, "Henry Lichenstein, Guilford, CT (US)" should read -- Henri Lichenstein, Guilford, CT (US) --.

Column 129,
Line 60, "a subject a compsition comprising a pharmaceutically" should read -- a subject a composition comprising a pharmaceutically --.

Signed and Sealed this

Fourteenth Day of March, 2006

JON W. DUDAS
*Director of the United States Patent and Trademark Office*

SEQUENCE LISTING

<160> NUMBER OF SEQ ID NOS: 14

<210> SEQ ID NO 1
<211> LENGTH: 633
<212> TYPE: DNA
<213> ORGANISM: Homo sapiens

<400> SEQUENCE: 1

```
atggctccct tagccgaagt cgggggcttt ctgggcggcc tggagggctt gggccagcag      60
gtgggttcgc atttcctgtt gcctcctgcc ggggagcggc cgccgctgct gggcgagcgc     120
aggagcgcgg cggagcggag cgcgcgcggc gggccggggg ctgcgcagct ggcgcacctg     180
cacggcatcc tgcgccgccg gcagctctat tgccgcaccg gcttccacct gcagatcctg     240
cccgacggca gcgtgcaggg cacccggcag gaccacagcc tcttcggtat cttggaattc     300
atcagtgtgg cagtgggact ggtcagtatt agaggtgtgg acagtggtct ctatcttgga     360
atgaatgaca aaggagaact ctatggatca gagaaactta cttccgaatg catctttagg     420
gagcagtttg aagagaactg gtataacacc tattcatcta acatatataa acatggagac     480
actggccgca ggtattttgt ggcacttaac aaagacggaa ctccaagaga tggcgccagg     540
tccaagaggc atcagaaatt tacacatttc ttacctagac cagtggatcc agaaagagtt     600
ccagaattgt acaaggacct actgatgtac act                                   633
```

<210> SEQ ID NO 2
<211> LENGTH: 211
<212> TYPE: PRT
<213> ORGANISM: Homo sapiens

<400> SEQUENCE: 2

```
Met Ala Pro Leu Ala Glu Val Gly Gly Phe Leu Gly Gly Leu Glu Gly
  1               5                  10                  15

Leu Gly Gln Gln Val Gly Ser His Phe Leu Leu Pro Pro Ala Gly Glu
             20                  25                  30

Arg Pro Pro Leu Leu Gly Glu Arg Arg Ser Ala Ala Glu Arg Ser Ala
         35                  40                  45

Arg Gly Gly Pro Gly Ala Ala Gln Leu Ala His Leu His Gly Ile Leu
     50                  55                  60

Arg Arg Arg Gln Leu Tyr Cys Arg Thr Gly Phe His Leu Gln Ile Leu
```

|     |     |     |     |     |     |     |     |     |     |     |     |     |     |     |
|-----|-----|-----|-----|-----|-----|-----|-----|-----|-----|-----|-----|-----|-----|-----|
| 65 | | | | | 70 | | | | | 75 | | | | 80 |
| Pro | Asp | Gly | Ser | Val | Gln | Gly | Thr | Arg | Gln | Asp | His | Ser | Leu | Phe | Gly |

Pro Asp Gly Ser Val Gln Gly Thr Arg Gln Asp His Ser Leu Phe Gly
                    85                      90                      95

Ile Leu Glu Phe Ile Ser Val Ala Val Gly Leu Val Ser Ile Arg Gly
                100                     105                     110

Val Asp Ser Gly Leu Tyr Leu Gly Met Asn Asp Lys Gly Glu Leu Tyr
            115                     120                     125

Gly Ser Glu Lys Leu Thr Ser Glu Cys Ile Phe Arg Glu Gln Phe Glu
    130                     135                     140

Glu Asn Trp Tyr Asn Thr Tyr Ser Ser Asn Ile Tyr Lys His Gly Asp
145                     150                     155                     160

Thr Gly Arg Arg Tyr Phe Val Ala Leu Asn Lys Asp Gly Thr Pro Arg
                165                     170                     175

Asp Gly Ala Arg Ser Lys Arg His Gln Lys Phe Thr His Phe Leu Pro
            180                     185                     190

Arg Pro Val Asp Pro Glu Arg Val Pro Glu Leu Tyr Lys Asp Leu Leu
        195                     200                     205

Met Tyr Thr
    210

<210> SEQ ID NO 3
<211> LENGTH: 1828
<212> TYPE: DNA
<213> ORGANISM: Homo sapiens

<400> SEQUENCE: 3

```
ctaaaaaata tgttctctac aacaccaagg ctcattaaaa tattttaaat attaatatac      60
atttcttctg tcagaaatac ataaaacttt attatatcag cgcagggcgg cgcggcgtcg     120
gtcccgggag cagaacccgg cttttttcttg gagcgacgct gtctctagtc gctgatccca    180
aatgcaccgg ctcatctttg tctacactct aatctgcgca aacttttgca gctgtcggga    240
cacttctgca accccgcaga gcgcatccat caaagctttg cgcaacgcca acctcaggcg    300
agatgagagc aatcacctca cagacttgta ccgaagagat gagaccatcc aggtgaaagg    360
aaacggctac gtgcagagtc ctagattccc gaacagctac cccaggaacc tgctcctgac    420
atggcggctt cactctcagg agaatacacg gatacagcta gtgtttgaca atcagtttgg    480
attagaggaa gcagaaaatg atatctgtag gtatgatttt gtggaagttg aagatatatc    540
cgaaaccagt accattatta gaggacgatg gtgtggacac aaggaagttc ctccaaggat    600
aaaatcaaga acgaaccaaa ttaaaatcac attcaagtcc gatgactact tgtggctaa    660
acctggattc aagatttatt attctttgct ggaagatttc caacccgcag cagcttcaga    720
gaccaactgg gaatctgtca caagctctat ttcagggggta tcctataact ctccatcagt    780
aacggatccc actctgattg cggatgctct ggacaaaaaa attgcagaat ttgatacagt    840
ggaagatctg ctcaagtact tcaatccaga gtcatggcaa gaagatcttg agaatatgta    900
tctggacacc cctcggtatc gaggcaggtc ataccatgac cggaagtcaa agttgacct    960
ggataggctc aatgatgatg ccaagcgtta cagttgcact cccaggaatt actcggtcaa   1020
tataagagaa gagctgaagt tggccaatgt ggtcttcttt ccacgttgcc tcctcgtgca   1080
gcgctgtgga ggaaattgtg gctgtggaac tgtcaactgg aggtcctgca catgcaattc   1140
agggaaaacc gtgaaaaagt atcatgaggt attacagttt gagcctggcc acatcaagag   1200
gaggggtaga gctaagacca tggctctagt tgacatccag ttggatcacc atgaacgatg   1260
```

-continued

```
tgattgtatc tgcagctcaa gaccacctcg ataagagaat gtgcacatcc ttacattaag      1320
cctgaaagaa cctttagttt aaggagggtg agataagaga ccctttcct accagcaacc       1380 aaacttacta ctagcctgca atgcaatgaa cacaagtggt tgctgagtct cagccttgct     1440
ttgttaatgc catggcaagt agaaaggtat atcatcaact tctataccta agaatatagg     1500
attgcattta ataatagtgt ttgaggttat atatgcacaa acacacacag aaatatattc     1560
atgtctatgt gtatatagat caaatgtttt ttttggtata tataaccagg tacaccagag     1620
cttacatatg tttgagttag actcttaaaa tcctttgcca aaataaggga tggtcaaata     1680
tatgaaacat gtcttagaa aatttaggag ataaatttat ttttaaattt tgaaacacaa      1740
aacaattttg aatcttgctc tcttaaagaa agcatcttgt atattaaaaa tcaaaagatg     1800
aggctttctt acatatacat cttagttg                                        1828
```

<210> SEQ ID NO 4
<211> LENGTH: 370
<212> TYPE: PRT
<213> ORGANISM: Homo sapiens

<400> SEQUENCE: 4

```
Met His Arg Leu Ile Phe Val Tyr Thr Leu Ile Cys Ala Asn Phe Cys
  1               5                  10                  15

Ser Cys Arg Asp Thr Ser Ala Thr Pro Gln Ser Ala Ser Ile Lys Ala
             20                  25                  30

Leu Arg Asn Ala Asn Leu Arg Arg Asp Glu Ser Asn His Leu Thr Asp
         35                  40                  45

Leu Tyr Arg Arg Asp Glu Thr Ile Gln Val Lys Gly Asn Gly Tyr Val
     50                  55                  60

Gln Ser Pro Arg Phe Pro Asn Ser Tyr Pro Arg Asn Leu Leu Leu Thr
 65                  70                  75                  80

Trp Arg Leu His Ser Gln Glu Asn Thr Arg Ile Gln Leu Val Phe Asp
                 85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270
```

-continued

```
Thr Pro Arg Asn Tyr Ser Val Asn Ile Arg Glu Glu Leu Lys Leu Ala
        275                 280                 285
Asn Val Val Phe Phe Pro Arg Cys Leu Leu Val Gln Arg Cys Gly Gly
    290                 295                 300
Asn Cys Gly Cys Gly Thr Val Asn Trp Arg Ser Cys Thr Cys Asn Ser
305                 310                 315                 320
Gly Lys Thr Val Lys Lys Tyr His Glu Val Leu Gln Phe Glu Pro Gly
                325                 330                 335
His Ile Lys Arg Arg Gly Arg Ala Lys Thr Met Ala Leu Val Asp Ile
            340                 345                 350
Gln Leu Asp His His Glu Arg Cys Asp Cys Ile Cys Ser Ser Arg Pro
        355                 360                 365
Pro Arg
    370
```

<210> SEQ ID NO 5
<211> LENGTH: 1587
<212> TYPE: DNA
<213> ORGANISM: Homo sapiens

<400> SEQUENCE: 5

| | | | | | |
|---|---|---|---|---|---|
| agaggctctc | aaattagatc | aagaaatgcc | tttaacagaa | gtgaagagtg | aacctgctcc | 60 |
| tgacatggcg | gcttcactct | caggagaata | cacggataca | gctagtgttt | gacaatcagt | 120 |
| ttggattaga | ggaagcagaa | atgatatct | gtaggtatga | ttttgtggaa | gttgaagata | 180 |
| tatccgaaac | cagtaccatt | attagaggac | gatggtgtgg | acacaaggaa | gttcctccaa | 240 |
| ggataaaatc | aagaacgaac | caaattaaaa | tcacattcaa | gtccgatgac | tactttgtgg | 300 |
| ctaaacctgg | attcaagatt | tattattctt | tgctggaaga | tttccaaccc | gcagcagctt | 360 |
| cagagaccaa | ctgggaatct | gtcacaagct | ctatttcagg | ggtatcctat | aactctccat | 420 |
| cagtaacgga | tcccactctg | attgcggatg | ctctggacaa | aaaaattgca | gaatttgata | 480 |
| cagtggaaga | tctgctcaag | tacttcaatc | agagtcatg | gcaagaagat | cttgagaata | 540 |
| tgtatctgga | cacccctcgg | tatcgaggca | ggtcatacca | tgaccggaag | tcaaaagttg | 600 |
| acctggatag | gctcaatgat | gatgccaagc | gttacagttg | cactcccagg | aattactcgg | 660 |
| tcaatataag | agaagagctg | aagttggcca | atgtggtctt | cttccacgt | tgcctcctcg | 720 |
| tgcagcgctg | tggaggaaat | tgtggctgtg | gaactgtcaa | ctggaggtcc | tgcacatgca | 780 |
| attcagggaa | aaccgtgaaa | aagtatcatg | aggtattaca | gtttgagcct | ggccacatca | 840 |
| agaggagggg | tagagctaag | accatggctc | tagttgacat | ccagttggat | caccatgaac | 900 |
| gatgtgattg | tatctgcagc | tcaagaccac | ctcgataaga | gaatgtgcac | atccttacat | 960 |
| taagcctgaa | agaacccttta | gtttaaggag | ggtgagataa | gagaccctt | tcctaccagc | 1020 |
| aaccaaactt | actactagcc | tgcaatgcaa | tgaacacaag | tggttgctga | gtctcagcct | 1080 |
| tgctttgtta | atgccatggc | aagtagaaag | gtatatcatc | aacttctata | cctaagaata | 1140 |
| taggattgca | tttaataata | gtgtttgagg | ttatatatgc | acaaacacac | acagaaatat | 1200 |
| attcatgtct | atgtgtatat | agatcaaatg | ttttttttgg | tatatataac | caggtacacc | 1260 |
| agagcttaca | tatgtttgag | ttagactctt | aaaatccttt | gccaaaataa | gggatggtca | 1320 |
| aatatatgaa | acatgtcttt | agaaaattta | ggagataaat | ttatttttaa | attttgaaac | 1380 |
| acaaaacaat | tttgaatctt | gctctcttaa | agaaagcatc | ttgtatatta | aaaatcaaaa | 1440 |
| gatgaggctt | tcttacatat | acatcttagt | tgattattaa | aaaaggaaaa | atatggtttc | 1500 |

-continued cagagaaaag gccaatacct aagcattttt tccatgagaa gcactgcata cttacctatg    1560
tggactataa taacctgtct ccaaaac                                        1587

<210> SEQ ID NO 6
<211> LENGTH: 132
<212> TYPE: PRT
<213> ORGANISM: Homo sapiens

<400> SEQUENCE: 6

Met Tyr Leu Asp Thr Pro Arg Tyr Arg Gly Arg Ser Tyr His Asp Arg
 1               5                  10                  15

Lys Ser Lys Val Asp Leu Asp Arg Leu Asn Asp Asp Ala Lys Arg Tyr
            20                  25                  30

Ser Cys Thr Pro Arg Asn Tyr Ser Val Asn Ile Arg Glu Glu Leu Lys
        35                  40                  45

Leu Ala Asn Val Val Phe Phe Pro Arg Cys Leu Leu Val Gln Arg Cys
    50                  55                  60

Gly Gly Asn Cys Gly Cys Gly Thr Val Asn Trp Arg Ser Cys Thr Cys
65                  70                  75                  80

Asn Ser Gly Lys Thr Val Lys Lys Tyr His Glu Val Leu Gln Phe Glu
                85                  90                  95

Pro Gly His Ile Lys Arg Arg Gly Arg Ala Lys Thr Met Ala Leu Val
            100                 105                 110

Asp Ile Gln Leu Asp His His Glu Arg Cys Asp Cys Ile Cys Ser Ser
        115                 120                 125

Arg Pro Pro Arg
    130

<210> SEQ ID NO 7
<211> LENGTH: 1113
<212> TYPE: DNA
<213> ORGANISM: Mus musculus

<400> SEQUENCE: 7
atgcaacggc tcgttttagt ctccattctc ctgtgcgcga actttagctg ctatccggac     60
acttttgcga ctccgcagag agcatccatc aaagctttgc gcaatgccaa cctcaggaga    120
gatgagagca tcaccctcac agacttgtac cagagagagg agaacattca ggtgacaagc    180
aatggccatg tgcagagtcc tcgcttcccg aacagctacc caaggaacct gcttctgaca    240
tggtggctcc gttcccagga gaaaacacgg atacaactgt cctttgacca tcaattcgga    300
ctagaggaag cagaaaatga catttgtagg tatgactttg tggaagttga agaagtctca    360
gagagcagca ctgttgtcag aggaagatgg tgtggccaca aggagatccc tccaaggata    420
acgtcaagaa caaaccagat taaaatcaca tttaagtctg atgactactt tgtggcaaaa    480
cctggattca gatttatta ttcatttgtg gaagatttcc aaccggaagc agcctcagag    540
accaactggg aatcagtcac aagctctttc tctggggtgt cctatcactc tccatcaata    600
acggacccca ctctcactgc tgatgccctg acaaaactg tcgcagaatt cgataccgtg    660
gaagatctac ttaagcactt caatccagtg tcttggcaag atgatctgga gaatttgtat    720
ctggacaccc ctcattatag aggcaggtca taccatgatc ggaagtccaa agtggacctg    780
gacaggctca atgatgatgt caagcgttac agttgcactc caggaatca ctctgtgaac    840 ctcagggagg agctgaagct gaccaatgca gtcttcttcc cacgatgcct cctcgtgcag    900
cgctgtggtg gcaactgtgg ttgcggaact gtcaactgga gtcctgcac atgcagctca    960

-continued

```
gggaagacag tgaagaagta tcatgaggta ttgaagtttg agcctggaca tttcaagaga    1020 agggggcaaag ctaagaatat ggctcttgtt gatatccagc tggatcatca tgagcgatgt   1080
gactgtatct gcagctcaag accacctcga taa                                 1113
```

<210> SEQ ID NO 8
<211> LENGTH: 370
<212> TYPE: PRT
<213> ORGANISM: Mus musculus

<400> SEQUENCE: 8

```
Met Gln Arg Leu Val Leu Val Ser Ile Leu Leu Cys Ala Asn Phe Ser
 1               5                  10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Glu Ser Asn His Leu Thr Asp
        35                  40                  45

Leu Tyr Gln Arg Glu Glu Asn Ile Gln Val Thr Ser Asn Gly His Val
    50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95

His Gln Phe Gly Leu Glu Glu Ala Glu Asn Asp Ile Cys Arg Tyr Asp
            100                 105                 110

Phe Val Glu Val Glu Val Ser Glu Ser Ser Thr Val Val Arg Gly
        115                 120                 125

Arg Trp Cys Gly His Lys Glu Ile Pro Pro Arg Ile Thr Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Ser Phe Ser Gly
            180                 185                 190

Val Ser Tyr His Ser Pro Ser Ile Thr Asp Pro Thr Leu Thr Ala Asp
        195                 200                 205

Ala Leu Asp Lys Thr Val Ala Glu Phe Asp Thr Val Glu Asp Leu Leu
    210                 215                 220

Lys His Phe Asn Pro Val Ser Trp Gln Asp Asp Leu Glu Asn Leu Tyr
225                 230                 235                 240

Leu Asp Thr Pro His Tyr Arg Gly Arg Ser Tyr His Asp Arg Lys Ser
                245                 250                 255

Lys Val Asp Leu Asp Arg Leu Asn Asp Asp Val Lys Arg Tyr Ser Cys
            260                 265                 270

Thr Pro Arg Asn His Ser Val Asn Leu Arg Glu Leu Lys Leu Thr
    275                 280                 285

Asn Ala Val Phe Phe Pro Arg Cys Leu Leu Val Gln Arg Cys Gly Gly
290                 295                 300

Asn Cys Gly Cys Gly Thr Val Asn Trp Lys Ser Cys Thr Cys Ser Ser
305                 310                 315                 320

Gly Lys Thr Val Lys Lys Tyr His Glu Val Leu Lys Phe Glu Pro Gly
                325                 330                 335

His Phe Lys Arg Arg Gly Lys Ala Lys Asn Met Ala Leu Val Asp Ile
            340                 345                 350
```

```
Gln Leu Asp His His Glu Arg Cys Asp Cys Ile Cys Ser Ser Arg Pro
        355                 360                 365

Pro Arg
    370

<210> SEQ ID NO 9
<211> LENGTH: 898
<212> TYPE: DNA
<213> ORGANISM: Mus musculus

<400> SEQUENCE: 9
atgcaacggc tcgttttagt ctccattctc ctgtgcgcga actttagctg ctatccggac      60
acttttgcga ctccgcagag agcatccatc aaagctttgc gcaatgccaa cctcaggaga     120
gatgagagca atcacctcac agacttgtac cagagagagg agaacattca ggtgacaagc     180
aatggccatg tgcagagtcc tcgcttcccg aacagctacc caaggaacct gcttctgaca     240
tggtggctcc gttcccagga gaaaacacgg atacaactgt cctttgacca tcaattcgga     300
ctagaggaag cagaaaatga catttgtagg tatgactttg tggaagttga agaagtctca     360
gagagcagca ctgttgtcag aggaagatgg tgtggccaca aggagatccc tccaaggata     420
acgtcaagaa caaaccagat taaaatcaca tttaagtctg atgactactt tgtggcaaaa     480
cctggattca agatttatta ttcatttgtg aagatttcc  aaccggaagc agcctcagag     540
accaactggg aatcagtcac aagctctttc tctggggtgt cctatcactc tccatcaata     600
acggacccca ctctcactgc tgatgccctg acaaaactg  tcgcagaatt cgataccgtg     660
gaagatctac ttaagcactt caatccagtg tcttggcaag atgatctgga gaatttgtat     720
ctggacaccc tcattatag  aggcaggtca taccatgatc ggaagtccaa aggtattgaa     780
gtttgagcct ggacatttca agagaagggg caaagctaag aatatggctc ttgttgatat     840
ccagctggat catcatgagc gatgtgactg tatctgcagc tcaagaccac ctcgataa      898

<210> SEQ ID NO 10
<211> LENGTH: 261
<212> TYPE: PRT
<213> ORGANISM: Mus musculus

<400> SEQUENCE: 10

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Glu Ser Asn His Leu Thr Asp
        35                  40                  45

Leu Tyr Gln Arg Glu Glu Asn Ile Gln Val Thr Ser Asn Gly His Val
    50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95

His Gln Phe Gly Leu Glu Glu Ala Glu Asn Asp Ile Cys Arg Tyr Asp
            100                 105                 110

Phe Val Glu Val Glu Glu Val Ser Glu Ser Ser Thr Val Val Arg Gly
        115                 120                 125

Arg Trp Cys Gly His Lys Glu Ile Pro Pro Arg Ile Thr Ser Arg Thr
    130                 135                 140
```

```
Asn Gln Ile Lys Ile Thr Phe Lys Ser Asp Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Phe Ser Gly
            180                 185                 190

Val Ser Tyr His Ser Pro Ser Ile Thr Asp Pro Thr Leu Thr Ala Asp
            195                 200                 205

Ala Leu Asp Lys Thr Val Ala Glu Phe Asp Thr Val Glu Asp Leu Leu
            210                 215                 220

Lys His Phe Asn Pro Val Ser Trp Gln Asp Asp Leu Glu Asn Leu Tyr
225                 230                 235                 240

Leu Asp Thr Pro His Tyr Arg Gly Arg Ser Tyr His Asp Arg Lys Ser
                245                 250                 255

Lys Gly Ile Glu Val
            260

<210> SEQ ID NO 11
<211> LENGTH: 462
<212> TYPE: DNA
<213> ORGANISM: Homo sapiens

<400> SEQUENCE: 11
atgcaccggc tcatcttgtt ctacactcta atctgcgcaa acttttgcag ctgtcgggac    60
acttctgcaa ccccgcagag cgcatccatc aaagctttgc gcaacgccaa cctcaggcga   120
gatgttgacc tggataggct caatgatgat gccaagcgtt acagttgcac tcccaggaat   180
tactcggtca atataagaga agagctgaag ttggccaatg tggtcttctt ccacgttgc    240
ctcctcgtgc agcgctgtgg aggaaattgt ggctgtggaa ctgtcaactg gaggtcctgc   300
acatgcaatt cagggaaaac cgtgaaaaag tatcatgagg tattacagtt tgagcctggc   360
cacatcaaga ggagggtag agctaagacc atggctctag ttgacatcca gttggatcac   420
catgaacgat gcgattgtat ctgcagctca agaccacctc ga                      462

<210> SEQ ID NO 12
<211> LENGTH: 154
<212> TYPE: PRT
<213> ORGANISM: Homo sapiens

<400> SEQUENCE: 12

Met His Arg Leu Ile Leu Phe Tyr Thr Leu Ile Cys Ala Asn Phe Cys
1               5                   10                  15

Ser Cys Arg Asp Thr Ser Ala Thr Pro Gln Ser Ala Ser Ile Lys Ala
                20                  25                  30

Leu Arg Asn Ala Asn Leu Arg Arg Asp Val Asp Leu Asp Arg Leu Asn
            35                  40                  45

Asp Asp Ala Lys Arg Tyr Ser Cys Thr Pro Arg Asn Tyr Ser Val Asn
        50                  55                  60

Ile Arg Glu Glu Leu Lys Leu Ala Asn Val Val Phe Phe Pro Arg Cys
65                  70                  75                  80

Leu Leu Val Gln Arg Cys Gly Gly Asn Cys Gly Cys Gly Thr Val Asn
                85                  90                  95

Trp Arg Ser Cys Thr Cys Asn Ser Gly Lys Thr Val Lys Lys Tyr His
                100                 105                 110

Glu Val Leu Gln Phe Glu Pro Gly His Ile Lys Arg Arg Gly Arg Ala
```

-continued

```
                115                 120                 125
Lys Thr Met Ala Leu Val Asp Ile Gln Leu Asp His His Glu Arg Cys
            130                 135                 140

Asp Cys Ile Cys Ser Ser Arg Pro Pro Arg
145                 150
```

<210> SEQ ID NO 13
<211> LENGTH: 415
<212> TYPE: DNA
<213> ORGANISM: Homo sapiens

<400> SEQUENCE: 13

```
atgcaccggc tcatctttgt ctacactcta atctgcgcaa acttttgcag ctgtcgggac      60
acttctgcaa ccccgcagag cgcatccatc aaagctttgc gcaacgccaa cctcaggcga     120
gatgagagca atcacctcac agacttgtac cgaagagatg agaccatcca ggtgaaagga     180
aacggctacg tgcagagtcc tagattcccg aacagctacc ccaggaacct gctcctgaca     240
tggcggcttc actctcagga gaatacacgg atacagctag tgtttgacaa tcagtttgga     300
ttagaggaag cagaaaatga tatctgtagg tagagctaag accatggctc tagttgacat     360
ccagttggat caccatgaac gatgcgattg tatctgcagc tcaagaccac ctcga          415
```

<210> SEQ ID NO 14
<211> LENGTH: 110
<212> TYPE: PRT
<213> ORGANISM: Homo sapiens

<400> SEQUENCE: 14

```
Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg
            100                 105                 110
```